United States Patent
Bevan et al.

(10) Patent No.: US 9,624,502 B2
(45) Date of Patent: Apr. 18, 2017

(54) METHODS OF CONTROLLING PLANT SEED AND ORGAN SIZE

(75) Inventors: Michael Bevan, Norwich (GB); Yunhai Li, Beijing (CN)

(73) Assignee: PLANT BIOSCIENCE LIMITED, Norfolk (GB)

( * ) Notice: Subject to any disclaimer, the term of this patent is extended or adjusted under 35 U.S.C. 154(b) by 574 days.

(21) Appl. No.: 12/734,114

(22) PCT Filed: Oct. 10, 2008

(86) PCT No.: PCT/GB2008/003444
§ 371 (c)(1),
(2), (4) Date: Apr. 12, 2010

(87) PCT Pub. No.: WO2009/047525
PCT Pub. Date: Apr. 16, 2009

(65) Prior Publication Data
US 2011/0004962 A1    Jan. 6, 2011

(30) Foreign Application Priority Data
Oct. 11, 2007 (GB) .................................. 0719919.3

(51) Int. Cl.
| | | |
|---|---|---|
| *A01H 3/00* | (2006.01) |
| *A01H 5/00* | (2006.01) |
| *C12N 15/82* | (2006.01) |
| *C07K 14/415* | (2006.01) |

(52) U.S. Cl.
CPC ........ *C12N 15/8261* (2013.01); *C07K 14/415* (2013.01)

(58) Field of Classification Search
CPC ................................................ C12N 15/8261
USPC ........................................................ 800/290
See application file for complete search history.

(56) References Cited

U.S. PATENT DOCUMENTS

2006/0048240 A1* 3/2006 Alexandrov et al. ......... 800/278

OTHER PUBLICATIONS

Li et al (2008,Genes & Development 22:1331-1336).*
Hurley et al., Ubiquitin—binding domains, 399 Biochem J., 361-372 (2006).*
Li et al., Control of final seed and organ size by the DA1 gene family in *Arabidopsis thaliana*, 22 Genes & Development 1331-1336 (2008).*
Disch et al., The E3 Ubiquitin Ligase Big Brother Controls Arabidopsis Organ Size in a Dosage-Dependent Manner, 16 Current Biology 272-279 (2006).*
Friedberg, Automated protein function prediction—the genomic challenge, 7 Briefings in Bioinformatics 225-242, at p. 232, right column (2006).*
Sharghi and Bagheri, Review of Morphology and Biologic in Canola (*Brassica napus* L.), 6 Research Journal of Fisheries and Hydrobiology No. 4, 608-610 (2011).*
Wang et al. Over expression of Zmda1-1 gene increases seed mass of corn African Journal of Biotechnology vol. 11(69), pp. 13387-13395, Aug. 28, 2012.
International Search Report for PCT/GB2008/003444, mailed Feb. 18, 2009.
Written Opinion of the International Searching Authority for PCT/GB2008/003444, mailed Feb. 18, 2009.
Li, Yunhai et al., "Control of final seed and organ size by the DA1 gene family in *Arabidopsis thaliana*", Genes & Development, vol. 22, No. 10, (May 2008), pp. 1331-1336.
Disch, Sabine et al., "The E3 Ubiquitin Ligase Big Brother Controls Arabidopsis Organ Size in a Dosage-Dependent Manner", Current Biology, Current Science, vol. 16, No. 3, (Feb. 7, 2006), pp. 272-279.

* cited by examiner

*Primary Examiner* — Li Zheng
(74) *Attorney, Agent, or Firm* — Nixon & Vanderhye P.C.

(57) ABSTRACT

This invention relates to the identification of a regulator protein (termed DA) which controls the size of plant seeds and organs in *Arabidopsis* and other plants. Manipulation of DA protein expression may useful, for example, in improving crop yield and increasing plant biomass.

16 Claims, 23 Drawing Sheets

```
Alignment B
UIM1
DA1
Q9LM05/295-314       DDTAL QQ    AM. MAQAAQ A
O74423/258-277       DSEAE QR    QL. KEEDEA R
VP27_YEAST/358       DEEELIE     EL. LKESEN S
Q05785/175-194       SYQDE EE    EE. RITAQE D
Q9P2G1/976-995       EDDENILI    QL. LQESGL A
AAK61871/105-1       EEEEL EE    AK. LNSCRP S
16741231/329-3       DEDLQ QI    SL. RQEHEK G
Q9XTL2/173-192       QEEDDIAE    EL. LKENEG S
2623826/295-31       SEEDQIAY    RM. LQQMGE E
Q9FJX8/64-84         BEAEQ DL    QEF RQEEEE E
Q9C9U5/139-158       EEENQIQI    EL. AREDPE A
YMI8_YEAST/651       NVDED QL    AL. LSEIN- -
Q9FJX8/119-138       EEDEI ARTI  EE. LKENNR R
AAK61871/80-99       TEEEQFAI    KM. EQEARE V
Q20187/2-21          SDEEE QI    EI. KKTFED E
Q9HCH8/758-777       EEEQE QQ    AQ. LQEQEA W
Q9V8R1/660-679       YVDFE AM    RL. QQEQRK F
O81340/323-343       GDDQE QI    QL. VQDSAK E
Q9TOE1/138-157       IEEEMIRA    EA. KKEAEG S
O74749/164-183       EEEEE QY    AL. LSESTA A
O35815/324-343       DDEDE QR    AM. RQEIDN E
O82143/323-343       VDDQE AI    QM. VQDAGG S
Q9HFR1/208-227       EMDFE AM    RM. LQEAQA Q
Q9FJX8/146-165       EKDEQ ALIV  QE. LNMEKY F
ENSG00000013375      EDDDL QE    QQ. LLEAGT E
YMI8_YEAST/517       ENDIQ EI    LE. QEACAR N
Q9MA77/5-34          QEDED KI    KM. MQYNPE E
Q9V8R1/510-529       DEDDM QY    EQ. LVETSG A
AAH11090/250-2       SEDEE QL    M AY. LSEMEA A
O13821/260-279       NEDEDIEE    EL. LKEMPQ S
O13821/304-323       DEDEE EE    AI. LEEAQE S
YMI8_YEAST/583       EDDEEFLE    RQ. RVEDER E
EP15_MOUSE/878       QEQEE EE    AL. KSEISE A
O35815/329-348       SEEDV RATV  TV. LETARD S
PSD4_ARATH/282       EDSAL DQ    AM. VGDVEN S
Q9FJX8/38-57         QEEADIQE K  QE. LATEKA E
VP27_YEAST/301       EEDFE EA    QE. LREAEE A
O74423/230-249       ENDFE QRV   EE. KEQAEE D
O82143/291-310       DDAQL QQ    AM. MEEGSS G
Q9LG27/1615-16       QEDEE AQ    AL. LGNSEE P
Q9HA18/233-252       GDDLE QM    EE. KEETGG K
O23197/65-84         FDEEEIEC    AL. LSEQEE V
O45266/382-401       SDSIE EY    EL. LLDSEE D
Q9H3M9/215-234       QEEEDFQE    EL. RQETNR E
YRA2_YEAST/162       SEDEE QE    KM. LFEYEE Q
YMI8_YEAST/547       DEDEQ EE    EE. QLIYEP Q
2623826/262-28       SEEAM QQ    AM. MQMNWT E
Q9HCH8/780-799       KEDDD EE    T EL. LQEFNN S
Q12518/165-184       ENDEE QE    SA. KLTAEE D
O75886/165-184       KEDEDIAE    EL. LQEQKQ Q
EP15_MOUSE/852       SEEEMIEW K  EE. EEEEEQ E
O23197/110-129       DEDEEYEE Q  LE. AAEEER E
Q9HCH8/656-675       SEEEI AAVI  EI. KEDASP S
Q9TOE1/170-189       EDDDDIAE V  TM. LESAEE E
Q03291/171-190       QEDEE EM    LE. LQELNT N
PSD4_DROME/212       NEDFE AI    EV. MEEQRQ E
Q9H3M9/235-252       EEDEE ESTI  EL. MQGSSG N
Q9VS85/226-245       SEDVE QI    SQ. EQDFKD F
```

Alignment C

Explanation of colour codes used by CHROMA

| Group name | Amino acids | Displayed as |
|---|---|---|
| Default | X | . |
| Single | X | ▮ |
| Alanine | A | ▨ |
| Cysteine | C | ▨ |
| Aspartic Acid | D | ▨ |
| Glutamic Acid | E | ▨ |
| Phenylalanine | F | ▨ |
| Glycine | G | ▨ |
| Histidine | H | ▮ |
| Isoleucine | I | ▯ |
| Lysine | K | ▮ |
| Leucine | L | ▨ |
| Methionine | M | ▯ |
| Asparagine | N | ▮ |
| Proline | P | ▯ |
| Glutamine | Q | ▮ |
| Arginine | R | ▮ |
| Serine | S | ▯ |
| Threonine | T | ▯ |
| Valine | V | ▨ |
| Tryptophan | W | ▯ |
| Tyrosine | Y | ▨ |
| Negative | D,E | - |
| Ser/Thr | S,T | = |
| Aliphatic | I,L,V | \| |
| Positive | H,K,R | + |
| Tiny | A,G,S | t |
| Aromatic | F,H,W,Y | a |
| Charged | D,E,H,K,R | c |
| Small | A,C,D,G,N,P,S,T,V | s |
| Polar | C,D,E,H,K,N,Q,R,S,T | p |
| Big | E,F,H,I,K,L,M,Q,R,W,Y | b |
| Hydrophobic | A,C,F,G,H,I,L,M,T,V,W,Y | h |

METHODS OF CONTROLLING PLANT SEED AND ORGAN SIZE

This application is the U.S. national phase of International Application No. PCT/GB2008/003444 filed 10 Oct. 2008, which designated the U.S. and claims priority to GB Application No. 0719919.3 filed 11 Oct. 2007, the entire contents of each of which are hereby incorporated by reference.

FIELD OF INVENTION

This invention relates to methods of controlling the size of the seeds and organs of plants.

BACKGROUND OF INVENTION

The size of seeds and organs is an agronomically and ecologically important trait that is under genetic control (Alonso-Blanco, C. Proc Natl Acad Sci USA 96, 4710-7 (1999); Song, X. J. Nat Genet 39, 623-30 (2007); Weiss, J. Int J Dev Biol 49, 513-25 (2005); Dinneny, J. R. Development 131, 1101-10 (2004); Disch, S. Curr Biol 16, 272-9 (2006); Science 289, 85-8 (2000); Horiquchi, G. Plant J 43, 68-78 (2005); Hu, Y Plant J 47, 1-9 (2006); Hu, Y. Plant Cell 15, 1951-61 (2003); Krizek, B. A. Dev Genet 25, 224-36 (1999); Mizukami, Y. Proc Natl Acad Sci USA 97, 942-7 (2000); Nath, U. Science 299, 1404-7 (2003); Ohno, C. K. Development 131, 1111-22 (2004); Szecsi, J. Embo J 25, 3912-20 (2006); White, D. W. Proc Natl Acad Sci USA 103, 13238-43 (2006); Horvath, B. M. Embo J 25, 4909-20 (2006); Garcia, D. Plant Cell 17, 52-60 (2005). The final size of seeds and organs is constant within a given species, whereas interspecies seed and organ size variation is remarkably large, suggesting that plants have regulatory mechanisms that control seed and organ growth in a coordinated and timely manner. Despite the importance of seed and organ size, however, little is known about the molecular and genetic mechanisms that control final organ and seed size in plants.

The genetic regulation of seed size has been investigated in plants, including in tomato, soybean, maize, and rice, using quantitative trait locus (QTL) mapping. To date, in the published literature, two genes (Song, X. J. Nat Genet 39, 623-30 (2007); Fan, C. Theor. Appl. Genet. 112, 1164-1171 (2006)), underlying two major QTLs for rice grain size, have been identified, although the molecular mechanisms of these genes remain to be elucidated. In Arabidopsis, eleven loci affecting seed weight and/or length in crosses between the accessions Lcr and Cvi, have been mapped {Alonso-Blanco, 1999 supra}, but the corresponding genes have not been identified. Recent studies have revealed that AP2 and ARF2 are involved in control of seed size. Unfortunately, however, apt and arf2 mutants have lower fertility than wild type (Schruff, M. C. Development 137, 251-261 (2006); Ohto, M. A. Proc. Natnl Acad. Sci USA 102, 3123-3128 (2005); Jofuku, K. D. Proc. Natnl Acad. Sci. USA 102, 3117-3122 (2005)). In addition, studies using mutant plants have identified several positive and negative regulators that influence organ size by acting on cell proliferation or expansion {Krizek, B. A. Dev Genet 25, 224-36 (1999); Mizukami, Y. Proc Natl Acad Sci USA 97, 942-7 (2000); Nath, U. Science 299, 1404-7 (2003); Ohno, C. K. Development 131, 1111-22 (2004); Szecsi, J. Embo J 25, 3912-20 (2006); White, D. W. Proc Natl Acad Sci USA 103, 13238-43 (2006); Horvath, B. M. Embo J 25, 4909-20 (2006); Garcia, D. Plant Cell 17, 52-60 (2005). Horiguchi, G. Plant J 43, 68-78 (2005); Hu, Y Plant J 47, 1-9 (2006) Dinneny, J. R. Development 131, 1101-10 (2004)).

Identification of a factor or factors that control the final size of both seeds and organs will not only advance understanding of the mechanisms of size control in plants, but may also have substantial practical applications for example in improving crop yield and plant biomass for generating biofuel.

SUMMARY OF INVENTION

The present inventors have identified a UIM and LIM domain-containing protein (termed DA1) which is a key regulator in controlling the final size of seeds and organs by restricting the duration of proliferative growth. An allele (termed the da1-1 allele) is shown herein to act as a dominant negative interfering mutation for DARs or DA1-related proteins. Over-expression of the da1-1 mutant gene (R358K) in wild type causes an increase in seed and organ size in wild type plants, indicating that the da1-1 allele interferes with DARs in a dosage dependent manner. Mutations that reduce or abolish the function of EOD1/BB, which encodes an E3 ubiquitin ligase, synergistically enhance the phenotypes of da1-1, indicating that DA1 acts in parallel with EOD1/BB to limit the size of seeds and organs. The functional characterization of DA1 and EOD1/BB provides insight into the mechanism of control of the final seed and organ size and may be a valuable tool for improving crop yield and increasing plant biomass.

Aspects of the invention provide an isolated protein which is DA1 and an isolated nucleic acid encoding a protein which is DA1. Also provided are DA1-related proteins and encoding nucleic acid. DA1 and DA1-related proteins (DARs) are collectively referred to herein as DA proteins.

Other aspects of the invention provide an isolated protein (DA1R358K) which interferes with the function of DA1 and DA1-related proteins and an isolated nucleic acid encoding such a protein.

Another aspect of the invention provides a method for producing plants having normal fertility but which have one or more features selected from longer life-span, enlarged organ size, enlarged seed size.

Another aspect of the invention provides a plant having normal fertility but which has a feature selected from longer life-span, enlarged organ size, enlarged seed size, and combinations of these features

BRIEF DESCRIPTION OF DRAWINGS

Figure 16B:
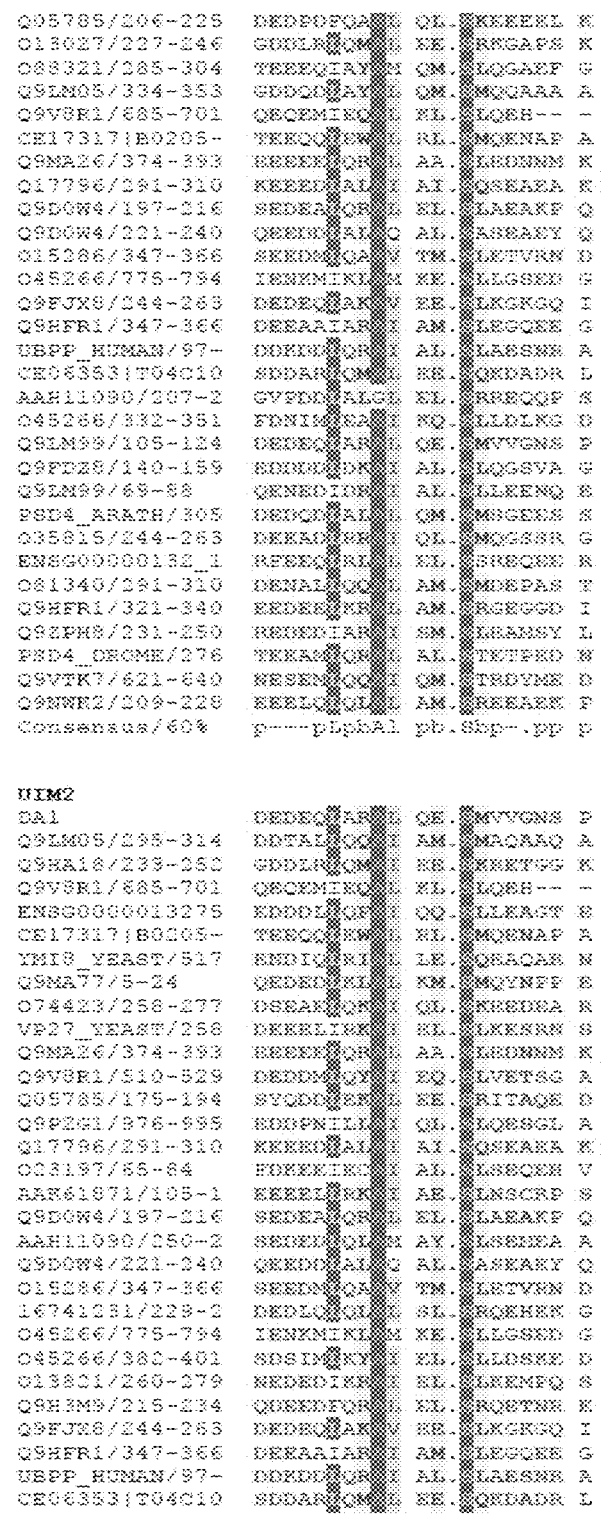
Figure 16C:
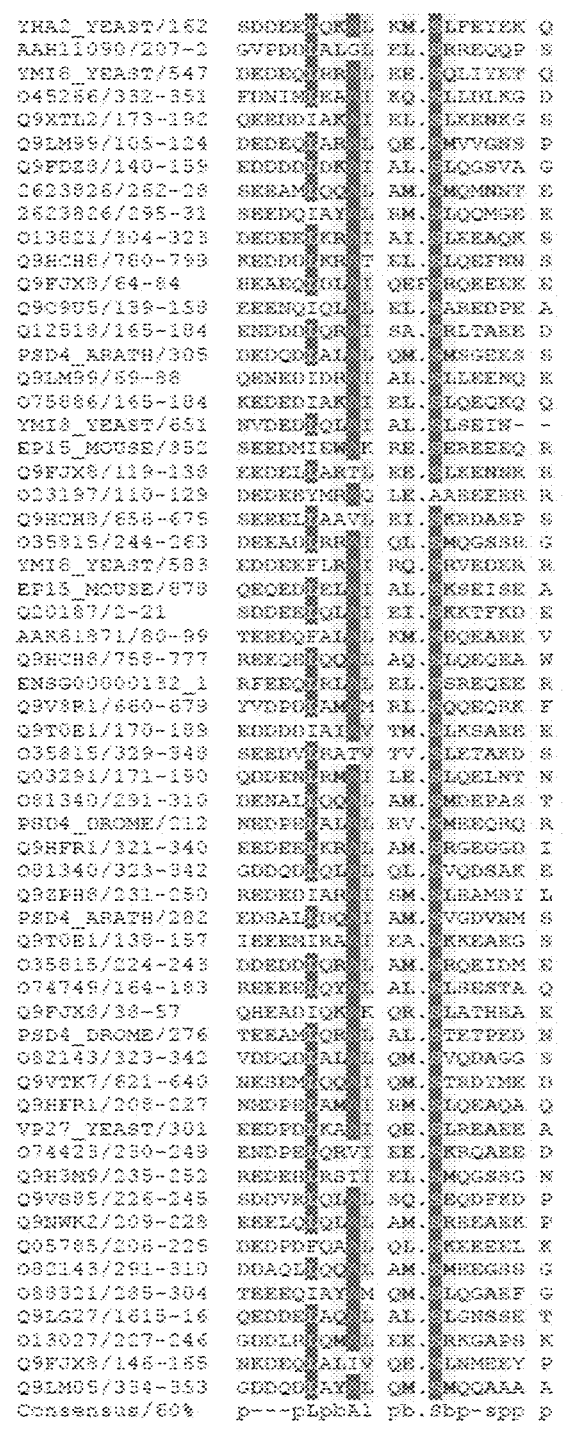

FIGS. 16 (A-C) show an alignment (alignment B) of UIM motifs among different UIM motif-containing proteins. UIM motifs were predicted by using SMART software. Sequences of FIG. 16A are listed in the Sequence Listing as SEQ ID NOs: 60-118, respectively. Sequences of FIG. 16B are listed in the Sequence Listing as SEQ ID NOs: 119-148, 3, 149, 61, 101, 123, 85, 124, 86, 87, 62, 63, 125, 80, 64, 65, 126, 102, 66, 127, 89, 128, 129, 61, 130, 103, 90, 104, 131, 132, 133, and 134, respectively. Sequences of FIG. 16C are listed in the Sequence Listing as SEQ ID NOs: 105, 135, 106, 136, 68, 137, 138, 107, 69, 91, 108, 70, 71, 109, 140, 139, 110, 72, 111, 73, 112, 113, 141, 92, 93, 75, 74, 76, 142, 77, 114, 94, 115, 143, 116, 144, 78, 145, 95, 79, 81, 80, 96, 146, 82, 147, 83, 97, 98, 117, 118, 148, 119, 99, 121, 100, 120, 84, 122, and 4, respectively.

Figure 17A:
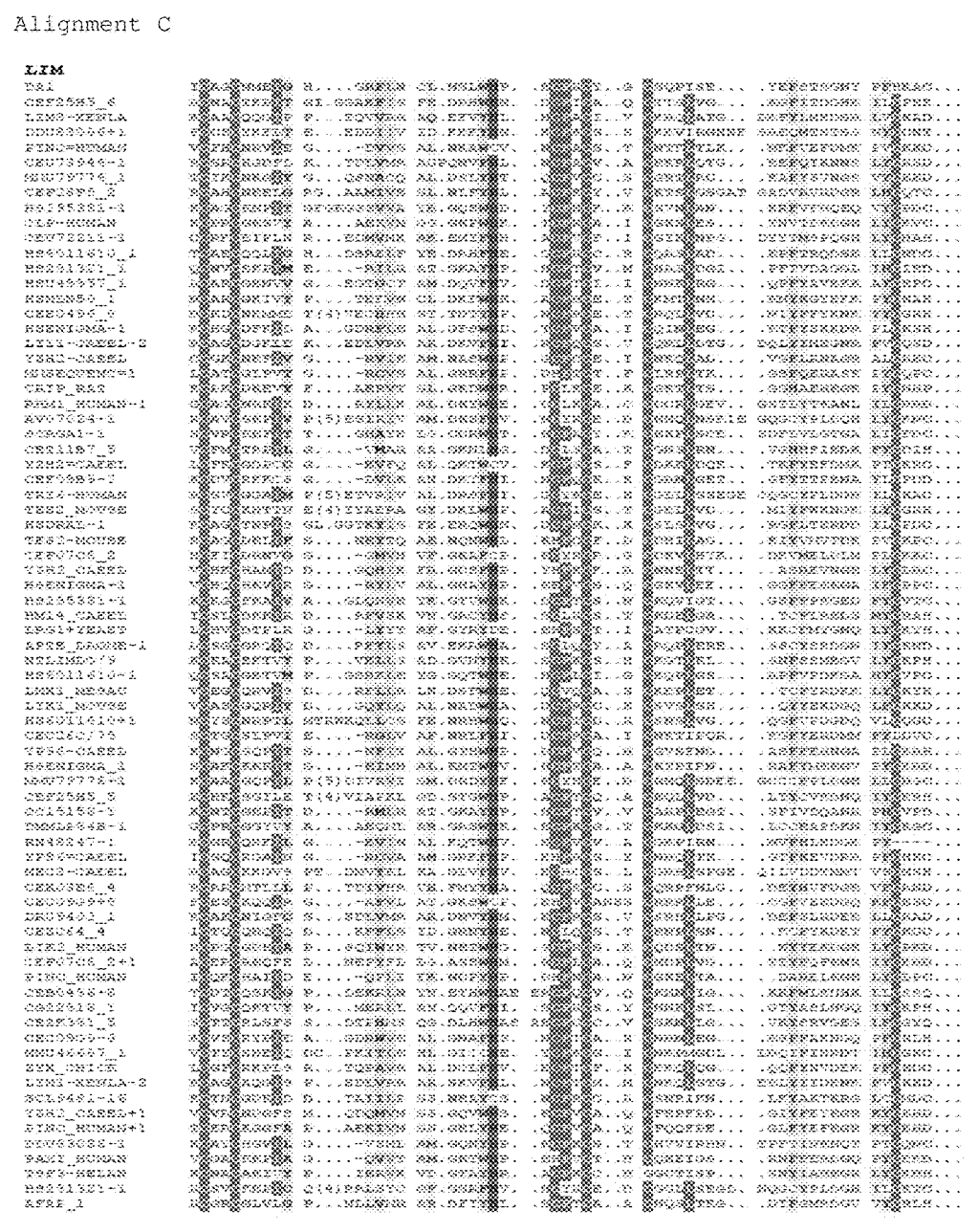
Figure 17B:
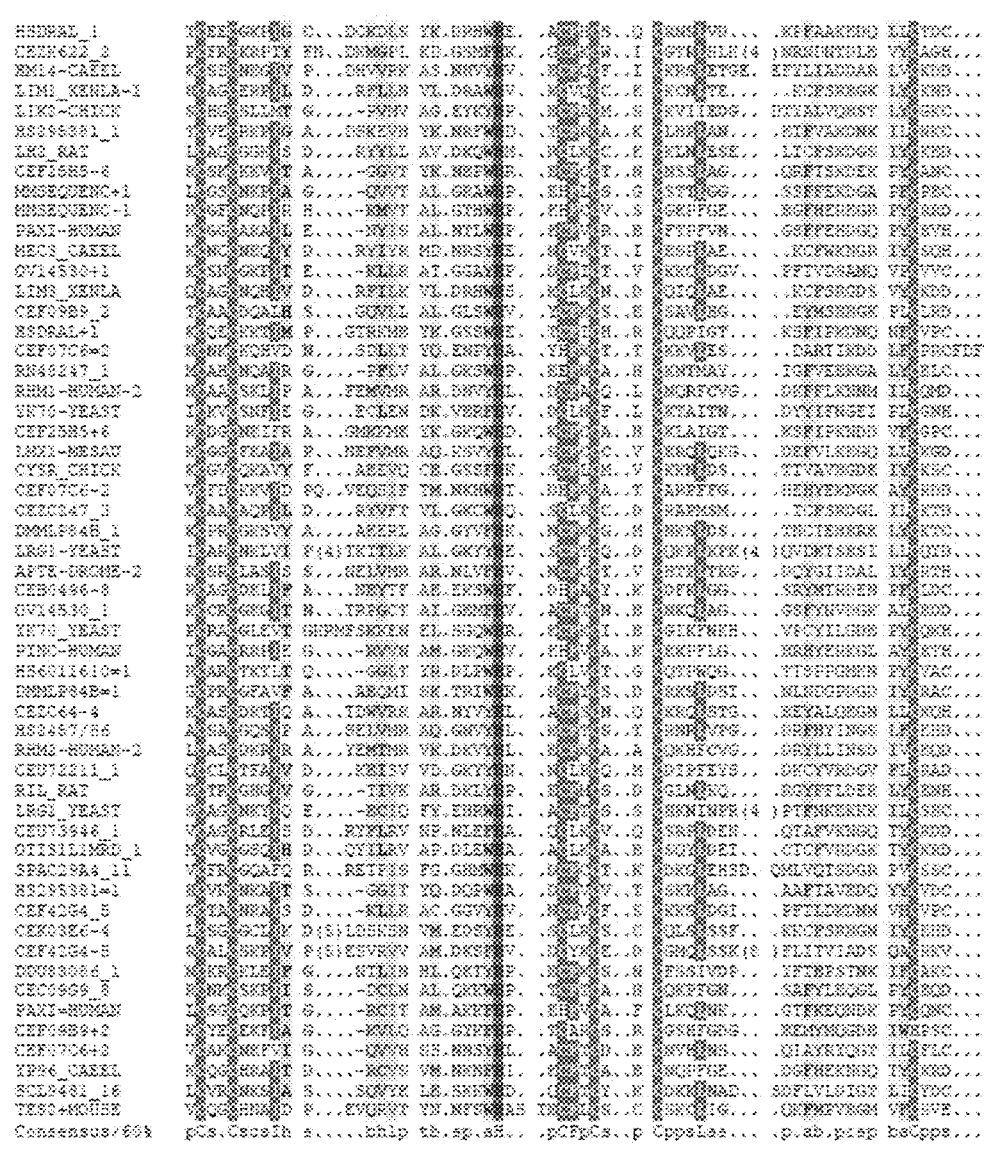

FIGS. 17 (A-C) show an alignment (alignment C) of LIM domains among LIM domain-containing proteins. In the LIM domain, there are seven conserved cysteine residues and one conserved histidine. The arrangement followed by these conserved residues is C-x(2)-C-x(16,23)-H-x(2)-[CH]-x(2)-C-x(2)-C-x(16,21)-C-x(2,3)-[CHD]. The LIM domain (E-value, 3.05e-10) was predicted by using SMART software. Sequences of FIG. 17A are listed in the Sequence Listing as SEQ ID NOs: 150, 151-164, 165 & 166 (CEB0496_8), 167-172, 173 & 174 (AV07024-1), 175-178, 179 & 180 (TRI6-HUMAN), 181 & 182 (TES2_MOUSE), 183-199, 200 & 201 (MXU79776-1), 202 & 203 (CEF25H5_5), 204-228, 229 & 230 (HS281321-1), and 231, respectively. Sequences of FIG. 17B are listed in the Sequence Listing as SEQ ID NOs: 232, 233 & 234 (CEZK622_2), 235-258, 259 & 260 & 261 (LRG1_YEAST), 262-273, 274 & 275 (LRG1_YEAST), 276-280, 281 & 282 (CEK03E6-4), 283 & 284 & 285 (CEF42G4-5), 286-293, and 5, respectively.

DETAILED DESCRIPTION OF EMBODIMENTS OF THE INVENTION

Figure 1:
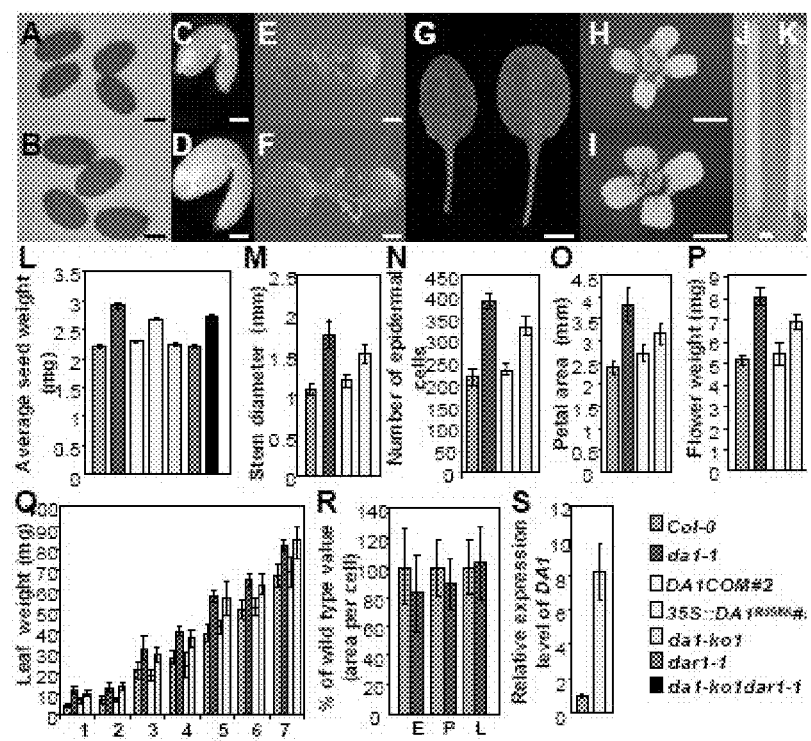
FIG. 1 shows that da1-1 has large seeds and organs. (A and B) Dry seeds of Col-0 (A) and da1-1 (B). (C and D) Mature embryos of Col-0 (C) and da1-1(D). (E and F) 9 d-old seedlings of Col-0 (E) and da1-1 (F). da1-1 has larger cotyledons than WT. (G) The fifth leaves of Col-0 (left) and da1-1 (right). da1-1 has larger and rounder leaves compared with wild type Col-0. (H and I) Flowers of Col-0 (H) and da1-1(I). (J and K) Siliques of Col-0 (J) and da1-1 (K). (L) Average seed weight of Col-0, da1-1, da1-ko1, dar1-1, and da1-ko1dar1-1 is given in mg per 100 seeds. Standard deviations (SD) are shown (n=5). Plants were grown under identical conditions. (M-O) stem diameter (M), epidermal cell number in stem cross sections (N), and petal area (0) of Col-0, da1-1, DA1COM#2, and 35.5::DA1$^{P358K}$#5. (P and Q) Mass of 5 fresh flowers (stage 14) (P) and leaves ($1^{st}$-$7^{th}$) of 35 d-old plants (Q). (R) Cell area of embryos (E), petals (P) and leaves (L) in Col-0 and da1-1. Values are given as mean±SD relative to the respective wild type value, set at 100%. (S) Relative expression levels of DA1 in Col-0 and 35S::DA1$^{R358K}$#5 seedlings were measured by quantitative real-time RT-PCR. Scale bars: 200 μm (A and B), 100 μm (C and D), 1 mm (E and F), 0.5 cm (G), 1 mm (H to K).

In various aspects, the invention provides isolated DA polypeptides encoded by DA genes and nucleic acid sequences described herein.

DA polypeptides include both DA-1 polypeptides and DA-1 related (DAR) polypeptides, and functional homologues thereof, as described herein.

DA polypeptides, including DA-1 polypeptides and DA-1 related (DAR) polypeptides, possess a characteristic domain structure.

A DA polypeptide may comprise a UIM1 domain and a UIM2 domain. A UIM1 domain may consist of the sequence of SEQ ID NO: 3 and a UIM2 domain may consist of the sequence of SEQ ID NO: 4.

```
p---pLpbAl pb.Sbp-.pp p      (SEQ ID NO: 3)

p---pLpbAl pb.Sbp-spp p      (SEQ ID NO: 4)
``` wherein;

p is a polar amino acid residue, for example, C, D, E, H, K, N, Q, R, S or T;

b is a big amino acid residue, for example, E, F, H, I, K, L, M, Q, R, W or Y;

s is a small amino acid residue, for example, A, C, D, G, N, P, S, T or V;

l is an aliphatic amino acid residue, for example, I, L or V;

. is absent or is any amino acid, and

- is any amino acid.

Examples of suitable UIM1 and UIM2 domain sequences are set out below. Further examples of UIM1 and UIM2 domain sequences may be identified using standard sequence analysis techniques as described herein (e.g. Simple Modular Architecture Research Tool (SMART); EMBL Heidelberg, DE).

A DA polypeptide may comprise an LIM domain. An LIM domain may consist of the sequence of SEQ ID NO: 5;

```
                                                          (SEQ ID NO: 5)
pCs.CscsIh s.....bhlp tb.sp.aH.. .pCFpCs..p CppsLss... .p.ab.pcsp baCpps...
``` wherein;

c is a charged amino acid residue, for example, D, E, H, K, R;

p is a polar amino acid residue, for example, C, D, E, H, K, N, Q, R, S or T;

h is a hydrophobic amino acid residue, for example, A, C, F, G, H, I, L, M, T, V, W and Y;

t is a tiny amino acid residue, for example, A, G or S;

a is an aromatic amino acid residue, for example, F, H, W or Y;

b is a big amino acid residue, for example, E, F, H, I, K, L, M, Q, R, W or Y;

s is a small amino acid residue, for example, A, C, D, G, N, P, S, T or V;

l is an aliphatic amino acid residue, for example, I, L or V;

. is absent or is any amino acid; and

- is any amino acid.

Examples of suitable LIM domain sequences are set out below. Further examples of LIM domain sequences may be identified using standard sequence analysis techniques (e.g. Simple Modular Architecture Research Tool (SMART); EMBL Heidelberg, DE).

A DA polypeptide may comprise a carboxyl terminal region having at least 20%, at least 30%, at least 40%, at least 50%, at least 60%, at least 70%, at least 80%, at least 90%, at least 95%, or at least 98% amino acid identity to residues 250 to 532 of SEQ ID NO: 1 that define the C terminal domain of DA1.

A DA polypeptide may further comprise R at a position equivalent to position 358 of SEQ ID NO: 1.

A position in an amino acid sequence which is equivalent to position 358 of SEQ ID NO: 1 can be readily identified using standard sequence analysis tools. Examples of sequences with an R residue at a position equivalent to position 358 of SEQ ID NO: 1 are shown elsewhere herein.

In some preferred embodiments, a DA polypeptide may comprise;
 a UIM domain of SEQ ID NO:3
 a UIM domain of SEQ ID NO:4
 a LIM domain of SEQ ID NO:5, and
 a C terminal region having at least 20% sequence identity to residues 250 to 532 of SEQ 112 NO: 1.

A preferred DA polypeptide may further comprise R at a position equivalent to position 358 of SEQ ID NO: 1.

For example, a DA polypeptide may comprise an amino acid sequence set out in a database entry selected from the group consisting of SGN-U317073, SGN-U277808, SGN-U325242, AT4G36860, SGN-U209255, AB082378.1, AT2G39830, CAN69394.1, OS03G16090, 9234.M000024, 29235.M000021, AT5G66620, AT5G66630, AT5G66610, AT5G66640, AT5G17890, SGN-U320806, AB096533.1, CAL53532.1, OS06G08400, SGN-U328968, OS03G42820 and OS12040490 or may be variant or a fragment of one of these sequences which retains DA activity.

A DA polypeptide may comprise an amino acid sequence of AtDA1, AtDAR1, AtDAR2, AtDAR3, AtDAR4, AtDAR5, AtDAR6, AtDAR7, BrDA1a, BrDA1b, BrDAR1, BrDAR2, BrDAR3-7, BrDAL1, BrDAL2, BrDAL3, OsDA1, OsDAR2, OsDAL3, OsDAL5, PpDAL1, PpDAL2, PpDAL3, PpDAL4, PpDAL5, PpDAL6, PpDAL7, PpDAL8, SmDAL1 and SmDAL2 (as shown in Alignment E).

Other examples of database entries of sequences of DA polypeptides are shown in Table 6 and Table 11. Other DA polypeptide sequences which include the characteristic features set out above may be identified using standard sequence analysis tools.

In some preferred embodiments, a DA polypeptide may comprise the amino acid sequence of SEQ ID NO: 1 (AT1G19270; NP_173361.1 GI: 15221983) or may be a fragment or variant of this sequence which retains DA activity.

A DA polypeptide which is a variant of a reference DA sequence, such as SEQ ID NO: 1 or a sequence shown in alignment E, may comprise an amino acid sequence having at least 20%, at least 30%, at least 40%, at least 50%, at least 60%, at least 70%, at least 80%, at least 90%, at least 95%, or at least 98% sequence identity to the reference sequence.

A DA polypeptide which is a variant of SEQ ID NO: 1 may comprise a UIM1 domain having the sequence QENEDIDRAIALSLLEENQE (SEQ ID NO: 6) and a UIM2 domain having the sequence DEDEQIARALQESMVVGNSP (SEQ ID NO: 7).

A DA polypeptide which is a variant of SEQ ID NO: 1 may comprise a LIM domain having the sequence:

(SEQ ID NO: 8)
ICAGCNMEIGHGRFLNCLNSLWHPECFRCYGCSQPISEYEFSTSGNYPF

HKAC

Particular amino acid sequence variants may differ from the DA-1 polypeptide of SEQ ID NO:1 by insertion, addition, substitution or deletion of 1 amino acid, 2, 3, 4, 5-10, 10-20 20-30, 30-50, or more than 50 amino acids.

Sequence similarity and identity are commonly defined with reference to the algorithm GAP (Wisconsin Package, Accelerys, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4.

Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Sequence comparison may be made over the full-length of the relevant sequence described herein.

In various aspects, the invention provides DA genes and nucleic acid sequences which encode DA polypeptides, as described herein.

For example, a nucleic acid encoding a DA polypeptide may comprise a nucleotide sequence set out in a database entry selected from the group consisting of SGN-U317073, SGN-U277808, SGN-U325242, AT4G36860, SGN-U209255, AB082378.1, AT2G39830, CAN69394.1, OS03G16090, 9234.M000024, 29235.M000021, AT5G66620, AT5G66630, AT5G66610, AT5G66640, AT5G17890, SGN-U320806, AB096533.1, CAL53532.1, OS06G08400, SGN-U328968, OS03G42820 and OS12G40490 or may be variant or a fragment of one of these sequences.

Other database entries of nucleic acid sequences which encode DA polypeptides are shown in Table 7.

In some preferred embodiments, a nucleic acid encoding a DA polypeptide may comprise the nucleotide sequence of SEQ ID NO: 2 or any one of SEQ ID NOS: 11 to 16 or may be a variant or fragment of this sequence which encodes a polypeptide which retains DA activity.

A variant sequence may be a mutant, homologue, or allele of a reference DA sequence, such as SEQ ID NO: 2; any one of SEQ ID NOS: 11 to 16; or a sequence having a database entry set out above, and may differ from the reference DA sequence by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included. A nucleic acid encoding a DA polypeptide may comprise a sequence having at least 20% or at least 30% sequence identity with the reference DA nucleic acid sequence, preferably at least 40%, at least 50%, at least 60%, at least 65%, at least 70%, at least 80%, at least 90%, at least 95% or at least 98%. Sequence identity is described above.

A fragment or variant may comprise a sequence which encodes a functional DA polypeptide i.e. a polypeptide which retains one or more functional characteristics of the polypeptide encoded by the wild-type DA gene, for example, the ability to modulate the duration of proliferative growth.

A nucleic acid comprising a nucleotide sequence which is a variant of a reference DA nucleic acid sequence, such as SEQ ID NO: 2 or any one of SEQ ID NOS: 11 to 16, may selectively hybridise under stringent conditions with this nucleic acid sequence or the complement thereof.

Stringent conditions include, e.g. for hybridization of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

An alternative, which may be particularly appropriate with plant nucleic acid preparations, is a solution of 5×SSPE (final 0.9 M NaCl, 0.05M sodium phosphate, 0.005M EDTA pH 7.7), 5×Denhardt's solution, 0.5% SDS, at 50° C. or 65° C. overnight. Washes may be performed in 0.2×SSC/0.1% SDS at 65° C. or at 50-60° C. in 1×SSC/0.1% SDS, as required.

Nucleic acids as described herein may be wholly or partially synthetic. In particular, they may be recombinant in that nucleic acid sequences which are not found together in nature (do not run contiguously) have been ligated or otherwise combined artificially. Alternatively, they may have been synthesised directly e.g. using an automated synthesiser.

The nucleic acid may of course be double- or single-stranded, cDNA or genomic DNA, or RNA. The nucleic acid may be wholly or partially synthetic, depending on design. Naturally, the skilled person will understand that where the nucleic acid includes RNA, reference to the sequence shown should be construed as reference to the RNA equivalent, with U substituted for T.

In various aspects, the invention provides dominant negative DA polypeptides and encoding nucleic acids. A dominant negative DA polypeptide may increase one or more of organ size, seed size or longevity without affecting fertility, upon expression in a plant.

A dominant negative allele of a DA polypeptide may comprise a DA polypeptide having a mutation, e.g. a substitution or deletion, at a position equivalent to position 358 of SEQ ID NO: 1.

For example, a dominant negative allele of a DA polypeptide may comprise a mutation of the conserved R residue at a position equivalent to position 358 of SEQ ID NO: 1. In preferred embodiments, the conserved R residue may be substituted for K. Position R358 of SEQ ID NO: 1 is located within the conserved C terminal region (amino acids 250 to 532 of SEQ ID NO: 1). An R residue at a position in a DA polypeptide sequence which is equivalent to position 358 of SEQ ID NO: 1 may be identified by aligning these conserved C terminal regions using standard sequence analysis and alignment tools.

Nucleic acid which encodes a dominant negative allele of a DA protein may be produced by any convenient technique. For example, site directed mutagenesis may be employed on a nucleic acid encoding a DA polypeptide to alter the conserved R residue at the equivalent position to R358 in SEQ ID NO: 1, for example to K. Reagents and kits for in vitro mutagenesis are commercially available. The mutated nucleic acid encoding the dominant negative allele of a DA protein and may be further cloned into an expression vector and expressed in plant cells as described below to alter plant phenotype.

The nucleic acid encoding the DA polypeptide may be expressed in the same plant species or variety from which it was originally isolated or in a different plant species or variety (i.e. a heterologous plant).

"Heterologous" indicates that the gene/sequence of nucleotides in question or a sequence regulating the gene/sequence in question, has been introduced into said cells of the plant or an ancestor thereof, using genetic engineering or recombinant means, i.e. by human intervention. Nucleotide sequences which are heterologous to a plant cell may be non-naturally occurring in cells of that type, variety or species (i.e. exogenous or foreign) or may be sequences which are non-naturally occurring in that sub-cellular or genomic environment of the cells or may be sequences which are non-naturally regulated in the cells i.e. operably linked to a non-natural regulatory element. "Isolated" indicate that the isolated molecule (e.g. polypeptide or nucleic acid) exists in an environment which is distinct from the environment in which it occurs in nature. For example, an isolated nucleic acid may be substantially isolated with respect to the genomic environment in which it naturally occurs. An isolated nucleic acid may exist in an environment other than the environment in which it occurs in nature.

A nucleic acid encoding a DA polypeptide as described herein may be operably linked to a heterologous regulatory sequence, such as a promoter, for example a constitutive, inducible, tissue-specific or developmental specific promoter.

Many suitable regulatory sequences are known in the art and may be used in accordance with the invention. Examples of suitable regulatory sequences may be derived from a plant virus, for example the Cauliflower Mosaic Virus 35S (CaMV 35S) gene promoter that is expressed at a high level in virtually all plant tissues (Benfey et al, (1990) EMBO J 9: 1677-1684). Other suitable constitutive regulatory elements include the cauliflower mosaic virus 19S promoter; the Figwort mosaic virus promoter; and the nopaline synthase (nos) gene promoter (Singer et al., Plant Mol. Biol. 14:433 (1990); An, Plant Physiol. 81:86 (1986)).

Constructs for expression of the DA genes under the control of a strong constitutive promoter (the 35S promoter) are exemplified below but those skilled in the art will appreciate that a wide variety of other promoters may be employed to advantage in particular contexts.

A tissue-specific promoter may be employed to express the dominant negative form of the DA polypeptide in a specific tissue or organ to increase size of that tissue or organ relative to tissues or organs in which the tissue-specific promoter is not active and the dominant negative form of the DA polypeptide is not expressed. For example, to increase the size of seeds, the dominant negative form of the DA polypeptide may be preferentially expressed in seed tissue, using a seed specific promoter. For example, the polypeptide may be expressed in developing integument using an integument-specific promoter such as the INC promoter (Meister R.M., Plant Journal 37: 426-438 (2004)) or in embryos using an embryo specific promoter such as the histone H4 promoter (Devic M. Plant Journal 9; 205-215 (1996)).

Alternatively, or in addition, one might select an inducible promoter. In this way, for example, the dominant negative form of the DA polypeptide may be expressed at specific times or places in order to obtain desired changes in organ growth. Inducible promoters include the alcohol inducible AlcA gene-expression system (Roslan et al., Plant Journal; 2001 Cct; 28(2):225-35) may be employed.

The DA nucleic acid may be contained on a nucleic acid construct or vector. The construct or vector is preferably suitable for transformation into and/or expression within a plant cell. A vector is, inter alia, any plasmid, cosmid, phage or *Agrobacterium* binary vector in double or single stranded linear or circular form, which may or may not be self transmissible or mobilizable, and which can transform prokaryotic or eukaryotic host, in particular a plant host, either by integration into the cellular genome or exist extrachromasomally (e.g. autonomous replicating plasmid with an origin of replication).

Specifically included are shuttle vectors by which is meant a DNA vehicle capable, naturally or by design, of replication in two different organisms, which may be selected from *Actinomyces* and related species, bacteria and eukaryotic (e.g. higher plant, mammalia, yeast or fungal) cells.

A construct or vector comprising nucleic acid as described above need not include a promoter or other regulatory sequence, particularly if the vector is to be used to introduce the nucleic acid into cells for recombination into the genome.

Constructs and vectors may further comprise selectable genetic markers consisting of genes that confer selectable phenotypes such as resistance to antibiotics such as kanamycin, hygromycin, phosphinotricin, chlorsulfuron, methotrexate, gentamycin, spectinomycin, imidazolinones, glyphosate and d-amino acids.

Those skilled in the art are well able to construct vectors and design protocols for recombinant gene expression, in particular in a plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook & Russell, 2001, Cold Spring Harbor Laboratory Press.

Those skilled in the art can construct vectors and design protocols for recombinant gene expression, for example in a microbial or plant cell. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 3rd edition, Sambrook et al, 2001, Cold Spring Harbor Laboratory Press and *Protocols in Molecular Biology*, Second Edition, Ausubel et al. eds. John Wiley & Sons, 1992. Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy R R D ed) Oxford, BIOS Scientific Publishers, pp 121-148.

When introducing a chosen gene construct into a cell, certain considerations must be taken into account, well known to those skilled in the art. The nucleic acid to be inserted should be assembled within a construct that contains effective regulatory elements that will drive transcription. There must be available a method of transporting the construct into the cell. Once the construct is within the cell membrane, integration into the endogenous chromosomal material either will or will not occur. Finally, the target cell type is preferably such that cells can be regenerated into whole plants.

Those skilled in the art will also appreciate that in producing constructs for achieving expression of the genes according to this invention, it is desirable to use a construct and transformation method which enhances expression of the nucleic acid encoding the dominant negative form of the DA polypeptide. Integration of a single copy of the gene into the genome of the plant cell may be beneficial to minimize gene silencing effects. Likewise, control of the complexity of integration may be beneficial in this regard. Of particular interest in this regard is transformation of plant cells utilizing a minimal gene expression construct according to, for example, EP Patent No. EP140700081, herein incorporated by reference for this purpose.

Techniques well known to those skilled in the art may be used to introduce nucleic acid constructs and vectors into plant cells to produce transgenic plants with the properties described herein.

*Agrobacterium* transformation is one method widely used by those skilled in the art to transform woody plant species, in particular hardwood species such as poplar. Production of stable, fertile transgenic plants is now routine in the art (see for example Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828; Nilsson, O. et al (1992) *Transgenic Research* 1, 209-220).

Other methods, such as microprojectile or particle bombardment (U.S. Pat. No. 5,100,792, EP-A-444882, EP-A-434616), electroporation (EP 290395, WO 8706614), microinjection (WO 92/09696, WO 94/00583, EP 331083, EP 175966, Green et al. (1987) *Plant Tissue and Cell Culture*, Academic Press), direct DNA uptake (DE 4005152, WO 9012096, U.S. Pat. No. 4,684,611), liposome mediated DNA uptake (e.g. Freeman et al. *Plant Cell Physiol.* 29: 1353 (1984)) or the vortexing method (e.g. Kindle, *PNAS U.S.A.* 87: 1228 (1990d)) may be preferred where *Agrobacterium* transformation is inefficient or ineffective, for example in some gymnosperm species.

Physical methods for the transformation of plant cells are reviewed in Oard, 1991, *Biotech. Adv.* 9: 1-11.

Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications,* Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

Another aspect of the invention provides a method of altering the phenotype of a plant comprising;

expressing a nucleic acid encoding a dominant-negative DA polypeptide within cells of said plant relative to control plants.

Suitable dominant-negative DA polypeptides and methods for expression in plant cells are described above.

A plant with altered phenotype produced as described above may have an extended period of proliferative growth and may display one or more of increased life-span, increased organ size and increased seed size relative to control plants. Preferably, the fertility of plants having the altered phenotype is normal. Methods described herein may be useful, for example, in increasing plant yields, improving grain yield in crop plants, and/or for increasing plant biomass, for example, in the production of biofuels.

The effect of dominant negative alleles of DA proteins is shown herein to be enhanced by reducing or abolishing the expression or function of the Big Brother (BB) protein in the plant.

Big Brother (BB) is an E3 ubiquitin ligase which is known to repress plant organ growth {Disch, 2006). A BB protein may comprise the amino acid sequence of SEQ ID NO: 9 (At3g63530 NP_001030922.1 GI: 79316205) or the sequence of a database entry shown in table 9, Of may be a fragment or variant of any one of these sequences which retains BB activity or is capable of interfering with the function of BB.

A BB polypeptide which is a variant of a reference BB sequence, for example SEQ ID NO: 9 or the sequence of a database entry shown in Table 9, may comprise an amino acid sequence having at least 20%, at least 30%, at least 40%, at least 50%, at least 60%, at least 70%, at least 80%, at least 90%, at least 95%, or at least 98% sequence identity to the reference sequence. Sequence identity is described in more detail above.

Particular amino acid sequence variants may differ from the BB polypeptide of SEQ ID NO:9 by insertion, addition, substitution or deletion of 1 amino acid, 2, 3, 4, 5-10, 10-20 20-30, 30-50, or more than 50 amino acids.

In some embodiments, a BB polypeptide may comprise an A at a position corresponding to position 44 of SEQ ID NO: 9.

A nucleic acid encoding the BB polypeptide may for example comprise a nucleotide set out in a database entry shown in table 10 or may be a variant or fragment thereof.

In some preferred embodiments, a nucleic acid encoding a BB polypeptide may comprise the nucleotide sequence of SEQ ID NO: 10 (NM_001035845.1 GI: 79316204) or may be a variant or fragment of this sequence which encodes a polypeptide which retains BB activity.

A variant sequence may be a mutant, homologue, or allele of a reference BB sequence, such as SEQ ID NO: 10 or a sequence having a database entry set out in table 10, and may differ from the reference BB sequence by one or more of addition, insertion, deletion or substitution of one or more nucleotides in the nucleic acid, leading to the addition, insertion, deletion or substitution of one or more amino acids in the encoded polypeptide. Of course, changes to the nucleic acid that make no difference to the encoded amino acid sequence are included. A nucleic acid encoding a BB polypeptide may comprise a sequence having at least 20% or at least 30% sequence identity with the reference BB nucleic acid sequence, preferably at least 40%, at least 50%, at least 60%, at least 65% at least 70%, at least 80%, at least 90%, at least 95% or at least 98%. Sequence identity is described above.

A fragment or variant may comprise a sequence which encodes a functional BB polypeptide i.e. a polypeptide which retains one or more functional characteristics of the polypeptide encoded by the wild-type BB gene, for example, E3 ubiquitin ligase activity. A method of altering a plant phenotype as described herein may further comprise reducing or abolishing the expression or activity of a BB polypeptide in said plant.

This may enhance or increase the effect of the expression of a dominant negative DA polypeptide on one or more of organ size, seed size or longevity.

Methods for reducing or abolishing the expression or activity of a BB polypeptide in said plant are well known in the art and are described in more detail below.

The expression of active protein may be abolished by mutating the nucleic acid sequences in the plant cell which encode the BB polypeptide and regenerating a plant from the mutated cell. The nucleic acids may be mutated by insertion or deletion of one or more nucleotides. Techniques for the inactivation or knockout of target genes are well-known in the art.

For example, an ECD1 allele of a BB polypeptide may be generated by introducing a mutation, such as a deletion, insertion or substitution, at a position corresponding to position 44 of SEQ ID NO: 9, for example, an A to T substitution. A position in a BB polypeptide sequence which is equivalent to position 44 of SEQ ID NO: 9 may be identified using standard sequence analysis and alignment tools. Others mutations suitable for abolishing expression of an active protein will be readily apparent to the skilled person.

The expression of active protein may be reduced using suppression techniques. The suppression of the expression of target polypeptides in plant cells is well-known in the art. Suitable suppressor nucleic acids may be copies of all or part of the target BB gene inserted in antisense or sense orientation or both relative to the BB gene, to achieve reduction in expression of the BB gene. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of this approach may be found in WO95/34668 (Biosource); Angell & Baulcombe (1997) The EMBO Journal 16, 12:3675-3684; and Voinnet & Baulcombe (1997) Nature 389: pg 553.

In some embodiments, the suppressor nucleic acids may be sense suppressors of expression of the BB polypeptide.

A suitable sense suppressor nucleic acid may be a double stranded RNA (Fire A. et al Nature, Vol 391, (1998)). dsRNA mediated silencing is gene specific and is often termed RNA interference (RNAi). RNAi is a two step process. First, dsRNA is cleaved within the cell to yield short interfering RNAs (siRNAs) of about 21-23 nt length with 5' terminal phosphate and 3' short overhangs (~2 nt). The siRNAs target the corresponding mRNA sequence specifically for destruction (Zamore P. D. Nature Structural Biology, 8, 9, 746-750, (2001)

siRNAs (sometimes called microRNAs) down-regulate gene expression by binding to complementary RNAs and either triggering mRNA elimination (RNAi) or arresting mRNA translation into protein. siRNA may be derived by processing of long double stranded RNAs and when found in nature are typically of exogenous origin. Micro-interfering RNAs (miRNA) are endogenously encoded small non-coding RNAs, derived by processing of short hairpins. Both siRNA and miRNA can inhibit the translation of mRNAs bearing partially complementary target sequences without RNA cleavage and degrade mRNAs bearing fully complementary sequences.

Accordingly, the present invention provides the use of RNAi sequences based on the BB nucleic acid sequence for suppression of the expression of the DA polypeptide. For example, an RNAi sequence may correspond to a fragment of SEQ ID NO: 10 or other BB nucleic acid sequence referred to above, or a variant thereof.

siRNA molecules are typically double stranded and, in order to optimise the effectiveness of RNA mediated down-regulation of the function of a target gene, it is preferred that the length and sequence of the siRNA molecule is chosen to ensure correct recognition of the siRNA by the RISC complex that mediates the recognition by the siRNA of the mRNA target and so that the siRNA is short enough to reduce a host response.

miRNA ligands are typically single stranded and have regions that are partially complementary enabling the ligands to form a hairpin.

miRNAs are RNA sequences which are transcribed from DNA, but are not translated into protein. A DNA sequence that codes for a miRNA is longer than the miRNA. This DNA sequence includes the miRNA sequence and an approximate reverse complement. When this DNA sequence is transcribed into a single-stranded RNA molecule, the miRNA sequence and its reverse-complement base pair to form a partially double stranded RNA segment. The design of microRNA sequences is discussed on John et al, PLoS Biology, 11(2), 1862-1879, 2004.

Typically, the RNA molecules intended to mimic the effects of siRNA or miRNA have between 10 and 40 ribonucleotides (or synthetic analogues thereof), more preferably between 17 and 30 ribonucleotides, more preferably between 19 and 25 ribonucleotides and most preferably between 21 and 23 ribonucleotides. In some embodiments of the invention employing double-stranded siRNA, the molecule may have symmetric 3' overhangs, e.g. of one or two (ribo)nucleotides, typically a UU of dTdT 3' overhang. Based on the disclosure provided herein, the skilled person can readily design suitable siRNA and miRNA sequences, for example using resources such as Ambion's siRNA finder, see URL ambion [dot]com/techlib/misc/siRNA_finder [dot] html. siRNA and miRNA sequences can be synthetically produced and added exogenously to cause gene downregulation or produced using expression systems (e.g. vectors). In a preferred embodiment, the siRNA is synthesized synthetically.

Longer double stranded RNAs may be processed in the cell to produce siRNAs (see for example Myers (2003) *Nature Biotechnology* 21:324-328). The longer dsRNA molecule may have symmetric 3' or 5' overhangs, e.g. of one or two (ribo) nucleotides, or may have blunt ends. The longer dsRNA molecules may be 25 nucleotides or longer. Preferably, the longer dsRNA molecules are between 25 and 30 nucleotides long. More preferably, the longer dsRNA molecules are between 25 and 27 nucleotides long. Most preferably, the longer dsRNA molecules are 27 nucleotides in length. dsRNAs 30 nucleotides or more in length may be expressed using the vector pDECAP (Shinagawa et al., Genes and Dev., 17, 1340-5, 2003).

Another alternative is the expression of a short hairpin RNA molecule (shRNA) in the cell. shRNAs are more stable than synthetic siRNAs. A shRNA consists of short inverted repeats separated by a small loop sequence. One inverted repeat is complementary to the gene target. In the cell the shRNA is processed by DICER into a siRNA which degrades the target gene mRNA and suppresses expression. In a preferred embodiment the shRNA is produced endogenously (within a cell) by transcription from a vector. shRNAs may be produced within a cell by transfecting the cell with a vector encoding the shRNA sequence under control of a RNA polymerase III promoter such as the human H1 or 7SK promoter or a RNA polymerase II promoter. Alternatively, the shRNA may be synthesised exogenously (in vitro) by transcription from a vector. The shRNA may then be introduced directly into the cell. Preferably, the shRNA molecule comprises a partial sequence of SHR. For example, the shRNA sequence is between 40 and 100 bases in length, more preferably between 40 and 70 bases in length. The stem of the hairpin is preferably between 19 and 30 base pairs in length. The stem may contain G-U pairings to stabilise the hairpin structure.

siRNA molecules, longer dsRNA molecules or miRNA molecules may be made recombinantly by transcription of a nucleic acid sequence, preferably contained within a vector. Preferably, the siRNA molecule, longer dsRNA molecule or miRNA molecule comprises a partial sequence of SEQ ID NO: 1, 3, 5, 7, 9, 11, 13, 15 or a variant thereof.

In other embodiments, the suppressor nucleic acids may be anti-sense suppressors of expression of the two or more DA polypeptides. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) Nature 334, 724-726; Zhang et al, (1992) *The Plant Cell* 4, 1575-1588, English et al., (1996) *The Plant Cell* 8, 179-188. Antisense technology is also reviewed in Bourque, (1995), Plant Science 105, 125-149, and Flavell (1994) PNAS USA 91, 3490-3496.

An anti-sense suppressor nucleic acid may comprise an anti-sense sequence of at least 10 nucleotides from a nucleotide sequence is a fragment of SEQ ID NO: 10 or other BB sequence referred to above, or a variant thereof.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

Suppressor nucleic acids may be operably linked to tissue-specific or inducible promoters. For example, integument and seed specific promoters can be used to specifically down-regulate two or more DA nucleic acids in developing ovules and seeds to increase final seed size.

Nucleic acid which suppresses expression of a BB polypeptide as described herein may be operably linked to a heterologous regulatory sequence, such as a promoter, for example a constitutive, inducible, tissue-specific or developmental specific promoter as described above.

The construct or vector may be transformed into plant cells and expressed as described above.

A plant expressing the dominant-negative form of the DA polypeptide and, optionally having reduced or abolished expression of a BB polypeptide, may be sexually or asexually propagated or off-spring or descendants may be grown.

Another aspect of the invention provides a method of producing a plant with an altered phenotype comprising:
  incorporating a heterologous nucleic acid which encodes a dominant-negative DA polypeptide into a plant cell by means of transformation, and;
  regenerating the plant from one or more transformed cells.

The altered phenotype of the plant produced by the method is described in more detail above. The method may be useful, for example, in producing plants having increased yields, for example, crop plants having improved grain yield, relative to control plants.

In some embodiments, a method may further comprise reducing or abolishing the expression or activity of a BB polypeptide in the plant cell or plant.

This may be carried out before, at the same time or after the incorporation of the nucleic acid which encodes the dominant-negative DA polypeptide. For example, in some embodiments, the expression or activity of a BB polypeptide may be abolished or reduced in one or more plant cells which already incorporate the nucleic acid encoding the dominant negative DA polypeptide. In other embodiments, the nucleic acid encoding the dominant negative DA polypeptide may be incorporated into one or more plant cells which have abolished or reduced expression of a BB polypeptide.

A plant thus produced may comprise a heterologous nucleic acid which encodes a dominant-negative DA polypeptide and may possess abolished or reduced expression or activity of a BB polypeptide in one or more of its plant cells.

The expression or activity of a BB polypeptide may be reduced or abolished as described above. For example, a method may comprise incorporating a heterologous nucleic acid into a plant cell by means of transformation, wherein the nucleic acid encodes a suppressor nucleic acid, such as an siRNA or shRNA, which reduces the expression of a BB polypeptide.

The heterologous nucleic acids encoding the dominant negative DA polypeptide and BB suppressor nucleic acid may be on the same or different expression vectors and may be incorporated into the plant cell by conventional techniques.

Dominant-negative DA polypeptides and BB suppressor nucleic acids are described in more detail above.

A plant produced as described above may be sexually or asexually propagated or grown to produce off-spring or descendants. Off-spring or descendants of the plant regenerated from the one or more cells may be sexually or asexually propagated or grown. The plant or its off-spring or descendents may be crossed with other plants or with itself.

A plant suitable for use in the present methods is preferably a higher plant, for example an agricultural plant selected from the group consisting of Lithospermum erythrorhizon, Taxus spp, tobacco, cucurbits, carrot, vegetable brassica, melons, capsicums, grape vines, lettuce, strawberry, oilseed brassica, sugar beet, wheat, barley, maize, rice, soyabeans, peas, sorghum, sunflower, tomato, potato, pepper, chrysanthemum, carnation, linseed, hemp and rye.

Another aspect of the invention provides a plant which expresses a dominant negative DA polypeptide and optionally has reduced or abolished expression of a BB polypeptide, wherein said plant displays an altered phenotype relative to controls.

The dominant negative DA polypeptide may be heterologous polypeptides.

A suitable plant may be produced by a method described herein

As described above, the plant may have one or more of increased life-span, increased organ size, increased duration of proliferative growth and increased seed size relative to control plants. The plant may have normal fertility relative to control plants.

A plant according to the present invention may be one which does not breed true in one or more properties. Plant varieties may be excluded, particularly registrable plant varieties according to Plant Breeders Rights.

In addition to a plant expressing a dominant negative DA polypeptide, for example, a plant produced by a method described herein, the invention encompasses any clone of such a plant, seed, selfed or hybrid progeny and descendants, and any part or propagule of any of these, such as cuttings and seed, which may be used in reproduction or propagation, sexual or asexual. Also encompassed by the invention is a plant which is a sexually or asexually propagated off-spring, clone or descendant of such a plant, or any part or propagule of said plant, off-spring, clone or descendant.

The present inventors have shown that reducing or abolishing the expression or activity of two or more DA polypeptides also produces an altered phenotype characterised by normal fertility and one or more of increased life-span, increased organ size, increased duration of proliferative growth and increased seed size.

Another aspect of the invention provides a method of altering the phenotype of a plant comprising;
  reducing or abolishing the expression or activity of two or more active DA proteins in one or more cells of the plant.

Another aspect of the invention provides a method of producing a plant with an altered phenotype comprising:
reducing or abolishing the expression or activity of two or more active DA proteins in a plant cell, and;
regenerating the plant from the plant cell.

The phenotype of the plant following reduction or abolition of expression is described in more detail above.

The expression of active protein may be abolished by mutating the nucleic acid sequences in the plant cell which encode the two or more DA proteins and regenerating a plant from the mutated cell. The nucleic acids may be mutated by insertion or deletion of one or more nucleotides. Techniques for the inactivation or knockout of target genes are well-known in the art.

The expression of target polypeptides in plant cells may be reduced by suppression techniques. The use of suppressor nucleic acids to suppress expression of target polypeptides in plant cells is well-known in the art and is described in more detail above.

Suppressor nucleic acids which reduce expression of two or more DA polypeptides may be operably linked to tissue-specific or inducible promoters. For example, integument and seed specific promoters can be used to specifically down-regulate two or more DA nucleic acids in developing ovules and seeds to increase final seed size.

Other aspects of the invention relate to the over-expression of DA polypeptides in plant cells. A method of altering the phenotype of a plant may comprise;
expressing a nucleic acid encoding a DA polypeptide within cells of said plant.

The plant may have an altered phenotype characterised by normal fertility and one or more of reduced life-span, reduced organ size, reduced duration of proliferative growth and reduced seed size relative to control plants.

Nucleic acid encoding a CA polypeptide may be expressed in a plant cell as described above mutatis mutandis for dominant negative DA polypeptides.

Another aspect of the invention provides a method of identifying a dominant negative DA polypeptide comprising;
providing an isolated nucleic acid encoding a DA polypeptide,
incorporating one or more mutations into the nucleic acid,
introducing the nucleic acid into a plant cell by means of transformation;
regenerating the plant from one or more transformed cells and, identifying the phenotype of the regenerated plant.

An altered phenotype which includes normal fertility and one or more of increased life-span, increased organ size and increased seed size relative to control plants is indicative that the mutated nucleic acid encodes a dominant negative DA allele.

Another aspect of the invention provides a method of producing a dominant-negative DA polypeptide comprising;
providing a nucleic acid sequence encoding a plant DA polypeptide,
identifying an R residue in the encoded plant DA polypeptide at a position equivalent to position 358 of SEQ ID NO: 1 and
mutating the nucleic acid to alter said R residue in the encoded plant DA polypeptide,
the mutant nucleic acid sequence encoding a dominant negative DA polypeptide.

Mutated nucleic acid encoding a dominant negative DA polypeptide which are identified or produced as described above may be used to produce plants having the altered phenotype, as described above.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Having generally described the invention above, certain aspects and embodiments of the invention will now be illustrated by way of example to extend the written description and enablement of the invention, and to ensure adequate disclosure of the best mode of practicing the invention. Those skilled in the art will appreciate, however, that the scope of this invention should not be interpreted as being limited by the specifics of these examples. Rather, variations, extensions, modifications and equivalents of these specifics and generic extensions of these details may be made without departing from the scope of the invention comprehended by this disclosure. Therefore, for an appreciation of the scope of this invention and the exclusive rights claimed herein, reference should be had to the claims appended to this disclosure, including equivalents thereof.

All documents mentioned in this specification are incorporated herein by reference in their entirety.

The contents of all database entries mentioned in this specification are also incorporated herein by reference in their entirety. This includes the versions of any sequences which are current at the filing date of this application.

Examples

The data set out below shows that "DA1" is a key regulator in terminating seed and organ growth, and encodes a novel protein containing UIM and LIM domains. DA1 is shown to control both seed and organ size by restricting the duration of proliferative growth. eod1, an enhancer of da1-1, is allelic to bb, suggesting that the DA1 and the E3 ubiquitin ligase BB, "Big Brother" {Disch, S. Curr Biol 16, 272-9 (2006); Science 289, 85-8 (2000)) can act in parallel pathways to control the final size of seeds and plant organs. It is possible that DA1 and EOC1/BB may share down stream components that control aced and organ size.

Previous study has shown that BB acts a negative regulator of organ growth, most likely by marking cellular proteins for degradation (Disch, S. Curr. Biol. 16, 272-279 (2006)). DA1 contains two predicted DIM motifs, which may have the function of binding ubiquitin and promoting ubiquitination (Hurley, J. H. Biochem. J. 399, 361-372 (2006)).

Expression of the DA1 gene is induced by the phytohormone abscisic acid (ABA), and the da1-1 mutant is insensitive to ABA, providing indication that ABA negatively regulates organ growth through DA1.

The inhibitory effects of ABA on growth have long been recognized as resulting from an inhibition of cell division (Lui, J. H. Planta 194, 368-373 (1994), consistent with the fact that ABA can induce the expression of a cyclin-dependent kinase inhibitor (ICK1), an important regulator of cell cycle progression (Wang, H. Cell Biol. Int. 27, 297-299 (2003)). In seed development, the transition from developing seeds to mature seeds is also correlated with an increase in seed ABA content (Finkelstein, R. R. Plant Cell 14 Suppl. S15-45 (2002)), which suggests that ABA may be one of environmental cues sensed by plants to control the final size of seeds and organs, by inducing negative growth regulators such as DA1. We herein report that one such negative growth regulator is DA1.

By conducting genetic analysis of abi4-1da1-1 and abi5-1da1-1 double mutants, we found that the large organ size phenotype of da1-1 is independent of ABI4 and ABI5 pathways.

We also show herein that suppressors of da1-1 (sod1) are molecules which have a second site mutation in the da1-1 mutant gene that are predicted to reduce gene function, indicating that the R358K mutation in DA1 is responsible for increased seed size and that the da1-1 allele interferes with activities of DARs.

We also show herein that the da1-1 R358K allele also interferes with DA1 functions in a dosage dependent manner, as evidenced by the fact that plants overexpressing da1-1 allele (35S::DA1R358K) in wild type have large seed and organ size. This result also demonstrates that the da1-1 mutant gene (DA1R358K) may be used to genetically engineer significant increases in seed weight and biomass.

To date, some mutants (e.g., ap2 and arf2) exhibiting large seeds usually have strong negative effects on their fertility and growth (Schruff, M. C. Development 137, 251-261 (2006); Ohto, M. A. Proc. Natnl Acad. Sci USA 102, 3123-3128 (2005); Jofuku, K. D. Proc. Natnl Acad. Sci. USA 102, 3117-3122 (2005)). However, the experiments set out below show that da1-1 has increased seed mass, large organ size, but normal fertility, compared with wild type.

Methods

Plant Materials

The *Arabidopsis thaliana* Columbia (Col-0) accession was used as a wild type. All mutants are in the Col-0 background, except for da1-1$^{Ler}$ and bb-1, which are in Landsberg erecta background. Before analysis, da1-1 and da1-1Lcr were backcrossed into Col-0 and Lcr six times, respectively. T-DNA insertion lines were obtained from SIGnAL (Salk Institute) and NASC (Nottingham).

Genetic Screen and Map-Based Cloning da1-1 was identified as a novel seed and organ size mutant from an ethyl-methanesulphonate (EMS)-treated M2 populations of Col-0 accession. sod1-1, sod1-2, sod1-3 and eod1-1 were identified as suppressor and enhancer of da1-1 from an ethyl-methanesulphonate (EMS)-treated M2 populations of da1-1, respectively. F2 mapping populations were generated from a single cross of Ler/da1-1, Ler/sod1-3da1-1, and da1-1Ler/eod1-1da1-1. A list of primer sequences is provided in Table 2.

Plasmids and Transgenic Plants

The following constructs were generated: DA1COM, 35S::DA1-HA, 35S::GFP-DA1, 35S::DA1-GFP, 35S::DA1R358K, pDA1::GUS, and 35S::EOD1.

Morphological and Cellular Analysis

Sample preparation, measurement, microscopy, and histochemical staining for β-glucuronidase activity used standard methods (Jefferson R., EMBO J. Embo J 6, 3901-3907 (1987).

DA1 Limits the Size of Seeds and Organs

To identify repressors of seed and/or organ growth, we screened for da mutants (DA means 'large' in Chinese) with large seed and/or organ size from an EMS mutagenized population in the Col-0 accession of *Arabidopsis thaliana*. da1-1 mutant has large seed and organ size, but normal fertility, compared with wild type (FIG. 1a-1p), providing indication that seed and organ growth share common regulatory mechanisms. Genetic analysis with reciprocal crosses between da1-1 and wild type plants revealed that da1-1 possesses a mutation in a single nuclear locus.

To reveal differences in seed size between wild type and da1-1 mutant, we examined da1-1 mutant seed size by fractionating seeds produced by individual wild type and da1-1 plants by using a series wire mesh screens. Seeds from wild type were retained only in 180-300 μm aperture meshes while the mutant seeds displayed a shift in range to larger exclusion sizes, 180-355 μm (FIGS. 5a and 5b). More than 80% of the wild type seeds were retained in 250 μm aperture meshes, whereas about 70% da1-1 seeds were retained in 300 μm aperture meshes. To determine whether the increase in seed size in da1-1 reflected an alternation in embryo size, we isolated mature embryos from wild type and da1-1 mutant seeds. da1-1 mature embryos were significantly fatter and longer than those of wild type (FIGS. 1c and 1d). We observed that the seed cavity in da1-1 seeds is larger throughout development than that in wild type (FIG. 6). In addition, the average seed mass of da1-1 mutant is increased to 132% of that of wild type (Table 5).

Figure 5:
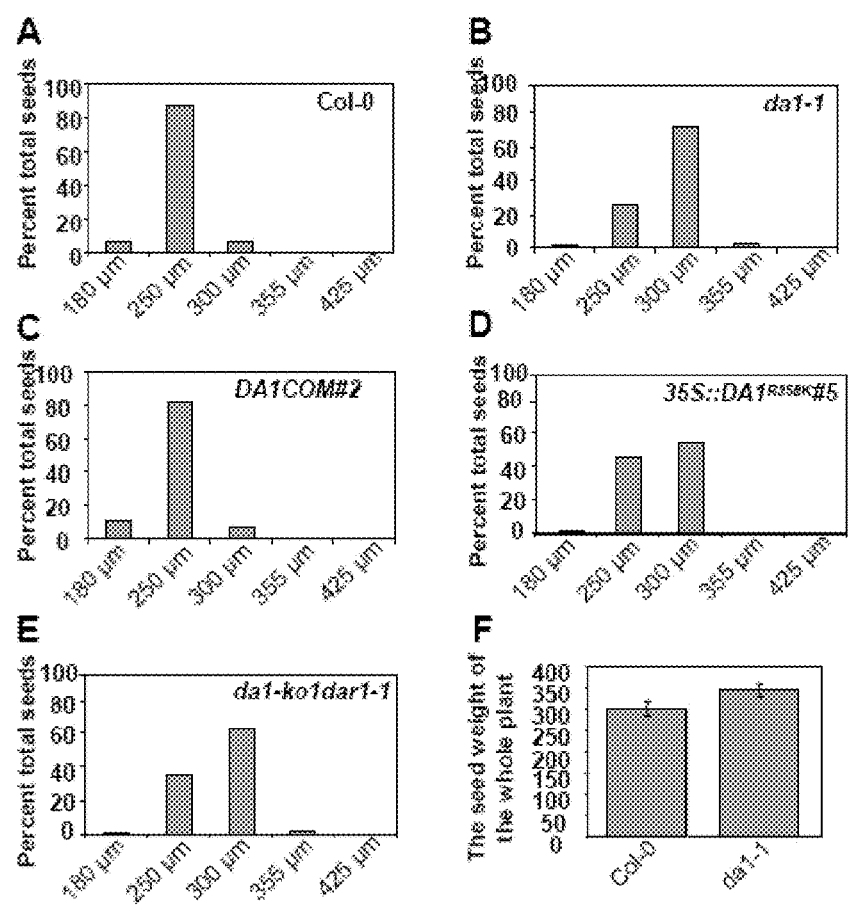
FIG. 5 shows that da1-1 has large seeds. Preweighed batches of wild type Col-0 (A), da1-1 (B), DA1COM#2 (C), 35.5::DA1$^{n358K}$#5 (D), and da1-ko1dar1-1 mutant seeds from individual plants were passed through a series of wire sieves of decreasing mesh size (in μm) as described in Supplementary methods. (E) The average seed weight per plant. Standard deviation values was given (n=5). Plants were grown under identical conditions.
Figure 6:
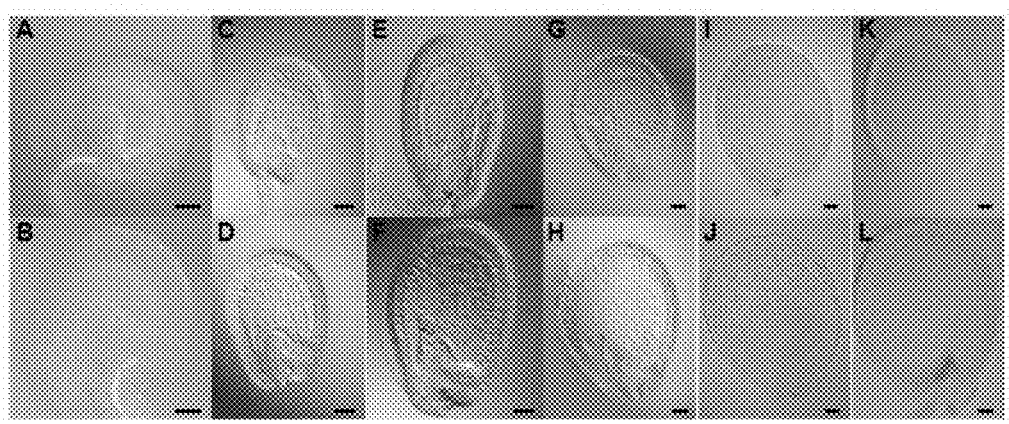
FIG. 6 shows seed development in wild type and da1-1 plants. (A to L). Cleared ovules (A,B) and seeds (C to L) of wild type (A, C, E, G, I and K), and da1-1 (B, D, F, H, J and L) imaged with differential contrast optics. Scale bars: 50 μm (A to L).

The fertility of da1-1 plant was found to be normal and the average seed weight per da1-1 plant is higher than that per wild type plant (FIG. 5). Therefore, we concluded that DA1 contributes to the determination of seed size and seed weight in *Arabidopsis*. We also identified examples of DA1 and DAR-related genes from crop plants that demonstrate related genes with related functions can be targeted by making the R358K dominant interfering mutation, or reducing expression of selected DA1- and DAR-related proteins using RNA interference methods described above.

We investigated whether DA1 acts maternally or zygotically. As shown in Table 1, the effect of the da1-1 mutation on seed mass was observed only when maternal plants were homozygous for the mutation. Seeds produced by a da1-1 mother, regardless of the genotype of the pollen donor, were consistently heavier than those produced by maternal wild type plants. In contrast, da1-1 mutant and wild type pollen produced seeds whose weight was comparable to that of wild type maternal plants. These results show that da1-1 is a maternal effect mutation that affects seed mass.

Figure 7:
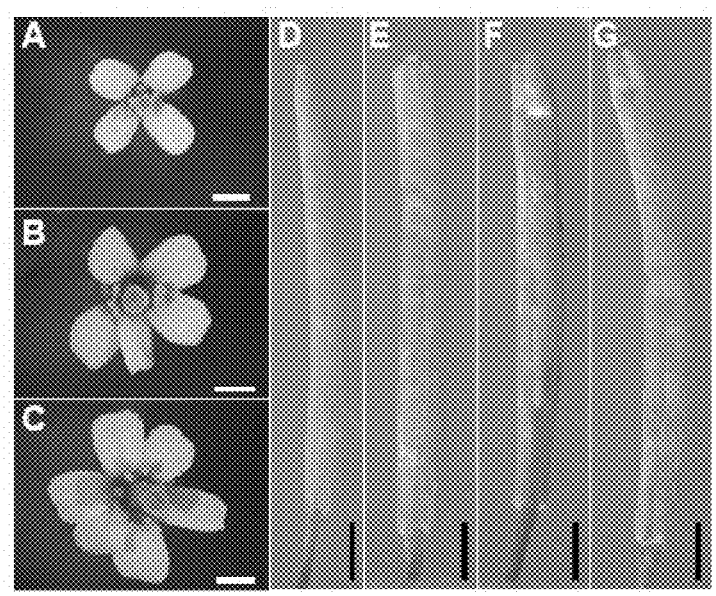
FIG. 7 shows that da1-1 plant has large flower with extra petals and deformed silique with extra carpels. (A) Wild type flower. (B and C) da1-1 flowers with extra petals. (D) Wild type silique, (E to G) da1-1 siliques with extra carpels. Scale bars: 1 mm (A to C), 2 mm (D to G).

In addition to the increased seed mass, the da1-1 mutant exhibited larger organ size than wild type (FIG. 1e-m and o). Compared with wild type, da1-1 plants have large flowers (FIG. 1h and i) that frequently have extra petals and carpels (FIG. 7). The average size of da1-1 petals was about 1.6-fold that of comparable wild-type petals (FIG. 1o). Siliques of the da1-1 mutant were wide, deformed and flattened, compared with the narrow, smooth, cylindrical shape of wild type siliques (FIGS. 1j and 1k). da1-1 mutant also forms larger cotyledons and leaves, as well as thicker stems than wild type (FIG. 1e-g i, and m). Consistent with this, da1-1 mutant accumulates more biomass in the form of flowers and leaves than wild type plants (FIGS. 1p and q). Taken together, these results indicated that DA1 limits the size of seeds and organs in *Arabidopsis*.

DA1 Restricts the Duration of Proliferative Growth

Seed and organ size is determined by both cell number and/or size. To understand which parameter is responsible for large seed and organ size in da1-1 mutant, we analyzed cell size of embryos, petals and leaves. As shown in FIG. 1r, the size of cells from da1-1 embryos, petals and leaves, were comparable with that of corresponding wild type cells. The epidermal cell number of stem in da1-1 mutant is increased to 180% that of wild type stems (FIG. 1n). These results indicate that da1-1 induced effects on seed mass and organ size are due to the increased cell number.

Figure 2:
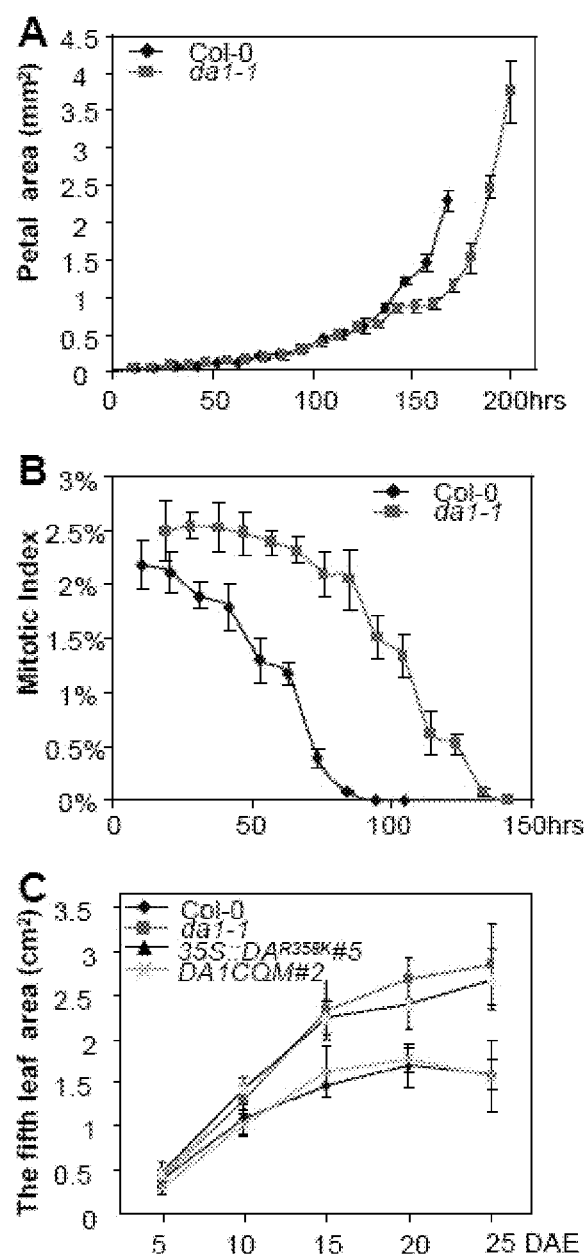
FIG. 2 shows kinematic analysis of petal and leaf growth. (A) Growth of Col-0 and da1-1 mutant petals. The largest petals of each series are from opened flowers (stage 14). (B) Mitotic index in WT and da1-1 mutant petals. Time axis in (B) corresponds to the one in (A). (C) Growth of the fifth leaf of Col-0, da1-1, DA1COM#2, and 35S::DA1$^{R359K}$#5 over time. DAE is days after emergence.
Figure 12:
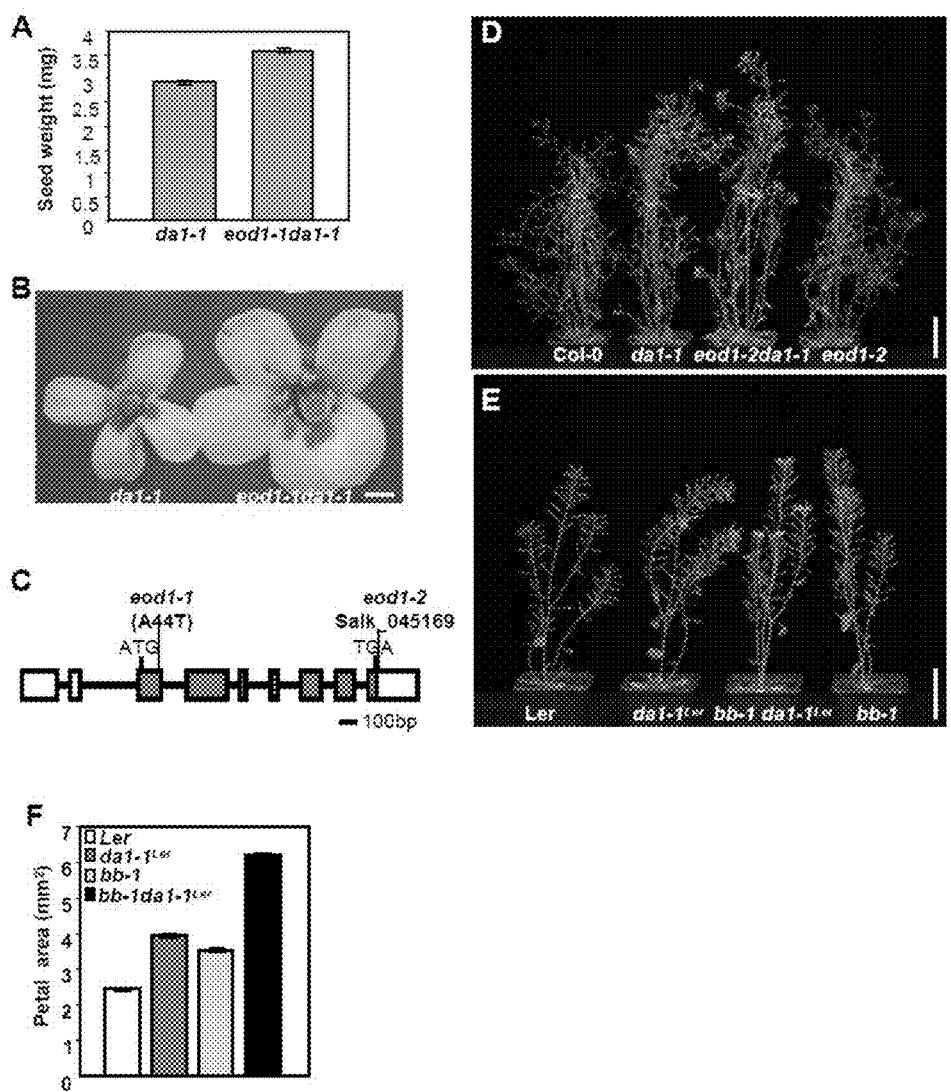
FIG. 12 shows that mutations in an enhancer of da1-1 (EOD1/BB) synergistically enhance the large seed and organ phenotypes of da1-1. (A) The eod1-1da1-1 double mutant has an increased seed weight compared with da1-1. Average seed weight of da1-1 and eod1-1da1-1 double mutant is given in mg per 100 seeds. Standard deviation values are shown (n=5). Plants were grown under identical conditions. (B) The eod1-1da1-1 double mutant has larger flower than da1-1. (C) EOD1/BB gene structure, showing the mutated sites of the two eod1 alleles. The start codon (ATG) and the stop codon (TGA) are indicated. Closed boxes indicate the coding sequence and lines between boxes indicate introns. The mutated site in eod1-1 and T-DNA insertion site in eod1-2 also are shown. (D) Eight week old plants of Col-0, da1-1, eod1-2, and eod1-2da1-1 plants are shown. The eod2-1da1-1 plant has a longer growing period than da1-1. (E) Eight week old plants of Ler, da1-1$^{Ler}$, bb-1, and bb-1da1-1$^{Ler}$ plants are shown. The bb-1da1-1$^{Ler}$ plant has a longer growing period than da1-1$^{Ler}$. Scale bars: 1 mm (B), 5 cm (D and E). (F) Petal areas of Ler, da1-1$^{Ler}$, bb-1, and bb-1da1-1$^{Ler}$ double mutants. Standard deviation values are shown (n>50). Mutations in BB synergistically enhance the petal size phenotype of da1-1, suggesting that DA1 and BB act in parallel pathways.
Figure 13:
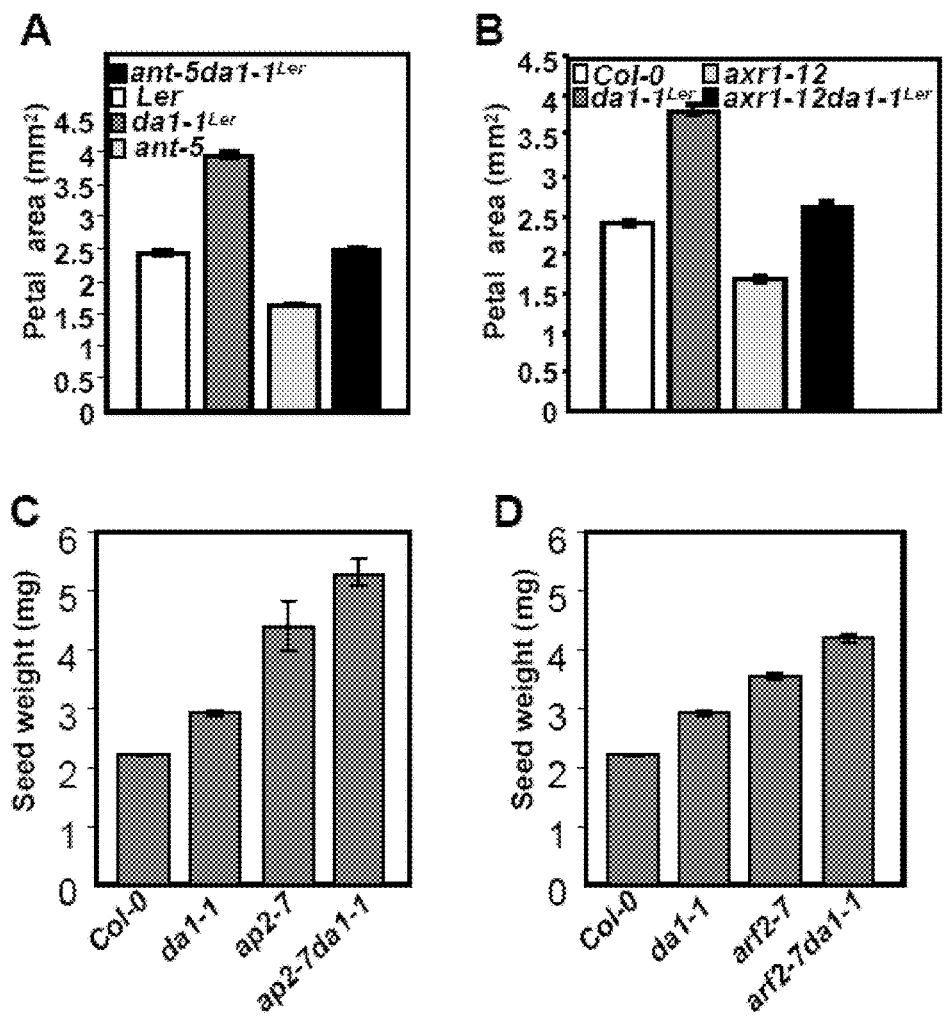
FIG. 13 shows that genetic analysis between da1-1 and ant-5, axr1-12, apt-7, and arf2-7. (A and B) The petal size phenotype of ant-5da1-1$^{Ler}$ and axr1-12da1-1 double mutant is essentially additive, compared to their parental lines. (C and D) The seed size phenotype of apt-7da1-1 and arf2-7da1-1 double mutants is also essentially additive, compared to their parental lines.

To determine how DA1 limits seed and organ size, we performed a kinematic analysis of embryos, petals, and leaves in wild type and the da1-1 mutant. We manually pollinated da1-1 mutant and wild type plants with their own pollen grains and examined the duration of seed development. Most of the wild-type seeds developed into desiccation stage in 8 days after fertilization, whereas most of the da1-1 seeds developed into mature stage in 10 days after fertilization in our growth conditions, suggesting that the period of seed development of da1-1 mutant was prolonged. Plotting the size of petal primordia and leaves over time revealed that the organ enlargement in da1-1 mutant is mainly due to a longer growing period of time (FIG. 2a, c). Consistent with this, da1-1 plants have younger and fresher organs in early developmental stages (FIG. 1g) and longer lifespan than wild type (FIG. 12 e, f).

Figure 8:
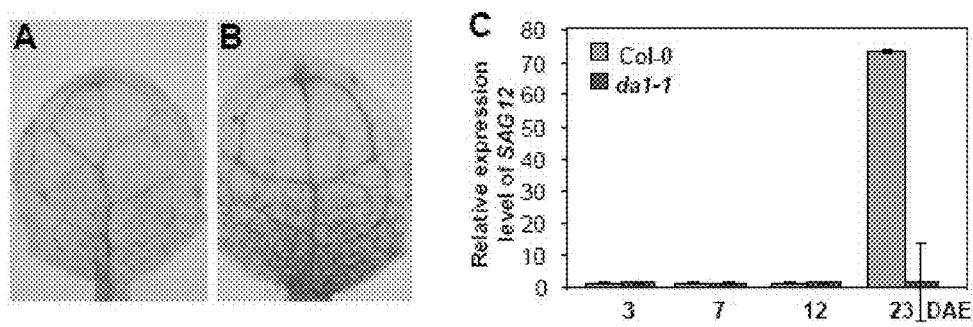
FIG. 8 shows that da1-1 mutant has the prolonged cell proliferation. (A and B) pCyclinB1;1::GUS activity in the first leaves (9 days after germination) of wild type (A) and da1-1 (B) seedlings grown on MS medium containing 1% glucose. (C) Expression level of SAG12 gene in the fifth leaves of wild type Col-0 and da1-1 plants was detected by using Quantitative real-time RT-PCR analysis. DAE is days after emergence.

To determine how cell division contributes to the observed growth dynamic, we measured the mitotic index of petals and leaves in wild type and mutant. A transgene marker of cell-cycle progression, a pCYCB1:1::GUS fusion, was used to compare the extent of cell proliferation in developing petals of wild type and da1-1 plants. The cells in da1-1 petals continue to proliferate for a longer time than those in wild-type petals (FIG. 2b). Similarly, the arrest of cell cycling in the cells of leaves was also delayed (FIG. 8). The analysis of ploidy level also indicated that da1-1 mutant exits cell cycle later than wild type. This result provided indication that da1-1 exhibits prolonged cell proliferation.

DA1 Encodes a Novel Protein Containing UIM and LIM Domains

Figure 3:
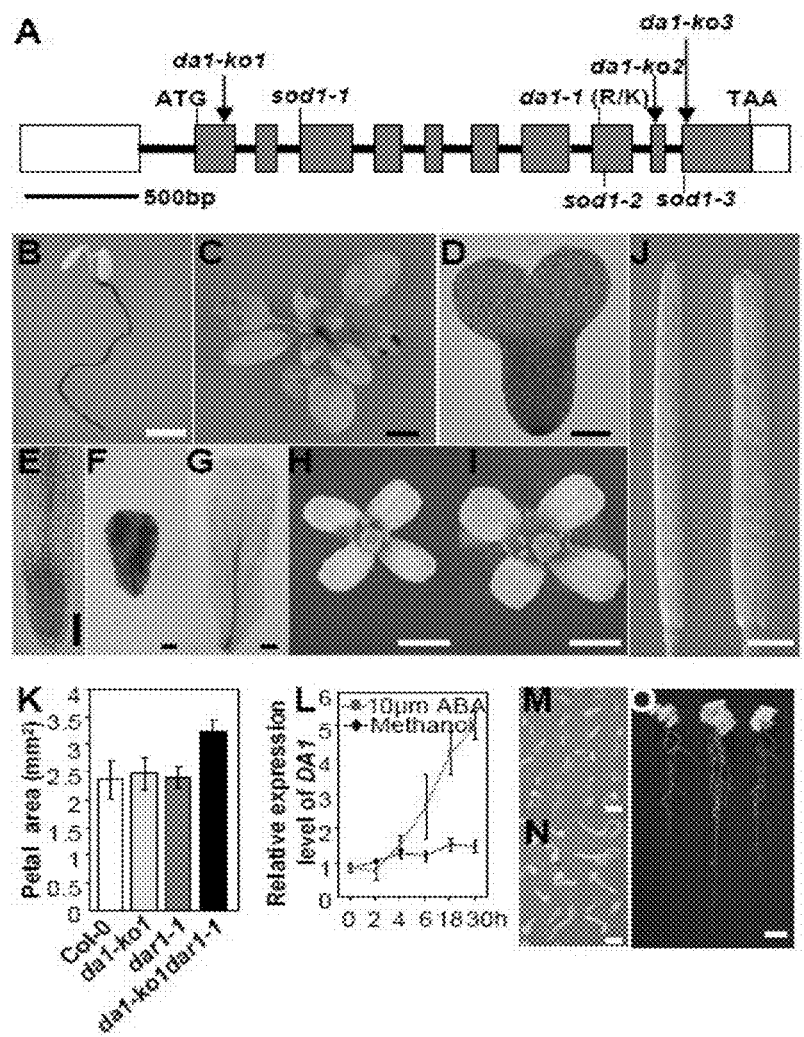
FIG. 3 shows the identification and expression of the DA1 gene. (A) DA1 gene structure, showing the mutated sites of da1-1, sod1-1, sod1-2, and sod1-3 alleles. The start codon (ATG) and the stop codon (TGA) are indicated. Closed boxes indicate the coding sequence and lines between boxes indicate introns. T-DNA insertion sites (da1-ko1, da1-ko2 and da1-ko3) in DA1 gene are shown. (B to G) DA1 promoter activity monitored by pDA1::GUS transgene expression. GUS staining in seedlings (B and C), an embryo (D), roots (E), and petals (F and G). (H and I) The flowers of Col-0 (H) and da1-ko1dar1-1 double mutant (I). (J) Siliques of Col-0 (left) and da1-ko1dar1-1 double mutant (right). (K) Petal area of Col-0, da1-ko1, dar1-1, da1-ko1dar1-1 double mutants. The da1-ko1dar1-1 double mutant displays a da1-1 phenotype including large flowers and petals, wide and flattened siliques, and short styles. (L) Quantitative RT-PCR analysis revealed that expression of DA1 is slowly induced by ABA. 7 d-old WT seedlings were treated with 10 μm ABA for 2, 4, 6, 18 and 30 hours. (M and N) Wild type Col-0 and da1-1 seeds were grown on MS medium with 2 μm ABA under constant light conditions. The da1-1 mutant (N) exhibits ABA-insensitive seedling establishment compared with wild type Col-0 (m). (O) 4 d-old seedlings of Col-0 (left), da1-1 (middle) and DA1COM #2 (right) were transferred to MS medium with 5 μm ABA for 3 weeks. da1-1 mutant seedlings continue to grow in the presence of low levels of ABA that inhibit the growth of wild type Col-0 seedlings. Scale bars: 1 mm (B, H, I, M, and N), 50 μm (C and E), 0.5 mm (C and J), 0.1 mm (F and G), 0.5 cm (0).
Figure 9:
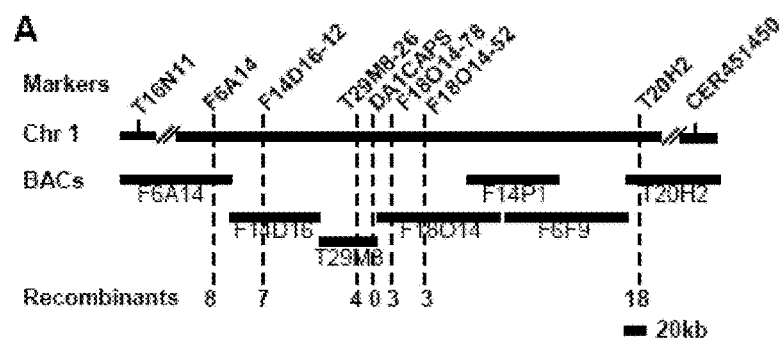
FIG. 9 shows map-based cloning of DAL (A) Fine mapping of the DA1 locus. The DA1 locus was mapped to chromosome 1 (Chr 1) between markers T16N11 and CER451450. The DA1 locus was further narrowed to a 30-kb genomic DNA region between markers T29M8-26 and F18O14-52 and co-segregated with CAPS marker DA1CAPS. The number of recombinants identified from F2 plants is shown. (B) The mutation in da1-1 was identified using the CAPS marker DA1CAPS1. (C to E) Expression levels of DA1 (C) and DAR1 (U) in wild type and T-DNA lines were revealed by RT-PCR analysis.
Figure 9:
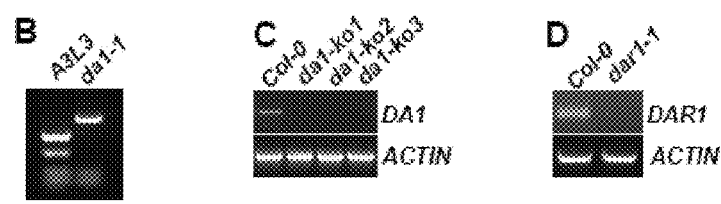

The DA1 locus was fine-mapped to an about 30-kilobase (kb) region using polymerase chain reaction-based markers (FIG. 9). DNA sequencing revealed that the da1-1 allele carries a single nucleotide mutation from G to A in the At1g19270 gene which cosegregated with the da1-1 phenotype and results in a change of an argine (R) to a lysine (K) at amino acid 358 of the predicted protein (FIG. 3a and FIG. 9a,b). A binary plasmid (DA1COM) carrying a 6.4-kb wild-type genomic fragment containing the entire ORF and a plasmid (35S::DA1) carrying 35S promoter plus At1g19270 cDNA were able to rescue the phenotypes of the da1-1 mutant (FIG. 1i-q and FIG. 2a), confirming that that At1g19270 is indeed the DA1 gene.

DA1 is predicted to encode a 532-amino acid protein containing two ubiquitin interaction motifs (DIM) (Hiyama, H. J. Bio. Chem. 274, 28019-28025 (1999)) and one zinc-binding domain (LIM) present in Lin-11, Isl-1, Mec-3 (Freyd, G. Nature 344, 876-879 (1990) at the N terminus (see Sequences). The UIM is a short peptide motif with the dual function of binding ubiquitin and promoting ubiquitination. This motif is conserved throughout eukaryotes and is present in numerous proteins involved in a wide variety of cellular processes including endocytosis, protein trafficking, and signal transduction (Hurley J. H. Biochem. J. 399, 361-372 (2006)). The LIM domain is a protein-protein interaction motif critically involved in a variety of fundamental biological process, including cytoskeleton organization, organ development and signal transduction (Dawid, I. B. Trends Genet. 14, 156-162 (1998); Dawid, I. B. CR Acad. Sci. III 318, 295-306 (1995); Kadrmas, J. L. Nat. Rev. Mol. Cell Biol. 5, 920-931 (2004)) Seven other predicted proteins in *Arabidopsis* share extensive amino acid similarity (>30% identity) with DA1 and have been named DA1-related proteins (DARs) (see sequence alignment D). The conserved regions among DA1 and DARs lie in the C terminal portion of the molecule, indicating that these conserved regions may be crucial for their function. Proteins that share significant homology with DA1 outside the UIM and LIM are also found in plants and green algae, but not animals.

The spatial expression patterns of DA1 were revealed by histochemical assays of β-glucuronidase (GUS) activity of transgenic plants containing DA1 promoter::GUS fusions (pDA1::GUS). Histochemical staining shows DA1 gene expression throughout the plant, including cotyledons, true leaves, flowers, and embryos (FIG. 3b-h), consistent with the large size phenotypes of da1-1 mutant plants. Relatively high levels of GUS activity were detected in proliferating tissues (FIG. 3c-f). In addition, the DA1 promoter is also active in roots (FIG. 3b, c). Given the effects of hormones on organ growth, we tested whether any major classes of phytohormones (abscisic acid, jasmonic acid, ethylene, auxin, cytokinin, gibberellin, brassinosteroids and glucose) could influence transcription of DA1 gene. The expression level of the DA1 gene was induced slowly by ABA (FIG. 3m), but not by other hormones, suggesting that the ABA signal may participate in regulation of DA1. Consistent with this, da1-1 mutant is insensitive to ABA (FIG. 3n), providing indication that ABA may be one of the environmental cues that regulate DA1 gene to limit seed and organ growth.

A green fluorescent protein (GFP)-DA1 translational fusion under the control of 35S promoter rescued the da1-1 phenotype. However, we could not detect GFP signal. Consistent with this, we also could not detect DA1 proteins of transgenic plants overexpressing DA1 with HA (35::DA1-HA) and GFP (35S::DA1-GFP) tags using western blot providing indication that the DA1 protein is readily degraded or cleaved in plants.

Da1-1 Acts as a Type of Dominant Negative Mutation for DA1-Related Proteins

Figure 10A:
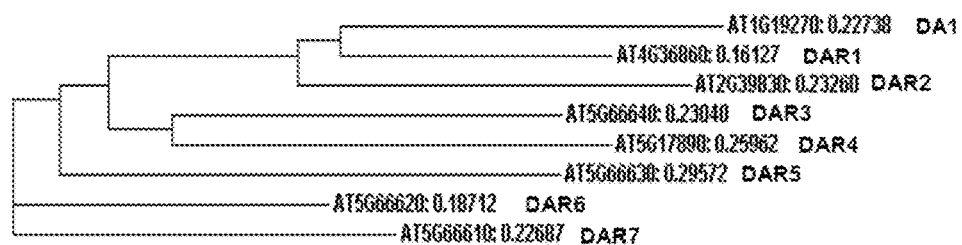
FIG. 10 shows the identification of DA1-related proteins in *Arabidopsis* and homologs of DA1 in other species. DA1-related proteins in *Arabidopsis* are shown in FIG. 10A and DA1-related proteins in other species are shown in FIG. 10B.
Figure 10B:
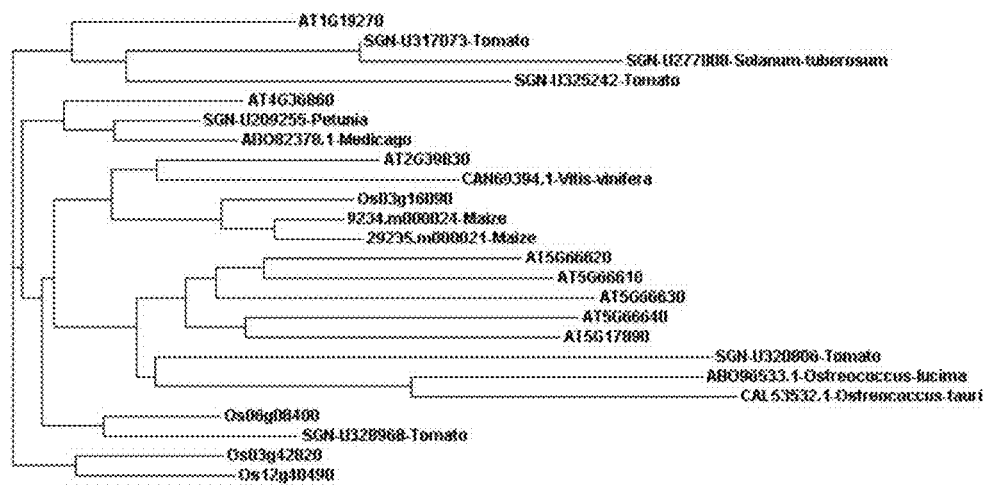

To identify the novel components of the DA1 pathway that determines the final size of seed and organ size, we screened for suppressors of the large seed and organ size phenotypes of da1-1 (sod) and found three sod1 alleles that were mapped to the original DA1 locus. We sequenced the DA1 gene from these lines and found that each harboured a second site mutation that is predicted to reduce or abolish gene function (FIG. 3A). That second site mutations in the da1-1 mutant gene suppress the da1-1 phenotype indicates that the (R358K) mutation within the DA1 coding sequence produces the large seed and organ size. Consistent with this, disruptions of the DA1 gene via T-DNA insertions (da1-ko1, da1-ko2 and da1-ko3) display no obvious phenotype (FIG. 10). To determine if one amino acid change found in the original da1-1 allele was necessary for the da1-1 phenotype, we crossed da1-1 with wild type or da1-ko lines. All heterozygotic lines (F1) from crosses between Col-0 and da1-1 exhibited the wild type phenotype, whereas all the F1 plants from crosses between da1-1 and T-DNA lines (da1-ko1, da1-ko2 and da1-ko3) exhibited similar phenotypes to da1-1 (Fig. S9). In addition, the da1-1 phenotype was also observed in wild type plants carrying the 35S::DA1R358K transgene (FIG. 1i-r). Therefore, the R358K mutation in DA1 is necessary and sufficient to cause the da1-1 phenotype.

The loss-of-function alleles display no obvious phenotype. We therefore postulated that DA1 may act redundantly with DARs and expression of da1-1 allele interferes with the ability of DARs to replace DA1. To test this hypothesis, we generated da1-ko1dar1-1 double mutants. The da1-ko1dar1-1 double mutant displayed the original da1-1 phenotype (FIG. 3i-1, Table 1 and FIG. 4e), indicating that da1-1 acts as a type of recessive interfering allele for DARs. Large seed and organ size phenotypes of plants overexpressing the da1-1 allele in Col-0 suggested that the da1-1 allele also interferes with the activity of DA1 in dosage-dependent manner (FIG. 1i-q).

DA1 Acts in Parallel with EOD1/BB, Independent of ANT, AXR1, ARF2 and AP2

Figure 4:
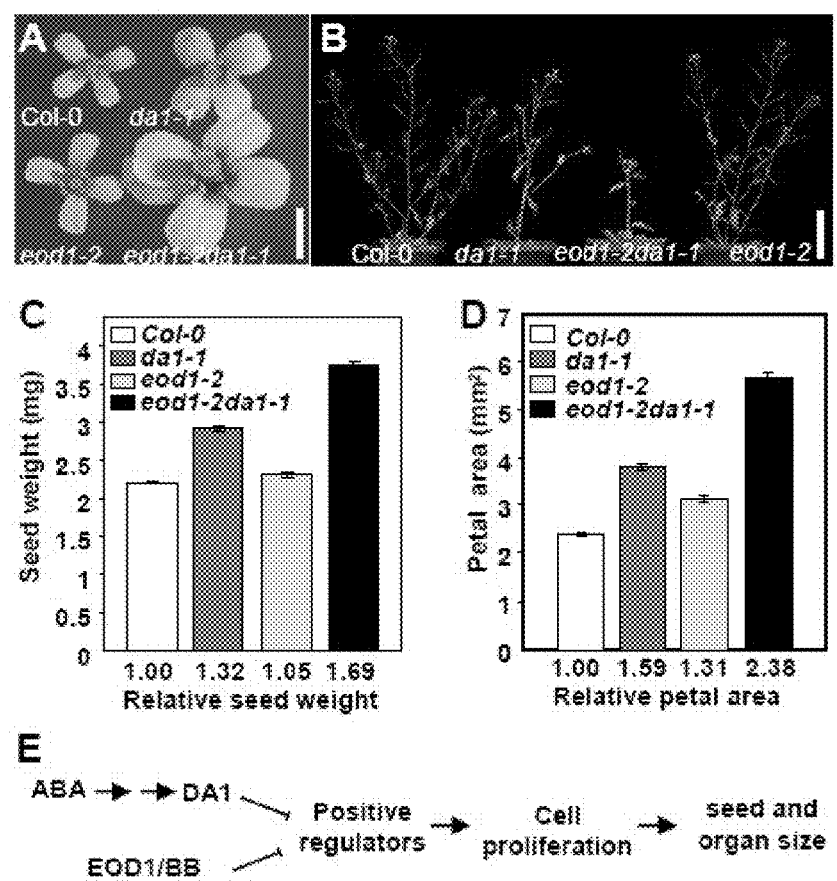
FIG. 4 show mutations in EOD1/BB synergistically enhance the phenotypes of da1-1. (A) Flowers of Col-0, da1-1, eod1-2 and eod1-2da1-1 double mutants. (B) Soil grown plants of Col-0, eod1-2, eod1-2 and eod1-2da1-1 double mutants. (C) Average seed weights of Col-0, da1-1, eod1-1 and eod1-2da1-1 double mutants are shown as mg per 100 seeds. Standard deviations are shown (n=5). Plants were grown under identical conditions. (D) Petal area of Col-0, da1-1, cod1-2 and eod1-2da1-1 double mutant. Standard deviation values are shown (n>50), (E) A model of DA1 and EOD1/BB in controlling seed and organ size. Scale bars: 2 mm (A), 50 mm (B).

In enhancer screens, we isolated one allele of a recessive enhancer of da1-1 (eod1-1). ecd1-1da1-1 plants exhibits larger seed and organ size, more extra petals and longer lifespan than da1-1 (FIG. 12a,b). We mapped the eod1-1 mutation and found that it was linked to Big Brother (BB) gene (At3g63530) that encodes an E3 ubiquitin ligase and represses organ growth in *Arabidopsis* {Disch, 2006}. Sequencing revealed that the eod1-1 allele carries a single nucleotide mutation from G to A in the At3g63530 and resulted in a change of an Alanine (A) to a Threonine (T) at amino acid 44 of the predicted BB protein (FIG. 12c). Both T-DNA insertion in the intron (eod1-2) and bb-1 also enhance da1-1 phenotypes (FIG. 4 and FIG. 12d, e). A binary plasmid (35S::EOD1) carrying 35S promoter plus At3g63530 cDNA was able to rescue the phenotype of the eod1 mutant, indicating that EOD1 is the BB gene. To determine the relationships between EOD1/BB and DA1 in limiting organ size, we analyzed the mRNA expression levels of DA1 in a bb-1 mutant and of BB in a da1-1 mutant. Expression of the DA1 gene in a bb-1 mutant and of the BB gene in a da1-1 plant is not significantly affected, compared with wild type (FIG. 12a,b).

Figure 11:
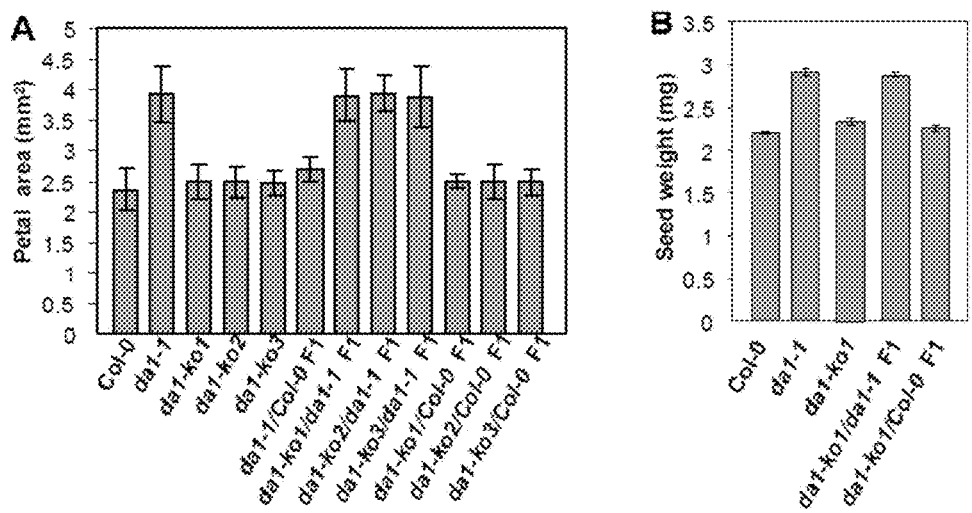
FIG. 11 shows that the R358K mutation in DA1 is responsible for increased seed and organ size. (A) Petal area of Col-0, da1-1, da1-ko1, da1-ko2, da1-ko3, da1-1/Col-0 F$_1$, da1-ko1/da1-1 F$_1$, da1-ko2/da1-1 F$_1$, da1-ko3/da1-1 F$_1$, da1-ko1/Col-0 F$_1$, da1-ko2/Col-0 F$_1$, da1-ko3/Col-0 F$_1$, and da1-ko1/da1-1 F$_1$. Standard deviation values are given (n>50). (B) Average seed weight of Col-0, da1-1, da1-ko1, da1-ko1/da1-1 F$_1$, and da1-ko1/Col-0 F$_1$ is given in mg per 100 seeds. Standard deviation values are given (n=5). Plants were grown under identical conditions.

To understand the genetic relationships between EOD1/BB and DA1, we measured seed and petal size in eod1-2da1-1 and bb-1da1-1$^{Ler}$ double mutants and found that mutations in EOD1/BE synergistically enhance the phenotype of da1-1 (FIG. 4, FIGS. 11 d, e and 12a), providing indication that the two genes act in parallel pathways to limit seed and organ size in plants (FIG. 4e).

aintegumenta (ant) alleles exhibit small petals and plants over-expressing ANT exhibit organ enlargement because of a prolonged period of organ growth {Krizek, B. A. *Dev Genet* 25, 224-36 (1999); Mizukami, Y. *Proc Natl Acad Sci USA* 97, 942-7 (2000)}, providing indication that DA1 and ANT could function antagonistically in a common pathway. To test this, we analyzed the mRNA expression levels of DA1 in ant mutants and of ANT and its downstream target CyclinD3;1 in da1-1 mutant. DA1 mRNA levels do not show robust changes in ant mutants (FIG. 12b). Similarly, the levels of both ANT and Cyclin3;1 mRNA are not significantly affected by the da1-1 mutation, as is the mRNA level of ARGOS {Hu, Y. *Plant Cell* 15, 1951-61 (2003)} (FIG. 11c, d, e). Genetic analysis also showed that the petal size phenotype of ant-5da1-1 mutant was essentially additive, providing indication that DA1 and ANT act in independent pathways. We also generated axr1-12da1-1, arf2-7da1-1 and ap2-7da1-1 double mutants, since axr1, arf2 and ap2 mutants have altered organ and/or seed size (Lincoln, C. Plant Cell 2, 1071-1080 (1990); Schruff, M. C. Development 137, 251-261 (2006); Ohto, M. A. Proc. Natnl Acad. Sci USA 102, 3123-3128 (2005); Jofuku, K. D. Proc. Natnl Acad. Sci. USA 102, 3117-3122 (2005)). Genetic analysis revealed that the petal size phenotype of axr1-12da1-1 mutant or the seed size phenotype of arf2-7da1-1 and ap2-7da1-1 were essentially additive (FIG. 12b,c,d,e), compared with their parental lines. Therefore, we concluded that DA1 appears to act in parallel with EOD1/BB, independent of ANT, ARX1, ARF2 and AP2.

The DA1 Protein Family in *Arabidopsis thaliana*

As described above, the DA1 gene is predicted to encode a 532-amino-acid protein containing two ubiquitin interaction motifs (UIM) typical of ubiquitin receptors and a single zinc-binding LIM domain defined by its conservation with the canonical Lin-11, Isl-1, and Mec-3 domains (Li et al. 2008). In *Arabidopsis*, seven other predicted proteins share extensive C-terminal (outside UIM and LIM domains) amino acid similarity with DA1 and have been named DA1-related (DAR) proteins, of which four (DAR3, DAR5-7) are found in a tandem cluster on chromosome 5. Using SMART (URL smart [dot]embl-heidel berg [dot]de/smart/show_motifs [dot]pl), the different functional domains were characterised (see Table 11).

UIM is the ubiquitin-interacting motif with two conserved serine residues required for binding and forms a short α-helix structure with ubiquitin (Haglund and Dikic 2005). LIM is a cysteine-rich protein interaction motif, has zinc-binding ability (Freyd et al. 1990). NB-ARC (stands for "a nucleotide-binding adaptor shared by APAF-1, certain R gene products and CED-4") links a protein-protein interaction module to an effector domain, it is a novel signalling motif shared by plant resistance gene products and regulators of cell death in animals. LRRs are leucine-rich repeats, they are short sequence motifs and are thought to be involved in protein-protein interactions. RPW8 belongs to a family that consists of several broad-spectrum mildew resistance proteins from *Arabidopsis thaliana*.

These diverse protein structures provide indication the family has diverse functions and has functionally diversified recently. Table 11 may be used to guide the formation of double and triple mutants eg DA1, DAR1 are similar and have been shown to function redundantly; it is possible that DA6 and DAR7 may also function redundantly with each other and DA1 and DAR1 because of their similar structures.

Characterisation of DA1-Like (DAL) Proteins in *Physcomitrella patens, Selaginella Moellendorffi, Brassica Rapa, Brachypodium Distachyon* and *Oryza sativa*

The amino acid sequences of *Arabidopsis* DA1 and DAR1-7 were used as queries to screen the available *Physcomitrella patens, Selaginella moellendorffi, Brassica rapa, Brachypodium distachyon* and *Oryza sativa* databases. Using different BLAST algorithms, candidate genes were then selected for preliminary phylogenetic analysis.

DA1-Like Proteins in Early Land Plants, *Physcomitrella patens* and *Selaginella moellendorffi*

The DA1 family orthologs in *P. patens* were searched by using DA1 amino acid sequence as query in NCBI BLAST, and then revised in JGI *P. patens* BLAST (URL: genome-dot-jgi-psf.org/cgi-bin/runAlignment?db=Phypal_1&advanced=1). Eight genes (PpDAL1-8) were selected based on scores, E-values and preliminary phylogenetic analysis. All *P. patens* DA1-like proteins are shorter than DA1 amino acid sequences, due to absence of the two UIM domains at the N-terminal (see FIG. 1), according to SMART (Simple Molecular Architecture Research Tool) program (URL: smart-dot-embl-heidelberg-dot-de/). The *S. moellendorffi* sequencing project provides us an opportunity to investigate DA1 family orthology in first vascular plant. By using JGI *S. moellendorffi* BLAST (URL: genome-dot-jgi-psf.org/cgi-bin/runAlignment?db=Selmol&advanced=1), two orthologs were found, and comparing with *P. patens* DA1-like proteins, they had similar amino acid sequences length with *Arabidopsis* DA1 family proteins. The regions preceding the LIM domain were predicted to be low-complexity regions by SMART, and no clear UIM protein sequence motifs were found. We can therefore conclude that the characteristic DA1 protein structure is not found in lower plants.

DA1-Like Proteins in *Brassica rapa*

Due to the close evolutionary relationships of *Arabidopsis* and *Brassica*, nucleotide BLAST methods for identifying *Brassica* DA1 family orthologs were used. In the *Brassica* database (URL: www-dot-*brassica*-dot-bbsrc-dot-ac-dot-uk/), full length cDNA sequences of *Arabidopsis* DA1 and DAR1-7 were used as queries. Because of a recent entire genome duplication, one *Arabidopsis* gene probably has 2 or 3 homologous genes in Brassica rapa. Two DA1 orthologs and one DAR2 orthologs were found (FIG. 1). These were called DAL (DA-Like) genes. The DAR3-7 Brassica orthologs were also found in a tandem cluster. The number of Brassica orthologs found is less than predicted probably due to incomplete genome sequencing. The partial sequences of Brassica DAL genes were used to design primers for the specific amplification of full-length DAL genes from B. rapa.

DA1-Like Proteins in the Grasses Brachypodium distachyon and Oryza sativa

In Brachypodium distachyon, three major DA1 family orthologs were identified, and in Oryza sativa, four DA1-like proteins were found using PROTEIN BLAST at NCBI. Rice DA1 and DAR2 orthologs were identified and named OsDA1 and OsDAR2. No rice gone was found to match Arabidopsis DAR1.

Figure 14:
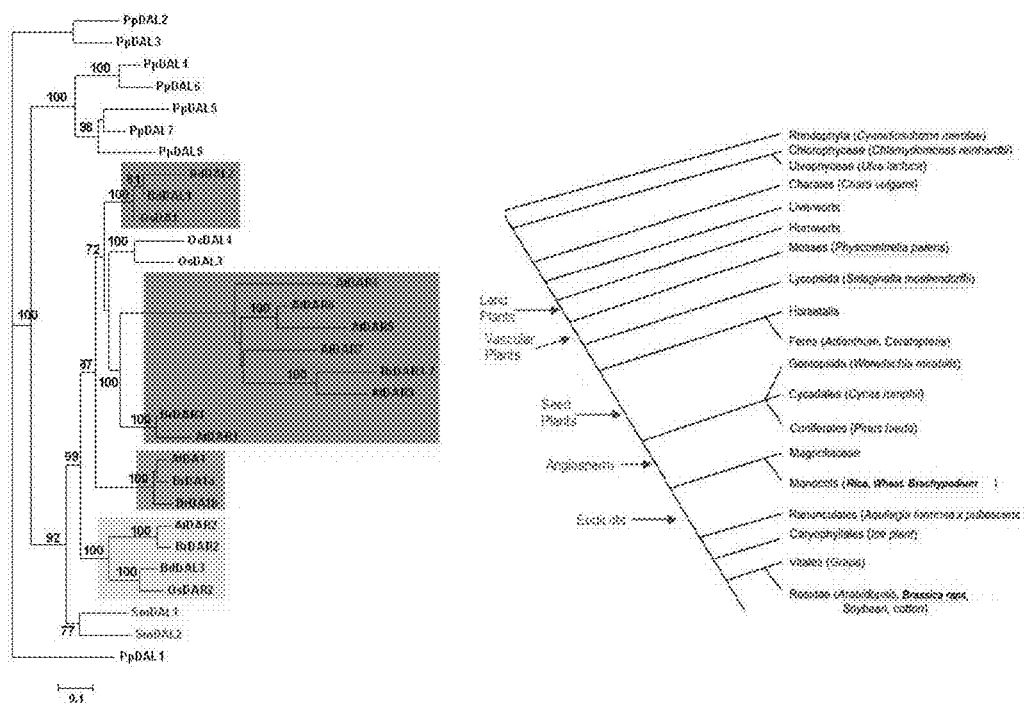
FIG. 14 shows a phylogenetic analysis of DA1-like proteins. Left graph: A distance matrix phylogenetic tree was created using PHYLIP software (VERSION 3.66) with the default settings (the JTT model of protein sequence evolution and the neighbour-joining algorithm). The tree was then imported into MEGA 4.0 software to rearrange. Bootstrap values (the numbers on the branches indicate the number of times the partition of the species into the two sets which are separated by that branch occurred among the trees, only shown over 70) were obtained by 100 replicates. The data for the tree was the C-terminal 250 amino acid region of full length DA1-like protein sequences. The right graph shows a simplified overview of plant evolution based on the hyperbolic tree presented at (URL: ucjeps-dot-berkeley-dot-edu/TreeofLife/hyperbolic-dot-php). Clades that are related with text are retained in the graph. Species that were analysed are underlined.

In the phylogenetic tree of FIG. 14 all DA-like proteins from vascular plants form one large clade. In that clade, S. moellendorffi DA-like proteins are highly divergent, but it is possible that DA-like proteins might originate from bryophytes, and function as size regulators since the evolution of the first vascular plants (Lycophytes). In the tree, a clade was formed by AtDAR2, BrDAR2, BdDAL3 and OsDAR2. These protein sequences show greater similarity, suggesting that DAR2 evolved before monocots originated (see right graph of FIG. 14) and is functionally conserve during evolution. Another clade consists of AtDA1, BrDA1a and BrDA1b. The high similarity between them suggests Brassica rapa DA1 proteins might have the same function as AtDA1. The clade consisting of OsDA1, BdDAL1 and BdDAL2 was placed apart from this clade (see FIG. 14), indicating that grass DA1 proteins may be slightly functionally divergent from those in the Brassicaceae. All Brassicaceae DAR1 and DAR3-7 were placed in one clade, indicating these genes probably arose from DA1 or DAR2 in the genome duplication within Brassicaccae. This hypothesis has been partially proved by genetic analysis, which demonstrated, in Arabidopsis, DA1 and DAR1 are functional redundant.

Functional Analysis of DA1-Like Proteins in Brassica rapa, Oryza Sativa

In silico, two Brassica rapa DA1-like genes (BrDA1a, BrDA1b) and one rice DA1-like gene (OsDA1) were identified. Full length cDNAs were synthesised and sequenced using directional TOPO vectors. The predicted biochemical characteristics of AtDA1, BrDA1a, BrDA1b and OsDA1 are shown in Table 12. The proteins these three genes encode have very similar biochemical characteristics, particularly the two Brassica ones. Interestingly, although analysis based on amino acid sequences shown BrDA1a is more close to AtDA1, BrDA1b was predicted to have more similar biochemical features to AtDA1 (Table 12).

The Phenotypes of Da1-1 are Rescued by BrDA1a, BrDA1b and OsDA1 Genes

Figure 15:
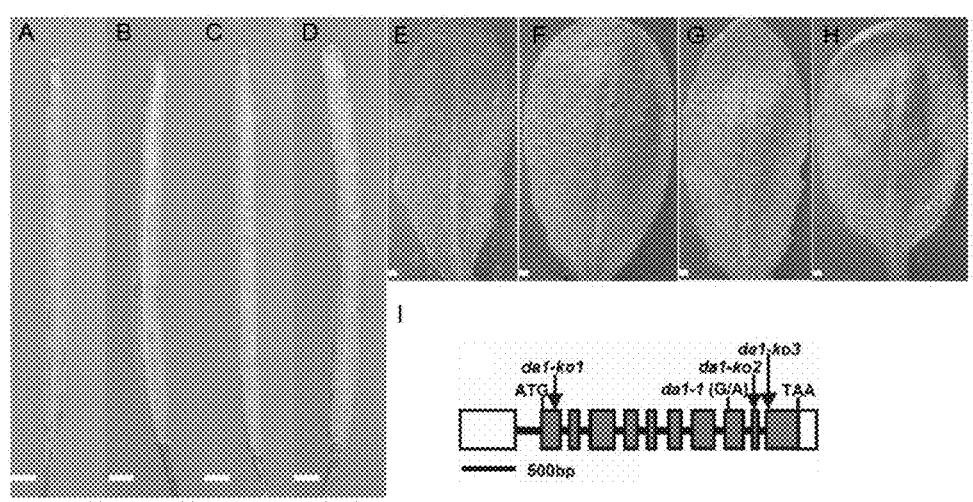
FIG. 15 (A-D) shows siliques of Col-0, BrDA1aCOM (35S:: BrDA1a transgenic line), OsDA1COM (35S:: OsDA1 transgenic line) and da1-1. (E-H) Rosette leaves of Col-0, da1-1, BrDA1bCOM (35S:: BrDA1b transgenic line) and 35S::BrDA1a$^{R/K}$ (overexpressing 35S::BrDA1a$^{R/K}$ in Col-0). (I) DA1 gene structure showing the mutated sites of da1-1 and T-DNA insertion sites (da1-ko1, da1-ko2 and da1-ko3).
Figure 18C:
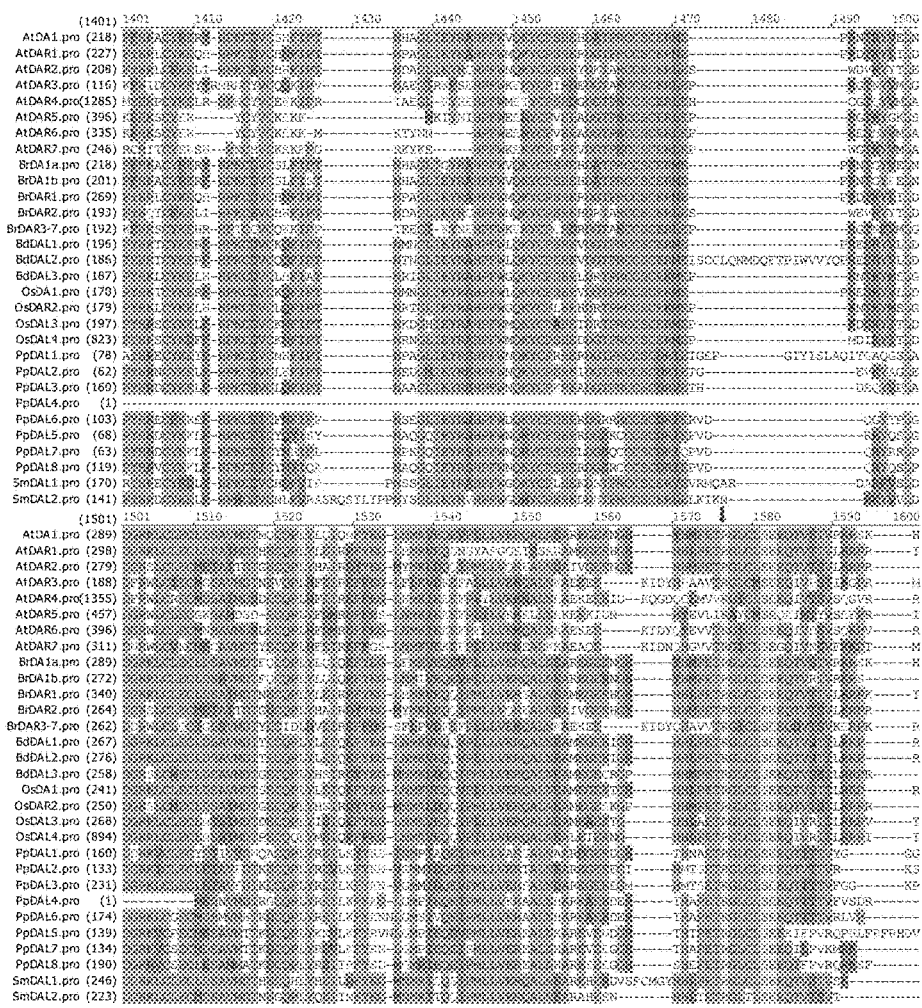
FIGS. 18 (A-D) shows an alignment (alignment E) of the amino acid sequences of DA1-like proteins. Full length amino acid sequences of DA1-like proteins from *Physcomitrella patens* (Pp), *Selaginella moellendorffi* (Sm), *Brassica rapa* (Br), *Arabidopsis thaliana* (At), *Brachypodium distachyon* (Bd) and *Oryza sativa* (Os) were aligned with default setting ClustalW (URL: ebi-dot-ac-dot-uk/Tools/clustalw2/index-dot-html), and edited display settings in VectorNTi. The red arrow shows the mutation in da1-1 allele. DAL stands for DA1-Like. Sequences of FIGS. 18A-18D are listed in the Sequence Listing as SEQ ID NOs: 301-330 (AtDA1.pro to SmDAL2.pro), respectively.
Figure 18D:
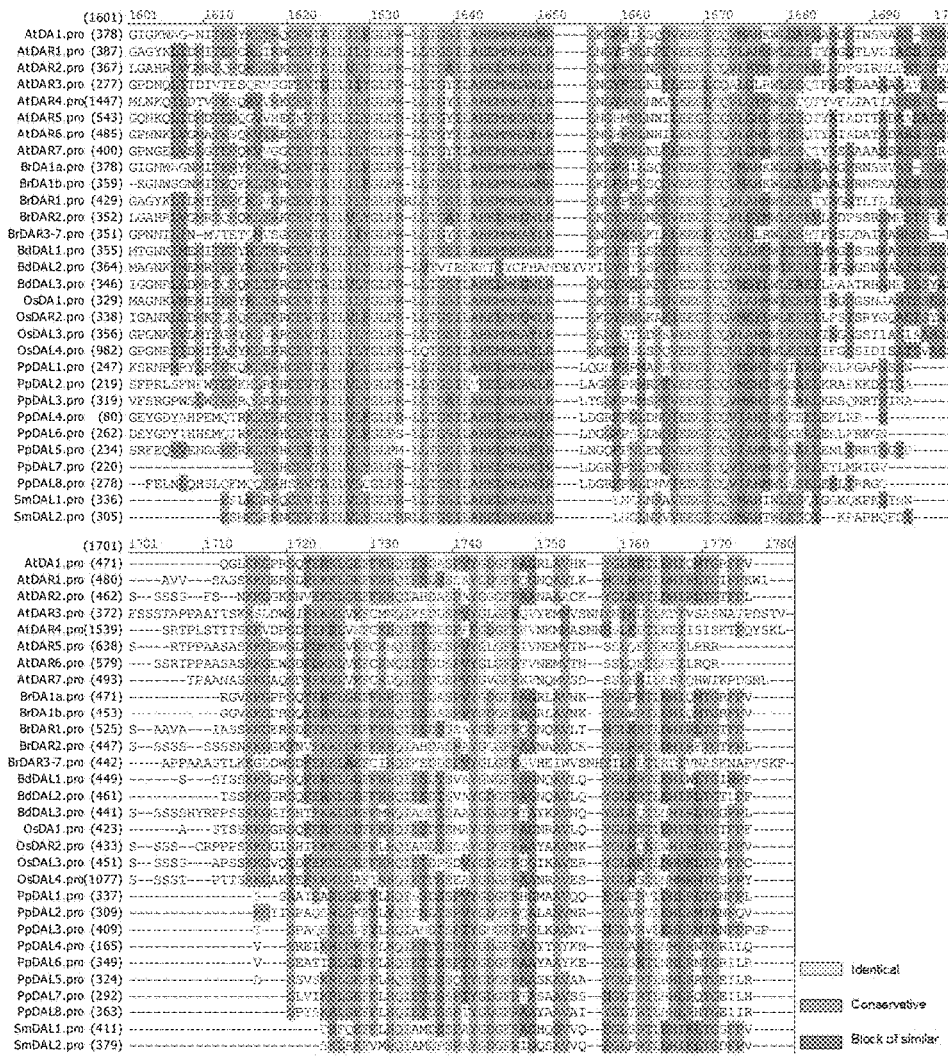

Full-length BrDA1a, BrDA1b and OsDA1 cDNAs were sub-cloned to TOPO vectors and transferred to pMDC32 binary destination vectors by LR recombination. These vectors express cDNAs from the constitutive 35S promoter. da1-1 plants were transformed to test whether the wild-type DAL genes from Brassica and rice could complement the large growth phenotypes of da1-1 plants. The 35S:: BrDA1a and 35S:: OsDA1 transgenic plants showed at least partial complementation (see FIG. 15A-D). Interestingly, although BrDA1b is not the closest homolog to AtDA1, the 35S:: BrDA1b transgenic plants showed full complementation of the da1-1 phenotype (see FIGS. 15E-G), consistent with the high biochemical similarity to AtDA1 (see Table 12). Two rounds of transformants were screened. In the first round, 10 out of 40 35S::BrDA1a and 3 out of 11 35S::OsDA1 T1 plants show the siliques phenotypes in FIG. 15A-D. In the second round, 30 out of 150 35S::BrDA1b have shown the rosette leaves phenotypes in FIG. 15E-G. This is convincing data that BrDA1b functions like Arabidopsis DA1. Consequently we have demonstrated that DA1 and related genes have similar functions in controlling organ and seed size in Brassica and rice, and probably many other types of plants.

BrDA1a$^{R355K}$ can Interfere with AtDA1 Function in Col-0 Plants

Site directed mutagenesis was used to generate the equivalent R358K mutation in the BrDA1a cDNA in the TOPO vector and then the mutated cDNA was transferred to pMDC32 destination vectors using the gateway system. Typical da1-1 phenotypes were observed in wildtype Col-0 plants expressing 35S:: BrDA1a$^{R358K}$ (see FIG. 15E,F,H), including large organ phenotypes. In this transformation experiment, 60 T1 transgenic plants were screened and 7 of these were found to have characteristic large organ phenotypes seen in da1-1 plants.

DA1 Protein Stability.

We have observed that transformants expressing fusions of the GFP protein with the C terminus of the full length DA1 protein complements the DA1$^{R358K}$ large organ phenotype, demonstrating that the fusion protein is fully functional. However, we did not detect GFP fluorescence in many transgenic lines, providing indication that DA1GFP protein levels are very low. This is supported by the observation that detection of DA1 protein with a good specific antibody in plant extracts is very difficult. We therefore tested the stability of DA1 protein in Arabidopsis using DA1 protein expressed in E. coli and cell-free protein extracts from Arabidopsis. Full length DA1 protein expressed and purified as an N-terminal GST fusion protein, was incubated with Arabidopsis protein extracts and ATP, and subjected to Western analysis using a specific DA1 antibody. DA1 protein was found to be rapidly degraded under these conditions. MG132, a specific inhibitor of the proteasome, was found to abolish this degradation. Therefore, DA1 is rapidly degraded by the proteasome in Arabidopsis. The UIM motifs of DA1 are predicted, based on knowledge of UIM function in animal cells, to be involved in ubiquitination. It may be that DA1 is ubiquitinated and targeted for degradation as part of the mechanism of growth control.

TABLE 1

DA1 acts maternally to control seed weight

| Parent | | $F_1$ |
| Female | male | seed weight |
| --- | --- | --- |
| Col-0 | Col-0 | 2.368 ± 0.023 |
| Col-0 | da1-1 | 2.427 ± 0.031 |
| da1-1 | Col-0 | 3.189 ± 0.042 |
| da1-1 | da1-1 | 3.231 ± 0.046 |

Average seed weight is given in mg per 100 seeds.

Standard deviation values was given (n = 5).

Plants were grown together in the same conditions.

TABLE 2

List of PCR-based molecular markers.
(SEQ ID NOs: 18-35)

| Marker | Forward Primer | Reverse Primer | Restriction Enzyme |
|---|---|---|---|
| T16N11 | TAATTTAATATTTCCTTCTTCCCC | TTACTTTGACTCACTTTCACCAC | |
| F6A14 | AATTAGAATAATAATGCAGCGTTG | CGTTTCGGTATCGCTTTGCG | |
| F14D16-12 | TTG GTT TTC GTT GGG TCA AGG | TGTTTCTGCAGAAGCGAGGG | |
| T29M8-26 | AATCACGTGGTGTTCTTAGCC | ACTCATTTTGGCAGCTTGGTG | |
| DA1CAPS | GACACCATGCAATGCCAACC | CTTTGAGCCTCATCCACGCA | MnlI |
| F18O14-78 | CTCAGGCTCAGGTAAATGCG | TTCACGTCCGAAACGCATCC | BsaHI |
| F18O14-52 | CTAACACGACCCACATGATGC | CTCGAGTTTCGTGGTTACGG | NspI |
| T20H2 | AGCATCCTCAAGGTATAAGCC | GGTGCTGCATTTCTGTCACC | |
| CER451450 | GGTTGCTCTAAATCACCTAACG | CTCACCAAGAATATGCATATGTG | |

Restriction enzymes for CAPS or dCAPS markers are indicated and others are SSLP markers

TABLE 3

List of Primers for RT-PCR and QRT-PCR
(SEQ ID NOs: 36-45)

| Gene Name | Forward Primer | Reverse Primer |
|---|---|---|
| RT-DA1 | ATGGGTTGGTTTAACAAGATCTTT | AACCGGGAATCTACCGGTCA |
| RT-DAR1 | ATGGAGTTTCTTCTCTTTCTTGG | TTAAATCCATTTAGGAAATGTACCG |
| RT-ACTIN | GAGAAGATGACTCAGATC | ATCCTTCCTGATATCGAC |
| QRT-DA1 | GACACCATGCAATGCCAACC | CTTTGAGCCTCATCCACGCA |
| QRT-TUB6 | GGTGAAGGAATGGACGAGAT | GTCATCTGCAGTTGCGTCTT |

TABLE 4

List of Primers for verifying T-DNA.
(SEQ ID NOs: 46-57)

| T-DNA Lines | LP | RP |
|---|---|---|
| SALK_126092 | AAGCCAGCTAAATATGATTGG | AATCCGTTTGGAACTCGTTTG |
| SALK_110232 | GAATTTGGTTCGGTTGGTTTG | TCACATGCCAGAAACAAGAGG |
| SALK_054295 | TCCTCTTGGTTGAGAGACAAGC | TCCATTTGGGTTCTTAAACCG |
| SALK_067100 | ATTTAGTCGAAGCCATGCATG | TTACAAGGAGCAGCATCATCC |
| SALK_016122 | TGAGGTGGCCTATTTTGATACC | CACAACCTTAGTCACTTCAGAAGG |
| SALK_045169 | GAGCGATGCATCTCTAACCAC | AGTAGGAACAGAAAGCAGGGG |
| Lba | TGGTTCACGTAGTGGGCCATCG | |

TABLE 5

DA1 controls seed weight

| Genotype | Average seed weight, mg | % increase over wild type |
|---|---|---|
| Col-0 | 2.206 ± 0.015 | |
| da1-1 | 2.915 ± 0.039 | +32 |
| DA1COM # 2 | 2.182 ± 0.022 | |
| DA1COM # 3 | 2.301 ± 0.018 | |
| 35S::DA1$^{R358K}$ # 2 | 2.513 ± 0.026 | +14 |
| 35S::DA1$^{R358K}$ # 5 | 2.672 ± 0.019 | +21 |
| da1-ko1 | 2.231 ± 0.029 | |
| dar1-1 | 2.199 ± 0.032 | |
| da1-ko1 dar1-1 | 2.727 ± 0.019 | +24 |

Plants were grown under identical conditions.
Average seed weight is given in mg per 100 seeds.
Standard deviation values was given (n = 5).
Percent increases in seed weight were calculated based on comparison with that of wild type seeds produced under similar growth conditions.

TABLE 6

1: CAO61229
unnamed protein product [*Vitis vinifera*]
gi|157335399|emb|CAO61229.1|[157335399]
2: EAZ36049
hypothetical protein OsJ_019532 [*Oryza sativa (japonica* cultivar-group)]
gi|125596269|gb|EAZ36049.1|[125596269]
3: EAY99923
hypothetical protein OsI_021156 [*Oryza sativa (indica* cultivar-group)]
gi|125554318|gb|EAY99923.1|[125554318]
4: NP_001056985
Os06g0182500 [*Oryza sativa (japonica* cultivar-group)]
gi|115466772|ref|NP_001056985.1|[115466772]
5: CAO22922
unnamed protein product [*Vitis vinifera*]
gi|157348212|emb|CAO22922.1|[157348212]
6: EAZ21100
hypothetical protein OsJ_035309 [*Oryza sativa (japonica* cultivar-group)]
gi|125579954|gb|EAZ21100.1|[125579954]
7: NP_001067188
Os12g0596800 [*Oryza sativa (japonica* cultivar-group)]
gi|115489402|ref|NP_001067188.1|[115489402]
8: CAO22921
unnamed protein product [*Vitis vinifera*]
gi|157348211|emb|CAO22921.1|[157348211]
9: AAW34243
putative LIM domain containing protein [*Oryza sativa (japonica* cultivar-group)]
gi|57164484|gb|AAW34243.1|[57164484]
10: AAW34242
putative LIM domain containing protein [*Oryza sativa (japonica* cultivar-group)]
gi|57164483|gb|AAW34242.1|[57164483]
11: NP_001050702
Os03g0626600 [*Oryza sativa (japonica* cultivar-group)]
gi|115454203|ref|NP_001050702.1|[115454203]
12: EAY83760
hypothetical protein OsI_037719 [*Oryza sativa (indica* cultivar-group)]
gi|125537272|gb|EAY83760.1|[125537272]
13: EAZ27845
hypothetical protein OsJ_011328 [*Oryza sativa (japonica* cultivar-group)]
gi|125587181|gb|EAZ27845.1|[125587181]
14: NP_001049668
Os03g0267800 [*Oryza sativa (japonica* cultivar-group)]
gi|115452135|ref|NP_001049668.1|[115452135]
15:
EAY91080
hypothetical protein OsI_012313 [*Oryza sativa (indica* cultivar-group)]
gi|125544941|gb|EAY91080.1|[125544941]
16:
AAP06895
hypothetical protein [*Oryza sativa (japonica* cultivar-group)]
gi|29893641|gb|AAP06895.1|[29893641]
17: EAY89390
hypothetical protein OsI_010623 [*Oryza sativa (indica* cultivar-group)]
gi|125543251|gb|EAY89390.1|[125543251]
18:
CAO16347
unnamed protein product [*Vitis vinifera*]
gi|157346464|emb|CAO16347.1|[157346464]
19: CAN64300
hypothetical protein [*Vitis vinifera*]
gi|147817187|emb|CAN64300.1|[147817187]
20: CAN69394
hypothetical protein [*Vitis vinifera*]
gi|147768077|emb|CAN69394.1|[147768077]

TABLE 7

*Oryza sativa (japonica* cultivar-group) Os06g0182500 (Os06g0182500) mRNA, complete cds
gi|115466771|ref|NM_001063520.1|[115466771]
*Oryza sativa (japonica* cultivar-group) cDNA clone: 001-201-F10, full insert sequence
gi|32990928|dbj|AK105719.1|[32990928]
*Oryza sativa (japonica* cultivar-group) cDNA clone: J023004G21, full insert sequence
gi|32979080|dbj|AK069056.1|[32979080]
*Oryza sativa (japonica* cultivar-group) Os12g0596800 (Os12g0596800) mRNA, complete cds
gi|115489401|ref|NM_001073720.1|[115489401]
*Oryza sativa (japonica* cultivar-group) cDNA clone: J013039D10, full insert sequence
gi|32975778|dbj|AK065760.1|[32975778]
*Oryza sativa (japonica* cultivar-group) cDNA clone: J013073O11, full insert sequence
gi|32976683|dbj|AK066665.1|[32976683]
*Oryza sativa (japonica* cultivar-group) Os03g0626600 (Os03g0626600) mRNA, partial cds
gi|115454202|ref|NM_001057237.1|[115454202]
*Oryza sativa (japonica* cultivar-group) cDNA clone: 001-043-H07, full insert sequence
gi|32972053|dbj|AK062035.1|[32972053]
*Oryza sativa (japonica* cultivar-group) Os03g0267800 (Os03g0267800) mRNA, complete cds
gi|115452134|ref|NM_001056203.1|[115452134]

TABLE 7-continued

*Oryza sativa* (*japonica* cultivar-group) cDNA clone: J023020C05, full
insert sequence
gi|32979610|dbj|AK069586.1|[32979610]
*Oryza sativa* (*japonica* cultivar-group) isolate 29050 unknown mRNA
gi|29368349|gb|AY224559.1|[29368349]
*Oryza sativa* (*japonica* cultivar-group) isolate 29050 disease
resistance-like protein mRNA, partial cds
gi|29367476|gb|AY224475.1|[29367476]
*Oryza sativa* (*japonica* cultivar-group) genomic DNA, chromosome 6
gi|58531193|dbj|AP008212.1|[58531193]
*Oryza sativa* (*japonica* cultivar-group) genomic DNA, chromosome 6,
BAC clone: OSJNBb0036B04
gi|50657316|dbj|AP007226.1|[50657316]
*Oryza sativa* (*japonica* cultivar-group) genomic DNA, chromosome 12
gi|58531199|dbj|AP008218.1|[58531199]
*Oryza sativa* chromosome 12, . BAC OSJNBa0056D07 of library OSJNBa from
chromosome 12 of cultivar Nipponbare of ssp. *japonica* of *Oryza sativa*
(rice), complete sequence
gi|23897123|emb|AL928754.2|[23897123]
*Oryza sativa* chromosome 12, . BAC OJ1306_H03 of library Monsanto from
chromosome 12 of cultivar Nipponbare of ssp. *japonica* of *Oryza sativa*
(rice), complete sequence
gi|20513132|emb|AL713904.3|[20513132]
*Oryza sativa* (*japonica* cultivar-group) genomic DNA, chromosome 3
gi|58530789|dbj|AP008209.1|[58530789]
*Oryza sativa* (*japonica* cultivar-group) chromosome 3 clone
OSJNBa0002I03 map E1419S, complete sequence
gi|57164481|gb|AC091246.8|[57164481]
*Oryza sativa* (*japonica* cultivar-group) chromosome 3 clone OJA1364E02,
complete sequence
gi|27901829|gb|AC139168.1|[27901829]
*Oryza sativa* (*japonica* cultivar-group) chromosome 3 clone OJ1364E02,
complete sequence
gi|27901828|gb|AC135208.3|[27901828]
*Oryza sativa* chromosome 3 BAC OSJNBb0013K08 genomic sequence, complete
sequence
gi|16356889|gb|AC092390.3|[16356889]
*Oryza sativa* (*indica* cultivar-group) clone OSE-97-192-H5 zn ion
binding protein mRNA, partial cds
gi|149390776|gb|EF575818.1|[149390776]
*Oryza sativa* (*indica* cultivar-group) cDNA clone: OSIGCRA102J03, full
insert sequence
gi|116633496|emb|CT833300.1|[116633496]
*Oryza sativa* (*japonica* cultivar-group) Os01g0916000 (Os01g0916000)
mRNA, complete cds
gi|115441820|ref|NM_001051725.1|[115441820]
*Oryza sativa* (*japonica* cultivar-group) genomic DNA, chromosome 1
gi|58530787|dbj|AP008207.1|[58530787]
*Oryza sativa* (*japonica* cultivar-group) genomic DNA, chromosome 1, PAC
clone: P0413C03
gi|19386744|dbj|AP003451.4|[19386744]
*Oryza sativa* (*japonica* cultivar-group) genomic DNA, chromosome 1, PAC
clone: P0004D12
gi|20804980|dbj|AP003433.3|[20804980]
*Oryza sativa* (*japonica* cultivar-group) cDNA clone: 002-101-C04, full
insert sequence
gi|32991509|dbj|AK106300.1|[32991509]
*Oryza sativa* (*japonica* cultivar-group) cDNA, clone: J100024O13, full
insert sequence
gi|116012466|dbj|AK243101.1|[116012466]
*Zea mays* clone EL01N0524A08.d mRNA sequence
gi|54653541|gb|BT018760.1|[54653541]
*Zea mays* PCO156068 mRNA sequence
gi|21212590|gb|AY109151.1|[21212590]
*Zea mays* clone EL01N0553E07 mRNA sequence
gi|85540336|gb|BT024085.1|[85540336]
*Zea mays* clone E04912705F06.c mRNA sequence
gi|54651736|gb|BT016955.1|[54651736]
*Zea mays* nitrate reductase gene, promoter region
gi|4894987|gb|AF141939.1|AF141939[4894987]
*Hordeum vulgare* subsp. vulgare cDNA clone: FLbaf82h16, mRNA sequence
gi|151419042|dbj|AK250393.1|[151419042]
*Vitis vinifera*, whole genome shotgun sequence, contig VV78X106678.4,
clone ENTAV 115
gi|123680846|emb|AM488121.1|[123680846]
*Vitis vinifera* contig VV78X222701.5, whole genome shotgun sequence
gi|147817185|emb|AM484789.2|[147817185]
*Vitis vinifera*, whole genome shotgun sequence, contig VV78X165152.5,
clone ENTAV 115
gi|123703056|emb|AM483648.1|[123703056]

TABLE 7-continued

*Vitis vinifera* contig VV78X263569.4, whole genome shotgun sequence
gi|147790377|emb|AM453516.2|[147790377]
*Vitis vinifera* contig VV78X179395.3, whole genome shotgun sequence
gi|147769864|emb|AM456337.2|[147769864]
*Vitis vinifera* contig VV78X219892.2, whole genome shotgun sequence
gi|147780236|emb|AM461946.2|[147780236]
*Vitis vinifera*, whole genome shotgun sequence, contig VV78X014445.8, clone ENTAV 115
gi|123704690|emb|AM483793.1|[123704690]
*Vitis vinifera* contig VV78X193742.9, whole genome shotgun sequence
gi|147768076|emb|AM435996.2|[147768076]
*Lotus japonicus* genomic DNA, chromosome 2, clone: LjB06D23, BM0787,
complete sequence
gi|37591131|dbj|AP006541.1|[37591131]
*Agropyron cristatum* isolate Bsyl y-type high-molecular-weight glutenin
subunit pseudogene, complete sequence
gi|71159564|gb|DQ073532.1|[71159564]
*Agropyron cristatum* isolate Btyl y-type high-molecular-weight glutenin
subunit pseudogene, complete sequence
gi|71159568|gb|DQ073535.1|[71159568]
*Agropyron cristatum* isolate Bfyl y-type high-molecular-weight glutenin
subunit pseudogene, complete sequence
gi|71159563|gb|DQ073531.1|[71159563]
*Pinus taeda* putative cell wall protein (lp5) gene, complete cds
gi|2317763|gb|AF013805.1|[2317763]
*Brassica rapa* subsp. pekinensis clone KBrH011G10, complete sequence
gi|110797257|gb|AC189577.1|[110797257]
*Brassica rapa* subsp. pekinensis KBrB032C14, complete sequence
gi|110796986|gb|AC189306.1|[110796986]
*Brassica rapa* subsp. pekinensis clone KBrB011P07, complete sequence
gi|110744010|gb|AC189225.1|[110744010]
*Poplar* cDNA sequences
gi|115416791|emb|CT029673.1|[115416791]
*Poplar* cDNA sequences
gi|115416790|emb|CT029672.1|[115416790]
*Coffea arabica* microsatellite DNA, clone 26-4CTG
gi|13398992|emb|AJ308799.1|[13398992]
*Medicago truncatula* clone mth2-34m14, complete sequence
gi|61675739|gb|AC126779.19|[61675739]
*Medicago truncatula* chromosome 5 clone mth2-5p5, COMPLETE SEQUENCE
gi|119359633|emb|CU302347.1|[119359633]
*Medicago truncatula* chromosome 8 clone mth2-14m21, complete sequence
gi|50355770|gb|AC148241.21|[50355770]
*Solanum lycopersicum* cDNA, clone: LEFL1035BC02, HTC in leaf
gi|148538338|dbj|AK247104.1|[148538338]
*Mimulus guttatus* clone MGBa-44P14, complete sequence
gi|150010729|gb|AC182564.2|[150010729]
*Mimulus guttatus* clone MGBa-64L10, complete sequence
gi|154350257|gb|AC182570.2|[154350257]
*Selaginella moellendorffii* clone JGIASXY-5I19, complete sequence
gi|62510100|gb|AC158187.2|[62510100]
*M. truncatula* DNA sequence from clone MTH2-170H18 on chromosome 3,
complete sequence
gi|115635794|emb|CT967314.8|[115635794]
*Vigna unguiculata* glutelin 2 mRNA, partial cds gi|4973069|gb|AF142332.1|AF142332[4973069]

TABLE 8

| Soybean cDNA clones |
| --- |
| gb|CX711863.1|CX711863 |
| gb|BM525343.1|BM525343 |
| gb|BG156297.1|BG156297 |
| gb|BM308148.1|BM308148 |
| gb|AI856660.1|AI856660 |
| gb|BF596520.1|BF596520 |
| gb|BI472193.1|BI472193 |
| gb|CO982042.1|CO982042 |
| gb|BM143278.1|BM143278 |
| gb|AW831270.1|AW831270 |
| gb|BE329874.1|BE329874 |
| gb|BG652163.1|BG652163 |
| gb|BI967821.1|BI967821 |
| gb|BI321493.1|BI321493 |
| gb|BU546579.1|BU546579 |
| gb|CO984945.1|CO984945 |
| gb|DW247614.1|DW247614 |
| gb|BG726202.1|BG726202 |
| gb|BI968915.1|BI968915 |
| gb|BG043212.1|BG043212 |
| gb|BG510065.1|BG510065 |
| gb|BG043153.1|BG043153 |
| gb|AW832591.1|AW832591 |
| gb|AI856369.1|AI856369 |
| gb|BI699452.1|BI699452 |
| gb|BG650019.1|BG650019 |
| gb|AW234002.1|AW234002 |
| gb|AW310220.1|AW310220 |
| gb|AW394699.1|AW394699 |
| gb|AW832462.1|AW832462 |
| gb|AW459788.1|AW459788 |
| gb|BM731310.1|BM731310 |
| gb|BI317518.1|BI317518 |

TABLE 8-continued

Soybean cDNA clones gb|AI988431.1|AI988431
gb|CA801874.1|CA801874
gb|BE057592.1|BE057592
gb|AW102002.1|AW102002
gb|CA938750.1|CA938750
gb|AW397679.1|AW397679

TABLE 9

BB polypeptides identified by Blastp emb|CAO40855.1| unnamed protein product [*Vitis vinifera*]
gb|EAY88740.1| hypothetical protein OsI_009973 [*Oryza sativa* (*indica* cultivar-group)]
gb|EAZ25768.1| hypothetical protein OsJ_009251 [*Oryza sativa* (*japonica* cultivar-group)]
ref|NP_001049123.1| Os03g0173900 [*Oryza sativa* (*japonica* cultivar-group)]
emb|CAO21927.1| unnamed protein product [*Vitis vinifera*]
emb|CAD41576.3| OSJNBa0088I22.8 [*Oryza sativa* (*japonica* cultivar-group)]
gb|EAY95219.1| hypothetical protein OsI_016452 [*Oryza sativa* (*indica* cultivar-group)]
emb|CAH67282.1| OSIGBa0111L12.9 [*Oryza sativa* (*indica* cultivar-group)]
ref|NP_001053604.1| Os04g0571200 [*Oryza sativa* (*japonica* cultivar-group)]
ref|NP_001063719.1| Os09g0525400 [*Oryza sativa* (*japonica* cultivar-group)]
gb|EAZ09811.1| hypothetical protein OsI_031043 [*Oryza sativa* (*indica* cultivar-group)]
gb|EAZ45411.1| hypothetical protein OsJ_028894 [*Oryza sativa* (*japonica* cultivar-group)]
ref|NP_001062434.1| Os08g0548300 [*Oryza sativa* (*japonica* cultivar-group)]
gb|EAZ07897.1| hypothetical protein OsI_029129 [*Oryza sativa* (*indica* cultivar-group)]
ref|NP_001063778.1| Os09g0535100 [*Oryza sativa* (*japonica* cultivar-group)]
emb|CAC10211.1| hypothetical protein [*Cicer arietinum*]
emb|CAO44394.1| unnamed protein product [*Vitis vinifera*]
gb|ABG73441.1| zinc finger C3HC4 type family protein [*Oryza brachyantha*]
ref|NP_001056653.1| Os06g0125800 [*Oryza sativa* (*japonica* cultivar-group)]
gb|EAZ09879.1| hypothetical protein OsI_031111 [*Oryza sativa* (*indica* cultivar-group)]
gb|EAZ45482.1| hypothetical protein OsJ_028965 [*Oryza sativa* (*japonica* cultivar-group)]
dbj|BAD82497.1| RING-H2 finger protein RHG1a-like [*Oryza sativa* (*japonica* cultivar-group)]
emb|CAN71989.1| hypothetical protein [*Vitis vinifera*]
dbj|BAD05399.1| DNA binding zinc finger protein-like [*Oryza sativa* (*japonica*
emb|CAH65886.1| OSIGBa0148J22.5 [*Oryza sativa* (*indica* cultivar-group)]
emb|CAE02518.2| OSJNBb0003A12.5 [*Oryza sativa* (*japonica* cultivar-group)]
ref|NP_001052192.1| Os04g0185500 [*Oryza sativa* (*japonica* cultivar-group)]
emb|CAO71872.1| unnamed protein product [*Vitis vinifera*]
emb|CAO39354.1| unnamed protein product [*Vitis vinifera*]
emb|CAE01827.2| OSJNBa0041A02.20 [*Oryza sativa* (*japonica* cultivar-group)]
emb|CAO71869.1| unnamed protein product [*Vitis vinifera*]
emb|CAA85320.1| C-terminal zinc-finger [*Glycine max*]
gb|EAZ08608.1| hypothetical protein OsI_029840 [*Oryza sativa* (*indica* cultivar-group)]
gb|EAY75305.1| hypothetical protein OsI_003152 [*Oryza sativa* (*indica* cultivar-group)]
ref|NP_001043810.1| Os01g0667700 [*Oryza sativa* (*japonica* cultivar-group)]
dbj|BAD73651.1| RING-finger protein-like [*Oryza sativa* (*japonica* cultivar-group)]
emb|CAO71875.1| unnamed protein product [*Vitis vinifera*]
ref|NP_001062870.1| Os09g0323100 [*Oryza sativa* (*japonica* cultivar-group)]
gb|EAZ35180.1| hypothetical protein OsJ_018663 [*Oryza sativa* (*japonica* cultivar-group)]
dbj|BAA74802.1| DNA binding zinc finger protein (Pspzf) [*Pisum sativum*]
ref|NP_001056239.1| Os05g0550000 [*Oryza sativa* (*japonica* cultivar-group)]
gb|EAY98923.1| hypothetical protein OsI_020156 [*Oryza sativa* (*indica* cultivar-group)]
emb|CAN83345.1| hypothetical protein [*Vitis vinifera*]
emb|CAO43928.1| unnamed protein product [*Vitis vinifera*]
emb|CAN79375.1| hypothetical protein [*Vitis vinifera*]

TABLE 10 nucleic acid encoding BB polypeptides identified by tBlastn ref|NM_001055658.1| *Oryza sativa* (*japonica* cultivar-group) Os03g0173900 (Os03g0173900) mRNA, complete cds
dbj|AK063978.1| *Oryza sativa* (*japonica* cultivar-group) cDNA clone:001-124-C08, full insert sequence
dbj|AP006425.1| *Lotus japonicus* genomic DNA, chromosome 1, clone: LjT39B10, TM0315, complete sequence
gb|AY110224.1| *Zea mays* CL5837_1 mRNA sequence
ref|NM_001060139.1| *Oryza sativa* (*japonica* cultivar-group) Os04g0571200 (Os04g0571200) mRNA, partial cds
dbj|AK071401.1| *Oryza sativa* (*japonica* cultivar-group) cDNA clone: J023097G23, full insert sequence
ref|NM_001068969.1| *Oryza sativa* (*japonica* cultivar-group) Os08g0548300 (Os08g0548300) mRNA, complete cds
dbj|AK073266.1| *Oryza sativa* (*japonica* cultivar-group) cDNA clone: J033029A20, full insert sequence
emb|CT832808.1| *Oryza sativa* (*indica* cultivar-group) cDNA clone: OSIGCSN035L02, full insert sequence
ref|NM_001070254.1| *Oryza sativa* (*japonica* cultivar-group) Os09g0525400 (Os09g0525400) mRNA, complete cds
dbj|AK104112.1| *Oryza sativa* (*japonica* cultivar-group) cDNA clone: 006-202-G09, full insert sequence
dbj|AK066238.1| *Oryza sativa* (*japonica* cultivar-group) cDNA clone: J013059J01, full insert sequence
emb|CT832015.1| *Oryza sativa* (*indica* cultivar-group) cDNA clone: OSIGCRA126H24, full insert sequence TABLE 10-continued nucleic acid encoding BB polypeptides identified by tBlastn dbj|AK250973.1| *Hordeum vulgare* subsp. *vulgare* cDNA clone: FLbaf101a03, mRNA sequence
dbj|AK249803.1| *Hordeum vulgare* subsp. *vulgare* cDNA clone: FLbaf58c16, mRNA sequence
emb|CT832014.1| *Oryza sativa* (*indica* cultivar-group) cDNA clone: OSIGCRA115D08, full insert sequence
gb|BT016451.1| *Zea mays* clone Contig284 mRNA sequence
emb|AJ299062.1|CAR299062 *Cicer arietinum* partial mRNA for hypothetical protein (ORF1), clone Can183
gb|AY109631.1| *Zea mays* CL5026_1 mRNA sequence
gb|AY108288.1| *Zea mays* PCO148716 mRNA sequence
ref|NM_001070313.1| *Oryza sativa* (*japonica* cultivar-group) Os09g0535100 (Os09g0535100) mRNA, complete cds
dbj|AK069888.1| *Oryza sativa* (*japonica* cultivar-group) cDNA clone: J023039O04, full insert sequence
gb|AY103990.1| *Zea mays* PCO093361 mRNA sequence
emb|AM485242.1| *Vitis vinifera*, whole genome shotgun sequence, contig VV78X218805.2, clone ENTAV 115
gb|BT018037.1| *Zea mays* clone EL01N0530G02.c mRNA sequence
emb|CT829435.1| *Oryza sativa* (*indica* cultivar-group) cDNA clone: OSIGCRA107A15, full insert sequence
ref|NM_001063188.1| *Oryza sativa* (*japonica* cultivar-group) Os06g0125800 (Os06g0125800) mRNA, complete cds
gb|AY225189.1| *Oryza sativa* (*indica* cultivar-group) zinc finger protein mRNA, complete cds
gb|AY207044.1| *Oryza sativa* (*indica* cultivar-group) zinc-finger protein mRNA, complete cds
dbj|AK104425.1| *Oryza sativa* (*japonica* cultivar-group) cDNA clone: 006-205-F10, full insert sequence
dbj|AK068302.1| *Oryza sativa* (*japonica* cultivar-group) cDNA clone: J013144A04, full insert sequence
gb|AY112568.1| *Zea mays* CL32837_1 mRNA sequence
emb|AM453896.2| *Vitis vinifera* contig VV78X100953.6, whole genome shotgun sequence
gb|AC157490.18| *Medicago truncatula* clone mth2-123f23, complete sequence
gb|AC151824.13| *Medicago truncatula* clone mth2-45n18, complete sequence
ref|NM_001058727.1| *Oryza sativa* (*japonica* cultivar-group) Os04g0185500 (Os04g0185500) mRNA, complete cds
gb|BT019187.1| *Zea mays* clone Contig858.F mRNA sequence
dbj|AK064939.1| *Oryza sativa* (*japonica* cultivar-group) cDNA clone: J013000P06,
gb|AY110468.1| *Zea mays* CL16240_2 mRNA sequence
gb|AY110685.1| *Zea mays* CL9024_1 mRNA sequence
dbj|AK246964.1| *Solanum lycopersicum* cDNA, clone: LEFL1004CA06, HTC in leaf
dbj|AP008214.1| *Oryza sativa* (*japonica* cultivar-group) genomic DNA, chromosome
ref|NM_001050479.1| *Oryza sativa* (*japonica* cultivar-group) Os01g0692700 (Os01g0692700) mRNA, partial cds
dbj|AK065626.1| *Oryza sativa* (*japonica* cultivar-group) cDNA clone: J013028F14,
dbj|AP004704.3| *Oryza sativa* (*japonica* cultivar-group) genomic DNA, chromosome 8, PAC clone: P0544G09
dbj|AP006265.2| *Oryza sativa* (*japonica* cultivar-group) genomic DNA, chromosome 8, BAC clone: OJ1112_E06

TABLE 11

|  | Length | Function Domains |
|---|---|---|
| DA1 | 532 aa | Two UIM, One LIM |
| DAR1 | 548 aa | three UIM, one LIM |
| DAR2 | 529 aa | One LIM |
| DAR3 | 451 aa | None |
| DAR4 | 1614 aa | one NB-ARC, one LRR3, three LRR1, one LIM |
| DAR5 | 703 aa | One RPW8, one LIM |
| DAR6 | 645 aa | Seven UIM, one LIM |
| DAR7 | 561 aa | Three UIM, one LIM |

TABLE 12

| Analysis | AtDA1 | BrDA1a | BrDA1b | OsDA1 |
|---|---|---|---|---|
| Length | 533 aa | 533 aa | 515 aa | 487 aa |
| Molecular Weight | 60470.46 | 60185.30 | 59041.38 | 55268.94 |
| Isoelectric Point | 5.98 | 5.89 | 5.96 | 6.08 |
| Charge at pH 7 | −12.15 | −13.24 | −13.04 | −8.57 |

Sequences

SEQ ID NO: 1

MGWFNKIFKGSNQRLRVGNNKHNHNVYYDNYPTASHDDEPSAADTDADNDEPHHTQEPST

SEDNTSNDQENEDIDRAIALSLLEENQEQTSISGKYSMPVDEDEQLARALQESMVVGNSP

RHKSGSTYDNGNAYGAGDLYGNGHMYGGGNVYANGDIYYPRPITFQMDFRICAGCNMEIG

HGRFLNCLNSLWHPECFRCYGCSQPISEYEFSTSGNYPFHKACYRERYHPKCDVCSHFIP

TNHAGLIEYRAHPFWVQKYCPSHEHDATPRCCSCERMEPRNTRYVELNDGRKLCLECLDS

AVMDTMQCQPLYLQIQNFYEGLNMKVEQEVPLLLVERQALNEAREGEKNGHYHMPETRGL

CLSEEQTVSTVRKRSKHGTGKWAGNITEPYKLTRQCEVTAILILFGLPRLLTGSILAHEM

MHAWMRLKGFRTLSQDVEEGICQVMAHKWLDAELAAGSTNSNAASSSSSQGLKKGPRSQ

YERKLGEFFKHQIESDASPVYGDGFRAGRLAVHKYGLRKTLEHIQMTGRFPV

SEQ ID NO: 2 atgggttggtttaacaagatctttaaaggctctaaccaaaggctccgggttgggaataat aagcacaatcacaatgtttattacgataattatccgactgcttcacatgatgatgagcct -continued

```
agtgcggcggatacagatgctgataatgatgaacctcatcatactcaggaaccatctaca tctgaggataatacatcgaatgaccaggaaaatgaagacatagaccgtgcaattgcattg tcgcttttagaagagaatcaagaacagacaagtataagcgggaaatactcgatgccggtg gatgaagatgagcaacttgctagagccctacaagaaagtatggtagttgggaattcaccc cgtcacaaaagtggaagtacatatgataatgggaatgcatatggagctggagatttatat gggaatggacatatgtatggaggagaaatgtatatgcaaatggagatatttattatcca agacctattacttttcaaatggatttcaggatttgtgctggctgtaatatggagattggc catggaagatttctgaattgccttaattcactatggcatccagaatgttttcgatgttat ggctgcagtcagccgatttctgagtacgagttttcaacatcagggaactacccttttcac aaggcttgttacagggagagatatcatcctaaatgtgatgtctgcagccactttatacca acaaatcatgctggtcttattgaatatagggcacatccttttgggttcagaagtattgt ccttctcacgaacacgatgctaccccgagatgttgcagttgtgaaagaatggagccacgg aatacgagatatgttgaacttaacgatggacggaaactttgccttgagtgtttggactcg gcggtcatggacaccatgcaatgccaacctctgtacttgcaaatacaaaatttctatgaa ggactcaacatgaaggtagagcaggaagttccactcctcttggttgagagacaagcactt aacgaagccagagaaggtgaaaagaatggtcactatcacatgccagaaacaagaggactc tgcctttcagaagaacaaactgttagtactgtaagaaagcgatcaaagcatggcacagga aaatgggccgggaatattacagaaccttacaagttaacacggcaatgtgaagttaccgcc attctcatcttattcgggctccctaggttacttactggttcgattctagctcatgagatg atgcatgcgtggatgaggctcaaaggattccgaacactgagccaagatgttgaagaaggt atatgtcaagtgatggctcataaatggttagatgctgagttagctgctggttcaacaaat agcaatgctgcatcatcatcctcctcttctcaaggactgaaaaagggaccgagatctcag tacgagagaaagcttggtgagttttcaagcaccaaatcgagtctgatgcttctccggtt tatggagacgggttcagagctgggaggttagctgttcacaagtacggtttgcgaaaaaca cttgagcatatacagatgaccggtagattcccggtttaa
```

SEQ ID NO: 3
p---pLpbAl pb.Sbp-.pp p

SEQ ID NO: 4
p---pLpbAl pb.Sbp-spp p

SEQ ID NO: 5
pCs.CscsIh s.....bhlp tb.sp.aH.. .pCFpCs..p CppsLss... .p.ab.pcsp
baCpps...
Wherein;
c is a charged amino acid residue, for example, D, E, H, K, R;
p is a polar amino acid residue, for example, C, D, E, H, K, N, Q,
R, S or T;
h is a hydrophobic amino acid residue, for example, A, C, F, G, H,
I, L, M, T, V, W and Y;
t is a tiny amino acid residue, for example, A, G or S
a is an aromatic amino acid residue, for example, F, H, W or Y;
b is a big amino acid residue, for example, E, F, H, I, K, L, M, Q,
R, W or Y;
s is a small amino acid residue, for example, A, C, D, G, N, P, S, T
or V;
l is an aliphatic amino acid residue, for example, I, L or V;
. is absent or is any amino acid; and
- is any amino acid.

SEQ ID NO: 6
QENEDIDRAIALSLLEENQE

SEQ ID NO: 7
DEDEQIARALQESMVVGNSP

-continued

SEQ ID NO: 8
ICAGCNMEIGHGRFLNCLNSLWHPECFRCYGCSQPISEYEFSTSGNYPFHKAC

SEQ ID NO: 9
```
  1 mngdnrpved ahytetgfpy aatgsymdfy ggaaqgplny dhaatmhpqd nlywtmntna
 61 ykfgfsgsdn asfygsydmn dhlsrmsigr tnwdyhpmvn vaddpentva rsvqigdtde
121 hseaeecian ehdpdspqvs wqddidpdtm tyeelvelge avgtesrgls qelietlptk
181 kykfgsifsr kragercvic qlkykigerq mnlpckhvyh seciskwlsi nkvcpvcnse
241 vfgepsih
```

SEQ ID NO: 10
```
   1 acactctttc ctctctcttt cttctctctt tcttttctct ctctctcctc tgctcctccg
  61 tctctcgtct acagtgccct ccgcatcacc ttttccttg tcctatgaat ttggtcgaaa
 121 tgcccttctc ctcctcctcc ttccactaat ctcaaaagat atatccttcg agactctccc
 181 ttgccgtctc caattgccac tcaccgctcc aactctcttc gaattagctg aaatgaatgg
 241 agataataga ccagtggaag atgctcatta acggagaca ggtttcccctt atgctgctac
 301 tggaagttac atggactttt atggtggtgc ggctcagggg cctcttaact acgatcatgc
 361 cgcaactatg catcctcagg acaatctgta ctggaccatg ataccaatg catacaagtt
 421 tgggttttca ggatcagata atgcttcttt ctatggttca tatgacatga acgatcattt
 481 atcgaggatg tccataggga gaacaaattg ggactatcat cccatggtga acgttgctga
 541 tgatcctgaa aacacagttg cacgttccgt ccaaatcgga gacacagatg agcactctga
 601 agctgaagaa tgcattgcaa atgagcatga tcccgacagt cctcaggtat cctggcaaga
 661 tgacattgat cctgatacaa tgacctatga ggaattagta gagctggggg aagcagtagg
 721 aacagaaagc agggggttgt ctcaggaact catagaaacg cttcccacta aaagtataa
 781 gtttgggagc atcttctcca ggaaaagagc tggggagagg tgtgtgatat gccagctcaa
 841 gtacaagata ggggagaggc aaatgaatct gccgtgcaag catgtgtatc attctgaatg
 901 catttccaaa tggctaagca tcaacaaggt ttgcccggtg tgtaacagcg aggtctttgg
 961 ggagcccagc attcattgat cggcacaagg ggctcctcct cttcttttct ttttggcttt
1021 ttatatcgag gctcatcaag taattgtttt agtgtagtga aaaccccaaa aaatagtcta
1081 aaagatgtcc acactatact ctctcatgtt cagtccttct ctgtacatgt aattttctt
1141 ctagttccat tttcgcttgt gtgtgcttta agtttaacag tcactcgtat tgtatactaa
1201 atgctaagtc aaaaacgctg aatccatat
```

(OsDAR2)
SEQ ID NO: 11
```
  1 atggcctact cctcacggtc ttgtgatcag tgcagtcacg agaggagatc cggcttcatg
 61 aagtggctct gcgctttcct gaaggggacg aaggacggcg aggccaaccg acggcgccct
121 cgggtgacgg caggagaaga gaccacgctc tgggaagaac cagttagacc aaagaaggaa
181 gaaccaccta gacataacaa tgaagaaatg gaccatgcac ttgcccttgc tcttgcagac
241 gatgccaaaa atacaaaaga gagaaaccat gacaagggag aaaacgatga gaactcgct
301 agagcaatac aggacagtct gaacatgaat ccttaccagc cttacaatcc ttgtgcaccc
361 tctcagaccc aggccaggtc gagaggatac agggtctgtg ggggttgcaa gcatgagata
421 gggcatggcc attacttgag ctgcttggga atgtactggc accctcagtg cttccgctgt
481 tcttcctgtc gccacccctat ccgtgagatg gagttcacct tgctaggtac agatccatac
541 cacaagctgt gctacaagga gcttcatcac ccaaagtgtg acgtctgcct tcaatttatc
601 ccaacgaaca ggactggttt gatagagtac agagcccatc cattctgggg acagaagtat
```

-continued

```
 661 tgtcctttgc atgagcatga tagaacacct cgttgctgta gctgtgagaa aatggagcca
 721 aggaacacaa agtatatgtc attagggat ggacgcagct tgtgcatgga atgcctggat
 781 tctgcaatca tggacaccgg tgaatgtcaa ccgctatacc attccatcag agactactac
 841 gaagggatga acatgaaact agaccagcag atacccatgc tcttggttga acgtcaagcc
 901 cttaatgaag ctatggaagg agaaagcaaa ggaccgcatc atatgcctga acacgaggc
 961 ctttgtctgt cagaggagca gactgtgacc agtatactta ggaggcccag aattggtgca
1021 aatcggttac tagatatgaa acccaaccg caaaagctaa ctaggagatg cgaagtcact
1081 gcaattcttg tattgtttgg cctccccagg ctgctaacgg ctccattct tgcccatgaa
1141 ttgatgcatg ggtggttgcg cctcaaaggt taccggaacc taaaggcgga gattgaggaa
1201 ggtatatgcc aggtcatgtc ttacctgtgg ctggagtcag agatccttcc atccacttca
1261 agatatggac aggcttcaac atcttacgct tcatcttcgt cgtcctcctg tcgaccaca
1321 ccgtccaaga agggtgggat ctctcacacc gagaagaagc ttggagaatt cttcctgcat
1381 cagatcgcca atgacacatc atcagcatac ggcgatggtt tcagagctgc ctatgcagct
1441 gtgaacaagt atggccttcg ccaatcactg aaccatatac ggctaaccgg aggctttcct
1501 gtgtaa
```
(BrDAR1)

SEQ ID NO: 12

```
   1 atggagtttc ttcttctctt gtttggatac attaagaatg tgtttctctt tgcaggtaag
  61 aggttgttgt tgatgccaat ggggtggctt actaagatcc ttaaaggttc tagtcataag
 121 tattcagatg gtcaagctaa cagaagatac aatagagagg atagaagcct ggacactcct
 181 cgttattccg cggaaggatc tgattttgac aaagaagaaa ttgaatgcgc cattgcactc
 241 tccctttctg aacaagaaca tgtgattcca caagatgaca aaggaaagaa agtcatcgga
 301 atacaaatct gaaactgaag aagatgatga tgaggatgag gatgaggatg aggaggatga
 361 tgatgaagaa cacatgagag ctcaggtgga agcagcagaa gaagaggaaa agaaggtagc
 421 tcaagctcaa atagaggaag aagagaaacg aagagctgaa gaagctgagc tagaagagtt
 481 agagaaacag cttgccaaag ctagactaga agaggaagaa gttagacgcg ccaaagctca
 541 acttgaggaa gatgagcagc tcgcaaaggc tattcaagaa agtatgaatg tgggatctcc
 601 tcctcctgga tatgattctg gaagtgtgtt tccatcatac ccttccttg ttccttctag
 661 agaatatgca ctggttgccg agctgagatt ggacatggaa ggtttctgag ttgcatgggt
 721 ggcgtttggc atcctgaatg ttttttgctgc cacgcttgtg ataagcccat catagactgt
 781 gaggtgttct caatgtcagg aaaccgtcct atcacaaac tgtgttacaa ggagcagcat
 841 catccaaaat gtgatgtttg tcataacttt attcctacaa atccagctgg tctcattgag
 901 tacagggcac atccctttg gatgcagaag tattgtcctt cacatgagcg tgatggaaca
 961 cctagatgct gcagctgtga gcgcatggag ccgaaagata caagtatct gatacttgat
1021 gatggtagaa aactgtgtct tgaatgtcta gactcagcca ttatggacac taatgaatgc
1081 caaccgttgt atctcgagat acgtgagttt tatgaaggct tgcacatgaa agtggaacag
1141 cagataccta tgctcttggt ggagagatca gctttaaacg aagctatgga aggagagaaa
1201 catggacatc atcacttacc tgagactaga ggactctgtt tgtctgaaga acaaactgtc
1261 acaacagtgt tgaggagacc aaagattggt gcaggctaca agttgataga catgatcact
1321 gagccttgca ggctggtgcg ccgttgtgaa gtcactgcta ttctcatctt atatggactt
1381 ccccgcgttt gttaactgga tcaatcctag ctcatgagat gatgcatgca tggcttcgac
1441 taaatggggt atccaaatct tagaccagaa gtggaagaag ggatatgtca ggttttagct
```

-continued

```
1501 cacatgtggt tggaatctga gacttatgct ggctctacat tgatagatat tgcatcttct
1561 tcttcgtctt catcatcagc cgctgtggcg attgcatcgt ccaagaaagg tgagaggtct
1621 gattttgaga agaaactcgg tgagttttc aagcaccaga tagagtcaga ttcttcttcg
1681 gcatatgggg atgggttcag gcaaggtaac caagctgttc ttacgcatgg tctgaagcga
1741 acccttgatc atattcgctt gaccggtaca tttccttaa
```

(BrDAR2)

SEQ ID NO: 13

```
   1 atggattctt cttcatatgg tgtttctcat gtcagccata tctccaatcc ttgtatcttt
  61 ggggctgggt cgtcgtcttc gccagagaag aaatggaact tgatgaaatg ggtgagtaaa
 121 cttttcaaga gtggctctaa cggtggcact ggtggtgctc gcactaaccg tcatcctcct
 181 cagtttcaag aggacgagaa tatggtcttt cctttacctc cttcctcttc ggacgatcgg
 241 tcgagagcct cacgggacaa agaagaacta gatcgtgcat tgtcagtttc tctagctgac
 301 gatacgaacc gaccatatgg atatggttgg tctatggata taattcaga tttccctagg
 361 ccttttcaca gtggattgaa tccatctttc attccacctt atgaaccgtc ctatcaagtc
 421 agacgaccac aaagaatatg tggcggttgc aatagcgata ttggattggg gaactatctg
 481 ggatgcatgg gaacattctt tcatcctgat tgcttctgtt gtgattcatg tcgttaccct
 541 atcactgagc atgagttctc tctatcagga accaaacctt accatcagat ttgtttcaaa
 601 gagctcactc atcctaaatg cgaagtttgt caccatttta tcccaactaa tgatgctggc
 661 ttgatcgaat atcgatgcca tccgttttgg aaccaaaagt attgcccctc tcacgaacac
 721 gatagaaccg ctcgttgctg tagctgcgaa cgtttggagt catgggaggt gagatattac
 781 acgttagacg atgggagaag tttatgttta gaatgcatgg aaactgcgat aaccgacact
 841 ggagattgtc aaccacttta ccatgcaata cgtgactatt acgaaggaat gtacatgaaa
 901 cttgagcaac aaatccccat gcttcttgtt cagcgagaag ctctcaacga cgctatcgtc
 961 ggagagaaac acgatacca tcacatgcct gagacaaggg gtttatgttt gtctgaagaa
1021 caaacagtca caagtgttct taaaagaccg agactgggcg ctcaccgtct tgttggtatg
1081 agaactcagc ctcaaaagct tacacgtaaa tgtgaagtca ctgcgattct cgttctttac
1141 ggcctcccta gactattaac tggagcaatt cttgcccacg agctgatgca tggatggcta
1201 aggctcaaag ggtataggaa ccttaaccct gaggtagagg aaggtatctg ccaagtcctc
1261 tcttacatgt ggcttgaatc tgaagttctc tcagatcctt cttcaagaag catgccctca
1321 acatcaactg ccacctcgtc atcatcatca tcatcatctt cttctaacaa gaaaggaggg
1381 aaaacaaacg tggagaagaa acttggagag ttctttaagc atcagatagc tcatgacgca
1441 tctcctgctt acgaggggg tttcagagca gcaaatgcag cggtttgtaa gtacggtctg
1501 cgtcgcacac ttgatcatat ccgcttcact ggaacgtttc ctttgtaa
```

BrDAR3-7

SEQ ID NO: 14

```
   1 atgccattga gagtgacata tctgatggaa gatcggaaaa gaaaaaggaa aaagcttttt
  61 gatttgggca gcggacttaa ccttaaacct gcaggatcct tttgaagctg aaactgatat
 121 cgtcaaacaa gtgtcatcga atgatgctca cgttcaagaa gatgaacagc ttgctttggc
 181 cattcaaaaa tctaaagaag acgaagagga agaaggccc accagggact agaagagca
 241 tgcacatgag agaggagaaa ggcaaaataa ttatgacaac tcttcttctt tgaaagacaa
 301 aaaagaagga cagacttctg aggagaaaac atgacaactt tcctctgaa gctcgcttgg
 361 atgagaatga ggagcagcgg attatctggg agagtttgaa ggataaaggt caaacaaagc
```

-continued

```
 421 catctgaaga tgaggtcatt cctcctcgta gagcaagtgt ggtggttgcc actctgagat
 481 tgaacaagga ggatcagtgg atgtctttgg tgttccttgg catcctgaat gtttctcttg
 541 tggtgcttgc cgtaacccaa ttgctgtcca cgaggttcaa aaccatgtct caaactcaag
 601 aggcaagttc cacaaaaact gctataaccg gtactgctat gtctgccaag agaaagttaa
 661 gattagagag tacaatagcc atcctttctg gaaggagata tactgccctg ctcacgaaac
 721 tgatggaact cccaagtgtt gcagctgcga gaggctagag cctagagaaa cggagttcgt
 781 aatgctagat gatggaaggt ggctatgtct agaatgtatg gactcagcgg ttatggatac
 841 tgacgaagtc cagcctcttc actttgaaat ccgtgacttc ttccatggct tgttcttgcc
 901 agttgagaaa gagttttctc ttcttttggt ggagaaacaa gccctgaata aagctgagga
 961 ggaagagaag attgtgtcaa aagggccaaa gatgggggag aacaagcagc taacaggaaa
1021 gaccacggaa tctcaaaggg ttgtgagtgg atgcccggtc actgcaattc tcatcttata
1081 tggacttcct agaggttact aacaggatct atcatggctc acgagatgat gcatgcttat
1141 cttagactca atgggacata taatttgaa caaggttctg gaagaaggaa tatgccaagt
1201 gctagggcac atgtggttgg agactcagag atacgcccct attgatgttg ctgcagcttc
1261 ttcttcttct tcgtcaaatg cggcaaagaa aggggagtgg tctgaactcg agaagaagct
1321 ggtggatttt tacaagtatg agatagaaac agatgagtca gctgtctatg gtgaagggtt
1381 taggaaagtt aactatatgg ttacaaactc cagcctccag gaaaccctca aagagattct
1441 tccccgccgg ggttga
```

BrDA1b

SEQ ID NO: 15

```
   1 atgggttggt taaacaagat cttcaaaggc tctaaccaaa ggcaccccct ggggaatgaa
  61 cactatcatc ataatggcgg ctattacgag aactacccgc acgaacattc tgagcctagt
 121 gcagagacag atgctgatca tacgcaggag ccatctactt ctgaggagga gacatggaat
 181 gggaaggaaa atgaagaagt agaccgtgta attgcattgt ctattttaga agaagagaat
 241 caaagaccag agactaatac aggcgcctgg aaacacgcaa tgatggatga cgatgagcaa
 301 cttgctagag ccatacaaga gagtatgata gctaggaatg gaactactta tgactttggg
 361 aatgcatatg ggaatggaca tatgcatgga ggaggcaatg tatatgacaa tggtgatatt
 421 tattatccaa gacctattgc tttctcaatg gacttcagga tctgtgctgg ctgcaatatg
 481 gagattggcc atggaagata tctgaattgc ctcaacgcac tatggcatcc acaatgtttt
 541 cgatgctatg gctgcagtca cccaatctct gagtacgagt tctcaacgtc tgggaattac
 601 ccttttcaca aagcttgtta cagggagagg ttccatccaa aatgtgatgt ctgcagcctc
 661 tttatttcaa caaaccatgc tggtcttatt gaatatagag cacatccttt ctgggtccag
 721 aagtattgcc cttctcacga acacgatgct acgccaagat gttgcagctg tgaaagaatg
 781 gagccgcgga atacaggata ttttgaactc aacgatggac ggaagctttg ccttgagtgt
 841 ctagactcat cggtgatgga cacttttcaa tgccagcctc tgtacttgca gatacaagag
 901 ttctatgaag gacttaacat gacggtagag caggaggttc cacttctctt agttgagcgg
 961 caggcactta acgaagccag agaaggtgaa aggaatggtc actatcacat gccagagaca
1021 agaggactct gtctgtcgga gaacaaaact gttagaactg tgagaaagag atcgaaggga
1081 aactggagtg ggaatatgat tacagagcaa ttcaagctaa ctcgtcgatg cgaggttact
1141 gccattctca tcttgtttgg tctccctagg ctactcactg gttcaattct agctcatgag
1201 atgatgcacg cgtggatgcg gctcaaaggg ttccggccac ttagccaaga tgttgaagag
1261 gggatatgtc aagtgatggc tcataagtgg ttagaagctg agttagctgc tggttcaaga
```

-continued

```
1321 aatagcaatg ctgcatcatc ttcatcatct tcttatggag gagtgaagaa gggaccaagg
1381 tctcagtacg agaggaagct tggtgagttt ttcaagcacc agatagagtc tgatgcttct
1441 ccggtttatg agatgggtt cagggccggg aggttagcgg ttaacaagta tggtttgtgg
1501 agaacacttg agcatataca gatgactggg agattcccgg tttaa
```

BrDA1a
SEQ ID NO: 16
```
   1 atgggttggt ttaacaagat cttcaaaggc tctacccaaa ggttccggct tgggaatgac
  61 catgaccaca atggctatta ccagagttat ccacatgatg agcctagtgc tgatactgat
 121 cctgatcctg atcctgatcc tgatgaaact catactcagg aaccatctac ctctgaggag
 181 gatacatccg gccaggaaaa cgaagacata gatcgtgcaa tcgcattgtc tcttatagaa
 241 aacagtcaag gacagactaa taatacatgc gctgccaacg cagggaagta cgcaatggtg
 301 gatgaagatg agcaacttgc tagagccata caagagagca tggtagttgg aatacaccg
 361 cgtcagaagc atgaagtag ttatgatatt gggaatgcat atggggctgg agacgtttac
 421 gggaatggac atatgcatgg aggtggaaat gtatatgcca atggagatat ttattatcca
 481 agacctactg cttttcccaat ggatttcagg atttgtgctg gctgcaatat ggagattgga
 541 catggaagat atctgaattg cttgaatgca ctatggcatc agaatgtttt tcgatgttat
 601 ggctgtaggc accccatttc tgagtacgag ttctcaacgt ctgggaacta cccttttcac
 661 aaagcttgtt atagggagag ataccatcca aaatgtgatg tctgcagcct ctttattcca
 721 acaaaccatg ctggtcttat tggatatagg gcacatcctt tttgggtcca gaagtattgc
 781 ccttctcacg aacacgatgc taccccaaga tgttgcagtt gcgaaagaat ggagccacgc
 841 aatacaggat atgttgaact taacgatgga cggaaacttt gccttgaatg tctggactca
 901 gcggtgatgg acacttttca atgccaacct ctgtatctgc agatacaaga attctacgaa
 961 ggtcttttca tgaaggtaga gcaggacgtt ccacttcttt tagttgagag caagcactc
1021 aacgaagcca gagaaggtga aaagaatggt cactatcaca tgccagagac aagaggactc
1081 tgcctttcag aagagcaaac tgttagcact gtaagaaaga gatcgaagca tggcacagga
1141 aactgggctg gaatatgat tacagagcct tacaagttga cacgtcaatg cgaggttact
1201 gccattctca tcttgtttgg gctccctagg ctactcaccg gttcgattct agctcatgag
1261 atgatgcacg cgtggatgcg gctcaaggga ttccggacgc tgagccaaga cgttgaagaa
1321 ggaatatgtc aagtgatggc tcataagtgg ttggaagcag agttagctgc tggttcaaga
1381 aacagcaatg ttgcgtcatc ttcatcttct agaggagta agaagggacc aagatcgcag
1441 tacgagagga agcttggtga gttttttcaag caccaaatcg agtctgatgc ttctccggtt
1501 tatgagacg ggttcagggc tgggaggtta gcggttaaca agtatggttt gccaaaaaca
1561 cttgagcata tacagatgac cggtagattc ccggtttaa
```

OsDA1
SEQ ID NO: 17
```
   1 atgggttggt tgaccaaatt ttttagaggt tcaacccaca aaatctcgga agggcaatac
  61 cacagcaaac ccgcggagga gacgatatgg aatggaccct ctaattccgc agttgtgacg
 121 gatgtcccgt cagaatttga caatgaagat atcgctcgtg ctatatcact ctctctatta
 181 gaggaggaac aaagaaaggc aaaggcaata gaaaaggaca tgcatttgga ggaggatgaa
 241 caacttgcaa gagctatcca ggaaagtttg aatgttgaat cgcctcctcg tgctcgtgaa
 301 aatggcaacg ccaatggtgg caatatgtat caaccactgc catttatgtt ttcttctgga
 361 ttcaggactt gtgccggatg tcacagtgag attggtcatg ggcgtttcct tagttgcatg
```

```
-continued
 421 ggagctgttt ggcatccaga atgttttcgc tgtcatgctt gtaatcaacc aatatatgac 481 tatgagttct ccatgtcggg aaaccatcca taccataaaa catgctacaa ggagcgcttt 541 cacccaaaat gtgatgtctg caagcaattt attcctacaa atatgaatgg cctgattgaa 601 tatagagcac atcctttctg gttacaaaaa tactgtccat cacatgaggt ggacggtact 661 ccaagatgct gtagttgtga aagaatggag ccaagggaat caagatatgt attgctggac 721 gatggtcgca aactctgcct ggagtgcctt gattctgcag ttatggatac gagcgagtgc 781 caacctcttt atcttgaaat acaggaattt tatgaaggcc taaatatgaa agtggaacaa 841 caagttccct tgcttcttgt agaaagacag gctttaaatg aagccatgga aggagagaag 901 actggtcacc accatcttcc agaaacaaga ggtttatgct tatcagaaga gcaaactgtc 961 agcacgatat tgaggagacc aagaatggct ggaaataaag ttatggaaat gataacggag 1021 ccatataggt tgactcgtcg atgtgaagtg actgcaattc tcattcttta tggtctccca 1081 agattgttga caggttcaat tttagctcat gagatgatgc atgcgtggtt gcgacttaaa 1141 ggatatcgca cacttagtcc agacgtagaa gagggcatat gccaagttct tgctcacatg 1201 tggattgagt cagagatcat tgcaggatca ggcagtaatg gtgcttcaac gtcttcatcc 1261 tcatcagcat ccacatcatc gaaaaagggg ggaagatctc agtttgagcg aaagcttggt 1321 gattttttca agcaccaaat tgagtcagat acctcaatgg cctatggcga tggttttaga 1381 gctggcaacc gagctgttct tcagtatggt ctaaagcgca cccttgagca tatccggtta 1441 acagggactt tcccattttg a
```

Sequence Alignments

A. amino acid (SEQ ID NO: 1) and nucleotide (SEQ ID NO: 2) sequences of DA1 and mutation sites of da1-1, sod1-1, sod1-2 and sod1-3. The domains predicted by using SMART software are shown. (SEQ ID NO:59)

B. Alignment of UIM motifs among different UIM motif-containing proteins. UIM motifs were predicted by using SMART software. The predicted UIM1 (E-value, 6.39e-02) and UIM2 (E-value, 7.34e-02) sequences are shown in A.

C. Alignment of LIM domains among LIM domain-containing proteins. In the LIM domain, there are seven conserved cysteine residues and one conserved histidine. The arrangement followed by these conserved residues is C-x(2)-C-x(16,23)-H-x(2)-[CH]-x(2)-C-x(2)-C-x(16,21)-C-x(2,3)-[CHD]. The LIM domain (E-value, 3.05e-10) was predicted by using SMART software and is shown in A.

D. Alignment of DA1 and DA1-related proteins in Arabidopsis. The conserved regions among DA1 and DARs are in their C-terminal regions. The da1-1 allele has a single nucleotide G to A transition in gene At1g19270 and is predicted to cause an arginine (R) to lysine change (K) in a conserved amino acid at position 358. An asterisk indicates identical amino acid residues in the alignment. A colon indicates conserved substitutions in the alignment and a period indicates semi-conserved substitutions in the alignment. Sequences of Alignment D are listed in the Sequence Listing as SEQ ID NOs: 1 (AT1G19270), 294 (AT4G36860), 295 (AT2G39830), 291 (AT5G66620), 297 (AT5G66630), 298 (AT5G66610), (AT5G66640) 300 (AT5G17890), and 299 (AT5G66640).

E: Amino acid alignments of DA1-like proteins. Full length amino acid sequences of DA1-like proteins from Physcomitrella patens (Pp), Selaginella moellendorffi (Sm), Brassica rapa (Br), Arabidopsis thaliana (At), Brachypodium distachyon (Bd) and Oryza sativa (Os) were aligned with default setting ClustalW (URL [dot]ebi [dot]ac [dot] uk/Tools/clustalw2/index.html), and edited display settings in VectorNTi. The red arrow shows the mutation in da1-1 allele. DAL stands for DA1-Like.

```
A                                                      cgtggggaacgttttttcctggaa gaagaagaagaagagctcaacaagctcaacgaccaaaaaacttcggacacgaagactttt taattcatttctcctcttttgttttttttcgttccaaaatattcgatactctcgatctctt cttcgtgatcctcattaaataaaaatacgattttttattctttttttgtgagtgcaccaaa tttttttgacttttggattagcgtagaattcaagcacattctgggtttattcgtgtatgagt agacattgattttgtcaaagttgcattcttttatataaaagaagtttaatttcctttttt cttttctttctctctttttttttttttcccccatgttatagattcttccccaaattttga agaaaggagagaactaaagagtcctttttgagattcttttgctgcttcccttgcttgatt
```

-continued

```
agatcattttttgtgattctggattttgtgggggtttcgtgaagcttattgggatcttatc tgattcaggattttctcaaggctgcattgccgtatgagcagatagttttatttaggcatt atgggttggtttaacaagatctttaaaggctctaaccaaaggctccgggttgggaataat
 M  G  W  F  N  K  I  F  K  G  S  N  Q  R  L  R  V  G  N  N aagcacaatcacaatgtttattacgataattatccgactgcttcacatgatgatgagcct
 K  H  N  H  N  V  Y  Y  D  N  Y  P  T  A  S  H  D  D  E  P agtgcggcggatacagatgctgataatgatgaacctcatcatactcaggaaccatctaca
 S  A  A  D  T  D  A  D  N  D  E  P  H  H  T  Q  E  P  S  T tctgaggataatacatcgaatgaccaggaaaatgaagacatagaccgtgcaattgcattg
 S  E  D  N  T  S  N  D  Q  E  N  E  D  I  D  R  A  I  A  L    UIM1 sod1-1(a)G/E
tcgcttttagaagagaatcaagaacaagtataagcgggaaatactcgatgccggtg
 S  L  L  E  E  N  Q  E  Q  T  S  I  S  G  K  Y  S  M  P  V gatgaagatgagcaacttgctagagccctacaagaaagtatggtagttgggaattcaccc
 D  E  D  E  Q  L  A  R  A  L  Q  E  S  M  V  V  G  N  S  P    UIM2 cgtcacaaaagtggaagtacatatgataatgggaatgcatatggagctggagatttatat
 R  H  K  S  G  S  T  Y  D  N  G  N  A  Y  G  A  G  D  L  Y gggaatggacatatgtatggaggaggaaatgtatatgcaaatggagatatttattatcca
 G  N  G  H  M  Y  G  G  G  N  V  Y  A  N  G  D  I  Y  Y  P agacctattacttttcaaatggatttcaggatttgtgctggctgtaatatggagattggc
 R  P  I  T  F  Q  M  D  F  R  I  C  A  G  C  N  M  E  I  G catggaagatttctgaattgccttaattcactatggcatccagaatgttttcgatgttat
 H  G  R  F  L  N  C  L  N  S  L  W  H  P  E  C  F  R  C  Y    LIM ggctgcagtcagccgatttctgagtacgagttttcaacatcagggaactacccttttcac
 G  C  S  Q  P  I  S  E  Y  E  F  S  T  S  G  N  Y  P  F  H aaggcttgttacagggagagatatcatcctaaatgtgatgtctgcagccactttatacca
 K  A  C  Y  R  E  R  Y  H  P  K  C  D  V  C  S  H  F  I  P acaaatcatgctggtcttattgaatatagggcacatcctttttgggttcagaagtattgt
 T  N  H  A  G  L  I  E  Y  R  A  H  P  F  W  V  Q  K  Y  C ccttctcacgaacacgatgctaccccgagatgttgcagttgtgaaagaatggagccacgg
 P  S  H  E  H  D  A  T  P  R  C  C  S  C  E  R  M  E  P  R aatacgagatatgttgaacttaacgatggacggaaactttgccttgagtgtttggactcg
 N  T  R  Y  V  E  L  N  D  G  R  K  L  C  L  E  C  L  D  S gcggtcatggacaccatgcaatgccaacctctgtacttgcaaatacaaaatttctatgaa
 A  V  M  D  T  M  Q  C  Q  P  L  Y  L  Q  I  Q  N  F  Y  E ggactcaacatgaaggtagagcaggaagttccactcctcttggttgagagacaagcactt
 G  L  N  M  K  V  E  Q  E  V  P  L  L  L  V  E  R  Q  A  L da1-1(a)(R/K)
aacgaagccagagaaggtgaaaagaatggtcactatcacatgccagaaacaagaggactc
 N  E  A  R  E  G  E  K  N  G  H  Y  H  M  P  E  T  R  G  L (t)(L/F)sod1-2
tgcctttcagaagaacaaactgttagtactgtaagaaagcgatcaaagcatggcacagga
 C  L  S  E  E  Q  T  V  S  T  V  R  K  R  S  K  H  G  T  G aaatgggccgggaatattacagaaccttacaagttaacacggcaatgtgaagttaccgcc
 K  W  A  G  N  I  T  E  P  Y  K  L  T  R  Q  C  E  V  T  A attctcatcttattcgggctccctaggttacttactggttcgattctagctcatgagatg
 I  L  I  L  F  G  L  P  R  L  L  T  G  S  I  L  A  H  E  M sod1-3(T)(Q/.)
atgcatgcgtggatgaggctcaaaggattccgaacactgagccaagatgttgaagaaggt
 M  H  A  W  M  R  L  K  G  F  R  T  L  S  Q  D  V  E  E  G atatgtcaagtgatggctcataaatggttagatgctgagttagctgctggttcaacaaat
 I  C  Q  V  M  A  H  K  W  L  D  A  E  L  A  A  G  S  T  N agcaatgctgcatcatcatcctcctcttctcaaggactgaaaaagggaccgagatctcag
 S  N  A  A  S  S  S  S  S  S  Q  G  L  K  K  G  P  R  S  Q tacgagagaaagcttggtgagttttttcaagcaccaaatcgagtctgatgcttctccggtt
```

-continued

```
                            Y E R K L G E F F K H Q I E S D A S P V tatggagacgggttcagagctggaggttagctgttcacaagtacggtttgcgaaaaaca
 Y  G  D  G  F  R  A  G  R  L  A  V  H  K  Y  G  L  R  K  T Cttgagcatatacagatgaccggtagattcccggtttaagaacccaaatggacaaggtct
 L  E  H  I  Q  M  T  G  R  F  P  V  - tctactttatttataggatccttggtagattcctcctatatgctctaattcttttggtgg aaaatgtactctcgaccatattcttattgtagtctcattcgatgattctttgtattcctc tgttaaaatccatcagaatcagattcagtgttttctttgtt
```

```
AT1G19270   ------------------------------------------------------------
AT4G36860   ------------------------------------------------------------
AT2G39830   ------------------------------------------------------------
AT5G66620   ------------------------------------------------------------
AT5G66630   ------------------------------------------------------------
AT5G66610   ------------------------------------------------------------
AT5G66640   ------------------------------------------------------------
AT5G17890   MEPPAARVTPSIKADCSHSVNIICEETVLHSLVSHLSAALRREGISVFVDACGLQETKFF       60

AT1G19270   ------------------------------------------------------------
AT4G36860   ------------------------------------------------------------
AT2G39830   ------------------------------------------------------------
AT5G66620   ------------------------------------------------------------
AT5G66630   ------------------------------------------------------------
AT5G66610   ------------------------------------------------------------
AT5G66640   ------------------------------------------------------------
AT5G17890   SIKQNQPLTDGARVLVVVISDEVEFYDPWFPKFLKVIQGWQNNGHVVVPVFYGVDSLTRV     120

AT1G19270   ------------------------------------------------------------
AT4G36860   ------------------------------------------------------------
AT2G39830   ------------------------------------------------------------
AT5G66620   ------------------------------------------------------------
AT5G66630   ------------------------------------------------------------
AT5G66610   ------------------------------------------------------------
AT5G66640   ------------------------------------------------------------
AT5G17890   YGILSNNVLTDSELVEEIVRDVYGKLYPAERVGIYARLLEIEKLLYKQHRDIRSIGIWGM     180

AT1G19270   ------------------------------------------------------------
AT4G36860   ------------------------------------------------------------
AT2G39830   ------------------------------------------------------------
AT5G66620   ------------------------------------------------------------
AT5G66630   ------------------------------------------------------------
AT5G66610   ------------------------------------------------------------
AT5G66640   ------------------------------------------------------------
AT5G17890   PGIGKTTLAKAVFNHMSTDYDASCFIENFDEAFHKEGLHRLLKERIGKILKDEFDIESSY     240

AT1G19270   ------------------------------------------------------------
AT4G36860   ------------------------------------------------------------
AT2G39830   ------------------------------------------------------------
AT5G66620   ------------------------------------------------------------
AT5G66630   ------------------------------------------------------------
AT5G66610   ------------------------------------------------------------
AT5G66640   ------------------------------------------------------------
AT5G17890   IMRPTLHRDKLYDKRILVVLDDVRDSLAAESFLKRLDWFGSGSLIIITSVDKQVFAFCQI     300

AT1G19270   ------------------------------------------------------------
AT4G36860   ------------------------------------------------------------
AT2G39830   ------------------------------------------------------------
AT5G66620   ------------------------------------------------------------
AT5G66630   ------------------------------------------------------------
AT5G66610   ------------------------------------------------------------
AT5G66640   ------------------------------------------------------------
AT5G17890   NQIYTVQGLNVHEALQLFSQSVFGINEPEQNDRKLSMKVIDYVNGNPLALSIYGRELMGK     360

AT1G19270   ------------------------------------------------------------
AT4G36860   ------------------------------------------------------------
AT2G39830   ------------------------------------------------------------
AT5G66620   ------------------------------------------------------------
AT5G66630   ------------------------------------------------------------
AT5G66610   ------------------------------------------------------------
AT5G66640   ------------------------------------------------------------
AT5G17890   KSEMETAFFELKHCPPLKIQDVLKNAYSALSDNEKNIVLDIAFFFKGETVNYVMQLLEES     420

AT1G19270   ------------------------------------------------------------
```

```
AT4G36860     ------------------------------------------------------------
AT2G39830     ------------------------------------------------------------
AT5G66620     ------------------------------------------------------------
AT5G66630     ------------------------------------------------------------
AT5G66610     ------------------------------------------------------------
AT5G66640     ------------------------------------------------------------
AT5G17890     HYFPRLAIDVLVDKCVLTISENTVQMNNLIQDTCQEIFNGEIETCTRMWEPSRIRYLLEY      480

AT1G19270     ------------------------------------------------------------
AT4G36860     ------------------------------------------------------------
AT2G39830     ------------------------------------------------------------
AT5G66620     ------------------------------------------------------------
AT5G66630     ------------------------------------------------------------
AT5G66610     ------------------------------------------------------------
AT5G66640     ------------------------------------------------------------
AT5G17890     DELEGSGETKAMPKSGLVAEHIESIFLDTSNVKFDVKHDAFKNMFNLKFLKIYNSCSKYI      540

AT1G19270     ------------------------------------------------------------
AT4G36860     ------------------------------------------------------------
AT2G39830     ------------------------------------------------------------
AT5G66620     ------------------------------------------------------------
AT5G66630     ------------------------------------------------------------
AT5G66610     ------------------------------------------------------------
AT5G66640     ------------------------------------------------------------
AT5G17890     SGLNFPKGLDSLPYELRLLHWENYPLQSLPQDFDFGHLVKLSMPYSQLHKLGTRVKDLVM      600

AT1G19270     ------------------------------------------------------------
AT4G36860     ------------------------------------------------------------
AT2G39830     ------------------------------------------------------------
AT5G66620     ------------------------------------------------------------
AT5G66630     ------------------------------------------------------------
AT5G66610     ------------------------------------------------------------
AT5G66640     ------------------------------------------------------------
AT5G17890     LKRLILSHSLQLVECDILIYAQNIELIDLQGCTGLQRFPDTSQLQNLRVVNLSGCTEIKC      660

AT1G19270     ------------------------------------------------------------
AT4G36860     ------------------------------------------------------------
AT2G39830     ------------------------------------------------------------
AT5G66620     ------------------------------------------------------------
AT5G66630     ------------------------------------------------------------
AT5G66610     ------------------------------------------------------------
AT5G66640     ------------------------------------------------------------
AT5G17890     FSGVPPNIEELHLQGTRIREIPIFNATHPPKVKLDRKKLWNLLENFSDVEHIDLECVTNL      720

AT1G19270     ------------------------------------------------------------
AT4G36860     ------------------------------------------------------------
AT2G39830     ------------------------------------------------------------
AT5G66620     ------------------------------------------------------------
AT5G66630     ------------------------------------------------------------
AT5G66610     ------------------------------------------------------------
AT5G66640     ------------------------------------------------------------
AT5G17890     ATVTSNNHVMGKLVCLNMKYCSNLRGLPDMVSLESLKVLYLSGCSELEKIMGFPRNLKKL      780

AT1G19270     ------------------------------------------------------------
AT4G36860     ------------------------------------------------------------
AT2G39830     ------------------------------------------------------------
AT5G66620     ------------------------------------------------------------
AT5G66630     ------------------------------------------------------------
AT5G66610     ------------------------------------------------------------
AT5G66640     ------------------------------------------------------------
AT5G17890     YVGGTAIRELPQLPNSLEFLNAHGCKHLKSINLDFEQLPRHFIFSNCYRFSSQVIAEFVE      840

AT1G19270     ------------------------------------------------------------
AT4G36860     ------------------------------------------------------------
AT2G39830     ------------------------------------------------------------
AT5G66620     ---------------------------------------------MASDYYSSDDEGFGE       15
AT5G66630     ---------------------------------------------MPISDVASLVGGAAL       15
AT5G66610     -----------------------------------------------------MWCLS---CFKP    9
AT5G66640     ------------------------------------------------------------
AT5G17890     KGLVASLARAKQEELIKAPEVIICIPMDTRQRSSFRLQAGRNAMTDLVPWMQKPISGFSM      900

AT1G19270     ---------------MGWFNKIFKGSNQRLRVGNNKHNHNVYYDNYPTASHDDEPSAAD       44
AT4G36860     --------------------------------------------DDDDDEDEDEEYMRAQ      16
AT2G39830     ------------------------------------------------------------
AT5G66620     KVGLIGEKDRFEAETIHVIEVSQHEADIQKAKQRSLATHEAEKLDLATHEAEQLDLAIQE       75
AT5G66630     GAPLSEIFKIVIEEAKKVKDFKPLSQDLASTMERLVPIFNEIDMMQQGSNRGTSELKVLT       75
AT5G66610     STKHDPSEDRFEEETNIVTGISLYEDVIIRQRR---------------SEADQIEWAIQD       54
AT5G66640     ------------------------------------------------------------
AT5G17890     SVVVSFQDDYHNDVGLRIRCVGTWKTWNNQPDRIVERFFQCWAPTEAPKVVADHIFVLYD      960

AT1G19270     TDADNDEPHHTQEPSISEDNTS-NDQENED------------------------------       73
```

```
                                                  -continued
AT4G36860  LEAAEEEERRVAQAQIEEEEKRRAEAQLEE------------------------------   46
AT2G39830  -------NMVFPLPPSSLDDRSRGARDKEE------------------------------   23
AT5G66620  FSRQEEEEERRRTRELENDAQIANVLQHEERERLIN--KKTALEDEEDELLARTLEESLK  133
AT5G66630  ETMERAGEMVHKCSRIQWYSIAKKALYTREIKAINQDFLKFCQIELQLIQHRNQLQYMRS  135
AT5G66610  SFNPQE---TSRCRQREEDDQIARGLQYVEETELD----KSVVDEE-------------   93
AT5G66640  ------------------------------------------------------------
AT5G17890  TKMHPSDSEENHISMWAHEVKFEFHTVSGENNPLGASCKVTECGVEVITAATGDISVSGI 1020

AT1G19270  ----------------------------------------------IDRAIALS        81
AT4G36860  ----------------------------------------------TEKLLAKA        54
AT2G39830  ----------------------------------------------LDRSISLS        31
AT5G66620  ENNRRKMFEEQVNKDEQLALIVQESLNMEEYPIRLEEYKSISRRAPLDVDEQFAKAVKES 193
AT5G66630  MGMASVSTKADLLSDIGNEFSKLCLVAQPEVVTKFWLKRPLMELKKMLFEDGVVTVVVSA 195
AT5G66610  ---------------------------------------------DQQLSKIVEES    104
AT5G66640  ------------------------------------------------------------
AT5G17890  IRESETITIIEKEDIIIDEEDTPLLSREPEETNRSRSSSELQKLSSTSSKPKNLRSRSRR 1080

AT1G19270  LLEENQEQISISGKYSMPVDEDEQLARALQES----------------------------  113
AT4G36860  RLEEEEMRRSK-----AQLEEDELLAKALQES----------------------------   81
AT2G39830  LADNTKRPHGYG----WSMDNNRDFPRPFHGG----------------------------   59
AT5G66620  LKNKGKG----KQFEDEQVKKDEQLALIVQES----------------------------  221
AT5G66630  PYALGKTILVTKLCHDADVKEKFKQIFFISVSKFPNVRLIGHKLLEHIGCKANEYENDLD  255
AT5G66610  LKEKGKS----KQFEDDQVENDEQQALMVQES----------------------------  132
AT5G66640  -----------MVRRKRQEEDEKIEIERVKEES---------------------------   22
AT5G17890  TTALEEALEEALKEREKLEDTRELQIALIESKK--------------------------- 1113
                  .                 .

AT1G19270  --MVVGNSPRHKSGSTYDNGNAYGAGDLYGNGHMY----------------------G    147
AT4G36860  --MNVGSPPR-------------------------------------------------   89
AT2G39830  --LNPSSFIP-------------------------------------------------   67
AT5G66620  --LNMVESPPRLEENNNISTRAP---VDEDE----------------------------  247
AT5G66630  AMLYIQQLLKQLGRNGSILLVLDDVWAEEES----------------------------  286
AT5G66610  --LYMVELSAQLEEDKNISTIPP---LNEDA----------------------------  158
AT5G66640  --LKLAKQAEEKRRLEESKEQGKRIQVDDD-----------------------------   50
AT5G17890  --IKKIKQADERDQIKHADEREQRKHSKDHEEEEIESNEKEERRHSKDYVIEELVLKGKG 1171
                  :                .

AT1G19270  GGNVYANGDIYYPRPIT----------------------------------FQM       167
AT4G36860  ----YDPGNILQPYPFL----------------------------------IPS       105
AT2G39830  ----------PYEPSYQ----------------------------------YRR        77
AT5G66620  QLAKAVEESLKGKGQIK----------------------QSKDEVEGDGML----LELNP 281
AT5G66630  LLQKFLIQLPDYKILVTSRFEFTSFGPTFHLKPLIDDEVECRDEIEENEKLP----EVNP 342
AT5G66610  QLQKVIWESAKGKGQIE----------------------HFKDPVEEDGNLPRVDLNVNH 196
AT5G66640  ---QLAKTTSKDKGQIN----------------------HSKDVVEE---------DVNP  76
AT5G17890  KRKQLDDDKADEKEQIK----------------------HSKDHVEE---------EVNP 1200

AT1G19270  DFRICAGCNMEIGHGRFLNCLNSLWHPECFRCYGCSQPISEYEFSTSGNYPFHKACYRER 227
AT4G36860  SHRICVGCQAEIGHGRFLSCMGGVWHPECFCCNACDKPIIDYEFSMSGNRPYHKLCYKEQ 165
AT2G39830  RQRICGGCNSDIGSGNYLGCMGTFFHPECFRCHSCGYAITEHEFSLSGTKPYHKLCFKEL 137
AT5G66620  PPSLCGGCNFAVEHGGSVNILGVLWHPECFCCRACHKPIAIHDIENHVSNSRGKFHFSCY 341
AT5G66630  PLSMCGGCNSAVKHEESVNILGVLWHPECFCCRCSCDKPIAIHELENHVSNSRGKFMKSCY 402
AT5G66610  PHSICDGCKSAIEYGRSVHALGVNWHPECFCCRYCDKPIAMH------------------ 238
AT5G66640  PPS-SIDGKSEIGDGTSVN-------PRCLCCFHCHRPFVMHEILKK-GKFHIDCYKEYY 127
AT5G17890  PLSKCKDCKSAIEDGISINAYGSVWHPQCFCCLRCREPIAMNEISDLRGMYHKPCYKELR 1260
             .   .  :    :       :      * *:  *    *        .:

AT1G19270  YHPKCDVCSHFIPTNHAGLIEYRAHPFWVQKYCPSHEHDATPRCCSCERMEPRNTRYVEL 287
AT4G36860  HHPKCDVCHNFIPTNPAGLIEYRAHPFWMQKYCPSHERDGTPRCCSCERMEPKDTKYLIL 225
AT2G39830  THPKCEVCHHFIPTNDAGLIEYRCHPFWNQKYCPSHEYDKTARCCSCERLESWDVRYYTL 197
AT5G66620  -ERYCYVCKEKK------MKTYNNHPFWEERYCPVHEADGTPKCCSCERLEPRESNYVML 394
AT5G66630  -ERYCYVCKEKK------MKTYNIHPFWEERYCPVHEADGTPKCCSCEPLEPRGTKYGKL 455
AT5G66610  ------------------EYKEHPFWKEKYCPFHEVDGTPKCCSCERLEPWGTKYVML   278
AT5G66640  RNRNCYVCQQKIPVNAEGIRKFSEHPFWKEKYCPIHDEDGTAKCCSCERLEPRGTNYVML 187
AT5G17890  -HPNCYVCEKKIPRTAEGL-KYHEHPFWMETYCPSHDGDGTPKCCSCERLEHCGTQYVML 1318
              :   ****  ***  *: *  *.:******:*      .*  *

AT1G19270  NDGRKLCLECLDSAVMDTMQCQPLYLQIQNFYEGLNMKVEQEVPLLLVERQALNEAREGE 347
AT4G36860  DDGRKLCLECLDSAIMDTHECQPLYLEIREFYEGLHMKVEQQIPMLLVERSALNEAMEGE 285
AT2G39830  EDGRSLCLECMETAITDTGECQPLYHAIRDYYEGMYMKLDQQIPMLLVQREALNDAIVGE 257
AT5G66620  ADGRWLCLECMNSAVMDSDECQPLHFDMRDFFEGLNMKIEKEFPFLLVEKQALNKAEKEE 454
AT5G66630  SDGRWLCLECGKS-AMDSDECQPLYFDMRDFFESLNMKIEKEFPLILVRKELLNKKE--E 512
AT5G66610  ADNRWLCVKCMECAVMDTYECQPLHFEIREFYEGLHMKVEKEFPLLLVEKALKKAEAQE  338
AT5G66640  GDFRWLCIECMGSAVMDTNEVQPLHFEIREFFEGLFLKVDKEFALLLVEKQALNKAEEEE 247
AT5G17890  ADFRWLCRECMDSAIMDSDECQPLHFEIREFFEGLHMKIEEEPPVYLVEKNALNKAEKEE 1378
             * ** :*        *: : ***:  ::::: .: :*:::::.. **.:.  ::     * da1-1 (R/K)
AT1G19270  KNGHYHMPETRGLCLSEEQTVSTVRKRSKH-GTG-KWAGNITEPYKLTRQCEVTAILILF 405
AT4G36860  KHGHHHLPETRGLCLSEEQTVTTVLRRPRI-GAGYKLIDMITEPCRLIRRCEVTAILILY 344
AT2G39830  KNGYHHMPETRGLCLSEEQTVTSVLRRPRL-GAH-RLVGMRTQPQRLTRKCEVTAILVLY 315
AT5G66620  KIDYQYEVVTRGICLSEEQIVDSVSQRPVR-GPNNKLVGMATESQKVTRECEVTAILILY 513
```

```
AT5G66630    KIDNHYEVLIRAYCMSEQKIMTYVSEEPRT-GQNKQLIDMDTEPQGVVHECKVTAILILY     571
AT5G66610    KIDNQHGVVTRGICLSEGQIVNSVFKKPTM-GPNGELVSLGTEPQKVVGGCEVTAILILY     397
AT5G66640    KIDYHRAAVTRGLCMSEEQIVIDSIIKGPRMGPDNQLITDIVTESQRVS-GFEVTGILITY     306
AT5G17890    KIGDQCLMVVRGICLSEEQIVTSVSQGVRR-MLNKQILDTVTESQRVVRKCEVTAILILY    1437
              * .       *. *:**   :         :           .   *:.  :   :**.**:::

AT1G19270    GLPRLLTGSILAHEMMHAWMRLKGFRTLSQDVEEGICQVMAHKWLDAELAAGSTNSNAAS     465
AT4G36860    GLPRLLTGSILAHEMMHAWLRLNGYPNLRPEVEEGICQVLAHMWLESETYAGSTLVDIAS     404
AT2G39830    GLPRLLTGAILAHELMHGWLRLNGFRNLNPEVEEGICQVLSYMWLESEVLSDPSTRNLPS     375
AT5G66620    GLPRLLTGYILAHEMMHAYLRLNGHRNLNNILEEGICQVLGHLWLDSQTYATADATADAS     573
AT5G66630    GLPRLLTGYILAHEMMHAWLRLNGHMNLNNILEEGICQVLGHLWLESQTYATADTTADAA     631
AT5G66610    GLPRLLTGYILAHEMMHAWLRLNGYRNLKLELEEGICQVLGHMWLESQTYS----SSAAA     453
AT5G66640    GLPRLLTGYILAHEMMHAWLRLNGYKNLKLELEEGLCQALGLRWLESQTFASTLAAAAAA     366
AT5G17890    GLPRLLTGYILAHEMMHAYLRLNGYRNLNMVLEEGLCQVLGHMWLECQTYVFD----TAT    1493
             ******** *****:**.::**:*. .*  :***:**::..  **::           ..

AT1G19270    SSSS-----------SQGLKKGP-RSQYERKLGEFFKHQIESDASPVYGDGFRAGRLAVH     513
AT4G36860    SSSSA-----VV---SASSKKGE-RSDFEKKLGEFFKHQIESDSSSAYGDGFRQGNQAVL     455
AT2G39830    TSSVA-----TSSSSSFSNKKGG-KSNVEKKLGEFFKHQIAHDASPAYGGGFRAANAAAC     429
AT5G66620    SSRTPPAASASKKGE-WSDFDKKLVEFCKNQIETDDSPVYGLGFRTVNEMVT     629
AT5G66630    SASSS---SSRTPPAASASKKGE-WSDFDKKLVEFCKNQIETDESPVYGLGFRTVNEMVT     687
AT5G66610    SSASS---SSRTP-AANASKKGA-QSDYEKKLVEFCKDQIETDDSPVYGFRKVNQMVS     508
AT5G66640    VASSSSFSSSTAPPAAITSKKSDDWSIFEKKLVEFCMNQIKEDDSPVYGLGFKQVYEMMV     426
AT5G17890    IASSS--SSSRTPLSTTTSKKVD-PSDFEKRLVNFCKHQIETDESPFFGDGFRKVNKMMA    1550
              ::              :   **   *   :::*  :*   .** *  *.  :* **:

AT1G19270    KY--GLRKTLEHIQMTGRFPV----                                       532
AT4G36860    KH--GLRRTLDHIRLTGTFPKWI--                                       476
AT2G39830    KY--GLRRTLDHIRLTGTFPL----                                       448
AT5G66620    NS--SLQETLKEILRQR--------                                       644
AT5G66630    NS--SLQETLKEILRRR--------                                       702
AT5G66610    DS--SLHKILKSIQHWTKPDSNL--                                       529
AT5G66640    SNNYNIKDTLKDIVSASNATPDSTV                                       451
AT5G17890    SNNHSLKDTLKEIISISKTPQYSKL                                      1575
```

The invention claimed is:

1. A method of altering the phenotype of a higher plant comprising;
expressing a nucleic acid encoding a dominant-negative DA polypeptide within cells of said plant,
wherein the dominant-negative DA polypeptide comprises any one of SEQ ID NOs: 1 and 301 to 330 with a mutation of R to K at a position corresponding to position 358 of SEQ ID NO: 1,
wherein the altered phenotype includes one or more traits selected from the group consisting of increased lifespan, increased organ size and increased seed size relative to a control plants.

2. The method according to claim 1 further comprising reducing or abolishing expression of a Big Brother (BB) polypeptide within cells of said plant,
wherein the BB polypeptide comprises an amino acid sequence having at least 90% sequence identity to SEQ ID NO: 9 and has E3 ubiquitin ligase activity.

3. A method of producing a higher plant with an altered phenotype comprising:
incorporating a heterologous nucleic acid which encodes a dominant-negative DA polypeptide into a higher plant cell by means of transformation, and;
regenerating the higher plant from one or more transformed cells, wherein the higher plant comprises the heterologous nucleic acid which encodes a dominant-negative DA polypeptide, and
wherein the dominant-negative DA polypeptide comprises any one of SEQ ID NOs: 1 and 301 to 330 with a mutation of R to K at a position corresponding to position 358 of SEQ ID NO:1, wherein the altered phenotype includes one or more traits selected from the group consisting of increased life-span, increased organ size and increased seed size relative to a control plants.

4. The method according to claim 3 further comprising incorporating a heterologous nucleic acid which expresses a suppressor nucleic acid which reduces expression of a BB polypeptide into said plant cell by means of transformation,
wherein the suppressor nucleic acid is a sense or antisense suppressor of BB polypeptide expression, and
wherein the BB polypeptide comprises an amino acid sequence having at least 90% sequence identity to SEQ ID NO: 9 and has E3 ubiquitin ligase activity.

5. The method according to claim 1 wherein the dominant-negative DA polypeptide comprises SEQ ID NO: 1 with a mutation of R to K at position 358.

6. The method according to claim 1 wherein the nucleic acid encoding the dominant negative DA polypeptide is operably linked to a heterologous promoter.

7. The method according to claim 6 wherein the promoter is a tissue-specific promoter.

8. The method according to claim 7 wherein the promoter is an inducible promoter.

9. The method according to claim 6 wherein the nucleic acid encoding the dominant negative DA polypeptide is comprised in one or more vectors.

10. The method according to claim 1 comprising sexually or asexually propagating or growing off-spring or descendants of the plant expressing the dominant-negative DA polypeptide.

11. The method according to claim 1 wherein the plant is an agricultural plant selected from the group consisting of *Lithospermum erythrorhizon*, *Taxus* spp, tobacco, cucurbits, carrot, vegetable *brassica*, melons, capsicums, grape vines, lettuce, strawberry, oilseed *brassica*, sugar beet, wheat, barley, maize, rice, soyabeans, peas, sorghum, sunflower, tomato, potato, pepper, *chrysanthemum*, carnation, linseed, hemp and rye.

12. A higher plant expressing a heterologous nucleic acid encoding a dominant-negative DA polypeptide within its cells,
wherein the dominant-negative DA polypeptide comprises any one of SEQ ID NOs:1 and 301 to 330 with a mutation of R to K at a position corresponding to position 358 of SEQ ID NO: 1,
wherein the plant has an altered phenotype that includes one or more traits selected from the group consisting of increased life-span, increased organ size and increased seed size relative to a control plants.

13. The higher plant according to claim 12 which is produced by a method comprising:
incorporating said heterologous nucleic acid which encodes a dominant-negative DA polypeptide into a higher plant cell by means of transformation, and
regenerating the higher plant from one or more transformed cells.

14. A method of producing a dominant-negative DA polypeptide comprising:
providing a nucleic acid sequence encoding a plant DA polypeptide,
identifying an R residue in the encoded plant DA polypeptide at a position corresponding to position 358 of SEQ ID NO: 1, and
mutating the nucleic acid to substitute said R residue for a K residue in the encoded plant DA polypeptide,
the mutant nucleic acid sequence encoding a dominant negative DA polypeptide,
wherein the DA polypeptide comprises any one of SEQ ID NOs: 1 and 301 to 330.

15. A higher plant comprising an isolated DA1 or DAR which comprises any one of SEQ ID NOs: 1 and 301 to 330 with a mutation of R to K at a position corresponding to position 358 of SEQ ID NO: 1.

16. A method of altering the phenotype of a higher plant comprising:
expressing a nucleic acid encoding a dominant-negative DA polypeptide within cells of said plant,
wherein the dominant-negative DA polypeptide comprises any one of SEQ ID NOS: 1 and 301 to 330 with a mutation of R to K at a position corresponding to position 358 of SEQ ID NO: 1,
wherein the altered phenotype includes one or more traits selected from the group consisting of increased life-span, increased organ size and increased seed size relative to a control plant.

* * * * *

SEQUENCE LISTING

<160> NUMBER OF SEQ ID NOS: 330

<210> SEQ ID NO 1
<211> LENGTH: 532
<212> TYPE: PRT
<213> ORGANISM: Arabidopsis thaliana

<400> SEQUENCE: 1

```
Met Gly Trp Phe Asn Lys Ile Phe Lys Gly Ser Asn Gln Arg Leu Arg
1               5                   10                  15

Val Gly Asn Asn Lys His Asn His Asn Val Tyr Tyr Asp Asn Tyr Pro
            20                  25                  30

Thr Ala Ser His Asp Asp Glu Pro Ser Ala Ala Asp Thr Asp Ala Asp
        35                  40                  45

Asn Asp Glu Pro His His Thr Gln Glu Pro Ser Thr Ser Glu Asp Asn
    50                  55                  60

Thr Ser Asn Asp Gln Glu Asn Glu Asp Ile Asp Arg Ala Ile Ala Leu
65                  70                  75                  80

Ser Leu Leu Glu Glu Asn Gln Glu Gln Thr Ser Ile Ser Gly Lys Tyr
                85                  90                  95

Ser Met Pro Val Asp Glu Asp Glu Gln Leu Ala Arg Ala Leu Gln Glu
            100                 105                 110

Ser Met Val Val Gly Asn Ser Pro Arg His Lys Ser Gly Ser Thr Tyr
        115                 120                 125

Asp Asn Gly Asn Ala Tyr Gly Ala Gly Asp Leu Tyr Gly Asn Gly His
    130                 135                 140

Met Tyr Gly Gly Gly Asn Val Tyr Ala Asn Gly Asp Ile Tyr Tyr Pro
145                 150                 155                 160

Arg Pro Ile Thr Phe Gln Met Asp Phe Arg Ile Cys Ala Gly Cys Asn
```

165                 170                 175
Met Glu Ile Gly His Gly Arg Phe Leu Asn Cys Leu Asn Ser Leu Trp
                    180                 185                 190

His Pro Glu Cys Phe Arg Cys Tyr Gly Cys Ser Gln Pro Ile Ser Glu
                195                 200                 205

Tyr Glu Phe Ser Thr Ser Gly Asn Tyr Pro Phe His Lys Ala Cys Tyr
            210                 215                 220

Arg Glu Arg Tyr His Pro Lys Cys Asp Val Cys Ser His Phe Ile Pro
225                 230                 235                 240

Thr Asn His Ala Gly Leu Ile Glu Tyr Arg Ala His Pro Phe Trp Val
                245                 250                 255

Gln Lys Tyr Cys Pro Ser His Glu His Asp Ala Thr Pro Arg Cys Cys
                260                 265                 270

Ser Cys Glu Arg Met Glu Pro Arg Asn Thr Arg Tyr Val Glu Leu Asn
                275                 280                 285

Asp Gly Arg Lys Leu Cys Leu Glu Cys Leu Asp Ser Ala Val Met Asp
            290                 295                 300

Thr Met Gln Cys Gln Pro Leu Tyr Leu Gln Ile Gln Asn Phe Tyr Glu
305                 310                 315                 320

Gly Leu Asn Met Lys Val Glu Gln Glu Val Pro Leu Leu Leu Val Glu
                325                 330                 335

Arg Gln Ala Leu Asn Glu Ala Arg Glu Gly Glu Lys Asn Gly His Tyr
            340                 345                 350

His Met Pro Glu Thr Arg Gly Leu Cys Leu Ser Glu Glu Gln Thr Val
                355                 360                 365

Ser Thr Val Arg Lys Arg Ser Lys His Gly Thr Gly Lys Trp Ala Gly
        370                 375                 380

Asn Ile Thr Glu Pro Tyr Lys Leu Thr Arg Gln Cys Glu Val Thr Ala
385                 390                 395                 400

Ile Leu Ile Leu Phe Gly Leu Pro Arg Leu Leu Thr Gly Ser Ile Leu
                405                 410                 415

Ala His Glu Met Met His Ala Trp Met Arg Leu Lys Gly Phe Arg Thr
            420                 425                 430

Leu Ser Gln Asp Val Glu Glu Gly Ile Cys Gln Val Met Ala His Lys
        435                 440                 445

Trp Leu Asp Ala Glu Leu Ala Ala Gly Ser Thr Asn Ser Asn Ala Ala
        450                 455                 460

Ser Ser Ser Ser Ser Ser Gln Gly Leu Lys Lys Gly Pro Arg Ser Gln
465                 470                 475                 480

Tyr Glu Arg Lys Leu Gly Glu Phe Phe Lys His Gln Ile Glu Ser Asp
                485                 490                 495

Ala Ser Pro Val Tyr Gly Asp Gly Phe Arg Ala Gly Arg Leu Ala Val
            500                 505                 510

His Lys Tyr Gly Leu Arg Lys Thr Leu Glu His Ile Gln Met Thr Gly
        515                 520                 525

Arg Phe Pro Val
    530

<210> SEQ ID NO 2
<211> LENGTH: 1599
<212> TYPE: DNA
<213> ORGANISM: Arabidopsis thaliana

<400> SEQUENCE: 2

```
atgggttggt taacaagat ctttaaaggc tctaaccaaa ggctccgggt tgggaataat    60
aagcacaatc acaatgttta ttacgataat tatccgactg cttcacatga tgatgagcct   120
agtgcggcgg atacagatgc tgataatgat gaacctcatc atactcagga accatctaca   180
tctgaggata tacatcgaa tgaccaggaa aatgaagaca tagaccgtgc aattgcattg   240
tcgcttttag aagagaatca agaacagaca agtataagcg ggaaatactc gatgccggtg   300
gatgaagatg agcaacttgc tagagcccta caagaaagta tggtagttgg gaattcaccc   360
cgtcacaaaa gtggaagtac atatgataat gggaatgcat atggagctgg agatttatat   420
gggaatggac atatgtatgg aggaggaaat gtatatgcaa atggagatat ttattatcca   480
agacctatta cttttcaaat ggatttcagg atttgtgctg gctgtaatat ggagattggc   540
catggaagat ttctgaattg ccttaattca ctatggcatc cagaatgttt tcgatgttat   600
ggctgcagtc agccgatttc tgagtacgag ttttcaacat cagggaacta cccttttcac   660
aaggcttgtt acaggagag atatcatcct aaatgtgatg tctgcagcca ctttatacca   720
acaaatcatg ctggtcttat tgaatatagg gcacatcctt tttgggttca gaagtattgt   780
ccttctcacg aacacgatgc taccccgaga tgttgcagtt gtgaaagaat ggagccacgg   840
aatacgagat atgttgaact taacgatgga cggaaacttt gccttgagtg tttggactcg   900
gcggtcatgg acaccatgca atgccaacct ctgtacttgc aaatacaaaa tttctatgaa   960
ggactcaaca tgaaggtaga gcaggaagtt ccactcctct tggttgagag acaagcactt  1020
aacgaagcca gagaaggtga aagaatggt cactatcaca tgccagaaac aagaggactc  1080
tgcctttcag aagaacaaac tgttagtact gtaagaaagc gatcaaagca tggcacagga  1140
aaatgggccg ggaatattac agaaccttac aagttaacac ggcaatgtga agttaccgcc  1200
attctcatct tattcgggct ccctaggtta cttactggtt cgattctagc tcatgagatg  1260
atgcatgcgt ggatgaggct caaaggattc cgaacactga gccaagatgt tgaagaaggt  1320
atatgtcaag tgatggctca taatggtta gatgctgagt tagctgctgg ttcaacaaat  1380
agcaatgctg catcatcatc ctcctcttct caaggactga aaaagggacc gagatctcag  1440
tacgagagaa agcttggtga gtttttcaag caccaaatcg agtctgatgc ttctccggtt  1500
tatggagacg ggttcagagc tgggaggtta gctgttcaca agtacggttt gcgaaaaaca  1560
cttgagcata tacagatgac cggtagattc ccggtttaa                         1599
```

<210> SEQ ID NO 3
<211> LENGTH: 21
<212> TYPE: PRT
<213> ORGANISM: Artificial sequence
<220> FEATURE:
<223> OTHER INFORMATION: Synthetic sequence: UIM1 domain
<220> FEATURE:
<221> NAME/KEY: VARIANT
<222> LOCATION: 1, 5, 7, 11, 16, 19..21
<223> OTHER INFORMATION: Xaa is a polar amino acid residue, for example,
      Cys, Asp, Glu, His, Lys, Asn, Gln, Arg, Ser or Thr
<220> FEATURE:
<221> NAME/KEY: VARIANT
<222> LOCATION: 2..4, 17
<223> OTHER INFORMATION: Xaa is any amino acid
<220> FEATURE:
<221> NAME/KEY: VARIANT
<222> LOCATION: 8, 12, 15
<223> OTHER INFORMATION: Xaa is a big amino acid residue, for example,
      Glu, Phe, His, Ile, Lys, Leu, Met, Gln, Arg, Trp, or Tyr
<220> FEATURE:
<221> NAME/KEY: VARIANT
<222> LOCATION: 10
<223> OTHER INFORMATION: Xaa is an aliphatic amino acid residue, for -continued

```
      example, Ile, Leu or Val
<220> FEATURE:
<221> NAME/KEY: VARIANT
<222> LOCATION: 13, 18
<223> OTHER INFORMATION: Xaa may be present or absent. If present, Xaa
      is any amino acid.

<400> SEQUENCE: 3

Xaa Xaa Xaa Xaa Xaa Leu Xaa Xaa Ala Xaa Xaa Xaa Xaa Ser Xaa Xaa
1               5                   10                  15

Xaa Xaa Xaa Xaa Xaa
            20

<210> SEQ ID NO 4
<211> LENGTH: 21
<212> TYPE: PRT
<213> ORGANISM: Artificial sequence
<220> FEATURE:
<223> OTHER INFORMATION: Synthetic sequence: UIM2 domain
<220> FEATURE:
<221> NAME/KEY: VARIANT
<222> LOCATION: 1, 5, 7, 11, 16, 19..21
<223> OTHER INFORMATION: Xaa is a polar amino acid residue, for example,
      Cys, Asp, Glu, His, Lys, Asn, Gln, Arg, Ser or Thr
<220> FEATURE:
<221> NAME/KEY: VARIANT
<222> LOCATION: 2..4, 17
<223> OTHER INFORMATION: Xaa is any amino acid
<220> FEATURE:
<221> NAME/KEY: VARIANT
<222> LOCATION: 8, 12, 15
<223> OTHER INFORMATION: Xaa is a big amino acid residue, for example,
      Glu, Phe, His, Ile, Lys, Leu, Met, Gln, Arg, Trp, or Tyr
<220> FEATURE:
<221> NAME/KEY: VARIANT
<222> LOCATION: 10
<223> OTHER INFORMATION: Xaa is an aliphatic amino acid residue, for
      example, Ile, Leu or Val
<220> FEATURE:
<221> NAME/KEY: VARIANT
<222> LOCATION: 13
<223> OTHER INFORMATION: Xaa may be present or absent. If present, Xaa
      is any amino acid.
<220> FEATURE:
<221> NAME/KEY: VARIANT
<222> LOCATION: 18
<223> OTHER INFORMATION: Xaa is a small amino acid residue, for example,
      Ala, Cys, Asp, Gly, Asn, Pro, Ser, Thr or Val

<400> SEQUENCE: 4

Xaa Xaa Xaa Xaa Xaa Leu Xaa Xaa Ala Xaa Xaa Xaa Xaa Ser Xaa Xaa
1               5                   10                  15

Xaa Xaa Xaa Xaa Xaa
            20

<210> SEQ ID NO 5
<211> LENGTH: 69
<212> TYPE: PRT
<213> ORGANISM: Artificial sequence
<220> FEATURE:
<223> OTHER INFORMATION: Synthetic sequence: LIM domain
<220> FEATURE:
<221> NAME/KEY: VARIANT
<222> LOCATION: 1, 20, 25, 32, 35, 40, 42, 43, 52, 57, 60, 64, 65
<223> OTHER INFORMATION: Xaa is a polar amino acid residue, for example,
      Cys, Asp, Glu, His, Lys, Asn, Gln, Arg, Ser or Thr
<220> FEATURE:
<221> NAME/KEY: VARIANT
<222> LOCATION: 3, 6, 8, 11, 24, 37, 44, 46, 47, 59, 66
<223> OTHER INFORMATION: Xaa is a small amino acid residue, for example,
      Ala, Cys, Asp, Gly, Asn, Pro, Ser, Thr or Val
<220> FEATURE:
<221> NAME/KEY: VARIANT
```

```
<222> LOCATION: 4, 12..16, 23, 26, 29..31, 38, 39, 48..51, 53, 56,
      67..69
<223> OTHER INFORMATION: Xaa may be present or absent. If present, Xaa
      is any amino acid.
<220> FEATURE:
<221> NAME/KEY: VARIANT
<222> LOCATION: 7, 58
<223> OTHER INFORMATION: Xaa is a charged amino acid residue, for
      example, Asp, Glu, His, Lys, Arg
<220> FEATURE:
<221> NAME/KEY: VARIANT
<222> LOCATION: 10, 18
<223> OTHER INFORMATION: Xaa is a hydrophobic amino acid residue, for
      example, Ala, Cys, Phe, Gly, His, Ile, Leu, Met, Thr, Val, Trp and
      Tyr
<220> FEATURE:
<221> NAME/KEY: VARIANT
<222> LOCATION: 17, 22, 55, 61
<223> OTHER INFORMATION: Xaa is a big amino acid residue, for example,
      Glu, Phe, His, Ile, Lys, Leu, Met, Gln, Arg, Trp, or Tyr
<220> FEATURE:
<221> NAME/KEY: VARIANT
<222> LOCATION: 19
<223> OTHER INFORMATION: Xaa is an aliphatic amino acid residue, for
      example, Ile, Leu or Val
<220> FEATURE:
<221> NAME/KEY: VARIANT
<222> LOCATION: 21
<223> OTHER INFORMATION: Xaa is a tiny amino acid residue, for example,
      Ala, Gly or Ser
<220> FEATURE:
<221> NAME/KEY: VARIANT
<222> LOCATION: 27, 54, 62
<223> OTHER INFORMATION: Xaa is an aromatic amino acid residue, for
      example, Phe, His, Trp or Tyr

<400> SEQUENCE: 5

Xaa Cys Xaa Xaa Cys Xaa Xaa Xaa Ile Xaa Xaa Xaa Xaa Xaa Xaa Xaa
1               5                   10                  15

Xaa Xaa Xaa Xaa Xaa Xaa Xaa Xaa Xaa Xaa His Xaa Xaa Xaa Xaa
            20                  25                  30

Cys Phe Xaa Cys Xaa Xaa Xaa Xaa Cys Xaa Xaa Xaa Leu Xaa Xaa Xaa
        35                  40                  45

Xaa Xaa Xaa Xaa Xaa Xaa Xaa Xaa Xaa Xaa Xaa Xaa Xaa Cys Xaa
    50                  55                  60

Xaa Xaa Xaa Xaa Xaa
65

<210> SEQ ID NO 6
<211> LENGTH: 20
<212> TYPE: PRT
<213> ORGANISM: Arabidopsis thaliana

<400> SEQUENCE: 6

Gln Glu Asn Glu Asp Ile Asp Arg Ala Ile Ala Leu Ser Leu Leu Glu
1               5                   10                  15

Glu Asn Gln Glu
            20

<210> SEQ ID NO 7
<211> LENGTH: 20
<212> TYPE: PRT
<213> ORGANISM: Arabidopsis thaliana

<400> SEQUENCE: 7

Asp Glu Asp Glu Gln Ile Ala Arg Ala Leu Gln Glu Ser Met Val Val
1               5                   10                  15

Gly Asn Ser Pro
```

```
<210> SEQ ID NO 8
<211> LENGTH: 53
<212> TYPE: PRT
<213> ORGANISM: Arabidopsis thaliana

<400> SEQUENCE: 8

Ile Cys Ala Gly Cys Asn Met Glu Ile Gly His Gly Arg Phe Leu Asn
1               5                   10                  15

Cys Leu Asn Ser Leu Trp His Pro Glu Cys Phe Arg Cys Tyr Gly Cys
                20                  25                  30

Ser Gln Pro Ile Ser Glu Tyr Glu Phe Ser Thr Ser Gly Asn Tyr Pro
            35                  40                  45

Phe His Lys Ala Cys
            50

<210> SEQ ID NO 9
<211> LENGTH: 248
<212> TYPE: PRT
<213> ORGANISM: Arabidopsis thaliana

<400> SEQUENCE: 9

Met Asn Gly Asp Asn Arg Pro Val Glu Asp Ala His Tyr Thr Glu Thr
1               5                   10                  15

Gly Phe Pro Tyr Ala Ala Thr Gly Ser Tyr Met Asp Phe Tyr Gly Gly
                20                  25                  30

Ala Ala Gln Gly Pro Leu Asn Tyr Asp His Ala Ala Thr Met His Pro
            35                  40                  45

Gln Asp Asn Leu Tyr Trp Thr Met Asn Thr Asn Ala Tyr Lys Phe Gly
        50                  55                  60

Phe Ser Gly Ser Asp Asn Ala Ser Phe Tyr Gly Ser Tyr Asp Met Asn
65                  70                  75                  80

Asp His Leu Ser Arg Met Ser Ile Gly Arg Thr Asn Trp Asp Tyr His
                85                  90                  95

Pro Met Val Asn Val Ala Asp Pro Glu Asn Thr Val Ala Arg Ser
            100                 105                 110

Val Gln Ile Gly Asp Thr Asp Glu His Ser Glu Ala Glu Cys Ile
        115                 120                 125

Ala Asn Glu His Asp Pro Asp Ser Pro Gln Val Ser Trp Gln Asp Asp
            130                 135                 140

Ile Asp Pro Asp Thr Met Thr Tyr Glu Glu Leu Val Glu Leu Gly Glu
145                 150                 155                 160

Ala Val Gly Thr Glu Ser Arg Gly Leu Ser Gln Glu Leu Ile Glu Thr
                165                 170                 175

Leu Pro Thr Lys Lys Tyr Lys Phe Gly Ser Ile Phe Ser Arg Lys Arg
            180                 185                 190

Ala Gly Glu Arg Cys Val Ile Cys Gln Leu Lys Tyr Lys Ile Gly Glu
            195                 200                 205

Arg Gln Met Asn Leu Pro Cys Lys His Val Tyr His Ser Glu Cys Ile
        210                 215                 220

Ser Lys Trp Leu Ser Ile Asn Lys Val Cys Pro Val Cys Asn Ser Glu
225                 230                 235                 240

Val Phe Gly Glu Pro Ser Ile His
                245
```

<210> SEQ ID NO 10
<211> LENGTH: 1229
<212> TYPE: DNA
<213> ORGANISM: Arabidopsis thaliana

<400> SEQUENCE: 10

```
acactctttc ctctctcttt cttctctctt tcttttctct ctctctcctc tgctcctccg      60
tctctcgtct acagtgccct ccgcatcacc ttttccttg tcctatgaat ttggtcgaaa      120
tgcccttctc ctcctcctcc ttccactaat ctcaaaagat atatccttcg agactctccc    180
ttgccgtctc caattgccac tcaccgctcc aactctcttc gaattagctg aaatgaatgg    240
agataataga ccagtggaag atgctcatta cacggagaca ggtttccctt atgctgctac    300
tggaagttac atggactttt atggtggtgc ggctcagggg cctcttaact acgatcatgc    360
cgcaactatg catcctcagg acaatctgta ctggaccatg ataccaatg catacaagtt    420
tgggttttca ggatcagata atgcttcttt ctatggttca tatgacatga cgatcattt    480
atcgaggatg tccatagggga gaacaaattg ggactatcat cccatggtga acgttgctga    540
tgatcctgaa acacagttg cacgttccgt ccaaatcgga gacacagatg agcactctga    600
agctgaagaa tgcattgcaa atgagcatga tcccgacagt cctcaggtat cctggcaaga    660
tgacattgat cctgatacaa tgacctatga ggaattagta gagctggggg aagcagtagg    720
aacagaaagc agggggttgt ctcaggaact catagaaacg cttccacta aaaagtataa    780
gtttgggagc atcttctcca ggaaaagagc tggggagagg tgtgtgatat gccagctcaa    840
gtacaagata ggggagaggc aaatgaatct gccgtgcaag catgtgtatc attctgaatg    900
catttccaaa tggctaagca tcaacaaggt ttgcccggtg tgtaacagcg aggtctttgg    960
ggagcccagc attcattgat cggcacaagg ggctcctcct cttctttct ttttggcttt   1020
ttatatcgag gctcatcaag taattgtttt agtgtagtga aaaccccaaa aaatagtcta   1080
aaagatgtcc acactatact ctctcatgtt cagtccttct ctgtacatgt aatttttctt   1140
ctagttccat tttcgcttgt gtgtgcttta agtttaacag tcactcgtat tgtatactaa   1200
atgctaagtc aaaaacgctg aatccatat                                     1229
```

<210> SEQ ID NO 11
<211> LENGTH: 1506
<212> TYPE: DNA
<213> ORGANISM: Oryza sativa

<400> SEQUENCE: 11

```
atggcctact cctcacggtc ttgtgatcag tgcagtcacg agaggagatc cggcttcatg      60
aagtggctct gcgctttcct gaaggggacg aaggacggcg aggccaaccg acggcgccct    120
cgggtgacgg caggagaaga gaccacgctc tgggaagaac cagttagacc aaagaaggaa    180
gaaccaccta gacataacaa tgaagaaatg gaccatgcac ttgcccttgc tcttgcagac    240
gatgccaaaa atacaaaaga gagaaaccat gacaagggga aaaacgatga agaactcgct    300
agagcaatac aggacagtct gaacatgaat ccttaccagc cttacaatcc ttgtgcaccc    360
tctcagaccc aggccaggtc gagaggatac agggtctgtg ggggttgcaa gcatgagata    420
gggcatggcc attacttgag ctgcttggga atgtactgga ccctcagtg cttccgctgt    480
tcttcctgtc gccacccctat ccgtgagatg gagttcacct tgctaggtac agatccatac    540
cacaagctgt gctacaagga gcttcatcac ccaaagtgtg acgtctgcct tcaatttatc    600
ccaacgaaca ggactggttt gatagagtac agagcccatc cattctgggg acagaagtat    660
```

```
tgtcctttgc atgagcatga tagaacacct cgttgctgta gctgtgagaa aatggagcca    720
aggaacacaa agtatatgtc attaggggat ggacgcagct tgtgcatgga atgcctggat    780
tctgcaatca tggacaccgg tgaatgtcaa ccgctatacc attccatcag agactactac    840
gaagggatga acatgaaact agaccagcag atacccatgc tcttggttga acgtcaagcc    900
cttaatgaag ctatggaagg agaaagcaaa ggaccgcatc atatgcctga acacgaggc    960
ctttgtctgt cagaggagca gactgtgacc agtatactta ggaggcccag aattggtgca   1020
aatcggttac tagatatgaa acccaaccg caaaagctaa ctaggagatg cgaagtcact   1080
gcaattcttg tatttgtttgg cctccccagg ctgctaacgg gctccattct tgcccatgaa   1140
ttgatgcatg ggtggttgcg cctcaaaggt taccggaacc taaaggcgga gattgaggaa   1200
ggtatatgcc aggtcatgtc ttacctgtgg ctggagtcag agatccttcc atccacttca   1260
agatatggac aggcttcaac atcttacgct tcatcttcgt cgtcctcctg tcgaccacca   1320
ccgtccaaga agggtgggat ctctcacacc gagaagaagc ttggagaatt cttcctgcat   1380
cagatcgcca atgacacatc atcagcatac ggcgatggtt tcagagctgc ctatgcagct   1440
gtgaacaagt atggccttcg ccaatcactg aaccatatac ggctaaccgg aggctttcct   1500
gtgtaa                                                               1506

<210> SEQ ID NO 12
<211> LENGTH: 1779
<212> TYPE: DNA
<213> ORGANISM: Brassica rapa

<400> SEQUENCE: 12
atggagtttc ttcttctctt gtttggatac attaagaatg tgtttctctt tgcaggtaag     60
aggttgttgt tgatgccaat ggggtggctt actaagatcc ttaaaggttc tagtcataag    120
tattcagatg gtcaagctaa cagaagatac aatagagagg atagaagcct ggacactcct    180
cgttattccg cggaaggatc tgattttgac aaagaagaaa ttgaatgcgc cattgcactc    240
tcccttctg aacaagaaca tgtgattcca caagatgaca aggaaagaa agtcatcgga    300
atacaaatct gaaactgaag aagatgatga tgaggatgag gatgaggatg aggaggatga    360
tgatgaagaa cacatgagag ctcaggtgga agcagcagaa gaagaggaaa agaaggtagc    420
tcaagctcaa atagaggaag aagagaaacg aagagctgaa gaagctgagc tagaagagtt    480
agagaaacag cttgccaaag ctagactaga agaggaagaa gttagacgcg ccaaagctca    540
acttgaggaa gatgagcagc tcgcaaaggc tattcaagaa agtatgaatg tgggatctcc    600
tcctcctgga tatgattctg gaagtgtgtt tccatcatac cccttccttg ttccttctag    660
agaatatgca ctggttgccg agctgagatt ggacatggaa ggtttctgag ttgcatgggt    720
ggcgtttggc atcctgaatg ttttgctgc cacgcttgtg ataagcccat catagactgt    780
gaggtgttct caatgtcagg aaaccgtcct tatcacaaac tgtgttacaa ggagcagcat    840
catccaaaat gtgatgtttg tcataacttt attcctacaa atccagctgg tctcattgag    900
tacagggcac atccctttg gatgcagaag tattgtcctt cacatgagcg tgatggaaca    960
cctagatgct gcagctgtga gcgcatgag ccgaaagata caagtatct gatacttgat   1020
gatggtagaa aactgtgtct tgaatgtcta gactcagcca ttatggacac taatgaatgc   1080
caaccgttgt atctcgagat acgtgagttt tatgaaggct tgcacatgaa agtggaacag   1140
cagatacccta tgctcttggt ggagagatca gctttaaacg aagctatgga aggagagaaa   1200
catggacatc atcacttacc tgagactaga ggactctgtt tgtctgaaga acaaactgtc   1260
```

```
acaacagtgt tgaggagacc aaagattggt gcaggctaca agttgataga catgatcact    1320
gagccttgca ggctggtgcg ccgttgtgaa gtcactgcta ttctcatctt atatggactt    1380
ccccgcgttt gttaactgga tcaatcctag ctcatgagat gatgcatgca tggcttcgac    1440
taaatggggt atccaaatct tagaccagaa gtggaagaag gatatgtca ggttttagct     1500 cacatgtggt tggaatctga gacttatgct ggctctacat tgatagatat tgcatcttct    1560
tcttcgtctt catcatcagc cgctgtggcg attgcatcgt ccaagaaagg tgagaggtct    1620
gattttgaga agaaactcgg tgagtttttc aagcaccaga tagagtcaga ttcttcttcg    1680
gcatatgggg atgggttcag gcaaggtaac caagctgttc ttacgcatgg tctgaagcga    1740
acccttgatc atattcgctt gaccggtaca tttccttaa                           1779
```

<210> SEQ ID NO 13
<211> LENGTH: 1548
<212> TYPE: DNA
<213> ORGANISM: Brassica rapa

<400> SEQUENCE: 13

```
atggattctt cttcatatgg tgtttctcat gtcagccata tctccaatcc ttgtatcttt      60
ggggctgggt cgtcgtcttc gccagagaag aaatggaact tgatgaaatg ggtgagtaaa    120
cttttcaaga gtggctctaa cggtggcact ggtggtgctc gcactaaccg tcatcctcct    180
cagtttcaag aggacgagaa tatggtcttt cctttacctc cttcctcttc ggacgatcgg    240
tcgagagcct cacgggacaa agaagaacta gatcgtgcat tgtcagtttc tctagctgac    300
gatacgaacc gaccatatgg atatggttgg tctatggata ataattcaga tttccctagg    360
ccttttcaca gtggattgaa tccatctttc attccacctt atgaaccgtc ctatcaagtc    420
agacgaccac aaagaatatg tggcggttgc aatagcgata ttggattggg gaactatctg    480
ggatgcatgg gaacattctt tcatcctgat tgcttctgtt gtgattcatg tcgttaccct    540
atcactgagc atgagttctc tctatcagga accaaacctt accatcagat ttgtttcaaa    600
gagctcactc atcctaaatg cgaagtttgt caccatttta tcccaactaa tgatgctggc    660
ttgatcgaat atcgatgcca tccgttttgg aaccaaaagt attgcccctc tcacgaacac    720
gatagaaccg ctcgttgctg tagctgcgaa cgtttggagt catgggaggt gagatattac    780
acgttagacg atgggagaag tttatgttta gaatgcatgg aaactgcgat aaccgacact    840
ggagattgtc aaccactttta ccatgcaata cgtgactatt acgaaggaat gtacatgaaa    900
cttgagcaac aaatccccat gcttcttgtt cagcgagaag ctctcaacga cgctatcgtc    960
ggagagaaac acggatacca tcacatgcct gagacaaggg gtttatgttt gtctgaagaa    1020
caaacagtca caagtgttct taaaagaccg agactgggcg ctcaccgtct tgttggtatg    1080
agaactcagc ctcaaaagct tacacgtaaa tgtgaagtca ctgcgattct cgttctttac    1140
ggcctcccta gactattaac tggagcaatt cttgcccacg agctgatgca tggatggcta    1200
aggctcaaag ggtataggaa ccttaaccct gaggtagagg aaggtatctg ccaagtcctc    1260
tcttacatgt ggcttgaatc tgaagttctc tcagatcctt cttcaagaag catgccctca    1320
acatcaactg ccacctcgtc atcatcatca tcatcatctt cttctaacaa gaaaggaggg    1380
aaaacaaacg tggagaagaa acttggagag ttctttaagc atcagatagc tcatgacgca    1440
tctcctgctt acgaggggggg tttcagagca gcaaatgcag cggtttgtaa gtacggtctg    1500
cgtcgcacac ttgatcatat ccgcttcact ggaacgtttc ctttgtaa                 1548
```

<210> SEQ ID NO 14
<211> LENGTH: 1456
<212> TYPE: DNA
<213> ORGANISM: Brassica rapa

<400> SEQUENCE: 14

| | |
|---|---|
| atgccattga gagtgacata tctgatggaa gatcggaaaa gaaaaaggaa aaagctttttt | 60 |
| gatttgggca gcggacttaa ccttaaacct gcaggatcct tttgaagctg aaactgatat | 120 |
| cgtcaaacaa gtgtcatcga atgatgctca cgttcaagaa gatgaacagc ttgctttggc | 180 |
| cattcaaaaa tctaaagaag acgaagagga agaaggcccc accagggact agaagagca | 240 |
| tgcacatgag agaggagaaa ggcaaaataa ttatgacaac tcttcttctt tgaaagacaa | 300 |
| aaaagaagga cagacttctg aggagaaaac atgacaacat ttcctctgaa gctcgcttgg | 360 |
| atgagaatga ggagcagcgg attatctggg agagtttgaa ggataaaggt caaacaaagc | 420 |
| catctgaaga tgaggtcatt cctcctcgta gagcaagtgt ggtggttgcc actctgagat | 480 |
| tgaacaagga ggatcagtgg atgtcttttgg tgttccttgg catcctgaat gtttctcttg | 540 |
| tggtgcttgc cgtaacccaa ttgctgtcca cgaggttcaa aaccatgtct caaactcaag | 600 |
| aggcaagttc cacaaaaact gctataaccg gtactgctat gtctgccaag agaaagttaa | 660 |
| gattagagag tacaatagcc atcctttctg gaaggagata tactgccctg ctcacgaaac | 720 |
| tgatggaact cccaagtgtt gcagctgcga gaggctagag cctagagaaa cggagttcgt | 780 |
| aatgctagat gatggaaggt ggctatgtct agaatgtatg gactcagcgg ttatggatac | 840 |
| tgacgaagtc cagcctcttc actttgaaat ccgtgacttc ttccatggct tgttcttgcc | 900 |
| agttgagaaa gagttttctc ttctttttggt ggagaaacaa gccctgaata agctgagga | 960 |
| ggaagagaag attgtgtcaa aagggccaaa gatggggag aacaagcagc taacaggaaa | 1020 |
| gaccacggaa tctcaaaggg ttgtgagtgg atgcccggtc actgcaattc tcatcttata | 1080 |
| tggacttcct agaggttact aacaggatct atcatggctc acgagatgat gcatgcttat | 1140 |
| cttagactca atgggacata taatttgaa caaggttctg gaagaaggaa tatgccaagt | 1200 |
| gctagggcac atgtggttgg agactcagag atacgcccct attgatgttg ctgcagcttc | 1260 |
| ttcttcttct tcgtcaaatg cggcaaagaa aggggagtgg tctgaactcg agaagaagct | 1320 |
| ggtggatttt tacaagtatg agatagaaac agatgagtca gctgtctatg gtgaagggtt | 1380 |
| taggaaagtt aactatatgg ttacaaactc cagcctccag gaaaccctca agagattct | 1440 |
| tccccgccgg ggttga | 1456 |

<210> SEQ ID NO 15
<211> LENGTH: 1545
<212> TYPE: DNA
<213> ORGANISM: Brassica rapa

<400> SEQUENCE: 15

| | |
|---|---|
| atgggttggt taaacaagat cttcaaaggc tctaaccaaa ggcaccccct ggggaatgaa | 60 |
| cactatcatc ataatggcgg ctattacgag aactacccgc acgaacattc tgagcctagt | 120 |
| gcagagacag atgctgatca tacgcaggag ccatctactt ctgaggagga gacatggaat | 180 |
| gggaaggaaa atgaagaagt agaccgtgta attgcattgt ctatttttaga agaagagaat | 240 |
| caaagaccag agactaatac aggcgcctgg aaacacgcaa tgatggatga cgatgagcaa | 300 |
| cttgctagag ccatacaaga gagtatgata gctaggaatg gaactactta tgactttggg | 360 |
| aatgcatatg ggaatggaca tatgcatgga ggaggcaatg tatatgacaa tggtgatatt | 420 |

```
tattatccaa gacctattgc tttctcaatg gacttcagga tctgtgctgg ctgcaatatg      480
gagattggcc atgaagata tctgaattgc ctcaacgcac tatggcatcc acaatgtttt      540
cgatgctatg gctgcagtca cccaatctct gagtacgagt tctcaacgtc tgggaattac     600 cctttcaca aagcttgtta cagggagagg ttccatccaa aatgtgatgt ctgcagcctc      660
tttatttcaa caaaccatgc tggtcttatt gaatatagag cacatccttt ctgggtccag     720
aagtattgcc cttctcacga acacgatgct acgccaagat gttgcagctg tgaaagaatg     780
gagccgcgga atacaggata ttttgaactc aacgatggac ggaagctttg ccttgagtgt     840
ctagactcat cggtgatgga cacttttcaa tgccagcctc tgtacttgca gatacaagag     900
ttctatgaag gacttaacat gacggtagag caggaggttc cacttctctt agttgagcgg     960
caggcactta acgaagccag agaaggtgaa aggaatggtc actatcacat gccagagaca    1020
agaggactct gtctgtcgga agaacaaact gttagaactg tgagaaagag atcgaaggga    1080
aactggagtg ggaatatgat tacagagcaa ttcaagctaa ctcgtcgatg cgaggttact    1140
gccattctca tcttgtttgg tctccctagg ctactcactg gttcaattct agctcatgag    1200
atgatgcacg cgtggatgcg gctcaaaggg ttccggccac ttagccaaga tgttgaagag    1260
gggatatgtc aagtgatggc tcataagtgg ttagaagctg agttagctgc tggttcaaga    1320
aatagcaatg ctgcatcatc ttcatcatct tcttatggag gagtgaagaa gggaccaagg    1380
tctcagtacg agaggaagct tggtgagttt ttcaagcacc agatagagtc tgatgcttct    1440
ccggtttatg gagatgggtt cagggccggg aggttagcgg ttaacaagta tggtttgtgg    1500
agaacacttg agcatataca gatgactggg agattcccgg tttaa                    1545
```

<210> SEQ ID NO 16
<211> LENGTH: 1599
<212> TYPE: DNA
<213> ORGANISM: Brassica rapa

<400> SEQUENCE: 16

```
atgggttggt ttaacaagat cttcaaaggc tctacccaaa ggttccggct tgggaatgac      60
catgaccaca atggctatta ccagagttat ccacatgatg agcctagtgc tgatactgat     120
cctgatcctg atcctgatcc tgatgaaact catactcagg aaccatctac ctctgaggag     180
gatacatccg gccaggaaaa cgaagacata gatcgtgcaa tcgcattgtc tcttatagaa     240
aacagtcaag gacagactaa taatacatgc gctgccaacg cagggaagta cgcaatggtg     300
gatgaagatg agcaacttgc tagagccata caagagagca tggtagttgg gaatacaccg     360
cgtcagaagc atggaagtag ttatgatatt gggaatgcat atgggctgg agacgtttac     420 gggaatggac atatgcatgg aagtggaaat gtatatgcca atgagatat ttattatcca     480 agacctactg ctttcccaat ggatttcagg atttgtgctg gctgcaatat ggagattgga     540 catgaagat atctgaattg cttgaatgca ctatggcatc cagaatgttt tcgatgttat     600
ggctgtaggc accccatttc tgagtacgag ttctcaacgt ctgggaacta ccctttcac     660 aaagcttgtt atagggagag ataccatcca aaatgtgatg tctgcagcct ctttattcca    720
acaaaccatg ctggtcttat tggatatagg gcacatcctt tttgggtcca gaagtattgc    780
ccttctcacg aacacgatgc taccccaaga tgttgcagtt gcgaaagaat ggagccacgc    840
aatacaggat atgttgaact taacgatgga cggaaacttt gccttgaatg tctggactca    900
gcggtgatgg acacttttca atgccaacct ctgtatctgc agatacaaga attctacgaa    960
```

| | |
|---|---|
| ggtcttttca tgaaggtaga gcaggacgtt ccacttcttt tagttgagag gcaagcactc | 1020 |
| aacgaagcca gagaaggtga aaagaatggt cactatcaca tgccagagac aagaggactc | 1080 |
| tgcctttcag aagagcaaac tgttagcact gtaagaaaga gatcgaagca tggcacagga | 1140 |
| aactgggctg ggaatatgat tacagagcct tacaagttga cacgtcaatg cgaggttact | 1200 |
| gccattctca tcttgtttgg gctccctagg ctactcaccg gttcgattct agctcatgag | 1260 |
| atgatgcacg cgtggatgcg gctcaaggga ttccggacgc tgagccaaga cgttgaagaa | 1320 |
| ggaatatgtc aagtgatggc tcataagtgg ttggaagcag agttagctgc tggttcaaga | 1380 |
| aacagcaatg ttgcgtcatc ttcatcttct agaggagtga agaagggacc aagatcgcag | 1440 |
| tacgagagga agcttggtga gttttttcaag caccaaatcg agtctgatgc ttctccggtt | 1500 |
| tatggagacg ggtccaggggc tgggaggtta gcggttaaca agtatggttt gccaaaaaca | 1560 |
| cttgagcata tacagatgac cggtagattc ccggtttaa | 1599 |

<210> SEQ ID NO 17
<211> LENGTH: 1461
<212> TYPE: DNA
<213> ORGANISM: Oryza sativa

<400> SEQUENCE: 17

| | |
|---|---|
| atgggttggt tgaccaaatt ttttagaggt tcaacccaca aaatctcgga agggcaatac | 60 |
| cacagcaaac ccgcggagga gacgatatgg aatggaccct ctaattccgc agttgtgacg | 120 |
| gatgtcccgt cagaatttga caatgaagat atcgctcgtg ctatatcact ctctctatta | 180 |
| gaggaggaac aaagaaaggc aaaggcaata gaaaaggaca tgcatttgga ggaggatgaa | 240 |
| caacttgcaa gagctatcca ggaaagtttg aatgttgaat cgcctcctcg tgctcgtgaa | 300 |
| aatggcaacg ccaatggtgg caatatgtat caaccactgc catttatgtt ttcttctgga | 360 |
| ttcaggactt gtgccggatg tcacagtgag attggtcatg ggcgtttcct tagttgcatg | 420 |
| ggagctgttt ggcatccaga atgttttcgc tgtcatgctt gtaatcaacc aatatatgac | 480 |
| tatgagttct ccatgtcggg aaaccatcca taccataaaa catgctacaa ggagcgcttt | 540 |
| cacccaaaat gtgatgtctg caagcaattt attcctacaa atatgaatgg cctgattgaa | 600 |
| tatagagcac atccttctg gttacaaaaa tactgtccat cacatgaggt ggacggtact | 660 |
| ccaagatgct gtagttgtga agaatggag ccaagggaat caagatatgt attgctggac | 720 |
| gatggtcgca aactctgcct ggagtgcctt gattctgcag ttatggatac gagcgagtgc | 780 |
| caacctcttt atcttgaaat acaggaattt tatgaaggcc taaatatgaa agtgaacaa | 840 |
| caagttccct tgcttcttgt agaaagacag gctttaaatg aagccatgga aggagagaag | 900 |
| actggtcacc accatcttcc agaaacaaga ggtttatgct atcagaaga gcaaactgtc | 960 |
| agcacgatat tgaggagacc aagaatggct ggaaataaag ttatggaaat gataacggag | 1020 |
| ccatataggt tgactcgtcg atgtgaagtg actgcaattc tcattctta tggtctccca | 1080 |
| agattgttga caggttcaat tttagctcat gagatgatgc atgcgtggtt gcgacttaaa | 1140 |
| ggatatcgca cacttagtcc agacgtagaa gagggcatat gccaagttct tgctcacatg | 1200 |
| tggattgagt cagagatcat tgcaggatca ggcagtaatg gtgcttcaac gtcttcatcc | 1260 |
| tcatcagcat ccacatcatc gaaaaagggg ggaagatctc agtttgagcg aaagcttggt | 1320 |
| gattttttca agcaccaaat tgagtcagat acctcaatgg cctatggcga tggttttaga | 1380 |
| gctggcaacc gagctgttct tcagtatggt ctaaagcgca ccccttgagca tatccggtta | 1440 |
| acagggactt tcccatttg a | 1461 |

<210> SEQ ID NO 18
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 18
taatttaata tttccttctt cccc                                          24

<210> SEQ ID NO 19
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 19
ttactttgac tcactttcac cac                                           23

<210> SEQ ID NO 20
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 20
aattagaata ataatgcagc gttg                                          24

<210> SEQ ID NO 21
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 21
cgtttcggta tcgctttgcg                                               20

<210> SEQ ID NO 22
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 22 ttggtttcg ttgggtcaag g                                              21

<210> SEQ ID NO 23
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 23
tgtttctgca gaagcgaggg                                               20

<210> SEQ ID NO 24
<211> LENGTH: 21
<212> TYPE: DNA
<213> ORGANISM: Artificial sequence
<220> FEATURE:

<223> OTHER INFORMATION: Synthetic sequence: Primer

<400> SEQUENCE: 24
aatcacgtgg tgttcttagc c                                              21

<210> SEQ ID NO 25
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 25
actcattttg gcagcttggt g                                              21

<210> SEQ ID NO 26
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 26
gacaccatgc aatgccaacc                                                20

<210> SEQ ID NO 27
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 27
ctttgagcct catccacgca                                                20

<210> SEQ ID NO 28
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 28
ctcaggctca ggtaaatgcg                                                20

<210> SEQ ID NO 29
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 29
ttcacgtccg aaacgcatcc                                                20

<210> SEQ ID NO 30
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 30
ctaacacgac ccacatgatg c                                              21

```
<210> SEQ ID NO 31
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 31
ctcgagtttc gtggttacgg                                               20

<210> SEQ ID NO 32
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 32
agcatcctca aggtataagc c                                             21

<210> SEQ ID NO 33
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 33
ggtgctgcat ttctgtcacc                                               20

<210> SEQ ID NO 34
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 34
ggttgctcta atcacctaa cg                                             22

<210> SEQ ID NO 35
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 35
ctcaccaaga atatgcatat gtg                                           23

<210> SEQ ID NO 36
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 36
atgggttggt ttaacaagat cttt                                          24

<210> SEQ ID NO 37
<211> LENGTH: 20
<212> TYPE: DNA
<213> ORGANISM: Artificial sequence
<220> FEATURE:
<223> OTHER INFORMATION: Synthetic sequence: Primer
```

<400> SEQUENCE: 37
aaccgggaat ctaccggtca          20

<210> SEQ ID NO 38
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 38
atggagtttc ttctctttct tgg          23

<210> SEQ ID NO 39
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 39
ttaaatccat ttaggaaatg taccg          25

<210> SEQ ID NO 40
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 40
gagaagatga ctcagatc          18

<210> SEQ ID NO 41
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 41
atccttcctg atatcgac          18

<210> SEQ ID NO 42
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 42
gacaccatgc aatgccaacc          20

<210> SEQ ID NO 43
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 43
ctttgagcct catccacgca          20

<210> SEQ ID NO 44
<211> LENGTH: 20

```
<212> TYPE: DNA
<213> ORGANISM: Artificial sequence
<220> FEATURE:
<223> OTHER INFORMATION: Synthetic sequence: Primer

<400> SEQUENCE: 44
ggtgaaggaa tggacgagat                                              20

<210> SEQ ID NO 45
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 45
gtcatctgca gttgcgtctt                                              20

<210> SEQ ID NO 46
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 46
aagccagcta aatatgattg g                                            21

<210> SEQ ID NO 47
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 47
aatccgtttg gaactcgttt g                                            21

<210> SEQ ID NO 48
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 48
gaatttggtt cggttggttt g                                            21

<210> SEQ ID NO 49
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 49
tcacatgcca gaaacaagag g                                            21

<210> SEQ ID NO 50
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 50
```

```
tcctcttggt tgagagacaa gc                                           22
```

<210> SEQ ID NO 51
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 51

```
tccatttggg ttcttaaacc g                                            21
```

<210> SEQ ID NO 52
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 52

```
atttagtcga agccatgcat g                                            21
```

<210> SEQ ID NO 53
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 53

```
ttacaaggag cagcatcatc c                                            21
```

<210> SEQ ID NO 54
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 54

```
tgaggtggcc tattttgata cc                                           22
```

<210> SEQ ID NO 55
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 55

```
cacaacctta gtcacttcag aagg                                         24
```

<210> SEQ ID NO 56
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 56

```
gagcgatgca tctctaacca c                                            21
```

<210> SEQ ID NO 57
<211> LENGTH: 21
<212> TYPE: DNA
<213> ORGANISM: Artificial sequence

```
<220> FEATURE:
<223> OTHER INFORMATION: Synthetic sequence: Primer

<400> SEQUENCE: 57
agtaggaaca gaaagcaggg g                                              21

<210> SEQ ID NO 58
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 58
tggttcacgt agtgggccat cg                                             22

<210> SEQ ID NO 59
<211> LENGTH: 2346
<212> TYPE: DNA
<213> ORGANISM: Arabidopsis thaliana
<220> FEATURE:
<221> NAME/KEY: CDS
<222> LOCATION: (565)..(2163)

<400> SEQUENCE: 59
cgtggggaac gttttttcct ggaagaagaa gaagaagagc tcaacaagct caacgaccaa     60
aaaacttcgg acacgaagac ttttaattc atttctcctc ttttgttttt ttcgttccaa    120
aatattcgat actctcgatc tcttcttcgt gatcctcatt aaataaaaat acgattttta    180 ttctttttt gtgagtgcac caaattttt gactttggat tagcgtagaa ttcaagcaca     240
ttctgggttt attcgtgtat gagtagacat tgattttgtc aaagttgcat tctttttatat    300 aaaaaaagtt taatttcctt ttttcttttc ttttctcttt ttttttttt tccccccatgt    360 tatagattct tccccaaatt tgaagaaag gagagaacta agagtccctt tttgagattc     420
ttttgctgct tcccttgctt gattagatca ttttttgtgat tctggatttt gtggggttt     480 cgtgaagctt attgggatct tatctgattc aggatttct caaggctgca ttgccgtatg      540
agcagatagt tttatttagg catt atg ggt tgg ttt aac aag atc ttt aaa      591
                            Met Gly Trp Phe Asn Lys Ile Phe Lys
                            1               5 ggc tct aac caa agg ctc cgg gtt ggg aat aat aag cac aat cac aat      639
Gly Ser Asn Gln Arg Leu Arg Val Gly Asn Asn Lys His Asn His Asn
 10                  15                  20                  25 gtt tat tac gat aat tat ccg act gct tca cat gat gat gag cct agt      687
Val Tyr Tyr Asp Asn Tyr Pro Thr Ala Ser His Asp Asp Glu Pro Ser
                 30                  35                  40 gcg gcg gat aca gat gct gat aat gat gaa cct cat cat act cag gaa      735
Ala Ala Asp Thr Asp Ala Asp Asn Asp Glu Pro His His Thr Gln Glu
             45                  50                  55 cca tct aca tct gag gat aat aca tcg aat gac cag gaa aat gaa gac      783
Pro Ser Thr Ser Glu Asp Asn Thr Ser Asn Asp Gln Glu Asn Glu Asp
         60                  65                  70 ata gac cgt gca att gca ttg tcg ctt tta gaa gag aat caa gaa cag      831
Ile Asp Arg Ala Ile Ala Leu Ser Leu Leu Glu Glu Asn Gln Glu Gln
     75                  80                  85 aca agt ata agc ggg aaa tac tcg atg ccg gtg gat gaa gat gag caa      879
Thr Ser Ile Ser Gly Lys Tyr Ser Met Pro Val Asp Glu Asp Glu Gln
 90                  95                 100                 105 ctt gct aga gcc cta caa gaa agt atg gta gtt ggg aat tca ccc cgt      927
Leu Ala Arg Ala Leu Gln Glu Ser Met Val Val Gly Asn Ser Pro Arg
                110                 115                 120
```

```
cac aaa agt gga agt aca tat gat aat ggg aat gca tat gga gct gga      975
His Lys Ser Gly Ser Thr Tyr Asp Asn Gly Asn Ala Tyr Gly Ala Gly
        125                 130                 135 gat tta tat ggg aat gga cat atg tat gga gga gga aat gta tat gca     1023
Asp Leu Tyr Gly Asn Gly His Met Tyr Gly Gly Gly Asn Val Tyr Ala
            140                 145                 150 aat gga gat att tat tat cca aga cct att act ttt caa atg gat ttc     1071
Asn Gly Asp Ile Tyr Tyr Pro Arg Pro Ile Thr Phe Gln Met Asp Phe
155                 160                 165 agg att tgt gct ggc tgt aat atg gag att ggc cat gga aga ttt ctg     1119
Arg Ile Cys Ala Gly Cys Asn Met Glu Ile Gly His Gly Arg Phe Leu
170                 175                 180                 185 aat tgc ctt aat tca cta tgg cat cca gaa tgt ttt cga tgt tat ggc     1167
Asn Cys Leu Asn Ser Leu Trp His Pro Glu Cys Phe Arg Cys Tyr Gly
                190                 195                 200 tgc agt cag ccg att tct gag tac gag ttt tca aca tca ggg aac tac     1215
Cys Ser Gln Pro Ile Ser Glu Tyr Glu Phe Ser Thr Ser Gly Asn Tyr
                    205                 210                 215 cct ttt cac aag gct tgt tac agg gag aga tat cat cct aaa tgt gat     1263
Pro Phe His Lys Ala Cys Tyr Arg Glu Arg Tyr His Pro Lys Cys Asp
            220                 225                 230 gtc tgc agc cac ttt ata cca aca aat cat gct ggt ctt att gaa tat     1311
Val Cys Ser His Phe Ile Pro Thr Asn His Ala Gly Leu Ile Glu Tyr
235                 240                 245 agg gca cat cct ttt tgg gtt cag aag tat tgt cct tct cac gaa cac     1359
Arg Ala His Pro Phe Trp Val Gln Lys Tyr Cys Pro Ser His Glu His
250                 255                 260                 265 gat gct acc ccg aga tgt tgc agt tgt gaa aga atg gag cca cgg aat     1407
Asp Ala Thr Pro Arg Cys Cys Ser Cys Glu Arg Met Glu Pro Arg Asn
                270                 275                 280 acg aga tat gtt gaa ctt aac gat gga cgg aaa ctt tgc ctt gag tgt     1455
Thr Arg Tyr Val Glu Leu Asn Asp Gly Arg Lys Leu Cys Leu Glu Cys
                    285                 290                 295 ttg gac tcg gcg gtc atg gac acc atg caa tgc caa cct ctg tac ttg     1503
Leu Asp Ser Ala Val Met Asp Thr Met Gln Cys Gln Pro Leu Tyr Leu
            300                 305                 310 caa ata caa aat ttc tat gaa gga ctc aac atg aag gta gag cag gaa     1551
Gln Ile Gln Asn Phe Tyr Glu Gly Leu Asn Met Lys Val Glu Gln Glu
315                 320                 325 gtt cca ctc ctc ttg gtt gag aga caa gca ctt aac gaa gca aga gaa     1599
Val Pro Leu Leu Leu Val Glu Arg Gln Ala Leu Asn Glu Ala Arg Glu
330                 335                 340                 345 ggt gaa aag aat ggt cac tat cac atg cca gaa aca aga gga ctc tgc     1647
Gly Glu Lys Asn Gly His Tyr His Met Pro Glu Thr Arg Gly Leu Cys
                350                 355                 360 ctt tca gaa gaa caa act gtt agt act gta aga aag cga tca aag cat     1695
Leu Ser Glu Glu Gln Thr Val Ser Thr Val Arg Lys Arg Ser Lys His
                    365                 370                 375 ggc aca gga aaa tgg gcc ggg aat att aca gaa cct tac aag tta aca     1743
Gly Thr Gly Lys Trp Ala Gly Asn Ile Thr Glu Pro Tyr Lys Leu Thr
            380                 385                 390 cgg caa tgt gaa gtt acc gcc att ctc atc tta ttc ggg ctc cct agg     1791
Arg Gln Cys Glu Val Thr Ala Ile Leu Ile Leu Phe Gly Leu Pro Arg
395                 400                 405 tta ctt act ggt tcg att cta gct cat gag atg atg cat gcg tgg atg     1839
Leu Leu Thr Gly Ser Ile Leu Ala His Glu Met Met His Ala Trp Met
410                 415                 420                 425 agg ctc aaa gga ttc cga aca ctg agc caa gat gtt gaa gaa ggt ata     1887
Arg Leu Lys Gly Phe Arg Thr Leu Ser Gln Asp Val Glu Glu Gly Ile
```

-continued

```
                    430                 435                 440
tgt caa gtg atg gct cat aaa tgg tta gat gct gag tta gct gct ggt     1935
Cys Gln Val Met Ala His Lys Trp Leu Asp Ala Glu Leu Ala Ala Gly
            445                 450                 455 tca aca aat agc aat gct gca tca tca tcc tct tct caa gga ctg         1983
Ser Thr Asn Ser Asn Ala Ala Ser Ser Ser Ser Ser Gln Gly Leu
        460                 465                 470 aaa aag gga ccg aga tct cag tac gag aga aag ctt ggt gag ttt ttc     2031
Lys Lys Gly Pro Arg Ser Gln Tyr Glu Arg Lys Leu Gly Glu Phe Phe
    475                 480                 485 aag cac caa atc gag tct gat gct tct ccg gtt tat gga gac ggg ttc     2079
Lys His Gln Ile Glu Ser Asp Ala Ser Pro Val Tyr Gly Asp Gly Phe
490                 495                 500                 505 aga gct ggg agg tta gct gtt cac aag tac ggt ttg cga aaa aca ctt     2127
Arg Ala Gly Arg Leu Ala Val His Lys Tyr Gly Leu Arg Lys Thr Leu
                510                 515                 520 gag cat ata cag atg acc ggt aga ttc ccg gtt taa gaacccaaat          2173
Glu His Ile Gln Met Thr Gly Arg Phe Pro Val
            525                 530 ggacaaggtc ttctacttta tttataggat ccttggtaga ttattattat atgctctaat   2233
tcttttggtg gaaaatgtac tctcgaccat attcttatgt gtagtctcat tcgatgattc   2293
tttgtattcc tctgttaaaa tccatcagaa tcagattcag tgttttcttt gtt          2346
```

<210> SEQ ID NO 60
<211> LENGTH: 20
<212> TYPE: PRT
<213> ORGANISM: Arabidopsis thaliana

<400> SEQUENCE: 60

Gln Glu Asn Glu Asp Ile Asp Arg Ala Ile Ala Leu Ser Leu Leu Glu
1               5                   10                  15

Glu Asn Gln Glu
            20

<210> SEQ ID NO 61
<211> LENGTH: 20
<212> TYPE: PRT
<213> ORGANISM: Unknown
<220> FEATURE:
<223> OTHER INFORMATION: UIM motif

<400> SEQUENCE: 61

Asp Asp Thr Ala Leu Leu Gln Gln Ala Ile Ala Met Ser Met Ala Gln
1               5                   10                  15

Ala Ala Gln Ala
            20

<210> SEQ ID NO 62
<211> LENGTH: 20
<212> TYPE: PRT
<213> ORGANISM: Unknown
<220> FEATURE:
<223> OTHER INFORMATION: UIM motif

<400> SEQUENCE: 62

Asp Ser Glu Ala Glu Leu Gln Lys Ala Ile Gln Leu Ser Lys Glu Glu
1               5                   10                  15

Asp Glu Ala Arg
            20

```
<210> SEQ ID NO 63
<211> LENGTH: 20
<212> TYPE: PRT
<213> ORGANISM: Unknown
<220> FEATURE:
<223> OTHER INFORMATION: UIM motif

<400> SEQUENCE: 63

Asp Glu Glu Glu Leu Ile Arg Lys Ala Ile Glu Leu Ser Leu Lys Glu
1               5                   10                  15

Ser Arg Asn Ser
            20

<210> SEQ ID NO 64
<211> LENGTH: 20
<212> TYPE: PRT
<213> ORGANISM: Unknown
<220> FEATURE:
<223> OTHER INFORMATION: UIM motif

<400> SEQUENCE: 64

Ser Tyr Gln Asp Asp Leu Glu Lys Ala Leu Glu Glu Ser Arg Ile Thr
1               5                   10                  15

Ala Gln Glu Asp
            20

<210> SEQ ID NO 65
<211> LENGTH: 20
<212> TYPE: PRT
<213> ORGANISM: Unknown
<220> FEATURE:
<223> OTHER INFORMATION: UIM motif

<400> SEQUENCE: 65

Glu Asp Asp Pro Asn Ile Leu Leu Ala Ile Gln Leu Ser Leu Gln Glu
1               5                   10                  15

Ser Gly Leu Ala
            20

<210> SEQ ID NO 66
<211> LENGTH: 20
<212> TYPE: PRT
<213> ORGANISM: Unknown
<220> FEATURE:
<223> OTHER INFORMATION: UIM motif

<400> SEQUENCE: 66

Glu Glu Glu Glu Leu Leu Arg Lys Ala Ile Ala Glu Ser Leu Asn Ser
1               5                   10                  15

Cys Arg Pro Ser
            20

<210> SEQ ID NO 67
<211> LENGTH: 20
<212> TYPE: PRT
<213> ORGANISM: Unknown
<220> FEATURE:
<223> OTHER INFORMATION: UIM motif

<400> SEQUENCE: 67

Asp Glu Asp Leu Gln Leu Gln Leu Ala Leu Ser Leu Ser Arg Gln Glu
1               5                   10                  15

His Glu Lys Gly
            20
```

```
<210> SEQ ID NO 68
<211> LENGTH: 20
<212> TYPE: PRT
<213> ORGANISM: Unknown
<220> FEATURE:
<223> OTHER INFORMATION: UIM motif

<400> SEQUENCE: 68

Gln Glu Glu Asp Asp Ile Ala Lys Ala Ile Glu Leu Ser Leu Lys Glu
1               5                   10                  15

Asn Lys Gly Ser
            20

<210> SEQ ID NO 69
<211> LENGTH: 20
<212> TYPE: PRT
<213> ORGANISM: Unknown
<220> FEATURE:
<223> OTHER INFORMATION: UIM motif

<400> SEQUENCE: 69

Ser Glu Glu Asp Gln Ile Ala Tyr Ala Leu Arg Met Ser Leu Gln Gln
1               5                   10                  15

Met Gly Glu Glu
            20

<210> SEQ ID NO 70
<211> LENGTH: 21
<212> TYPE: PRT
<213> ORGANISM: Unknown
<220> FEATURE:
<223> OTHER INFORMATION: UIM motif

<400> SEQUENCE: 70

His Glu Ala Glu Gln Leu Asp Leu Ala Ile Gln Glu Phe Ser Arg Gln
1               5                   10                  15

Glu Glu Glu Glu Glu
            20

<210> SEQ ID NO 71
<211> LENGTH: 20
<212> TYPE: PRT
<213> ORGANISM: Unknown
<220> FEATURE:
<223> OTHER INFORMATION: UIM motif

<400> SEQUENCE: 71

Glu Glu Glu Asn Gln Ile Gln Leu Ala Leu Gly Leu Ser Ala Arg Glu
1               5                   10                  15

Asp Pro Glu Ala
            20

<210> SEQ ID NO 72
<211> LENGTH: 20
<212> TYPE: PRT
<213> ORGANISM: Unknown
<220> FEATURE:
<223> OTHER INFORMATION: UIM motif
<220> FEATURE:
<221> NAME/KEY: Variant
<222> LOCATION: (19)..(20)
<223> OTHER INFORMATION: Xaa is any amino acid

<400> SEQUENCE: 72

Asn Val Asp Glu Asp Leu Gln Leu Ala Ile Ala Leu Ser Leu Ser Glu
```

```
                 1               5                  10                 15
Ile Asn Xaa Xaa
            20

<210> SEQ ID NO 73
<211> LENGTH: 20
<212> TYPE: PRT
<213> ORGANISM: Unknown
<220> FEATURE:
<223> OTHER INFORMATION: UIM motif

<400> SEQUENCE: 73

Glu Glu Asp Glu Leu Leu Ala Arg Thr Leu Glu Glu Ser Leu Lys Glu
1               5                   10                  15

Asn Asn Arg Arg
            20

<210> SEQ ID NO 74
<211> LENGTH: 20
<212> TYPE: PRT
<213> ORGANISM: Unknown
<220> FEATURE:
<223> OTHER INFORMATION: UIM motif

<400> SEQUENCE: 74

Thr Glu Glu Glu Gln Phe Ala Leu Ala Leu Lys Met Ser Glu Gln Glu
1               5                   10                  15

Ala Arg Glu Val
            20

<210> SEQ ID NO 75
<211> LENGTH: 20
<212> TYPE: PRT
<213> ORGANISM: Unknown
<220> FEATURE:
<223> OTHER INFORMATION: UIM motif

<400> SEQUENCE: 75

Ser Asp Asp Glu Glu Leu Gln Leu Ala Ile Glu Ile Ser Lys Lys Thr
1               5                   10                  15

Phe Lys Asp Glu
            20

<210> SEQ ID NO 76
<211> LENGTH: 20
<212> TYPE: PRT
<213> ORGANISM: Unknown
<220> FEATURE:
<223> OTHER INFORMATION: UIM motif

<400> SEQUENCE: 76

Arg Glu Glu Gln Glu Leu Gln Gln Ala Leu Ala Gln Ser Leu Gln Glu
1               5                   10                  15

Gln Glu Ala Trp
            20

<210> SEQ ID NO 77
<211> LENGTH: 20
<212> TYPE: PRT
<213> ORGANISM: Unknown
<220> FEATURE:
<223> OTHER INFORMATION: UIM motif

<400> SEQUENCE: 77
```

```
Tyr Val Asp Pro Asp Leu Ala Met Ala Met Arg Leu Ser Gln Gln Glu
1               5                   10                  15

Gln Arg Lys Phe
            20

<210> SEQ ID NO 78
<211> LENGTH: 20
<212> TYPE: PRT
<213> ORGANISM: Unknown
<220> FEATURE:
<223> OTHER INFORMATION: UIM motif

<400> SEQUENCE: 78

Gly Asp Asp Gln Asp Leu Gln Leu Ala Leu Gln Leu Ser Val Gln Asp
1               5                   10                  15

Ser Ala Lys Glu
            20

<210> SEQ ID NO 79
<211> LENGTH: 20
<212> TYPE: PRT
<213> ORGANISM: Unknown
<220> FEATURE:
<223> OTHER INFORMATION: UIM motif

<400> SEQUENCE: 79

Ile Glu Glu Glu Met Ile Arg Ala Ala Ile Glu Ala Ser Lys Lys Glu
1               5                   10                  15

Ala Glu Gly Ser
            20

<210> SEQ ID NO 80
<211> LENGTH: 20
<212> TYPE: PRT
<213> ORGANISM: Unknown
<220> FEATURE:
<223> OTHER INFORMATION: UIM motif

<400> SEQUENCE: 80

Arg Glu Glu Glu Leu Gln Tyr Ala Leu Ala Leu Ser Leu Ser Glu
1               5                   10                  15

Ser Thr Ala Gln
            20

<210> SEQ ID NO 81
<211> LENGTH: 20
<212> TYPE: PRT
<213> ORGANISM: Unknown
<220> FEATURE:
<223> OTHER INFORMATION: UIM motif

<400> SEQUENCE: 81

Asp Asp Glu Asp Asp Leu Gln Arg Ala Leu Ala Met Ser Arg Gln Glu
1               5                   10                  15

Ile Asp Met Glu
            20

<210> SEQ ID NO 82
<211> LENGTH: 20
<212> TYPE: PRT
<213> ORGANISM: Unknown
<220> FEATURE:
<223> OTHER INFORMATION: UIM motif

<400> SEQUENCE: 82
```

-continued

Val Asp Asp Gln Asp Leu Ala Leu Ala Leu Gln Met Ser Val Gln Asp
1               5                   10                  15

Ala Gly Gly Ser
        20

<210> SEQ ID NO 83
<211> LENGTH: 20
<212> TYPE: PRT
<213> ORGANISM: Unknown
<220> FEATURE:
<223> OTHER INFORMATION: UIM motif

<400> SEQUENCE: 83

Asn Met Asp Pro Glu Leu Ala Met Ala Ile Arg Met Ser Leu Gln Glu
1               5                   10                  15

Ala Gln Ala Gln
        20

<210> SEQ ID NO 84
<211> LENGTH: 20
<212> TYPE: PRT
<213> ORGANISM: Unknown
<220> FEATURE:
<223> OTHER INFORMATION: UIM motif

<400> SEQUENCE: 84

Asn Lys Asp Glu Gln Leu Ala Leu Ile Val Gln Glu Ser Leu Asn Met
1               5                   10                  15

Glu Glu Tyr Pro
        20

<210> SEQ ID NO 85
<211> LENGTH: 20
<212> TYPE: PRT
<213> ORGANISM: Unknown
<220> FEATURE:
<223> OTHER INFORMATION: UIM motif

<400> SEQUENCE: 85

Glu Asp Asp Asp Leu Leu Gln Phe Ala Ile Gln Gln Ser Leu Leu Glu
1               5                   10                  15

Ala Gly Thr Glu
        20

<210> SEQ ID NO 86
<211> LENGTH: 20
<212> TYPE: PRT
<213> ORGANISM: Unknown
<220> FEATURE:
<223> OTHER INFORMATION: UIM motif

<400> SEQUENCE: 86

Glu Asn Asp Ile Gln Leu Arg Ile Ala Leu Leu Glu Ser Gln Glu Ala
1               5                   10                  15

Gln Ala Arg Asn
        20

<210> SEQ ID NO 87
<211> LENGTH: 20
<212> TYPE: PRT
<213> ORGANISM: Unknown
<220> FEATURE:
<223> OTHER INFORMATION: UIM motif -continued

```
<400> SEQUENCE: 87

Gln Glu Asp Glu Asp Leu Lys Leu Ala Leu Lys Met Ser Met Gln Tyr
1               5                   10                  15

Asn Pro Pro Glu
            20

<210> SEQ ID NO 88
<211> LENGTH: 20
<212> TYPE: PRT
<213> ORGANISM: Unknown
<220> FEATURE:
<223> OTHER INFORMATION: UIM motif

<400> SEQUENCE: 88

Asp Glu Asp Asp Met Leu Gln Tyr Ala Ile Glu Gln Ser Leu Val Glu
1               5                   10                  15

Thr Ser Gly Ala
            20

<210> SEQ ID NO 89
<211> LENGTH: 20
<212> TYPE: PRT
<213> ORGANISM: Unknown
<220> FEATURE:
<223> OTHER INFORMATION: UIM motif

<400> SEQUENCE: 89

Ser Glu Asp Glu Asp Leu Gln Leu Ala Met Ala Tyr Ser Leu Ser Glu
1               5                   10                  15

Met Glu Ala Ala
            20

<210> SEQ ID NO 90
<211> LENGTH: 20
<212> TYPE: PRT
<213> ORGANISM: Unknown
<220> FEATURE:
<223> OTHER INFORMATION: UIM motif

<400> SEQUENCE: 90

Asn Glu Asp Glu Asp Ile Lys Arg Ala Ile Glu Leu Ser Leu Lys Glu
1               5                   10                  15

Met Pro Gln Ser
            20

<210> SEQ ID NO 91
<211> LENGTH: 20
<212> TYPE: PRT
<213> ORGANISM: Unknown
<220> FEATURE:
<223> OTHER INFORMATION: UIM motif

<400> SEQUENCE: 91

Asp Glu Asp Glu Glu Leu Lys Arg Ala Ile Ala Ile Ser Leu Glu Glu
1               5                   10                  15

Ala Gln Lys Ser
            20

<210> SEQ ID NO 92
<211> LENGTH: 20
<212> TYPE: PRT
<213> ORGANISM: Unknown
<220> FEATURE:
<223> OTHER INFORMATION: UIM motif
```

-continued

<400> SEQUENCE: 92

Glu Asp Asp Glu Glu Phe Leu Arg Ala Ile Arg Gln Ser Arg Val Glu
1               5                   10                  15

Asp Glu Arg Arg
            20

<210> SEQ ID NO 93
<211> LENGTH: 20
<212> TYPE: PRT
<213> ORGANISM: Mus musculus

<400> SEQUENCE: 93

Gln Glu Gln Glu Asp Leu Glu Leu Ala Ile Ala Leu Ser Lys Ser Glu
1               5                   10                  15

Ile Ser Glu Ala
            20

<210> SEQ ID NO 94
<211> LENGTH: 20
<212> TYPE: PRT
<213> ORGANISM: Unknown
<220> FEATURE:
<223> OTHER INFORMATION: UIM motif

<400> SEQUENCE: 94

Ser Glu Glu Asp Val Leu Arg Ala Thr Val Thr Val Ser Leu Glu Thr
1               5                   10                  15

Ala Lys Asp Ser
            20

<210> SEQ ID NO 95
<211> LENGTH: 20
<212> TYPE: PRT
<213> ORGANISM: Arabidopsis thaliana

<400> SEQUENCE: 95

Glu Asp Ser Ala Leu Leu Asp Gln Ala Ile Ala Met Ser Val Gly Asp
1               5                   10                  15

Val Asn Met Ser
            20

<210> SEQ ID NO 96
<211> LENGTH: 20
<212> TYPE: PRT
<213> ORGANISM: Unknown
<220> FEATURE:
<223> OTHER INFORMATION: UIM motif

<400> SEQUENCE: 96

Gln His Glu Ala Asp Ile Gln Lys Ala Lys Gln Arg Ser Leu Ala Thr
1               5                   10                  15

His Glu Ala Glu
            20

<210> SEQ ID NO 97
<211> LENGTH: 20
<212> TYPE: PRT
<213> ORGANISM: Unknown
<220> FEATURE:
<223> OTHER INFORMATION: UIM motif

<400> SEQUENCE: 97

-continued

Glu Glu Asp Pro Asp Leu Lys Ala Ala Ile Gln Glu Ser Leu Arg Glu
1               5                   10                  15

Ala Glu Glu Ala
            20

<210> SEQ ID NO 98
<211> LENGTH: 20
<212> TYPE: PRT
<213> ORGANISM: Unknown
<220> FEATURE:
<223> OTHER INFORMATION: UIM motif

<400> SEQUENCE: 98

Glu Asn Asp Pro Glu Leu Gln Arg Val Ile Glu Glu Ser Lys Arg Gln
1               5                   10                  15

Ala Glu Glu Asp
            20

<210> SEQ ID NO 99
<211> LENGTH: 20
<212> TYPE: PRT
<213> ORGANISM: Unknown
<220> FEATURE:
<223> OTHER INFORMATION: UIM motif

<400> SEQUENCE: 99

Asp Asp Ala Gln Leu Leu Gln Gln Ala Leu Ala Met Ser Met Glu Glu
1               5                   10                  15

Gly Ser Ser Gly
            20

<210> SEQ ID NO 100
<211> LENGTH: 20
<212> TYPE: PRT
<213> ORGANISM: Unknown
<220> FEATURE:
<223> OTHER INFORMATION: UIM motif

<400> SEQUENCE: 100

Gln Glu Asp Asp Glu Leu Ala Gln Ala Leu Ala Leu Ser Leu Gly Asn
1               5                   10                  15

Ser Ser Glu Thr
            20

<210> SEQ ID NO 101
<211> LENGTH: 20
<212> TYPE: PRT
<213> ORGANISM: Unknown
<220> FEATURE:
<223> OTHER INFORMATION: UIM motif

<400> SEQUENCE: 101

Gly Asp Asp Leu Arg Leu Gln Met Ala Ile Glu Glu Ser Lys Arg Glu
1               5                   10                  15

Thr Gly Gly Lys
            20

<210> SEQ ID NO 102
<211> LENGTH: 20
<212> TYPE: PRT
<213> ORGANISM: Unknown
<220> FEATURE:
<223> OTHER INFORMATION: UIM motif

<400> SEQUENCE: 102

```
Phe Asp Lys Glu Glu Ile Glu Cys Ala Ile Ala Leu Ser Leu Ser Glu
1               5                   10                  15

Gln Glu His Val
            20

<210> SEQ ID NO 103
<211> LENGTH: 20
<212> TYPE: PRT
<213> ORGANISM: Unknown
<220> FEATURE:
<223> OTHER INFORMATION: UIM motif

<400> SEQUENCE: 103

Ser Asp Ser Ile Met Leu Lys Tyr Ala Ile Glu Leu Ser Leu Leu Asp
1               5                   10                  15

Ser Lys Glu Asp
            20

<210> SEQ ID NO 104
<211> LENGTH: 20
<212> TYPE: PRT
<213> ORGANISM: Unknown
<220> FEATURE:
<223> OTHER INFORMATION: UIM motif

<400> SEQUENCE: 104

Gln Asp Glu Glu Asp Phe Gln Arg Ala Leu Glu Leu Ser Arg Gln Glu
1               5                   10                  15

Thr Asn Arg Glu
            20

<210> SEQ ID NO 105
<211> LENGTH: 20
<212> TYPE: PRT
<213> ORGANISM: Unknown
<220> FEATURE:
<223> OTHER INFORMATION: UIM motif

<400> SEQUENCE: 105

Ser Asp Asp Glu Glu Leu Gln Lys Ala Leu Lys Met Ser Leu Phe Glu
1               5                   10                  15

Tyr Glu Lys Gln
            20

<210> SEQ ID NO 106
<211> LENGTH: 20
<212> TYPE: PRT
<213> ORGANISM: Unknown
<220> FEATURE:
<223> OTHER INFORMATION: UIM motif

<400> SEQUENCE: 106

Asp Glu Asp Glu Gln Leu Arg Arg Ala Leu Glu Glu Ser Gln Leu Ile
1               5                   10                  15

Tyr Glu Thr Gln
            20

<210> SEQ ID NO 107
<211> LENGTH: 20
<212> TYPE: PRT
<213> ORGANISM: Unknown
<220> FEATURE:
<223> OTHER INFORMATION: UIM motif
```

```
<400> SEQUENCE: 107

Ser Glu Glu Ala Met Leu Gln Gln Ala Leu Ala Met Ser Met Gln Met
1               5                   10                  15

Asn Asn Thr Glu
            20

<210> SEQ ID NO 108
<211> LENGTH: 20
<212> TYPE: PRT
<213> ORGANISM: Unknown
<220> FEATURE:
<223> OTHER INFORMATION: UIM motif

<400> SEQUENCE: 108

Lys Glu Asp Asp Leu Lys Arg Ala Thr Glu Leu Ser Leu Gln Glu
1               5                   10                  15

Phe Asn Asn Ser
            20

<210> SEQ ID NO 109
<211> LENGTH: 20
<212> TYPE: PRT
<213> ORGANISM: Unknown
<220> FEATURE:
<223> OTHER INFORMATION: UIM motif

<400> SEQUENCE: 109

Glu Asn Asp Asp Leu Gln Arg Ala Ile Ser Ala Ser Arg Leu Thr
1               5                   10                  15

Ala Glu Glu Asp
            20

<210> SEQ ID NO 110
<211> LENGTH: 20
<212> TYPE: PRT
<213> ORGANISM: Unknown
<220> FEATURE:
<223> OTHER INFORMATION: UIM motif

<400> SEQUENCE: 110

Lys Glu Asp Glu Asp Ile Ala Lys Ala Ile Glu Leu Ser Leu Gln Glu
1               5                   10                  15

Gln Lys Gln Gln
            20

<210> SEQ ID NO 111
<211> LENGTH: 20
<212> TYPE: PRT
<213> ORGANISM: Mus musculus

<400> SEQUENCE: 111

Ser Glu Glu Asp Met Ile Glu Trp Ala Lys Arg Glu Ser Glu Arg Glu
1               5                   10                  15

Glu Glu Gln Arg
            20

<210> SEQ ID NO 112
<211> LENGTH: 20
<212> TYPE: PRT
<213> ORGANISM: Unknown
<220> FEATURE:
<223> OTHER INFORMATION: UIM motif

<400> SEQUENCE: 112
```

```
Asp Glu Asp Glu Glu Tyr Met Arg Ala Gln Leu Glu Ala Ala Glu Glu
1               5                   10                  15

Glu Glu Arg Arg
            20

<210> SEQ ID NO 113
<211> LENGTH: 20
<212> TYPE: PRT
<213> ORGANISM: Unknown
<220> FEATURE:
<223> OTHER INFORMATION: UIM motif

<400> SEQUENCE: 113

Ser Glu Glu Glu Leu Leu Ala Ala Val Leu Glu Ile Ser Lys Arg Asp
1               5                   10                  15

Ala Ser Pro Ser
            20

<210> SEQ ID NO 114
<211> LENGTH: 20
<212> TYPE: PRT
<213> ORGANISM: Unknown
<220> FEATURE:
<223> OTHER INFORMATION: UIM motif

<400> SEQUENCE: 114

Glu Asp Asp Asp Asp Ile Ala Ile Ala Val Thr Met Ser Leu Lys Ser
1               5                   10                  15

Ala Glu Glu Glu
            20

<210> SEQ ID NO 115
<211> LENGTH: 20
<212> TYPE: PRT
<213> ORGANISM: Unknown
<220> FEATURE:
<223> OTHER INFORMATION: UIM motif

<400> SEQUENCE: 115

Gln Asp Asp Glu Asn Leu Arg Met Ala Ile Leu Glu Ser Leu Gln Glu
1               5                   10                  15

Leu Asn Thr Asn
            20

<210> SEQ ID NO 116
<211> LENGTH: 20
<212> TYPE: PRT
<213> ORGANISM: Drosophila melanogaster

<400> SEQUENCE: 116

Asn Glu Asp Pro Glu Leu Ala Leu Ala Leu Arg Val Ser Met Glu Glu
1               5                   10                  15

Gln Arg Gln Arg
            20

<210> SEQ ID NO 117
<211> LENGTH: 20
<212> TYPE: PRT
<213> ORGANISM: Unknown
<220> FEATURE:
<223> OTHER INFORMATION: UIM motif

<400> SEQUENCE: 117
```

Arg Glu Asp Glu His Leu Arg Ser Thr Ile Glu Leu Ser Met Gln Gly
1               5                   10                  15

Ser Ser Gly Asn
            20

<210> SEQ ID NO 118
<211> LENGTH: 20
<212> TYPE: PRT
<213> ORGANISM: Unknown
<220> FEATURE:
<223> OTHER INFORMATION: UIM motif

<400> SEQUENCE: 118

Ser Asp Asp Val Arg Leu Gln Leu Ala Leu Ser Gln Ser Glu Gln Asp
1               5                   10                  15

Phe Lys Asp Pro
            20

<210> SEQ ID NO 119
<211> LENGTH: 20
<212> TYPE: PRT
<213> ORGANISM: Unknown
<220> FEATURE:
<223> OTHER INFORMATION: UIM motif

<400> SEQUENCE: 119

Asp Glu Asp Pro Asp Phe Gln Ala Ala Leu Gln Leu Ser Lys Glu Glu
1               5                   10                  15

Glu Glu Leu Lys
            20

<210> SEQ ID NO 120
<211> LENGTH: 20
<212> TYPE: PRT
<213> ORGANISM: Unknown
<220> FEATURE:
<223> OTHER INFORMATION: UIM motif

<400> SEQUENCE: 120

Gly Asp Asp Leu Arg Leu Gln Met Ala Leu Glu Glu Ser Arg Lys Gly
1               5                   10                  15

Ala Pro Ser Lys
            20

<210> SEQ ID NO 121
<211> LENGTH: 20
<212> TYPE: PRT
<213> ORGANISM: Unknown
<220> FEATURE:
<223> OTHER INFORMATION: UIM motif

<400> SEQUENCE: 121

Thr Glu Glu Glu Gln Ile Ala Tyr Ala Met Gln Met Ser Leu Gln Gly
1               5                   10                  15

Ala Glu Phe Gly
            20

<210> SEQ ID NO 122
<211> LENGTH: 20
<212> TYPE: PRT
<213> ORGANISM: Unknown
<220> FEATURE:
<223> OTHER INFORMATION: UIM motif

<400> SEQUENCE: 122

-continued

Gly Asp Asp Gln Asp Leu Ala Tyr Ala Leu Gln Met Ser Met Gln Gln
1               5                   10                  15

Ala Ala Ala Ala
            20

<210> SEQ ID NO 123
<211> LENGTH: 20
<212> TYPE: PRT
<213> ORGANISM: Unknown
<220> FEATURE:
<223> OTHER INFORMATION: UIM motif
<220> FEATURE:
<221> NAME/KEY: Variant
<222> LOCATION: (18)..(20)
<223> OTHER INFORMATION: Xaa is any amino acid

<400> SEQUENCE: 123

Gln Glu Gln Glu Met Ile Glu Gln Ala Leu Lys Leu Ser Leu Gln Glu
1               5                   10                  15

His Xaa Xaa Xaa
            20

<210> SEQ ID NO 124
<211> LENGTH: 20
<212> TYPE: PRT
<213> ORGANISM: Unknown
<220> FEATURE:
<223> OTHER INFORMATION: UIM motif

<400> SEQUENCE: 124

Thr Glu Glu Gln Gln Leu Glu Trp Ala Leu Arg Leu Ser Met Gln Glu
1               5                   10                  15

Asn Ala Pro Ala
            20

<210> SEQ ID NO 125
<211> LENGTH: 20
<212> TYPE: PRT
<213> ORGANISM: Unknown
<220> FEATURE:
<223> OTHER INFORMATION: UIM motif

<400> SEQUENCE: 125

Glu Glu Glu Glu Glu Leu Gln Arg Ala Leu Ala Ala Ser Leu Glu Asp
1               5                   10                  15

Asn Asn Met Lys
            20

<210> SEQ ID NO 126
<211> LENGTH: 20
<212> TYPE: PRT
<213> ORGANISM: Unknown
<220> FEATURE:
<223> OTHER INFORMATION: UIM motif

<400> SEQUENCE: 126

Lys Glu Glu Glu Asp Leu Ala Leu Ala Ile Ala Ile Ser Gln Ser Glu
1               5                   10                  15

Ala Glu Ala Lys
            20

<210> SEQ ID NO 127
<211> LENGTH: 20
<212> TYPE: PRT

```
<213> ORGANISM: Unknown
<220> FEATURE:
<223> OTHER INFORMATION: UIM motif

<400> SEQUENCE: 127

Ser Glu Asp Glu Ala Leu Gln Arg Ala Leu Glu Leu Ser Leu Ala Glu
1               5                   10                  15

Ala Lys Pro Gln
            20

<210> SEQ ID NO 128
<211> LENGTH: 20
<212> TYPE: PRT
<213> ORGANISM: Unknown
<220> FEATURE:
<223> OTHER INFORMATION: UIM motif

<400> SEQUENCE: 128

Gln Glu Glu Asp Asp Leu Ala Leu Ala Gln Ala Leu Ser Ala Ser Glu
1               5                   10                  15

Ala Glu Tyr Gln
            20

<210> SEQ ID NO 129
<211> LENGTH: 20
<212> TYPE: PRT
<213> ORGANISM: Unknown
<220> FEATURE:
<223> OTHER INFORMATION: UIM motif

<400> SEQUENCE: 129

Ser Glu Glu Asp Met Leu Gln Ala Ala Val Thr Met Ser Leu Glu Thr
1               5                   10                  15

Val Arg Asn Asp
            20

<210> SEQ ID NO 130
<211> LENGTH: 20
<212> TYPE: PRT
<213> ORGANISM: Unknown
<220> FEATURE:
<223> OTHER INFORMATION: UIM motif

<400> SEQUENCE: 130

Ile Glu Asn Lys Met Ile Lys Leu Ala Met Lys Glu Ser Leu Leu Gly
1               5                   10                  15

Ser Glu Asp Gly
            20

<210> SEQ ID NO 131
<211> LENGTH: 20
<212> TYPE: PRT
<213> ORGANISM: Unknown
<220> FEATURE:
<223> OTHER INFORMATION: UIM motif

<400> SEQUENCE: 131

Asp Glu Asp Glu Gln Leu Ala Lys Ala Val Glu Glu Ser Leu Lys Gly
1               5                   10                  15

Lys Gly Gln Ile
            20

<210> SEQ ID NO 132
<211> LENGTH: 20
```

<212> TYPE: PRT
<213> ORGANISM: Unknown
<220> FEATURE:
<223> OTHER INFORMATION: UIM motif

<400> SEQUENCE: 132

Asp Glu Glu Ala Ala Ile Ala Arg Ala Ile Ala Met Ser Leu Glu Gly
1               5                   10                  15

Gln Glu Glu Gly
        20

<210> SEQ ID NO 133
<211> LENGTH: 20
<212> TYPE: PRT
<213> ORGANISM: Homo sapiens

<400> SEQUENCE: 133

Asp Asp Lys Asp Asp Leu Gln Arg Ala Ile Ala Leu Ser Leu Ala Glu
1               5                   10                  15

Ser Asn Arg Ala
        20

<210> SEQ ID NO 134
<211> LENGTH: 20
<212> TYPE: PRT
<213> ORGANISM: Unknown
<220> FEATURE:
<223> OTHER INFORMATION: UIM motif

<400> SEQUENCE: 134

Ser Asp Asp Ala Arg Leu Gln Met Ala Leu Glu Glu Ser Gln Lys Asp
1               5                   10                  15

Ala Asp Arg Leu
        20

<210> SEQ ID NO 135
<211> LENGTH: 20
<212> TYPE: PRT
<213> ORGANISM: Unknown
<220> FEATURE:
<223> OTHER INFORMATION: UIM motif

<400> SEQUENCE: 135

Gly Val Pro Asp Asp Leu Ala Leu Gly Leu Glu Leu Ser Arg Arg Glu
1               5                   10                  15

Gln Gln Pro Ser
        20

<210> SEQ ID NO 136
<211> LENGTH: 20
<212> TYPE: PRT
<213> ORGANISM: Unknown
<220> FEATURE:
<223> OTHER INFORMATION: UIM motif

<400> SEQUENCE: 136

Phe Asp Asn Ile Met Leu Glu Ala Ala Ile Lys Gln Ser Leu Leu Asp
1               5                   10                  15

Leu Lys Gly Asp
        20

<210> SEQ ID NO 137
<211> LENGTH: 20
<212> TYPE: PRT

-continued

```
<213> ORGANISM: Unknown
<220> FEATURE:
<223> OTHER INFORMATION: UIM motif

<400> SEQUENCE: 137

Asp Glu Asp Glu Gln Leu Ala Arg Ala Leu Gln Glu Ser Met Val Val
1               5                   10                  15

Gly Asn Ser Pro
            20

<210> SEQ ID NO 138
<211> LENGTH: 20
<212> TYPE: PRT
<213> ORGANISM: Unknown
<220> FEATURE:
<223> OTHER INFORMATION: UIM motif

<400> SEQUENCE: 138

Glu Asp Asp Asp Asp Leu Asp Lys Ala Ile Ala Leu Ser Leu Gln Gly
1               5                   10                  15

Ser Val Ala Gly
            20

<210> SEQ ID NO 139
<211> LENGTH: 20
<212> TYPE: PRT
<213> ORGANISM: Unknown
<220> FEATURE:
<223> OTHER INFORMATION: UIM motif

<400> SEQUENCE: 139

Gln Glu Asn Glu Asp Ile Asp Arg Ala Ile Ala Leu Ser Leu Leu Glu
1               5                   10                  15

Glu Asn Gln Glu
            20

<210> SEQ ID NO 140
<211> LENGTH: 20
<212> TYPE: PRT
<213> ORGANISM: Arabidopsis thaliana

<400> SEQUENCE: 140

Asp Glu Asp Gln Asp Leu Ala Leu Ala Leu Gln Met Ser Met Ser Gly
1               5                   10                  15

Glu Glu Ser Ser
            20

<210> SEQ ID NO 141
<211> LENGTH: 20
<212> TYPE: PRT
<213> ORGANISM: Unknown
<220> FEATURE:
<223> OTHER INFORMATION: UIM motif

<400> SEQUENCE: 141

Asp Glu Glu Ala Asp Leu Arg Arg Ala Ile Gln Leu Ser Met Gln Gly
1               5                   10                  15

Ser Ser Arg Gly
            20

<210> SEQ ID NO 142
<211> LENGTH: 20
<212> TYPE: PRT
<213> ORGANISM: Unknown
```

```
<220> FEATURE:
<223> OTHER INFORMATION: UIM motif

<400> SEQUENCE: 142

Arg Phe Glu Glu Gln Leu Arg Leu Ala Leu Glu Leu Ser Ser Arg Glu
1               5                   10                  15

Gln Glu Glu Arg
            20

<210> SEQ ID NO 143
<211> LENGTH: 20
<212> TYPE: PRT
<213> ORGANISM: Unknown
<220> FEATURE:
<223> OTHER INFORMATION: UIM motif

<400> SEQUENCE: 143

Asp Glu Asn Ala Leu Leu Gln Gln Ala Leu Ala Met Ser Met Asp Glu
1               5                   10                  15

Pro Ala Ser Thr
            20

<210> SEQ ID NO 144
<211> LENGTH: 20
<212> TYPE: PRT
<213> ORGANISM: Unknown
<220> FEATURE:
<223> OTHER INFORMATION: UIM motif

<400> SEQUENCE: 144

Glu Glu Asp Glu Glu Leu Lys Arg Ala Leu Ala Met Ser Arg Gly Glu
1               5                   10                  15

Gly Gly Asp Ile
            20

<210> SEQ ID NO 145
<211> LENGTH: 20
<212> TYPE: PRT
<213> ORGANISM: Unknown
<220> FEATURE:
<223> OTHER INFORMATION: UIM motif

<400> SEQUENCE: 145

Arg Glu Asp Glu Asp Ile Ala Arg Ala Ile Ser Met Ser Leu Glu Ala
1               5                   10                  15

Met Ser Tyr Leu
            20

<210> SEQ ID NO 146
<211> LENGTH: 20
<212> TYPE: PRT
<213> ORGANISM: Drosophila melanogaster

<400> SEQUENCE: 146

Thr Glu Glu Ala Met Leu Gln Arg Ala Leu Ala Leu Ser Thr Glu Thr
1               5                   10                  15

Pro Glu Asp Asn
            20

<210> SEQ ID NO 147
<211> LENGTH: 20
<212> TYPE: PRT
<213> ORGANISM: Unknown
<220> FEATURE:
```

<223> OTHER INFORMATION: UIM motif

<400> SEQUENCE: 147

Asn Glu Ser Glu Met Leu Gln Gln Ala Ile Gln Met Ser Thr Arg Asp
1               5                   10                  15

Tyr Met Glu Asp
            20

<210> SEQ ID NO 148
<211> LENGTH: 20
<212> TYPE: PRT
<213> ORGANISM: Unknown
<220> FEATURE:
<223> OTHER INFORMATION: UIM motif

<400> SEQUENCE: 148

Glu Glu Glu Leu Gln Leu Gln Leu Ala Leu Ala Met Ser Arg Glu Glu
1               5                   10                  15

Ala Glu Lys Pro
            20

<210> SEQ ID NO 149
<211> LENGTH: 20
<212> TYPE: PRT
<213> ORGANISM: Arabidopsis thaliana

<400> SEQUENCE: 149

Asp Glu Asp Glu Gln Leu Ala Arg Ala Leu Gln Glu Ser Met Val Val
1               5                   10                  15

Gly Asn Ser Pro
            20

<210> SEQ ID NO 150
<211> LENGTH: 53
<212> TYPE: PRT
<213> ORGANISM: Arabidopsis thaliana

<400> SEQUENCE: 150

Ile Cys Ala Gly Cys Asn Met Glu Ile Gly His Gly Arg Phe Leu Asn
1               5                   10                  15

Cys Leu Asn Ser Leu Trp His Pro Glu Cys Phe Arg Cys Tyr Gly Cys
                20                  25                  30

Ser Gln Pro Ile Ser Glu Tyr Glu Phe Ser Thr Ser Gly Asn Tyr Pro
            35                  40                  45

Phe His Lys Ala Cys
        50

<210> SEQ ID NO 151
<211> LENGTH: 56
<212> TYPE: PRT
<213> ORGANISM: Unknown
<220> FEATURE:
<223> OTHER INFORMATION: LIM domain

<400> SEQUENCE: 151

Arg Cys Asn Ala Cys Thr Lys Pro Ile Thr Gly Ile Gly Gly Ala Lys
1               5                   10                  15

Phe Ile Ser Phe Glu Asp Arg His Trp His Asn Asp Cys Phe Ile Cys
                20                  25                  30

Ala Gln Cys Thr Thr Ser Leu Val Gly Lys Gly Phe Ile Thr Asp Gly
            35                  40                  45

His Glu Ile Leu Cys Pro Glu Lys
    50              55

<210> SEQ ID NO 152
<211> LENGTH: 56
<212> TYPE: PRT
<213> ORGANISM: Xenopus laevis

<400> SEQUENCE: 152

Lys Cys Ala Ala Cys Gln Gln Gly Ile Pro Pro Thr Gln Val Val Arg
1               5                   10                  15

Arg Ala Gln Glu Phe Val Tyr His Leu His Cys Phe Ala Cys Ile Val
            20                  25                  30

Cys Lys Arg Gln Leu Ala Thr Gly Asp Glu Phe Tyr Leu Met Glu Asp
        35                  40                  45

Ser Arg Leu Val Cys Lys Ala Asp
    50              55

<210> SEQ ID NO 153
<211> LENGTH: 58
<212> TYPE: PRT
<213> ORGANISM: Unknown
<220> FEATURE:
<223> OTHER INFORMATION: LIM domain

<400> SEQUENCE: 153

Phe Cys Cys Ser Cys Tyr Lys Phe Leu Thr Glu Glu Asp Asp Ile Ile
1               5                   10                  15

Val Ile Asp Lys Glu Lys Tyr His Asn Lys Cys Phe Lys Cys Ser Ser
            20                  25                  30

Cys Lys Glu Val Ile Arg Gly Asn Asn Phe Ser Arg Glu Gln Met Thr
        35                  40                  45

Ser Thr Ser Ser Asn Tyr Cys Cys Asn Thr
    50              55

<210> SEQ ID NO 154
<211> LENGTH: 54
<212> TYPE: PRT
<213> ORGANISM: Homo sapiens
<220> FEATURE:
<221> NAME/KEY: Variant
<222> LOCATION: (12)..(12)
<223> OTHER INFORMATION: Xaa is any amino acid

<400> SEQUENCE: 154

Val Cys Phe His Cys Asn Arg Val Ile Glu Gly Xaa Asp Val Val Ser
1               5                   10                  15

Ala Leu Asn Lys Ala Trp Cys Val Asn Cys Phe Ala Cys Ser Thr Cys
            20                  25                  30

Asn Thr Lys Leu Thr Leu Lys Asn Lys Phe Val Glu Phe Asp Met Lys
        35                  40                  45

Pro Val Cys Lys Lys Cys
    50

<210> SEQ ID NO 155
<211> LENGTH: 56
<212> TYPE: PRT
<213> ORGANISM: Unknown
<220> FEATURE:
<223> OTHER INFORMATION: LIM domain

<400> SEQUENCE: 155

```
Arg Cys Ser Arg Cys His Gly Asp Phe Asp Lys Thr Asp Leu Val Met
1               5                   10                  15
Arg Ala Gly Pro Gln Asn Val Phe His Leu Asn Cys Phe Ala Cys Val
            20                  25                  30
Ala Cys Glu Lys Arg Leu Gln Thr Gly Glu Glu Phe Gln Ile Lys Asn
        35                  40                  45
Asn Ser Leu Tyr Cys Arg Ser Asp
    50                  55
```

<210> SEQ ID NO 156
<211> LENGTH: 54
<212> TYPE: PRT
<213> ORGANISM: Unknown
<220> FEATURE:
<223> OTHER INFORMATION: LIM domain

<400> SEQUENCE: 156

```
Thr Cys Ile Lys Cys Asn Lys Gly Ile Tyr Gly Gln Ser Asn Ala Cys
1               5                   10                  15
Gln Ala Leu Asp Ser Leu Tyr His Thr Gln Cys Phe Val Cys Cys Ser
            20                  25                  30
Cys Gly Arg Thr Leu Arg Cys Lys Ala Phe Tyr Ser Val Asn Gly Ser
        35                  40                  45
Val Tyr Cys Glu Glu Asp
    50
```

<210> SEQ ID NO 157
<211> LENGTH: 59
<212> TYPE: PRT
<213> ORGANISM: Unknown
<220> FEATURE:
<223> OTHER INFORMATION: LIM domain

<400> SEQUENCE: 157

```
Arg Cys Ala His Cys Asn Glu Glu Leu Gly Arg Gly Ala Ala Met Ile
1               5                   10                  15
Val Glu Ser Leu Asn Leu Phe Tyr His Leu Ala Cys Phe Lys Cys Tyr
            20                  25                  30
Val Cys Lys Thr Ser Leu Gly Ser Gly Ala Thr Gly Ala Asp Val Arg
        35                  40                  45
Val Arg Asp Gly Arg Leu His Cys Gln Thr Cys
    50                  55
```

<210> SEQ ID NO 158
<211> LENGTH: 57
<212> TYPE: PRT
<213> ORGANISM: Unknown
<220> FEATURE:
<223> OTHER INFORMATION: LIM domain

<400> SEQUENCE: 158

```
Lys Cys Ala Gly Cys Lys Asn Pro Ile Thr Gly Phe Gly Lys Gly Ser
1               5                   10                  15
Ser Val Val Ala Tyr Glu Gly Gln Ser Trp His Asp Tyr Cys Phe His
            20                  25                  30
Cys Lys Lys Cys Ser Val Asn Leu Ala Asn Lys Arg Phe Val Phe His
        35                  40                  45
Gln Glu Gln Val Tyr Cys Pro Asp Cys
    50                  55
```

```
<210> SEQ ID NO 159
<211> LENGTH: 53
<212> TYPE: PRT
<213> ORGANISM: Homo sapiens

<400> SEQUENCE: 159

Lys Cys Pro Arg Cys Gly Lys Ser Val Tyr Ala Ala Glu Lys Val Met
1               5                   10                  15

Gly Gly Gly Lys Pro Trp His Lys Thr Cys Phe Arg Cys Ala Ile Cys
            20                  25                  30

Gly Lys Ser Leu Glu Ser Thr Asn Val Thr Asp Lys Asp Gly Glu Leu
        35                  40                  45

Tyr Cys Lys Val Cys
    50

<210> SEQ ID NO 160
<211> LENGTH: 56
<212> TYPE: PRT
<213> ORGANISM: Unknown
<220> FEATURE:
<223> OTHER INFORMATION: LIM domain

<400> SEQUENCE: 160

Cys Cys Arg Lys Cys Glu Ile Pro Leu Asn Arg Glu Asp Met Val Met
1               5                   10                  15

Lys Ala Lys Glu Met Ile Phe His His Ala Cys Phe Val Cys Phe Ile
            20                  25                  30

Cys Gly Ile Lys Leu Asn Pro Gly Asp Tyr Tyr Thr Met Ser Pro Gln
        35                  40                  45

Gly His Leu Tyr Cys His Ala His
    50                  55

<210> SEQ ID NO 161
<211> LENGTH: 54
<212> TYPE: PRT
<213> ORGANISM: Unknown
<220> FEATURE:
<223> OTHER INFORMATION: LIM domain

<400> SEQUENCE: 161

Thr Cys Ala Glu Cys Gln Gln Leu Ile Gly His Asp Ser Arg Glu Leu
1               5                   10                  15

Phe Tyr Glu Asp Arg His Phe His Glu Gly Cys Phe Arg Cys Cys Arg
            20                  25                  30

Cys Gln Arg Ser Leu Ala Asp Glu Pro Phe Thr Arg Gly Asp Ser Glu
        35                  40                  45

Leu Leu Cys Asn Asp Cys
    50

<210> SEQ ID NO 162
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 162

Gln Cys Asn Val Cys Ser Lys Pro Ile Met Glu Xaa Arg Ile Leu Arg
1               5                   10                  15
```

-continued

```
Ala Thr Gly Lys Ala Tyr His Pro His Cys Phe Thr Cys Val Met Cys
                20                  25                  30

His Arg Ser Leu Asp Gly Ile Pro Phe Thr Val Asp Ala Gly Gly Leu
            35                  40                  45

Ile His Cys Ile Glu Asp
        50

<210> SEQ ID NO 163
<211> LENGTH: 54
<212> TYPE: PRT
<213> ORGANISM: Unknown
<220> FEATURE:
<223> OTHER INFORMATION: LIM domain

<400> SEQUENCE: 163

Arg Cys Ala Arg Cys Gly Glu Asn Val Val Gly Glu Gly Thr Gly Cys
1               5                   10                  15

Thr Ala Met Asp Gln Val Phe His Val Asp Cys Phe Thr Cys Ile Ile
                20                  25                  30

Cys Asn Asn Lys Leu Arg Gly Gln Pro Phe Tyr Ala Val Glu Lys Lys
            35                  40                  45

Ala Tyr Cys Glu Pro Cys
        50

<210> SEQ ID NO 164
<211> LENGTH: 53
<212> TYPE: PRT
<213> ORGANISM: Unknown
<220> FEATURE:
<223> OTHER INFORMATION: LIM domain

<400> SEQUENCE: 164

Asn Cys Ala Arg Cys Gly Lys Ile Val Tyr Pro Thr Glu Lys Val Asn
1               5                   10                  15

Cys Leu Asp Lys Phe Trp His Lys Ala Cys Phe His Cys Glu Thr Cys
                20                  25                  30

Lys Met Thr Leu Asn Met Lys Asn Tyr Lys Gly Tyr Glu Lys Lys Pro
            35                  40                  45

Tyr Cys Asn Ala His
        50

<210> SEQ ID NO 165
<211> LENGTH: 11
<212> TYPE: PRT
<213> ORGANISM: Unknown
<220> FEATURE:
<223> OTHER INFORMATION: LIM domain

<400> SEQUENCE: 165

Asp Cys Lys Asp Cys Asn Glu Met Met Glu Thr
1               5                   10

<210> SEQ ID NO 166
<211> LENGTH: 43
<212> TYPE: PRT
<213> ORGANISM: Unknown
<220> FEATURE:
<223> OTHER INFORMATION: LIM domain

<400> SEQUENCE: 166

Val Glu Cys His His His Ser Thr Thr Asp Thr Tyr His Pro Asn Cys
1               5                   10                  15
```

Phe Arg Cys Glu Thr Cys Arg Gln Leu Leu Val Asp Asn Ile Tyr Phe
                20                  25                  30

Phe Tyr Lys Asn Lys Tyr Tyr Cys Gly Arg His
            35                  40

<210> SEQ ID NO 167
<211> LENGTH: 54
<212> TYPE: PRT
<213> ORGANISM: Unknown
<220> FEATURE:
<223> OTHER INFORMATION: LIM domain

<400> SEQUENCE: 167

Lys Cys His Gly Cys Asp Phe Lys Ile Asp Ala Gly Asp Arg Phe Leu
1               5                   10                  15

Glu Ala Leu Gly Phe Ser Trp His Asp Thr Cys Phe Val Cys Ala Ile
                20                  25                  30

Cys Gln Ile Asn Leu Glu Gly Lys Thr Phe Tyr Ser Lys Lys Asp Arg
            35                  40                  45

Pro Leu Cys Lys Ser His
    50

<210> SEQ ID NO 168
<211> LENGTH: 56
<212> TYPE: PRT
<213> ORGANISM: Caenorhabditis elegans

<400> SEQUENCE: 168

Arg Cys Ala Gly Cys Asp Gly Lys Leu Glu Lys Glu Asp Leu Val Arg
1               5                   10                  15

Arg Ala Arg Asp Lys Val Phe His Ile Arg Cys Phe Gln Cys Ser Val
                20                  25                  30

Cys Gln Arg Leu Leu Asp Thr Gly Asp Gln Leu Tyr Ile Met Glu Gly
            35                  40                  45

Asn Arg Phe Val Cys Gln Ser Asp
    50                  55

<210> SEQ ID NO 169
<211> LENGTH: 53
<212> TYPE: PRT
<213> ORGANISM: Caenorhabditis elegans
<220> FEATURE:
<221> NAME/KEY: Variant
<222> LOCATION: (12)..(12)
<223> OTHER INFORMATION: Xaa is any amino acid

<400> SEQUENCE: 169

Cys Cys Gly Lys Cys Asn Glu Phe Ile Val Gly Xaa Arg Val Ile Lys
1               5                   10                  15

Ala Met Asn Ala Ser Trp His Pro Gly Cys Phe Cys Cys Glu Ile Cys
                20                  25                  30

Asn Lys Gln Leu Ala Asp Val Gly Phe Leu Arg Asn Ala Gly Arg Ala
            35                  40                  45

Leu Cys Arg Glu Cys
    50

<210> SEQ ID NO 170
<211> LENGTH: 53
<212> TYPE: PRT
<213> ORGANISM: Unknown
<220> FEATURE:

```
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 170

Leu Cys Ala Thr Cys Gly Leu Pro Val Thr Gly Xaa Arg Cys Val Ser
1               5                   10                  15

Ala Leu Gly Arg Arg Phe His Pro Asp His Phe Thr Cys Thr Phe Cys
            20                  25                  30

Leu Arg Pro Leu Thr Lys Gly Ser Phe Gln Glu Arg Ala Ser Lys Pro
        35                  40                  45

Tyr Cys Gln Pro Cys
    50

<210> SEQ ID NO 171
<211> LENGTH: 53
<212> TYPE: PRT
<213> ORGANISM: Rattus sp.

<400> SEQUENCE: 171

Lys Cys Pro Lys Cys Asp Lys Glu Val Tyr Phe Ala Glu Arg Val Thr
1               5                   10                  15

Ser Leu Gly Lys Asp Trp His Arg Pro Cys Leu Lys Cys Glu Lys Cys
            20                  25                  30

Gly Lys Thr Leu Thr Ser Gly Gly His Ala Glu His Glu Gly Lys Pro
        35                  40                  45

Tyr Cys Asn His Pro
    50

<210> SEQ ID NO 172
<211> LENGTH: 55
<212> TYPE: PRT
<213> ORGANISM: Homo sapiens

<400> SEQUENCE: 172

Gly Cys Ala Gly Cys Asn Arg Lys Ile Lys Asp Arg Tyr Leu Leu Lys
1               5                   10                  15

Ala Leu Asp Lys Tyr Trp His Glu Asp Cys Leu Lys Cys Ala Cys Cys
            20                  25                  30

Asp Cys Arg Leu Gly Glu Val Gly Ser Thr Leu Tyr Thr Lys Ala Asn
        35                  40                  45

Leu Ile Leu Cys Arg Arg Asp
    50                  55

<210> SEQ ID NO 173
<211> LENGTH: 11
<212> TYPE: PRT
<213> ORGANISM: Unknown
<220> FEATURE:
<223> OTHER INFORMATION: LIM domain

<400> SEQUENCE: 173

Arg Cys Ala Val Cys Ser Lys Pro Ile Val Pro
1               5                   10

<210> SEQ ID NO 174
<211> LENGTH: 47
<212> TYPE: PRT
<213> ORGANISM: Unknown
<220> FEATURE:
```

<223> OTHER INFORMATION: LIM domain

<400> SEQUENCE: 174

Glu Ser Ile Arg Ile Val Ala Met Asp Lys Ser Phe His Val Asn Cys
1               5                   10                  15

Tyr Arg Cys Glu Asp Cys Asn Met Gln Leu Asn Ser Lys Ile Glu Gly
                20                  25                  30

Gln Gly Cys Tyr Pro Leu Asp Gln His Leu Tyr Cys Lys Asn Cys
        35                  40                  45

<210> SEQ ID NO 175
<211> LENGTH: 55
<212> TYPE: PRT
<213> ORGANISM: Unknown
<220> FEATURE:
<223> OTHER INFORMATION: LIM domain

<400> SEQUENCE: 175

Ser Cys Val Arg Cys Lys Glu Phe Ile Thr Thr Gly His Ala Tyr Glu
1               5                   10                  15

Leu Gly Cys Asp Arg Trp His Thr His Cys Phe Ala Cys Tyr Lys Cys
                20                  25                  30

Glu Lys Pro Leu Ser Cys Glu Ser Asp Phe Leu Val Leu Gly Thr Gly
        35                  40                  45

Ala Leu Ile Cys Phe Asp Cys
        50                  55

<210> SEQ ID NO 176
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 176

Val Cys Phe Met Cys Thr Arg Pro Ile Leu Gly Xaa Val Met Ala Arg
1               5                   10                  15

Ala Ala Gly Lys Asn Leu His Gly Asp Cys Leu Ser Cys Ala Thr Cys
                20                  25                  30

Gly Asn Ser Leu Arg Asn Val Gly His His Phe Ile Glu Asp Lys Phe
        35                  40                  45

Tyr Cys Asp Ile His
        50

<210> SEQ ID NO 177
<211> LENGTH: 54
<212> TYPE: PRT
<213> ORGANISM: Caenorhabditis elegans
<220> FEATURE:
<221> NAME/KEY: Variant
<222> LOCATION: (12)..(12)
<223> OTHER INFORMATION: Xaa is any amino acid

<400> SEQUENCE: 177

Leu Cys Phe Lys Cys Gly Asp Pro Cys Cys Gly Xaa Glu Val Phe Gln
1               5                   10                  15

Ala Leu Gln Lys Thr Trp Cys Val Lys Cys Phe Ser Cys Ser Phe Cys
                20                  25                  30

```
Asp Lys Lys Leu Asp Gln Lys Thr Lys Phe Tyr Glu Phe Asp Met Lys
         35                  40                  45

Pro Thr Cys Lys Arg Cys
     50

<210> SEQ ID NO 178
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 178

Lys Cys Asp Val Cys Arg Lys Lys Cys Ser Gly Xaa Asp Val Leu Lys
1               5                  10                  15

Ala Asn Asp Lys Tyr Phe His Ile Asn Cys Phe Gln Cys Lys Lys Cys
            20                  25                  30

Gly Arg Asn Leu Gly Glu Thr Gly Phe Tyr Thr Thr Pro Glu Asn Ala
         35                  40                  45

Tyr Leu Cys Pro Asp Asp
     50

<210> SEQ ID NO 179
<211> LENGTH: 11
<212> TYPE: PRT
<213> ORGANISM: Unknown
<220> FEATURE:
<223> OTHER INFORMATION: LIM domain

<400> SEQUENCE: 179

Arg Cys Ser Val Cys Gly Gly Ala Ile Met Pro
1               5                  10

<210> SEQ ID NO 180
<211> LENGTH: 47
<212> TYPE: PRT
<213> ORGANISM: Homo sapiens

<400> SEQUENCE: 180

Glu Thr Val Arg Ile Val Ala Leu Asp Arg Ser Phe His Ile Gly Cys
1               5                  10                  15

Tyr Lys Cys Glu Glu Cys Gly Leu Leu Leu Ser Ser Glu Gly Glu Cys
            20                  25                  30

Gln Gly Cys Tyr Pro Leu Asp Gly His Ile Leu Cys Lys Ala Cys
         35                  40                  45

<210> SEQ ID NO 181
<211> LENGTH: 11
<212> TYPE: PRT
<213> ORGANISM: Mus musculus

<400> SEQUENCE: 181

Ser Cys Tyr Cys Cys Lys His Thr Thr Asn Glu
1               5                  10

<210> SEQ ID NO 182
<211> LENGTH: 43
<212> TYPE: PRT
<213> ORGANISM: Mus musculus
```

-continued

<400> SEQUENCE: 182

Ile Tyr Ala Glu Arg Ala Gly Tyr Asp Lys Leu Trp His Pro Ala Cys
1               5                   10                  15

Phe Ile Cys Ser Thr Cys Gly Glu Leu Leu Val Asp Met Ile Tyr Phe
                20                  25                  30

Trp Lys Asn Gly Lys Leu Tyr Cys Gly Arg His
                35                  40

<210> SEQ ID NO 183
<211> LENGTH: 56
<212> TYPE: PRT
<213> ORGANISM: Unknown
<220> FEATURE:
<223> OTHER INFORMATION: LIM domain

<400> SEQUENCE: 183

Lys Cys Ala Gly Cys Thr Asn Pro Ile Ser Gly Leu Gly Gly Thr Lys
1               5                   10                  15

Tyr Ile Ser Phe Glu Glu Arg Gln Trp His Asn Asp Cys Phe Asn Cys
                20                  25                  30

Lys Lys Cys Ser Leu Ser Leu Val Gly Arg Gly Phe Leu Thr Glu Arg
                35                  40                  45

Asp Asp Ile Leu Cys Pro Asp Cys
            50                  55

<210> SEQ ID NO 184
<211> LENGTH: 53
<212> TYPE: PRT
<213> ORGANISM: Mus musculus

<400> SEQUENCE: 184

Arg Cys Ala Gly Cys Asp Glu Leu Ile Phe Ser Asn Glu Tyr Thr Gln
1               5                   10                  15

Ala Glu Asn Gln Asn Trp His Leu Lys His Phe Cys Cys Phe Asp Cys
                20                  25                  30

Asp His Ile Leu Ala Gly Lys Ile Tyr Val Met Val Thr Asp Lys Pro
                35                  40                  45

Val Cys Lys Pro Cys
            50

<210> SEQ ID NO 185
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 185

His Cys Phe Ile Cys Asp Arg Asn Val Gly Gly Xaa Gly Met Val His
1               5                   10                  15

Val Phe Gly Lys Ala Phe Cys Pro Glu Cys Tyr Arg Cys Arg Gly Cys
                20                  25                  30

Asp Lys Val Leu His Tyr Lys Asp Lys Val Met Glu Leu Asp Leu Met
                35                  40                  45

Pro Leu Cys Lys Lys Cys
        50

```
<210> SEQ ID NO 186
<211> LENGTH: 52
<212> TYPE: PRT
<213> ORGANISM: Caenorhabditis elegans

<400> SEQUENCE: 186

Val Cys His Lys Cys His Ala Met Ile Asp Asp Gly Gln His Ile Lys
1               5                   10                  15

Phe Arg Gly Asp Ser Phe His Pro Tyr His Phe Lys Cys Lys Arg Cys
                20                  25                  30

Asn Asn Glu Leu Thr Thr Ala Ser Arg Glu Val Asn Gly Glu Leu Tyr
            35                  40                  45

Cys Leu Arg Cys
    50

<210> SEQ ID NO 187
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 187

Val Cys His Gln Cys His Lys Val Ile Arg Gly Xaa Arg Tyr Leu Val
1               5                   10                  15

Ala Leu Gly His Ala Tyr His Pro Glu Glu Phe Val Cys Ser Gln Cys
                20                  25                  30

Gly Lys Val Leu Glu Glu Gly Gly Phe Phe Glu Glu Lys Gly Ala Ile
            35                  40                  45

Phe Cys Pro Pro Cys
    50

<210> SEQ ID NO 188
<211> LENGTH: 54
<212> TYPE: PRT
<213> ORGANISM: Unknown
<220> FEATURE:
<223> OTHER INFORMATION: LIM domain

<400> SEQUENCE: 188

Lys Cys Lys Gly Cys Phe Lys Ala Ile Val Ala Gly Asp Gln Asn Val
1               5                   10                  15

Glu Tyr Lys Gly Thr Val Trp His Lys Asp Cys Phe Thr Cys Ser Asn
                20                  25                  30

Cys Lys Gln Val Ile Gly Thr Gly Ser Phe Phe Pro Lys Gly Glu Asp
            35                  40                  45

Phe Tyr Cys Val Thr Cys
    50

<210> SEQ ID NO 189
<211> LENGTH: 52
<212> TYPE: PRT
<213> ORGANISM: Caenorhabditis elegans

<400> SEQUENCE: 189

Ile Cys Ser Leu Cys Asp Lys Lys Ile Arg Asp Arg Phe Val Ser Lys
1               5                   10                  15
```

```
Val Asn Gly Arg Cys Tyr His Ser Ser Cys Leu Arg Cys Ser Thr Cys
         20                  25                  30

Lys Asp Glu Leu Gly Ala Thr Cys Phe Leu Arg Glu Asp Ser Met Tyr
         35                  40                  45

Cys Arg Ala His
         50

<210> SEQ ID NO 190
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 190

Leu Cys His Val Cys Asp Thr Pro Leu Arg Gly Xaa Leu Tyr Tyr Thr
1               5                   10                  15

Ala Phe Gly Tyr Arg Tyr Asp Glu Glu His Phe Ser Cys Thr Ile Cys
         20                  25                  30

Ala Thr Pro Cys Gly Val Lys Lys Cys Phe Met Tyr Gly Asn Gln Leu
         35                  40                  45

Tyr Cys Lys Tyr His
         50

<210> SEQ ID NO 191
<211> LENGTH: 54
<212> TYPE: PRT
<213> ORGANISM: Drosophila melanogaster

<400> SEQUENCE: 191

Asp Cys Ser Gly Cys Gly Arg Gln Ile Gln Asp Arg Phe Tyr Leu Ser
1               5                   10                  15

Ala Val Glu Lys Arg Trp His Ala Ser Cys Leu Gln Cys Tyr Ala Cys
         20                  25                  30

Arg Gln Pro Leu Glu Arg Glu Ser Ser Cys Tyr Ser Arg Asp Gly Asn
         35                  40                  45

Ile Tyr Cys Lys Asn Asp
         50

<210> SEQ ID NO 192
<211> LENGTH: 53
<212> TYPE: PRT
<213> ORGANISM: Unknown
<220> FEATURE:
<223> OTHER INFORMATION: LIM domain

<400> SEQUENCE: 192

Lys Cys Lys Ala Cys Glu Lys Thr Val Tyr Pro Val Glu Leu Leu Ser
1               5                   10                  15

Ala Asp Gly Val Asn Tyr His Lys Ser Cys Phe Lys Cys Ser His Cys
         20                  25                  30

Lys Gly Thr Leu Lys Leu Ser Asn Phe Ser Ser Met Glu Gly Val Leu
         35                  40                  45

Tyr Cys Lys Pro His
         50

<210> SEQ ID NO 193
```

```
<211> LENGTH: 54
<212> TYPE: PRT
<213> ORGANISM: Unknown
<220> FEATURE:
<223> OTHER INFORMATION: LIM domain

<400> SEQUENCE: 193

Gln Cys Ser Ala Cys Gly Glu Thr Val Met Pro Gly Ser Arg Lys Leu
1               5                   10                  15

Glu Tyr Gly Gly Gln Thr Trp His Glu His Cys Phe Leu Cys Ile Gly
            20                  25                  30

Cys Glu Gln Pro Leu Gly Ser Arg Pro Phe Val Pro Asp Lys Gly Ala
        35                  40                  45

His Tyr Cys Val Pro Cys
        50

<210> SEQ ID NO 194
<211> LENGTH: 52
<212> TYPE: PRT
<213> ORGANISM: Unknown
<220> FEATURE:
<223> OTHER INFORMATION: LIM domain

<400> SEQUENCE: 194

Val Cys Glu Gly Cys Gln Arg Val Ile Ser Asp Arg Phe Leu Leu Arg
1               5                   10                  15

Leu Asn Asp Ser Phe Trp His Glu Gln Cys Val Gln Cys Ala Ser Cys
            20                  25                  30

Lys Glu Pro Leu Glu Thr Thr Cys Phe Tyr Arg Asp Lys Lys Leu Tyr
        35                  40                  45

Cys Lys Tyr His
        50

<210> SEQ ID NO 195
<211> LENGTH: 52
<212> TYPE: PRT
<213> ORGANISM: Mus musculus

<400> SEQUENCE: 195

Val Cys Ala Ser Cys Gly Gln Arg Ile Tyr Asp Gly Gln Tyr Leu Gln
1               5                   10                  15

Ala Leu Asn Ala Asp Trp His Ala Asp Cys Phe Arg Cys Cys Glu Cys
            20                  25                  30

Ser Val Ser Leu Ser His Gln Tyr Tyr Glu Lys Asp Gly Gln Leu Phe
        35                  40                  45

Cys Lys Lys Asp
        50

<210> SEQ ID NO 196
<211> LENGTH: 57
<212> TYPE: PRT
<213> ORGANISM: Unknown
<220> FEATURE:
<223> OTHER INFORMATION: LIM domain

<400> SEQUENCE: 196

Asn Cys Tyr Ser Cys Asn Arg Pro Thr Leu Met Thr Arg Trp Lys Gln
1               5                   10                  15

Leu Leu Cys Ser Phe Glu Asn Arg His Trp His Gln Asn Cys Phe Thr
            20                  25                  30

Cys Asp Arg Cys Ser Asn Ser Leu Val Gly Gln Gly Phe Val Pro Asp
```

```
                35                  40                  45

Gly Asp Gln Val Leu Cys Gln Gly Cys
     50                  55

<210> SEQ ID NO 197
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 197

Ser Cys Thr Gly Cys Ser Leu Pro Val Ile Glu Xaa Arg Gly Leu Val
1               5                   10                  15

Ala Phe Asn Arg Leu Phe His Ile Asp Cys Phe Arg Cys Ala Ile Cys
            20                  25                  30

Asn Lys Thr Ile Pro Gln Arg Lys Gly Phe Tyr Glu Arg Asp Met Met
        35                  40                  45

Phe Tyr Asp Asp Val Cys
     50

<210> SEQ ID NO 198
<211> LENGTH: 53
<212> TYPE: PRT
<213> ORGANISM: Caenorhabditis elegans
<220> FEATURE:
<221> NAME/KEY: Variant
<222> LOCATION: (12)..(12)
<223> OTHER INFORMATION: Xaa is any amino acid

<400> SEQUENCE: 198

Lys Cys Asn Gly Cys Ser Gln Pro Ile Thr Ser Xaa Asn Phe Ile Thr
1               5                   10                  15

Ala Leu Gly Thr His Trp His Pro Asp Cys Phe Val Cys Gln His Cys
            20                  25                  30

Gly Val Ser Phe Asn Gly Ala Ser Phe Phe Glu His Asn Gly Ala Pro
        35                  40                  45

Leu Cys Glu Arg His
     50

<210> SEQ ID NO 199
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 199

Ser Cys Ala Lys Cys Lys Lys Ile Thr Gly Xaa Glu Ile Met His
1               5                   10                  15

Ala Leu Lys Met Thr Trp His Val His Cys Phe Thr Cys Ala Ala Cys
            20                  25                  30

Lys Thr Pro Ile Arg Asn Arg Ala Phe Tyr Met Glu Glu Gly Val Pro
        35                  40                  45

Tyr Cys Glu Arg Asp
```

<210> SEQ ID NO 200
<211> LENGTH: 11
<212> TYPE: PRT
<213> ORGANISM: Unknown
<220> FEATURE:
<223> OTHER INFORMATION: LIM domain

<400> SEQUENCE: 200

Lys Cys Ala Ala Cys Gly Gln Pro Ile Leu Pro
1               5                   10

<210> SEQ ID NO 201
<211> LENGTH: 46
<212> TYPE: PRT
<213> ORGANISM: Unknown
<220> FEATURE:
<223> OTHER INFORMATION: LIM domain

<400> SEQUENCE: 201

Asp Ile Val Arg Val Ile Ser Met Asp Arg Asp Tyr His Phe Glu Cys
1               5                   10                  15

Tyr His Cys Glu Asp Cys Arg Met Gln Leu Ser Asp Glu Glu Gly Cys
            20                  25                  30

Cys Cys Phe Pro Leu Asp Gly His Leu Leu Cys His Gly Cys
        35                  40                  45

<210> SEQ ID NO 202
<211> LENGTH: 11
<212> TYPE: PRT
<213> ORGANISM: Unknown
<220> FEATURE:
<223> OTHER INFORMATION: LIM domain

<400> SEQUENCE: 202

Glu Cys His Lys Cys Ser Gly Ile Leu Glu Thr
1               5                   10

<210> SEQ ID NO 203
<211> LENGTH: 43
<212> TYPE: PRT
<213> ORGANISM: Unknown
<220> FEATURE:
<223> OTHER INFORMATION: LIM domain

<400> SEQUENCE: 203

Val Ile Ala Pro Lys Leu Gly Asp Ser Thr Gly Trp His Pro Ala Cys
1               5                   10                  15

Phe Thr Cys Gln Ala Cys Glu Gln Leu Leu Val Asp Leu Thr Tyr Cys
            20                  25                  30

Val Lys Asp Asn Gln Ile Tyr Cys Glu Arg His
            35                  40

<210> SEQ ID NO 204
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 204

```
Lys Cys Asn Thr Cys Gly Glu Pro Ile Thr Asp Xaa Arg Met Leu Arg
1               5                   10                  15

Ala Thr Gly Lys Ala Tyr His Pro His Cys Phe Thr Cys Val Val Cys
                20                  25                  30

Ala Arg Pro Leu Glu Gly Thr Ser Phe Ile Val Asp Gln Ala Asn Arg
            35                  40                  45

Pro His Cys Val Pro Asp
        50

<210> SEQ ID NO 205
<211> LENGTH: 54
<212> TYPE: PRT
<213> ORGANISM: Unknown
<220> FEATURE:
<223> OTHER INFORMATION: LIM domain

<400> SEQUENCE: 205

Gly Cys Pro Arg Cys Gly Gly Tyr Val Tyr Ala Ala Glu Gln Met Leu
1               5                   10                  15

Ala Arg Gly Arg Ser Trp His Lys Glu Cys Phe Lys Cys Gly Thr Cys
                20                  25                  30

Lys Lys Gly Leu Asp Ser Ile Leu Cys Cys Glu Ala Pro Asp Lys Asn
            35                  40                  45

Ile Tyr Cys Lys Gly Cys
        50

<210> SEQ ID NO 206
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid
<220> FEATURE:
<221> NAME/KEY: Variant
<222> LOCATION: (50)..(53)
<223> OTHER INFORMATION: Xaa is any amino acid

<400> SEQUENCE: 206

Glu Cys Gly Arg Cys Gln Arg Lys Ile Leu Gly Xaa Glu Val Ile Asn
1               5                   10                  15

Ala Leu Lys Gln Thr Trp His Val Ser Cys Phe Val Cys Val Ala Cys
                20                  25                  30

Gly Lys Pro Ile Arg Asn Asn Val Phe His Leu Glu Asp Gly Glu Pro
            35                  40                  45

Tyr Xaa Xaa Xaa Xaa
        50

<210> SEQ ID NO 207
<211> LENGTH: 53
<212> TYPE: PRT
<213> ORGANISM: Caenorhabditis elegans
<220> FEATURE:
<221> NAME/KEY: Variant
<222> LOCATION: (12)..(12)
<223> OTHER INFORMATION: Xaa is any amino acid

<400> SEQUENCE: 207

Ile Cys Ser Gln Cys Arg Gly Ala Ile Asn Gly Xaa Arg Cys Val Ala
1               5                   10                  15
```

Ala Met Gly Arg Lys Phe His Pro Glu His Phe Arg Cys Ser Tyr Cys
            20                  25                  30

Asn His Gln Leu Thr Lys Gly Thr Phe Lys Glu Val Asp Arg Arg Pro
        35                  40                  45

Phe Cys His Lys Cys
    50

<210> SEQ ID NO 208
<211> LENGTH: 58
<212> TYPE: PRT
<213> ORGANISM: Caenorhabditis elegans

<400> SEQUENCE: 208

Arg Cys Ala Gly Cys Lys Lys Gly Val Ser Pro Thr Asp Met Val Tyr
1               5                   10                  15

Lys Leu Lys Ala Gly Leu Val Phe His Val Glu Cys His Cys Cys Ser
            20                  25                  30

Leu Cys Gly Arg His Leu Ser Pro Gly Glu Gln Ile Leu Val Asp Asp
        35                  40                  45

Thr Met Met Thr Val Ser Cys Met Ser His
    50                  55

<210> SEQ ID NO 209
<211> LENGTH: 55
<212> TYPE: PRT
<213> ORGANISM: Unknown
<220> FEATURE:
<223> OTHER INFORMATION: LIM domain

<400> SEQUENCE: 209

Arg Cys Arg Arg Cys Met Thr Leu Leu Leu Pro Thr Asp Ile Val His
1               5                   10                  15

Arg Val His Phe Met Tyr Tyr His Ala Gln Cys Phe Ser Cys Cys Ser
            20                  25                  30

Cys Gln Arg Pro Phe Asn Leu Gly Asp Glu Tyr His Val Phe Asp Gly
        35                  40                  45

Glu Val Phe Cys Arg Asn Asp
    50                  55

<210> SEQ ID NO 210
<211> LENGTH: 55
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 210

Phe Cys Glu Ser Cys Lys Gln Gln Ile Arg Gly Xaa Ala Phe Val Leu
1               5                   10                  15

Ala Thr Gly Lys Ser Trp Cys Pro Glu His Phe Val Cys Ala Asn Ser
            20                  25                  30

Ser Cys Arg Arg Arg Leu Leu Glu Cys Gly Phe Val Glu Glu Asp Gly
        35                  40                  45

Gln Lys Phe Cys Glu Ser Cys
    50                  55

-continued

```
<210> SEQ ID NO 211
<211> LENGTH: 55
<212> TYPE: PRT
<213> ORGANISM: Unknown
<220> FEATURE:
<223> OTHER INFORMATION: LIM domain

<400> SEQUENCE: 211
```

Lys Cys Ala Lys Cys Asn Ile Gly Phe Cys Ser Ser Asp Leu Val Met
1               5                   10                  15

Arg Ala Arg Asp Asn Val Tyr His Met Glu Cys Phe Cys Ser Val
            20                  25                  30

Cys Ser Arg His Leu Leu Pro Gly Asp Glu Phe Ser Leu Arg Asp Glu
        35                  40                  45

Glu Leu Leu Cys Arg Ala Asp
    50              55

```
<210> SEQ ID NO 212
<211> LENGTH: 52
<212> TYPE: PRT
<213> ORGANISM: Unknown
<220> FEATURE:
<223> OTHER INFORMATION: LIM domain

<400> SEQUENCE: 212
```

Ile Cys Thr Gln Cys Gln His Gln Ile Gln Asp Lys Phe Phe Leu Ser
1               5                   10                  15

Ile Asp Gly Arg Asn Tyr His Glu Asn Cys Leu Gln Cys Ser Thr Cys
            20                  25                  30

Glu Asn Pro Leu Ser Asn Lys Cys Phe Tyr Lys Asp Lys Thr Phe Tyr
        35                  40                  45

Cys Lys Gly Cys
    50

```
<210> SEQ ID NO 213
<211> LENGTH: 53
<212> TYPE: PRT
<213> ORGANISM: Homo sapiens

<400> SEQUENCE: 213
```

Arg Cys Pro Gly Cys Gly Asp His Ile Ala Pro Ser Gln Ile Trp Tyr
1               5                   10                  15

Arg Thr Val Asn Glu Thr Trp His Gly Ser Cys Phe Arg Cys Ser Glu
            20                  25                  30

Cys Gln Asp Ser Leu Thr Asn Trp Tyr Tyr Glu Lys Asp Gly Lys Leu
        35                  40                  45

Tyr Cys Pro Lys Asp
    50

```
<210> SEQ ID NO 214
<211> LENGTH: 54
<212> TYPE: PRT
<213> ORGANISM: Unknown
<220> FEATURE:
<223> OTHER INFORMATION: LIM domain

<400> SEQUENCE: 214
```

Ala Cys Glu Arg Cys Arg Glu Gln Phe Glu Leu Asn Glu Pro Tyr Phe
1               5                   10                  15

Leu Leu Gly Ala Ser Ser Trp His Met Arg Cys Phe Leu Cys Ala Gln
            20                  25                  30

```
Cys Met Asp Pro Leu Val Gly Thr Thr Tyr Phe Gln Phe Glu Asn Arg
            35                  40                  45

Ile Tyr Cys Glu His Asp
    50

<210> SEQ ID NO 215
<211> LENGTH: 52
<212> TYPE: PRT
<213> ORGANISM: Homo sapiens
<220> FEATURE:
<221> NAME/KEY: Variant
<222> LOCATION: (12)..(12)
<223> OTHER INFORMATION: Xaa is any amino acid

<400> SEQUENCE: 215

Ile Cys Gln Lys Cys His Ala Ile Ile Asp Glu Xaa Gln Pro Leu Ile
1               5                   10                  15

Phe Lys Asn Asp Pro Tyr His Pro Asp His Phe Asn Cys Ala Asn Cys
            20                  25                  30

Gly Lys Glu Leu Thr Ala Asp Ala Arg Glu Leu Lys Gly Glu Leu Tyr
            35                  40                  45

Cys Leu Pro Cys
    50

<210> SEQ ID NO 216
<211> LENGTH: 56
<212> TYPE: PRT
<213> ORGANISM: Unknown
<220> FEATURE:
<223> OTHER INFORMATION: LIM domain

<400> SEQUENCE: 216

Thr Cys Asp Thr Cys Gln Ser Lys Ile Gly Pro Asp Glu Lys Arg Leu
1               5                   10                  15

Asn Tyr Asn Glu Thr His Trp His Ala Glu Glu Arg Cys Phe Gln Cys
            20                  25                  30

Val Gln Cys Lys Met Asn Leu Ile Gly Lys Lys Phe Met Leu Lys Asn
            35                  40                  45

His Lys Leu Leu Cys Ser Ser Gln
    50                  55

<210> SEQ ID NO 217
<211> LENGTH: 53
<212> TYPE: PRT
<213> ORGANISM: Unknown
<220> FEATURE:
<223> OTHER INFORMATION: LIM domain

<400> SEQUENCE: 217

Ile Cys Val Gly Cys Gln Lys Thr Val Tyr Pro Met Glu Arg Leu Leu
1               5                   10                  15

Ala Asn Gln Gln Val Phe His Ile Ser Cys Phe Arg Cys Ser Tyr Cys
            20                  25                  30

Asn Asn Lys Leu Ser Leu Gly Thr Tyr Ala Ser Leu His Gly Gln Ile
            35                  40                  45

Tyr Cys Lys Pro His
    50

<210> SEQ ID NO 218
<211> LENGTH: 56
<212> TYPE: PRT
<213> ORGANISM: Unknown
```

```
<220> FEATURE:
<223> OTHER INFORMATION: LIM domain

<400> SEQUENCE: 218

Ser Cys Thr Thr Cys Arg Leu Ser Phe Ser Ser Asp Thr Pro His Met
1               5                   10                  15

Ser Gln Gly Asp Leu His Trp His Ala Ser Ala Glu Cys Phe Cys Cys
            20                  25                  30

Cys Val Cys Ser Lys Asn Leu Leu Gly Val Lys Tyr Ser Arg Val Gly
        35                  40                  45

Glu Ser Leu Phe Cys Gly Tyr Gln
    50                  55

<210> SEQ ID NO 219
<211> LENGTH: 54
<212> TYPE: PRT
<213> ORGANISM: Unknown
<220> FEATURE:
<223> OTHER INFORMATION: LIM domain

<400> SEQUENCE: 219

Lys Cys Val Ser Cys Arg Tyr Pro Ile Glu Ala Gly Asp Arg Trp Val
1               5                   10                  15

Glu Ala Leu Gly Asn Ala Phe His Ser Asn Cys Phe Thr Cys Ala Arg
            20                  25                  30

Cys Asn His Asn Leu Glu Gly Glu Ser Phe Phe Ala Lys Asn Gly Gln
        35                  40                  45

Pro Phe Cys Arg Leu His
    50

<210> SEQ ID NO 220
<211> LENGTH: 57
<212> TYPE: PRT
<213> ORGANISM: Unknown
<220> FEATURE:
<223> OTHER INFORMATION: LIM domain

<400> SEQUENCE: 220

Val Cys Thr Tyr Cys Ser His Glu Ile Gln Asp Cys Pro Lys Ile Thr
1               5                   10                  15

Leu Glu His Leu Gly Ile Cys Cys His Glu Tyr Cys Phe Lys Cys Gly
            20                  25                  30

Ile Cys Asn Lys Pro Met Gly Asp Leu Leu Asp Gln Ile Phe Ile His
        35                  40                  45

Arg Asp Thr Ile His Cys Gly Lys Cys
    50                  55

<210> SEQ ID NO 221
<211> LENGTH: 54
<212> TYPE: PRT
<213> ORGANISM: Gallus gallus

<400> SEQUENCE: 221

Leu Cys Gly Phe Cys Arg Lys Pro Leu Ser Arg Thr Gln Pro Ala Val
1               5                   10                  15

Arg Ala Leu Asp Cys Leu Phe His Val Glu Cys Phe Thr Cys Phe Lys
            20                  25                  30

Cys Glu Lys Gln Leu Gln Gly Gln Gln Phe Tyr Asn Val Asp Glu Lys
        35                  40                  45

Pro Phe Cys Glu Asp Cys
    50
```

```
                                          50
```

<210> SEQ ID NO 222
<211> LENGTH: 56
<212> TYPE: PRT
<213> ORGANISM: Xenopus laevis

<400> SEQUENCE: 222

Lys Cys Ala Gly Cys Ala Gln Gly Ile Ser Pro Ser Asp Leu Val Arg
1               5                   10                  15

Arg Ala Arg Ser Lys Val Phe His Leu Asn Cys Phe Thr Cys Met Met
                20                  25                  30

Cys Asn Lys Gln Leu Ser Thr Gly Glu Glu Leu Tyr Ile Ile Asp Glu
            35                  40                  45

Asn Lys Phe Val Cys Lys Glu Asp
        50                  55

<210> SEQ ID NO 223
<211> LENGTH: 54
<212> TYPE: PRT
<213> ORGANISM: Unknown
<220> FEATURE:
<223> OTHER INFORMATION: LIM domain

<400> SEQUENCE: 223

Lys Cys Thr Asn Cys Gly Asp Lys Ile Asp Thr Ala Ile Ile Leu
1               5                   10                  15

Pro Ser Ser Asn Glu Ala Tyr Cys Ser Asn Cys Phe Arg Cys Cys Arg
                20                  25                  30

Cys Ser Asn Arg Ile Lys Asn Leu Lys Tyr Ala Lys Thr Lys Arg Gly
            35                  40                  45

Leu Cys Cys Met Asp Cys
        50

<210> SEQ ID NO 224
<211> LENGTH: 54
<212> TYPE: PRT
<213> ORGANISM: Caenorhabditis elegans

<400> SEQUENCE: 224

Val Cys Val Arg Cys Asn Asp Gly Phe Ser Met Gln Asp Gln Met Val
1               5                   10                  15

Asn Ser Ser Gly Gln Val Trp His Ser Glu Cys Phe Val Cys Ala Gln
                20                  25                  30

Cys Phe Glu Pro Phe Pro Asp Gly Ile Tyr Phe Glu Tyr Glu Gly Arg
            35                  40                  45

Lys Tyr Cys Glu His Asp
        50

<210> SEQ ID NO 225
<211> LENGTH: 54
<212> TYPE: PRT
<213> ORGANISM: Homo sapiens

<400> SEQUENCE: 225

Thr Cys Glu Arg Cys Lys Gly Gly Phe Ala Pro Ala Glu Lys Ile Val
1               5                   10                  15

Asn Ser Asn Gly Glu Leu Tyr His Glu Gln Cys Phe Val Cys Ala Gln
                20                  25                  30

Cys Phe Gln Gln Phe Pro Glu Gly Leu Phe Tyr Glu Phe Glu Gly Arg

-continued

```
                    35                   40                   45

Lys Tyr Cys Glu His Asp
    50

<210> SEQ ID NO 226
<211> LENGTH: 55
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 226

Lys Cys Ala Tyr Cys His Gly Val Ile Leu Gly Xaa Val Ser Met Leu
1               5                   10                  15

Ala Met Gly Gln Asn Tyr His Pro Lys Cys Phe Lys Cys Ser Thr Cys
                20                  25                  30

His Val Val Ile Arg His Asn Thr Pro Phe Thr Ile Asn Lys Asn Gln
            35                  40                  45

Thr Pro Thr Cys Gln Asn Cys
    50                  55

<210> SEQ ID NO 227
<211> LENGTH: 53
<212> TYPE: PRT
<213> ORGANISM: Homo sapiens
<220> FEATURE:
<221> NAME/KEY: Variant
<222> LOCATION: (12)..(12)
<223> OTHER INFORMATION: Xaa is any amino acid

<400> SEQUENCE: 227

Val Cys Gly Ala Cys Lys Lys Pro Ile Ala Gly Xaa Gln Val Val Thr
1               5                   10                  15

Ala Met Gly Lys Thr Trp His Pro Glu His Phe Val Cys Thr His Cys
                20                  25                  30

Gln Glu Glu Ile Gly Ser Arg Asn Phe Phe Glu Arg Asp Gly Gln Pro
            35                  40                  45

Tyr Cys Glu Lys Asp
    50

<210> SEQ ID NO 228
<211> LENGTH: 53
<212> TYPE: PRT
<213> ORGANISM: Unknown
<220> FEATURE:
<223> OTHER INFORMATION: LIM domain

<400> SEQUENCE: 228

Lys Cys Asn Ala Cys Ala Lys Ile Val Tyr Pro Ile Glu Arg Val Lys
1               5                   10                  15

Val Asp Gly Thr Ala Tyr His Arg Ala Cys Phe Lys Cys Cys His Gly
                20                  25                  30

Gly Cys Thr Ile Ser Pro Ser Asn Tyr Ile Ala His Glu Gly Arg Leu
            35                  40                  45

Tyr Cys Lys His His
    50

<210> SEQ ID NO 229
```

```
<211> LENGTH: 11
<212> TYPE: PRT
<213> ORGANISM: Unknown
<220> FEATURE:
<223> OTHER INFORMATION: LIM domain

<400> SEQUENCE: 229

Arg Cys Ser Val Cys Lys Glu Pro Ile Cys Gln
1               5                   10

<210> SEQ ID NO 230
<211> LENGTH: 46
<212> TYPE: PRT
<213> ORGANISM: Unknown
<220> FEATURE:
<223> OTHER INFORMATION: LIM domain

<400> SEQUENCE: 230

Arg Arg Leu Ser Tyr Cys Gly Phe Gly Ser Arg Phe His Val His Cys
1               5                   10                  15

Tyr Arg Cys Glu Asp Cys Gly Gly Leu Leu Ser Glu Gly Asp Asn Gln
            20                  25                  30

Gly Cys Tyr Pro Leu Asp Gly His Ile Leu Cys Lys Thr Cys
        35                  40                  45

<210> SEQ ID NO 231
<211> LENGTH: 55
<212> TYPE: PRT
<213> ORGANISM: Unknown
<220> FEATURE:
<223> OTHER INFORMATION: LIM domain

<400> SEQUENCE: 231

Arg Cys Gly Arg Cys Gly Leu Val Leu Gly Pro Asn Asp Leu Val Met
1               5                   10                  15

Arg Ala Arg Asp Phe Ile Tyr His Leu Ser Cys Phe Thr Cys Ala Ala
            20                  25                  30

Cys Asn Gln Ser Leu Thr Lys Gly Asp Ile Phe Gly Met Arg Asp Gly
        35                  40                  45

Val Val Tyr Cys Arg Leu His
    50                  55

<210> SEQ ID NO 232
<211> LENGTH: 54
<212> TYPE: PRT
<213> ORGANISM: Unknown
<220> FEATURE:
<223> OTHER INFORMATION: LIM domain

<400> SEQUENCE: 232

Thr Cys Glu Glu Cys Gly Lys Pro Ile Gly Cys Asp Cys Lys Asp Leu
1               5                   10                  15

Ser Tyr Lys Asp Arg His Trp His Glu Ala Cys Phe His Cys Ser Gln
            20                  25                  30

Cys Arg Asn Ser Leu Val Asp Lys Pro Phe Ala Ala Lys Glu Asp Gln
        35                  40                  45

Leu Leu Cys Thr Asp Cys
    50

<210> SEQ ID NO 233
<211> LENGTH: 41
<212> TYPE: PRT
<213> ORGANISM: Unknown
```

```
<220> FEATURE:
<223> OTHER INFORMATION: LIM domain

<400> SEQUENCE: 233

Pro Cys Phe Arg Cys Lys Arg Pro Thr Tyr Phe Asn Asp Lys Met Gly
1               5                   10                  15

Pro Leu Lys Asp Gly Ser Met Phe His Lys Gly Cys Phe Lys Cys Trp
            20                  25                  30

Ile Cys Gly Thr Arg Leu Ser Leu Lys
        35                  40

<210> SEQ ID NO 234
<211> LENGTH: 15
<212> TYPE: PRT
<213> ORGANISM: Unknown
<220> FEATURE:
<223> OTHER INFORMATION: LIM domain

<400> SEQUENCE: 234

Asn Arg Asn Asp Asn Thr Asp Leu Glu Val Tyr Cys Ala Gly His
1               5                   10                  15

<210> SEQ ID NO 235
<211> LENGTH: 57
<212> TYPE: PRT
<213> ORGANISM: Caenorhabditis elegans

<400> SEQUENCE: 235

Lys Cys Ser Ser Cys Asn Glu Gly Ile Val Pro Asp His Val Val Arg
1               5                   10                  15

Lys Ala Ser Asn His Val Tyr His Val Glu Cys Phe Gln Cys Phe Ile
            20                  25                  30

Cys Lys Arg Ser Leu Glu Thr Gly Glu Glu Phe Tyr Leu Ile Ala Asp
        35                  40                  45

Asp Ala Arg Leu Val Cys Lys Asp Asp
    50                  55

<210> SEQ ID NO 236
<211> LENGTH: 52
<212> TYPE: PRT
<213> ORGANISM: Xenopus laevis

<400> SEQUENCE: 236

His Cys Ala Gly Cys Glu Arg Pro Ile Leu Asp Arg Phe Leu Leu Asn
1               5                   10                  15

Val Leu Asp Arg Ala Trp His Val Lys Cys Val Gln Cys Cys Glu Cys
            20                  25                  30

Lys Cys Asn Leu Thr Glu Lys Cys Phe Ser Arg Glu Gly Lys Leu Tyr
        35                  40                  45

Cys Lys Asn Asp
    50

<210> SEQ ID NO 237
<211> LENGTH: 55
<212> TYPE: PRT
<213> ORGANISM: Gallus gallus
<220> FEATURE:
<221> NAME/KEY: Variant
<222> LOCATION: (12)..(12)
<223> OTHER INFORMATION: Xaa is any amino acid

<400> SEQUENCE: 237
```

-continued

Ser Cys His Gly Cys Ser Leu Leu Met Thr Gly Xaa Pro Val Met Val
1               5                   10                  15

Ala Gly Glu Tyr Lys Tyr His Pro Glu Cys Phe Ala Cys Met Ser Cys
            20                  25                  30

Lys Val Ile Ile Glu Asp Gly Asp Thr Tyr Ala Leu Val Gln His Ser
        35                  40                  45

Thr Leu Tyr Cys Gly Lys Cys
    50                  55

<210> SEQ ID NO 238
<211> LENGTH: 54
<212> TYPE: PRT
<213> ORGANISM: Unknown
<220> FEATURE:
<223> OTHER INFORMATION: LIM domain

<400> SEQUENCE: 238

Thr Cys Val Glu Cys Arg Lys Pro Ile Gly Ala Asp Ser Lys Glu Val
1               5                   10                  15

His Tyr Lys Asn Arg Phe Trp His Asp Thr Cys Phe Arg Cys Ala Lys
            20                  25                  30

Cys Leu His Pro Leu Ala Asn Glu Thr Phe Val Ala Lys Asp Asn Lys
        35                  40                  45

Ile Leu Cys Asn Lys Cys
    50

<210> SEQ ID NO 239
<211> LENGTH: 54
<212> TYPE: PRT
<213> ORGANISM: Rattus sp.

<400> SEQUENCE: 239

Leu Cys Ala Gly Cys Gly Gly Lys Ile Ser Asp Arg Tyr Tyr Leu Leu
1               5                   10                  15

Ala Val Asp Lys Gln Trp His Met Arg Cys Leu Lys Cys Cys Glu Cys
            20                  25                  30

Lys Leu Asn Leu Glu Ser Glu Leu Thr Cys Phe Ser Lys Asp Gly Ser
        35                  40                  45

Ile Tyr Cys Lys Glu Asp
    50

<210> SEQ ID NO 240
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 240

Arg Cys Ser Lys Cys Lys Lys Val Ile Thr Ala Xaa Gly Gly Val Thr
1               5                   10                  15

Tyr Lys Asn Glu Pro Trp His Arg Glu Cys Phe Cys Cys Thr Asn Cys
            20                  25                  30

Asn Ser Ser Leu Ala Gly Gln Arg Phe Thr Ser Lys Asp Glu Lys Pro
        35                  40                  45

Tyr Cys Ala Asn Cys
    50

<210> SEQ ID NO 241
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 241

```
Leu Cys Gly Ser Cys Asn Lys Pro Ile Ala Gly Xaa Gln Val Val Thr
1               5                   10                  15

Ala Leu Gly Arg Ala Trp His Pro Glu His Phe Leu Cys Ser Gly Cys
            20                  25                  30

Ser Thr Thr Leu Gly Gly Ser Ser Phe Glu Lys Asp Gly Ala Pro
        35                  40                  45

Phe Cys Pro Glu Cys
    50
```

<210> SEQ ID NO 242
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 242

```
Arg Cys Gly Phe Cys Asn Gln Pro Ile Arg His Xaa Lys Met Val Thr
1               5                   10                  15

Ala Leu Gly Thr His Trp His Pro Glu His Phe Cys Cys Val Ser Cys
            20                  25                  30

Gly Glu Pro Phe Gly Glu Gly Phe His Glu Arg Glu Gly Arg Pro
        35                  40                  45

Tyr Cys Arg Arg Asp
    50
```

<210> SEQ ID NO 243
<211> LENGTH: 53
<212> TYPE: PRT
<213> ORGANISM: Homo sapiens
<220> FEATURE:
<221> NAME/KEY: Variant
<222> LOCATION: (12)..(12)
<223> OTHER INFORMATION: Xaa is any amino acid

<400> SEQUENCE: 243

```
Lys Cys Gly Gly Cys Ala Arg Ala Ile Leu Glu Xaa Asn Tyr Ile Ser
1               5                   10                  15

Ala Leu Asn Thr Leu Trp His Pro Glu Cys Phe Val Cys Arg Glu Cys
            20                  25                  30

Phe Thr Pro Phe Val Asn Gly Ser Phe Phe Glu His Asp Gly Gln Pro
        35                  40                  45

Tyr Cys Glu Val His
    50
```

<210> SEQ ID NO 244

```
<211> LENGTH: 52
<212> TYPE: PRT
<213> ORGANISM: Caenorhabditis elegans

<400> SEQUENCE: 244

Lys Cys Asn Cys Cys Asn Glu Gln Ile Tyr Asp Arg Tyr Ile Tyr Arg
1               5                   10                  15

Met Asp Asn Arg Ser Tyr His Glu Asn Cys Val Lys Cys Thr Ile Cys
                20                  25                  30

Glu Ser Pro Leu Ala Glu Lys Cys Phe Trp Lys Asn Gly Arg Ile Tyr
            35                  40                  45

Cys Ser Gln His
    50

<210> SEQ ID NO 245
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 245

Lys Cys Ser Asn Cys Gly Lys Pro Ile Thr Glu Xaa Lys Leu Leu Arg
1               5                   10                  15

Ala Thr Gly Gly Ala Tyr His Pro Asp Cys Phe Ile Cys Thr Val Cys
                20                  25                  30

Lys Lys Cys Leu Asp Gly Val Pro Phe Thr Val Asp Ser Ala Asn Gln
            35                  40                  45

Val Pro Cys Val Val Cys
    50

<210> SEQ ID NO 246
<211> LENGTH: 52
<212> TYPE: PRT
<213> ORGANISM: Xenopus laevis

<400> SEQUENCE: 246

Gln Cys Ala Gly Cys Asn Gln His Ile Val Asp Arg Phe Ile Leu Lys
1               5                   10                  15

Val Leu Asp Arg His Trp His Ser Lys Cys Leu Lys Cys Asn Asp Cys
                20                  25                  30

Gln Ile Gln Leu Ala Glu Lys Cys Phe Ser Arg Gly Asp Ser Val Tyr
            35                  40                  45

Cys Lys Asp Asp
    50

<210> SEQ ID NO 247
<211> LENGTH: 52
<212> TYPE: PRT
<213> ORGANISM: Unknown
<220> FEATURE:
<223> OTHER INFORMATION: LIM domain

<400> SEQUENCE: 247

Thr Cys Ala Ala Cys Asp Gln Ala Leu His Ser Gly Gln Val Leu Leu
1               5                   10                  15

Ala Leu Gly Leu Ser Trp His Val Tyr Cys Phe Lys Cys Ser Glu Cys
                20                  25                  30
```

Ser Ala Val Leu His Gly Glu Tyr Met Ser His His Gly Lys Pro Leu
        35                  40                  45

Cys Leu Arg Asp
    50

<210> SEQ ID NO 248
<211> LENGTH: 54
<212> TYPE: PRT
<213> ORGANISM: Unknown
<220> FEATURE:
<223> OTHER INFORMATION: LIM domain

<400> SEQUENCE: 248

Lys Cys Gln Glu Cys Lys Lys Thr Ile Met Pro Gly Thr Arg Lys Met
1               5                   10                  15

Glu Tyr Lys Gly Ser Ser Trp His Glu Thr Cys Phe Ile Cys His Arg
            20                  25                  30

Cys Gln Gln Pro Ile Gly Thr Lys Ser Phe Ile Pro Lys Asp Asn Gln
        35                  40                  45

Asn Phe Cys Val Pro Cys
    50

<210> SEQ ID NO 249
<211> LENGTH: 55
<212> TYPE: PRT
<213> ORGANISM: Unknown
<220> FEATURE:
<223> OTHER INFORMATION: LIM domain

<400> SEQUENCE: 249

Asn Cys Asn Lys Cys Lys Gln His Val Asp Asn Ser Asp Leu Leu Thr
1               5                   10                  15

Tyr Gln Glu Asn Pro Tyr His Ala Tyr His Phe Lys Cys Thr Thr Cys
            20                  25                  30

Lys Lys Val Leu Glu Ser Asp Ala Arg Thr Ile Lys Asp Asp Leu Phe
        35                  40                  45

Cys Pro Arg Cys Phe Asp Phe
    50                  55

<210> SEQ ID NO 250
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 250

Met Cys Ala His Cys Asn Gln Ala Ile Arg Gly Xaa Pro Phe Leu Val
1               5                   10                  15

Ala Leu Gly Lys Ser Trp His Pro Glu Glu Phe Asn Cys Ala His Cys
            20                  25                  30

Lys Asn Thr Met Ala Tyr Ile Gly Phe Val Glu Glu Lys Gly Ala Leu
        35                  40                  45

Tyr Cys Glu Leu Cys
    50

<210> SEQ ID NO 251

```
<211> LENGTH: 55
<212> TYPE: PRT
<213> ORGANISM: Homo sapiens

<400> SEQUENCE: 251

Asn Cys Ala Ala Cys Ser Lys Leu Ile Pro Ala Phe Glu Met Val Met
1               5                   10                  15

Arg Ala Arg Asp Asn Val Tyr His Leu Asp Cys Phe Ala Cys Gln Leu
            20                  25                  30

Cys Asn Gln Arg Phe Cys Val Gly Asp Lys Phe Phe Leu Lys Asn Asn
        35                  40                  45

Met Ile Leu Cys Gln Met Asp
    50                  55

<210> SEQ ID NO 252
<211> LENGTH: 53
<212> TYPE: PRT
<213> ORGANISM: Unknown
<220> FEATURE:
<223> OTHER INFORMATION: LIM domain

<400> SEQUENCE: 252

Ile Cys Lys Val Cys Ser Asn Phe Ile Glu Gly Glu Cys Leu Glu Asn
1               5                   10                  15

Asp Lys Val Glu Arg Phe His Val Asp Cys Leu Asn Cys Phe Leu Cys
            20                  25                  30

Lys Thr Ala Ile Thr Asn Asp Tyr Tyr Ile Phe Asn Gly Glu Ile Pro
        35                  40                  45

Leu Cys Gly Asn His
    50

<210> SEQ ID NO 253
<211> LENGTH: 54
<212> TYPE: PRT
<213> ORGANISM: Unknown
<220> FEATURE:
<223> OTHER INFORMATION: LIM domain

<400> SEQUENCE: 253

Arg Cys Asp Gly Cys Asn Glu Ile Phe Arg Ala Gly Met Lys Lys Met
1               5                   10                  15

Glu Tyr Lys Gly Lys Gln Trp His Asp Lys Cys Phe Cys Cys Ala His
            20                  25                  30

Cys Lys Leu Ala Ile Gly Thr Lys Ser Phe Ile Pro Lys Asn Asp Asp
        35                  40                  45

Val Phe Cys Gly Pro Cys
    50

<210> SEQ ID NO 254
<211> LENGTH: 55
<212> TYPE: PRT
<213> ORGANISM: Unknown
<220> FEATURE:
<223> OTHER INFORMATION: LIM domain

<400> SEQUENCE: 254

Lys Cys Gly Gly Cys Phe Glu Ala Ile Ala Pro Asn Glu Phe Val Met
1               5                   10                  15

Arg Ala Gln Lys Ser Val Tyr His Leu Ser Cys Phe Cys Cys Cys Val
            20                  25                  30

Cys Glu Arg Gln Leu Gln Lys Gly Asp Glu Phe Val Leu Lys Glu Gly
```

```
      35                  40                  45
Gln Leu Leu Cys Lys Gly Asp
    50                  55

<210> SEQ ID NO 255
<211> LENGTH: 53
<212> TYPE: PRT
<213> ORGANISM: Gallus gallus

<400> SEQUENCE: 255

Lys Cys Gly Val Cys Gln Lys Ala Val Tyr Phe Ala Glu Glu Val Gln
1               5                   10                  15

Cys Glu Gly Ser Ser Phe His Lys Ser Cys Phe Leu Cys Met Val Cys
            20                  25                  30

Lys Lys Asn Leu Asp Ser Thr Thr Val Ala Val His Gly Asp Glu Ile
        35                  40                  45

Tyr Cys Lys Ser Cys
    50

<210> SEQ ID NO 256
<211> LENGTH: 55
<212> TYPE: PRT
<213> ORGANISM: Unknown
<220> FEATURE:
<223> OTHER INFORMATION: LIM domain

<400> SEQUENCE: 256

Val Cys Phe Asp Cys Lys Lys Val Ile Asp Pro Gln Val Glu Gln Ser
1               5                   10                  15

Ile Phe Thr Met Asn Lys His Trp His Thr Asp His Phe Arg Cys Ala
            20                  25                  30

Thr Cys Ala Arg Pro Phe Phe Gly His Glu His Tyr Glu Lys Asn Gly
        35                  40                  45

Lys Ala Tyr Cys Arg Asp Asp
    50                  55

<210> SEQ ID NO 257
<211> LENGTH: 52
<212> TYPE: PRT
<213> ORGANISM: Unknown
<220> FEATURE:
<223> OTHER INFORMATION: LIM domain

<400> SEQUENCE: 257

Glu Cys Ala Ala Cys Ala Gln Pro Ile Leu Asp Arg Tyr Val Phe Thr
1               5                   10                  15

Val Leu Gly Lys Cys Trp His Gln Ser Cys Leu Arg Cys Cys Asp Cys
            20                  25                  30

Arg Ala Pro Met Ser Met Thr Cys Phe Ser Arg Asp Gly Leu Ile Leu
        35                  40                  45

Cys Lys Thr Asp
    50

<210> SEQ ID NO 258
<211> LENGTH: 53
<212> TYPE: PRT
<213> ORGANISM: Unknown
<220> FEATURE:
<223> OTHER INFORMATION: LIM domain

<400> SEQUENCE: 258
```

```
Lys Cys Pro Arg Cys Gly Lys Ser Val Tyr Ala Ala Glu Glu Arg Leu
1               5                   10                  15

Ala Gly Gly Tyr Val Phe His Lys Asn Cys Phe Lys Cys Gly Met Cys
            20                  25                  30

Asn Lys Ser Leu Asp Ser Thr Asn Cys Thr Glu His Glu Arg Glu Leu
        35                  40                  45

Tyr Cys Lys Thr Cys
    50

<210> SEQ ID NO 259
<211> LENGTH: 11
<212> TYPE: PRT
<213> ORGANISM: Unknown
<220> FEATURE:
<223> OTHER INFORMATION: LIM domain

<400> SEQUENCE: 259

Ile Cys Ala Arg Cys Asn Lys Leu Val Ile Pro
1               5                   10

<210> SEQ ID NO 260
<211> LENGTH: 29
<212> TYPE: PRT
<213> ORGANISM: Unknown
<220> FEATURE:
<223> OTHER INFORMATION: LIM domain

<400> SEQUENCE: 260

Thr Lys Thr Thr Leu Lys Ala Leu Gly Lys Tyr Tyr His Glu Ser Cys
1               5                   10                  15

Phe Thr Cys Gln Asp Cys Gln Lys Pro Leu Lys Pro Lys
            20                  25

<210> SEQ ID NO 261
<211> LENGTH: 15
<212> TYPE: PRT
<213> ORGANISM: Unknown
<220> FEATURE:
<223> OTHER INFORMATION: LIM domain

<400> SEQUENCE: 261

Gln Val Asp Lys Thr Ser Glu Ser Ile Leu Leu Cys Gln Tyr Asp
1               5                   10                  15

<210> SEQ ID NO 262
<211> LENGTH: 55
<212> TYPE: PRT
<213> ORGANISM: Drosophila melanogaster

<400> SEQUENCE: 262

Arg Cys Ser Arg Cys Leu Ala Ser Ile Ser Ser Asn Glu Leu Val Met
1               5                   10                  15

Arg Ala Arg Asn Leu Val Phe His Val Asn Cys Phe Cys Cys Thr Val
            20                  25                  30

Cys His Thr Pro Leu Thr Lys Gly Asp Gln Tyr Gly Ile Ile Asp Ala
        35                  40                  45

Leu Ile Tyr Cys Arg Thr His
    50                  55

<210> SEQ ID NO 263
<211> LENGTH: 53
<212> TYPE: PRT
<213> ORGANISM: Unknown
```

<220> FEATURE:
<223> OTHER INFORMATION: LIM domain

<400> SEQUENCE: 263

Arg Cys Ala Gly Cys Asp Glu Leu Ile Phe Ala Asn Glu Tyr Thr Phe
1               5                   10                  15

Ala Glu Glu Lys Ser Trp His Phe Asp His Phe Ala Cys Tyr Lys Cys
            20                  25                  30

Asp Phe Lys Leu Gly Gly Ser Arg Tyr Met Thr Arg Asp Glu Asn Pro
        35                  40                  45

Phe Cys Leu Asp Cys
    50

<210> SEQ ID NO 264
<211> LENGTH: 54
<212> TYPE: PRT
<213> ORGANISM: Unknown
<220> FEATURE:
<223> OTHER INFORMATION: LIM domain

<400> SEQUENCE: 264

Lys Cys Cys Arg Cys Gly Glu Gly Ile Thr Asn Thr Arg Pro Gly Cys
1               5                   10                  15

Thr Ala Ile Gly Glu Met Phe His Val Ala Cys Phe Thr Cys Asn Glu
            20                  25                  30

Cys Asn Lys Gln Leu Ala Gly Gly Ser Phe Tyr Asn Val Asp Gly Lys
        35                  40                  45

Ala Leu Cys Glu Asp Asp
    50

<210> SEQ ID NO 265
<211> LENGTH: 58
<212> TYPE: PRT
<213> ORGANISM: Unknown
<220> FEATURE:
<223> OTHER INFORMATION: LIM domain

<400> SEQUENCE: 265

Pro Cys Arg Ala Cys Gly Leu Glu Val Thr Gly Lys Arg Met Phe Ser
1               5                   10                  15

Lys Lys Glu Asn Glu Leu Ser Gly Gln Trp His Arg Glu Cys Phe Lys
            20                  25                  30

Cys Ile Glu Cys Gly Ile Lys Phe Asn Lys His Val Pro Cys Tyr Ile
        35                  40                  45

Leu Gly Asp Glu Pro Tyr Cys Gln Lys His
    50                  55

<210> SEQ ID NO 266
<211> LENGTH: 53
<212> TYPE: PRT
<213> ORGANISM: Homo sapiens
<220> FEATURE:
<221> NAME/KEY: Variant
<222> LOCATION: (12)..(12)
<223> OTHER INFORMATION: Xaa is any amino acid

<400> SEQUENCE: 266

Ile Cys Gly Ala Cys Arg Arg Pro Ile Glu Gly Xaa Arg Val Val Asn
1               5                   10                  15

Ala Met Gly Lys Gln Trp His Val Glu His Phe Val Cys Ala Lys Cys
            20                  25                  30

```
Glu Lys Pro Phe Leu Gly His Arg His Tyr Glu Arg Lys Gly Leu Ala
        35                  40                  45

Tyr Cys Glu Thr His
    50

<210> SEQ ID NO 267
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 267

Arg Cys Ala Arg Cys Thr Lys Thr Leu Thr Gln Xaa Gly Gly Leu Thr
1               5                  10                  15

Tyr Arg Asp Leu Pro Trp His Pro Lys Cys Leu Val Cys Thr Gly Cys
            20                  25                  30

Gln Thr Pro Trp Gln Gly Thr Thr Ser Pro Pro Gly Met Lys Asn Pro
        35                  40                  45

Tyr Cys Val Ala Cys
    50

<210> SEQ ID NO 268
<211> LENGTH: 54
<212> TYPE: PRT
<213> ORGANISM: Unknown
<220> FEATURE:
<223> OTHER INFORMATION: LIM domain

<400> SEQUENCE: 268

Gly Cys Pro Arg Cys Gly Phe Ala Val Phe Ala Ala Glu Gln Met Ile
1               5                  10                  15

Ser Lys Thr Arg Ile Trp His Lys Arg Cys Phe Tyr Cys Ser Asp Cys
            20                  25                  30

Arg Lys Ser Leu Asp Ser Thr Asn Leu Asn Asp Gly Pro Asp Gly Asp
        35                  40                  45

Ile Tyr Cys Arg Ala Cys
    50

<210> SEQ ID NO 269
<211> LENGTH: 55
<212> TYPE: PRT
<213> ORGANISM: Unknown
<220> FEATURE:
<223> OTHER INFORMATION: LIM domain

<400> SEQUENCE: 269

Lys Cys Ala Ser Cys Asp Arg Thr Ile Gln Ala Thr Asp Trp Val Arg
1               5                  10                  15

Arg Ala Arg Asn Tyr Val Tyr His Leu Ala Cys Phe Ser Cys Asn Gln
            20                  25                  30

Cys Lys Arg Gln Leu Ser Thr Gly Glu Glu Tyr Ala Leu Gln Glu Gly
        35                  40                  45

Asn Leu Leu Cys Lys Gln His
    50                  55

<210> SEQ ID NO 270
<211> LENGTH: 55
```

```
<212> TYPE: PRT
<213> ORGANISM: Unknown
<220> FEATURE:
<223> OTHER INFORMATION: LIM domain

<400> SEQUENCE: 270

Ala Cys Ser Ala Cys Gly Gln Ser Ile Pro Ala Ser Glu Leu Val Met
1               5                   10                  15

Arg Ala Gln Gly Asn Val Tyr His Leu Lys Cys Phe Thr Cys Ser Thr
            20                  25                  30

Cys Arg Asn Arg Leu Val Pro Gly Asp Arg Phe His Tyr Ile Asn Gly
        35                  40                  45

Ser Leu Phe Cys Glu His Asp
    50                  55

<210> SEQ ID NO 271
<211> LENGTH: 55
<212> TYPE: PRT
<213> ORGANISM: Homo sapiens

<400> SEQUENCE: 271

Leu Cys Ala Ser Cys Asp Lys Arg Ile Arg Ala Tyr Glu Met Thr Met
1               5                   10                  15

Arg Val Lys Asp Lys Val Tyr His Leu Glu Cys Phe Lys Cys Ala Ala
            20                  25                  30

Cys Gln Lys His Phe Cys Val Gly Asp Arg Tyr Leu Leu Ile Asn Ser
        35                  40                  45

Asp Ile Val Cys Glu Gln Asp
    50                  55

<210> SEQ ID NO 272
<211> LENGTH: 54
<212> TYPE: PRT
<213> ORGANISM: Unknown
<220> FEATURE:
<223> OTHER INFORMATION: LIM domain

<400> SEQUENCE: 272

Gln Cys Cys Leu Cys Thr Phe Ala Ile Val Asp Lys Glu Ile Ser Val
1               5                   10                  15

Val Asp Gly Lys Tyr Tyr His Asn Asn Cys Leu Arg Cys Gln Met Cys
            20                  25                  30

Asp Ile Pro Phe Glu Tyr Ser Asp Lys Cys Tyr Val Arg Asp Gly Val
        35                  40                  45

Phe Leu Cys Arg Ala Asp
    50

<210> SEQ ID NO 273
<211> LENGTH: 53
<212> TYPE: PRT
<213> ORGANISM: Rattus sp.
<220> FEATURE:
<221> NAME/KEY: Variant
<222> LOCATION: (12)..(12)
<223> OTHER INFORMATION: Xaa is any amino acid

<400> SEQUENCE: 273

Glu Cys Thr Arg Cys Gly His Gly Ile Val Gly Xaa Thr Ile Val Lys
1               5                   10                  15

Ala Arg Asp Lys Leu Tyr His Pro Glu Cys Phe Met Cys Ser Asp Cys
            20                  25                  30
```

Gly Leu Asn Leu Lys Gln Arg Gly Tyr Phe Leu Asp Glu Arg Leu
            35                  40                  45

Tyr Cys Glu Asn His
    50

<210> SEQ ID NO 274
<211> LENGTH: 39
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 274

Ser Cys Ala Gly Cys Asn Lys Tyr Ile Gln Glu Xaa Glu Cys Ile Gln
1               5                   10                  15

Phe Tyr Glu His Arg Trp His Ile Ala Cys Phe Thr Cys Ser Ser Cys
            20                  25                  30

His Lys Asn Ile Asn Pro Arg
        35

<210> SEQ ID NO 275
<211> LENGTH: 15
<212> TYPE: PRT
<213> ORGANISM: Unknown
<220> FEATURE:
<223> OTHER INFORMATION: LIM domain

<400> SEQUENCE: 275

Pro Thr Phe Asn Lys Glu Lys Lys Ile Leu Cys Ser His Cys
1               5                   10                  15

<210> SEQ ID NO 276
<211> LENGTH: 55
<212> TYPE: PRT
<213> ORGANISM: Unknown
<220> FEATURE:
<223> OTHER INFORMATION: LIM domain

<400> SEQUENCE: 276

Val Cys Ala Gly Cys Arg Leu Glu Ile Ser Asp Arg Tyr Phe Leu Arg
1               5                   10                  15

Val Asn Pro Asn Leu Glu Phe His Ala Gln Cys Leu Lys Cys Val Gln
            20                  25                  30

Cys Ser Arg Pro Leu Asp Glu Asn Gln Thr Ala Phe Val Lys Asn Gly
        35                  40                  45

Gln Thr Tyr Cys Arg Asp Asp
    50                  55

<210> SEQ ID NO 277
<211> LENGTH: 55
<212> TYPE: PRT
<213> ORGANISM: Unknown
<220> FEATURE:
<223> OTHER INFORMATION: LIM domain

<400> SEQUENCE: 277

Met Cys Val Gly Cys Gly Ser Gln Ile His Asp Gln Tyr Ile Leu Arg
1               5                   10                  15

Val Ala Pro Asp Leu Glu Trp His Ala Ala Cys Leu Lys Cys Ala Glu
            20                  25                  30

Cys Ser Gln Tyr Leu Asp Glu Thr Cys Thr Cys Phe Val Arg Asp Gly
            35                  40                  45

Lys Thr Tyr Cys Lys Arg Asp
    50                  55

<210> SEQ ID NO 278
<211> LENGTH: 57
<212> TYPE: PRT
<213> ORGANISM: Unknown
<220> FEATURE:
<223> OTHER INFORMATION: LIM domain

<400> SEQUENCE: 278

Val Cys Phe Arg Cys Gly Gln Ala Phe Gln Arg Arg Glu Thr Pro Ile
1               5                   10                  15

Ser Phe Gly Gly His Met Trp His Lys Asp Cys Phe Cys Cys Thr Lys
            20                  25                  30

Cys Asp Lys Gly Leu Glu His Ser Asp Gln Met Leu Val Gln Thr Ser
            35                  40                  45

Asp Gly Arg Pro Val Cys Ser Ser Cys
    50                  55

<210> SEQ ID NO 279
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 279

His Cys Val Lys Cys Asn Lys Ala Ile Thr Ser Xaa Gly Gly Ile Thr
1               5                   10                  15

Tyr Gln Asp Gln Pro Trp His Ala Asp Cys Phe Val Cys Val Thr Cys
            20                  25                  30

Ser Lys Lys Leu Ala Gly Ala Ala Phe Thr Ala Val Glu Asp Gln Tyr
            35                  40                  45

Tyr Cys Val Asp Cys
    50

<210> SEQ ID NO 280
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 280

Lys Cys Thr Ala Cys Asn Arg Ala Ile Ser Asp Xaa Lys Leu Leu Arg
1               5                   10                  15

Ala Cys Gly Gly Val Tyr His Val Asn Cys Phe Val Cys Phe Ser Cys
            20                  25                  30

Lys Lys Ser Leu Asp Gly Ile Pro Phe Thr Leu Asp Lys Asp Asn Asn
            35                  40                  45

Val His Cys Val Pro Cys

<210> SEQ ID NO 281
<211> LENGTH: 11
<212> TYPE: PRT
<213> ORGANISM: Unknown
<220> FEATURE:
<223> OTHER INFORMATION: LIM domain

<400> SEQUENCE: 281

Leu Cys Ser Gly Cys Gly Cys Leu Ile Lys Asp
1               5                   10

<210> SEQ ID NO 282
<211> LENGTH: 44
<212> TYPE: PRT
<213> ORGANISM: Unknown
<220> FEATURE:
<223> OTHER INFORMATION: LIM domain

<400> SEQUENCE: 282

Leu Asp Ser Lys Ser Asn Val Met Glu Asp Ser Tyr His Glu Ser Cys
1               5                   10                  15

Leu Arg Cys Ser Cys Gln Leu Ser Leu Ser Ser Phe Lys Lys Cys
            20                  25                  30

Phe Ser Arg His Gly Asn Ile Tyr Cys Glu His Asp
        35                  40

<210> SEQ ID NO 283
<211> LENGTH: 11
<212> TYPE: PRT
<213> ORGANISM: Unknown
<220> FEATURE:
<223> OTHER INFORMATION: LIM domain

<400> SEQUENCE: 283

Arg Cys Ala Leu Cys Ser Lys Pro Ile Val Pro
1               5                   10

<210> SEQ ID NO 284
<211> LENGTH: 29
<212> TYPE: PRT
<213> ORGANISM: Unknown
<220> FEATURE:
<223> OTHER INFORMATION: LIM domain

<400> SEQUENCE: 284

Glu Ser Val Arg Val Val Ala Met Asp Lys Ser Phe His Val Asp Cys
1               5                   10                  15

Tyr Lys Cys Glu Asp Cys Gly Met Gln Leu Ser Ser Lys
            20                  25

<210> SEQ ID NO 285
<211> LENGTH: 15
<212> TYPE: PRT
<213> ORGANISM: Unknown
<220> FEATURE:
<223> OTHER INFORMATION: LIM domain

<400> SEQUENCE: 285

Phe Leu Ile Thr Val Ile Ala Asp Ser Gln Ala Cys Arg Lys Val
1               5                   10                  15

<210> SEQ ID NO 286
<211> LENGTH: 54

```
<212> TYPE: PRT
<213> ORGANISM: Unknown
<220> FEATURE:
<223> OTHER INFORMATION: LIM domain

<400> SEQUENCE: 286

Asn Cys Lys Arg Cys Lys Leu Glu Ile Phe Gly Asn Thr Leu Ile Asn
1               5                   10                  15

His Leu Gln Glu Thr Tyr His Pro Glu Cys Phe Lys Cys Ser Asn Cys
            20                  25                  30

Phe Ser Ser Ile Val Asp Pro Tyr Phe Thr Glu Pro Ser Thr Asn Lys
        35                  40                  45

Ile Phe Cys Ala Lys Cys
    50

<210> SEQ ID NO 287
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 287

Arg Cys Asn Lys Cys Ser Lys Pro Ile Ile Ser Xaa Asp Cys Leu Asn
1               5                   10                  15

Ala Leu Gln Lys Lys Trp His Pro Thr Cys Phe Thr Cys Ala His Cys
            20                  25                  30

Gln Lys Pro Phe Gly Asn Ser Ala Phe Tyr Leu Glu Gln Gly Leu Pro
        35                  40                  45

Tyr Cys Glu Gln Asp
    50

<210> SEQ ID NO 288
<211> LENGTH: 53
<212> TYPE: PRT
<213> ORGANISM: Homo sapiens
<220> FEATURE:
<221> NAME/KEY: Variant
<222> LOCATION: (12)..(12)
<223> OTHER INFORMATION: Xaa is any amino acid

<400> SEQUENCE: 288

Leu Cys Ser Gly Cys Gln Lys Pro Ile Thr Gly Xaa Arg Cys Ile Thr
1               5                   10                  15

Ala Met Ala Lys Lys Phe His Pro Glu His Phe Val Cys Ala Phe Cys
            20                  25                  30

Leu Lys Gln Leu Asn Lys Gly Thr Phe Lys Glu Gln Asn Asp Lys Pro
        35                  40                  45

Tyr Cys Gln Asn Cys
    50

<210> SEQ ID NO 289
<211> LENGTH: 54
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
```

<223> OTHER INFORMATION: Xaa is any amino acid

<400> SEQUENCE: 289

Lys Cys Tyr Glu Cys Glu Lys Phe Ile Ala Gly Xaa Lys Val Leu Gln
1               5                   10                  15

Ala Gly Gly Tyr Lys Phe His Pro Thr Cys Ala Arg Cys Ser Arg Cys
            20                  25                  30

Gly Ser His Phe Gly Asp Gly Glu Met Tyr Met Gln Gly Asp Glu
        35                  40                  45

Ile Trp His Pro Ser Cys
    50

<210> SEQ ID NO 290
<211> LENGTH: 53
<212> TYPE: PRT
<213> ORGANISM: Unknown
<220> FEATURE:
<223> OTHER INFORMATION: LIM domain
<220> FEATURE:
<221> NAME/KEY: Variant
<222> LOCATION: (12)..(12)
<223> OTHER INFORMATION: Xaa is any amino acid

<400> SEQUENCE: 290

Val Cys Ala Lys Cys Asn Glu Phe Val Ile Gly Xaa Gln Val Val His
1               5                   10                  15

Ser Ser Asn Asn Ser Tyr His Leu Ala Cys Phe Thr Cys Asp Glu Cys
            20                  25                  30

Asn Val His Leu Asn Ser Gln Ile Ala Tyr Arg Tyr Gln Gly Thr Ile
        35                  40                  45

Leu Cys Phe Leu Cys
    50

<210> SEQ ID NO 291
<211> LENGTH: 53
<212> TYPE: PRT
<213> ORGANISM: Caenorhabditis elegans
<220> FEATURE:
<221> NAME/KEY: Variant
<222> LOCATION: (12)..(12)
<223> OTHER INFORMATION: Xaa is any amino acid

<400> SEQUENCE: 291

Lys Cys Gln Gly Cys His Arg Ala Ile Thr Asp Xaa Arg Cys Val Ser
1               5                   10                  15

Val Met Asn Lys Asn Phe His Ile Glu Cys Phe Thr Cys Ala Glu Cys
            20                  25                  30

Asn Gln Pro Phe Gly Glu Asp Gly Phe His Glu Lys Asn Gly Gln Thr
        35                  40                  45

Tyr Cys Lys Arg Asp
    50

<210> SEQ ID NO 292
<211> LENGTH: 55
<212> TYPE: PRT
<213> ORGANISM: Unknown
<220> FEATURE:
<223> OTHER INFORMATION: LIM domain

<400> SEQUENCE: 292

Leu Cys Val Arg Cys Asn Lys Ser Ile Ala Ser Ser Gln Val Tyr Glu
1               5                   10                  15

```
Leu Glu Ser Lys Lys Trp His Asp Gln Cys Phe Thr Cys Lys Cys
            20                  25                  30

Asp Lys Lys Leu Asn Ala Asp Ser Asp Phe Leu Val Leu Asp Ile Gly
            35                  40                  45

Thr Leu Ile Cys Tyr Asp Cys
 50                  55

<210> SEQ ID NO 293
<211> LENGTH: 56
<212> TYPE: PRT
<213> ORGANISM: Mus musculus

<400> SEQUENCE: 293

Val Cys Gln Gly Cys His Asn Ala Ile Asp Pro Glu Val Gln Arg Val
 1               5                  10                  15

Thr Tyr Asn Asn Phe Ser Trp His Ala Ser Thr Glu Cys Phe Leu Cys
            20                  25                  30

Ser Cys Cys Ser Lys Cys Leu Ile Gly Gln Lys Phe Met Pro Val Glu
            35                  40                  45

Gly Met Val Phe Cys Ser Val Glu
 50                  55

<210> SEQ ID NO 294
<211> LENGTH: 476
<212> TYPE: PRT
<213> ORGANISM: Arabidopsis thaliana

<400> SEQUENCE: 294

Asp Asp Asp Asp Asp Glu Asp Glu Asp Glu Tyr Met Arg Ala Gln
 1               5                  10                  15

Leu Glu Ala Ala Glu Glu Glu Arg Arg Val Ala Gln Ala Gln Ile
            20                  25                  30

Glu Glu Glu Glu Lys Arg Arg Ala Glu Ala Gln Leu Glu Thr Glu
            35                  40                  45

Lys Leu Leu Ala Lys Ala Arg Leu Glu Glu Glu Met Arg Arg Ser
 50                  55                  60

Lys Ala Gln Leu Glu Glu Asp Glu Leu Leu Ala Lys Ala Leu Gln Glu
 65                  70                  75                  80

Ser Met Asn Val Gly Ser Pro Arg Tyr Asp Pro Gly Asn Ile Leu
            85                  90                  95

Gln Pro Tyr Pro Phe Leu Ile Pro Ser Ser His Arg Ile Cys Val Gly
                100                 105                 110

Cys Gln Ala Glu Ile Gly His Gly Arg Phe Leu Ser Cys Met Gly Gly
                115                 120                 125

Val Trp His Pro Glu Cys Phe Cys Asn Ala Cys Asp Lys Pro Ile
            130                 135                 140

Ile Asp Tyr Glu Phe Ser Met Ser Gly Asn Arg Pro Tyr His Lys Leu
145                 150                 155                 160

Cys Tyr Lys Glu Gln His His Pro Lys Cys Asp Val Cys His Asn Phe
                165                 170                 175

Ile Pro Thr Asn Pro Ala Gly Leu Ile Glu Tyr Arg Ala His Pro Phe
                180                 185                 190

Trp Met Gln Lys Tyr Cys Pro Ser His Glu Arg Asp Gly Thr Pro Arg
                195                 200                 205

Cys Cys Ser Cys Glu Arg Met Glu Pro Lys Asp Thr Lys Tyr Leu Ile
                210                 215                 220
```

Leu Asp Asp Gly Arg Lys Leu Cys Leu Glu Cys Leu Asp Ser Ala Ile
225                 230                 235                 240

Met Asp Thr His Glu Cys Gln Pro Leu Tyr Leu Glu Ile Arg Glu Phe
            245                 250                 255

Tyr Glu Gly Leu His Met Lys Val Glu Gln Gln Ile Pro Met Leu Leu
        260                 265                 270

Val Glu Arg Ser Ala Leu Asn Glu Ala Met Glu Gly Glu Lys His Gly
    275                 280                 285

His His His Leu Pro Glu Thr Arg Gly Leu Cys Leu Ser Glu Glu Gln
290                 295                 300

Thr Val Thr Thr Val Leu Arg Arg Pro Arg Ile Gly Ala Gly Tyr Lys
305                 310                 315                 320

Leu Ile Asp Met Ile Thr Glu Pro Cys Arg Leu Ile Arg Arg Cys Glu
            325                 330                 335

Val Thr Ala Ile Leu Ile Leu Tyr Gly Leu Pro Arg Leu Leu Thr Gly
        340                 345                 350

Ser Ile Leu Ala His Glu Met Met His Ala Trp Leu Arg Leu Asn Gly
    355                 360                 365

Tyr Pro Asn Leu Arg Pro Glu Val Glu Glu Gly Ile Cys Gln Val Leu
370                 375                 380

Ala His Met Trp Leu Glu Ser Glu Thr Tyr Ala Gly Ser Thr Leu Val
385                 390                 395                 400

Asp Ile Ala Ser Ser Ser Ser Ala Val Val Ser Ala Ser Ser Lys
            405                 410                 415

Lys Gly Glu Arg Ser Asp Phe Glu Lys Lys Leu Gly Phe Phe Lys
        420                 425                 430

His Gln Ile Glu Ser Asp Ser Ser Ala Tyr Gly Asp Gly Phe Arg
    435                 440                 445

Gln Gly Asn Gln Ala Val Leu Lys His Gly Leu Arg Arg Thr Leu Asp
450                 455                 460

His Ile Arg Leu Thr Gly Thr Phe Pro Lys Trp Ile
465                 470                 475

<210> SEQ ID NO 295
<211> LENGTH: 448
<212> TYPE: PRT
<213> ORGANISM: Arabidopsis thaliana

<400> SEQUENCE: 295

Asn Met Val Phe Pro Leu Pro Pro Ser Ser Leu Asp Asp Arg Ser Arg
1               5                   10                  15

Gly Ala Arg Asp Lys Glu Glu Leu Asp Arg Ser Ile Ser Leu Ser Leu
            20                  25                  30

Ala Asp Asn Thr Lys Arg Pro His Gly Tyr Gly Trp Ser Met Asp Asn
        35                  40                  45

Asn Arg Asp Phe Pro Arg Pro Phe His Gly Leu Asn Pro Ser Ser
    50                  55                  60

Phe Ile Pro Pro Tyr Glu Pro Ser Tyr Gln Tyr Arg Arg Gln Arg
65                  70                  75                  80

Ile Cys Gly Gly Cys Asn Ser Asp Ile Gly Ser Gly Asn Tyr Leu Gly
            85                  90                  95

Cys Met Gly Thr Phe Phe His Pro Glu Cys Phe Arg Cys His Ser Cys
        100                 105                 110

Gly Tyr Ala Ile Thr Glu His Glu Phe Ser Leu Ser Gly Thr Lys Pro
    115                 120                 125

Tyr His Lys Leu Cys Phe Lys Glu Leu Thr His Pro Lys Cys Glu Val
            130                 135                 140

Cys His His Phe Ile Pro Thr Asn Asp Ala Gly Leu Ile Glu Tyr Arg
145                 150                 155                 160

Cys His Pro Phe Trp Asn Gln Lys Tyr Cys Pro Ser His Glu Tyr Asp
                165                 170                 175

Lys Thr Ala Arg Cys Cys Ser Cys Glu Arg Leu Glu Ser Trp Asp Val
            180                 185                 190

Arg Tyr Tyr Thr Leu Glu Asp Gly Arg Ser Leu Cys Leu Glu Cys Met
        195                 200                 205

Glu Thr Ala Ile Thr Asp Thr Gly Glu Cys Gln Pro Leu Tyr His Ala
    210                 215                 220

Ile Arg Asp Tyr Tyr Glu Gly Met Tyr Met Lys Leu Asp Gln Gln Ile
225                 230                 235                 240

Pro Met Leu Leu Val Gln Arg Glu Ala Leu Asn Asp Ala Ile Val Gly
                245                 250                 255

Glu Lys Asn Gly Tyr His His Met Pro Glu Thr Arg Gly Leu Cys Leu
            260                 265                 270

Ser Glu Glu Gln Thr Val Thr Ser Val Leu Arg Arg Pro Arg Leu Gly
        275                 280                 285

Ala His Arg Leu Val Gly Met Arg Thr Gln Pro Gln Arg Leu Thr Arg
    290                 295                 300

Lys Cys Glu Val Thr Ala Ile Leu Val Leu Tyr Gly Leu Pro Arg Leu
305                 310                 315                 320

Leu Thr Gly Ala Ile Leu Ala His Glu Leu Met His Gly Trp Leu Arg
                325                 330                 335

Leu Asn Gly Phe Arg Asn Leu Asn Pro Glu Val Glu Glu Gly Ile Cys
            340                 345                 350

Gln Val Leu Ser Tyr Met Trp Leu Glu Ser Glu Val Leu Ser Asp Pro
        355                 360                 365

Ser Thr Arg Asn Leu Pro Ser Thr Ser Ser Val Ala Thr Ser Ser Ser
    370                 375                 380

Ser Ser Phe Ser Asn Lys Lys Gly Gly Lys Ser Asn Val Glu Lys Lys
385                 390                 395                 400

Leu Gly Glu Phe Phe Lys His Gln Ile Ala His Asp Ala Ser Pro Ala
                405                 410                 415

Tyr Gly Gly Gly Phe Arg Ala Ala Asn Ala Ala Cys Lys Tyr Gly
            420                 425                 430

Leu Arg Arg Thr Leu Asp His Ile Arg Leu Thr Gly Thr Phe Pro Leu
        435                 440                 445

<210> SEQ ID NO 296
<211> LENGTH: 644
<212> TYPE: PRT
<213> ORGANISM: Arabidopsis thaliana

<400> SEQUENCE: 296

Met Ala Ser Asp Tyr Tyr Ser Ser Asp Glu Gly Phe Gly Glu Lys
1               5                   10                  15

Val Gly Leu Ile Gly Glu Lys Asp Arg Phe Glu Ala Glu Thr Ile His
            20                  25                  30

Val Ile Glu Val Ser Gln His Glu Ala Asp Ile Gln Lys Ala Lys Gln
        35                  40                  45

Arg Ser Leu Ala Thr His Glu Ala Glu Lys Leu Asp Leu Ala Thr His

-continued

```
                50                  55                  60
Glu Ala Glu Gln Leu Asp Leu Ala Ile Gln Glu Phe Ser Arg Gln Glu
 65                  70                  75                  80

Glu Glu Glu Glu Arg Arg Thr Arg Glu Leu Glu Asn Asp Ala Gln
                 85                  90                  95

Ile Ala Asn Val Leu Gln His Glu Glu Arg Glu Arg Leu Ile Asn Lys
                    100                 105                 110

Lys Thr Ala Leu Glu Asp Glu Glu Asp Glu Leu Leu Ala Arg Thr Leu
                    115                 120                 125

Glu Glu Ser Leu Lys Glu Asn Asn Arg Arg Lys Met Phe Glu Glu Gln
                    130                 135                 140

Val Asn Lys Asp Glu Gln Leu Ala Leu Ile Val Gln Glu Ser Leu Asn
145                 150                 155                 160

Met Glu Glu Tyr Pro Ile Arg Leu Glu Gly Tyr Lys Ser Ile Ser Arg
                    165                 170                 175

Arg Ala Pro Leu Asp Val Asp Glu Gln Phe Ala Lys Ala Val Lys Glu
                    180                 185                 190

Ser Leu Lys Asn Lys Gly Lys Gly Lys Gln Phe Glu Asp Glu Gln Val
                    195                 200                 205

Lys Lys Asp Glu Gln Leu Ala Leu Ile Val Gln Glu Ser Leu Asn Met
210                 215                 220

Val Glu Ser Pro Pro Arg Leu Glu Glu Asn Asn Asn Ile Ser Thr Arg
225                 230                 235                 240

Ala Pro Val Asp Glu Asp Glu Gln Leu Ala Lys Ala Val Glu Glu Ser
                    245                 250                 255

Leu Lys Gly Lys Gly Gln Ile Lys Gln Ser Lys Asp Glu Val Glu Gly
                    260                 265                 270

Asp Gly Met Leu Leu Glu Leu Asn Pro Pro Ser Leu Cys Gly Gly
                    275                 280                 285

Cys Asn Phe Ala Val Glu His Gly Gly Ser Val Asn Ile Leu Gly Val
                    290                 295                 300

Leu Trp His Pro Gly Cys Phe Cys Cys Arg Ala Cys His Lys Pro Ile
305                 310                 315                 320

Ala Ile His Asp Ile Glu Asn His Val Ser Asn Ser Arg Gly Lys Phe
                    325                 330                 335

His Lys Ser Cys Tyr Glu Arg Tyr Cys Tyr Val Cys Lys Glu Lys Lys
                    340                 345                 350

Met Lys Thr Tyr Asn Asn His Pro Phe Trp Glu Glu Arg Tyr Cys Pro
                    355                 360                 365

Val His Glu Ala Asp Gly Thr Pro Lys Cys Cys Ser Cys Glu Arg Leu
                    370                 375                 380

Glu Pro Arg Glu Ser Asn Tyr Val Met Leu Ala Asp Gly Arg Trp Leu
385                 390                 395                 400

Cys Leu Glu Cys Met Asn Ser Ala Val Met Asp Ser Asp Glu Cys Gln
                    405                 410                 415

Pro Leu His Phe Asp Met Arg Asp Phe Glu Gly Leu Asn Met Lys
                    420                 425                 430

Ile Glu Lys Glu Phe Pro Phe Leu Leu Val Glu Lys Gln Ala Leu Asn
                    435                 440                 445

Lys Ala Glu Lys Glu Glu Lys Ile Asp Tyr Gln Tyr Glu Val Val Thr
                    450                 455                 460

Arg Gly Ile Cys Leu Ser Glu Glu Gln Ile Val Asp Ser Val Ser Gln
465                 470                 475                 480
```

```
Arg Pro Val Arg Gly Pro Asn Lys Leu Val Gly Met Ala Thr Glu
                485                 490                 495

Ser Gln Lys Val Thr Arg Glu Cys Glu Val Thr Ala Ile Leu Ile Leu
            500                 505                 510

Tyr Gly Leu Pro Arg Leu Leu Thr Gly Tyr Ile Leu Ala His Glu Met
            515                 520                 525

Met His Ala Tyr Leu Arg Leu Asn Gly His Arg Asn Leu Asn Asn Ile
    530                 535                 540

Leu Glu Glu Gly Ile Cys Gln Val Leu Gly His Leu Trp Leu Asp Ser
545                 550                 555                 560

Gln Thr Tyr Ala Thr Ala Asp Ala Thr Ala Asp Ala Ser Ser Ser Ala
                565                 570                 575

Ser Ser Ser Ser Arg Thr Pro Pro Ala Ala Ser Ala Ser Lys Lys Gly
            580                 585                 590

Glu Trp Ser Asp Phe Asp Lys Lys Leu Val Glu Phe Cys Lys Asn Gln
            595                 600                 605

Ile Glu Thr Asp Asp Ser Pro Val Tyr Gly Leu Gly Phe Arg Thr Val
            610                 615                 620

Asn Glu Met Val Thr Asn Ser Ser Leu Gln Glu Thr Leu Lys Glu Ile
625                 630                 635                 640

Leu Arg Gln Arg

<210> SEQ ID NO 297
<211> LENGTH: 702
<212> TYPE: PRT
<213> ORGANISM: Arabidopsis thaliana

<400> SEQUENCE: 297

Met Pro Ile Ser Asp Val Ala Ser Leu Val Gly Gly Ala Ala Leu Gly
1               5                   10                  15

Ala Pro Leu Ser Glu Ile Phe Lys Leu Val Ile Glu Glu Ala Lys Lys
            20                  25                  30

Val Lys Asp Phe Lys Pro Leu Ser Gln Asp Leu Ala Ser Thr Met Glu
        35                  40                  45

Arg Leu Val Pro Ile Phe Asn Glu Ile Asp Met Met Gln Gln Gly Ser
    50                  55                  60

Asn Arg Gly Thr Ser Glu Leu Lys Val Leu Thr Glu Thr Met Glu Arg
65                  70                  75                  80

Ala Gly Glu Met Val His Lys Cys Ser Arg Ile Gln Trp Tyr Ser Ile
                85                  90                  95

Ala Lys Lys Ala Leu Tyr Thr Arg Glu Ile Lys Ala Ile Asn Gln Asp
            100                 105                 110

Phe Leu Lys Phe Cys Gln Ile Glu Leu Gln Leu Ile Gln His Arg Asn
        115                 120                 125

Gln Leu Gln Tyr Met Arg Ser Met Gly Met Ala Ser Val Ser Thr Lys
    130                 135                 140

Ala Asp Leu Leu Ser Asp Ile Gly Asn Glu Phe Ser Lys Leu Cys Leu
145                 150                 155                 160

Val Ala Gln Pro Glu Val Val Thr Lys Phe Trp Leu Lys Arg Pro Leu
                165                 170                 175

Met Glu Leu Lys Lys Met Leu Phe Glu Asp Gly Val Val Thr Val Val
            180                 185                 190

Val Ser Ala Pro Tyr Ala Leu Gly Lys Thr Thr Leu Val Thr Lys Leu
        195                 200                 205
```

```
Cys His Asp Ala Asp Val Lys Glu Lys Phe Lys Gln Ile Phe Phe Ile
    210                 215                 220

Ser Val Ser Lys Phe Pro Asn Val Arg Leu Ile Gly His Lys Leu Leu
225                 230                 235                 240

Glu His Ile Gly Cys Lys Ala Asn Glu Tyr Glu Asn Asp Leu Asp Ala
                    245                 250                 255

Met Leu Tyr Ile Gln Gln Leu Leu Lys Gln Leu Gly Arg Asn Gly Ser
                260                 265                 270

Ile Leu Leu Val Leu Asp Asp Val Trp Ala Glu Glu Ser Leu Leu
                275                 280                 285

Gln Lys Phe Leu Ile Gln Leu Pro Asp Tyr Lys Ile Leu Val Thr Ser
    290                 295                 300

Arg Phe Glu Phe Thr Ser Phe Gly Pro Thr Phe His Leu Lys Pro Leu
305                 310                 315                 320

Ile Asp Asp Glu Val Glu Cys Arg Asp Glu Ile Glu Glu Asn Glu Lys
                    325                 330                 335

Leu Pro Glu Val Asn Pro Pro Leu Ser Met Cys Gly Cys Asn Ser
                340                 345                 350

Ala Val Lys His Glu Glu Ser Val Asn Ile Leu Gly Val Leu Trp His
            355                 360                 365

Pro Gly Cys Phe Cys Cys Arg Ser Cys Asp Lys Pro Ile Ala Ile His
    370                 375                 380

Glu Leu Glu Asn His Val Ser Asn Ser Arg Gly Lys Phe His Lys Ser
385                 390                 395                 400

Cys Tyr Glu Arg Tyr Cys Tyr Val Cys Lys Glu Lys Lys Met Lys Thr
                    405                 410                 415

Tyr Asn Ile His Pro Phe Trp Glu Glu Arg Tyr Cys Pro Val His Glu
                420                 425                 430

Ala Asp Gly Thr Pro Lys Cys Cys Ser Cys Glu Arg Leu Glu Pro Arg
            435                 440                 445

Gly Thr Lys Tyr Gly Lys Leu Ser Asp Gly Arg Trp Leu Cys Leu Glu
    450                 455                 460

Cys Gly Lys Ser Ala Met Asp Ser Asp Glu Cys Gln Pro Leu Tyr Phe
465                 470                 475                 480

Asp Met Arg Asp Phe Phe Glu Ser Leu Asn Met Lys Ile Glu Lys Glu
                485                 490                 495

Phe Pro Leu Ile Leu Val Arg Lys Glu Leu Leu Asn Lys Lys Glu Glu
                500                 505                 510

Lys Ile Asp Asn His Tyr Glu Val Leu Ile Arg Ala Tyr Cys Met Ser
            515                 520                 525

Glu Gln Lys Ile Met Thr Tyr Val Ser Glu Pro Arg Thr Gly Gln
    530                 535                 540

Asn Lys Gln Leu Ile Asp Met Asp Thr Glu Pro Gln Gly Val Val His
545                 550                 555                 560

Glu Cys Lys Val Thr Ala Ile Leu Ile Leu Tyr Gly Leu Pro Arg Leu
                565                 570                 575

Leu Thr Gly Tyr Ile Leu Ala His Glu Met Met His Ala Trp Leu Arg
                580                 585                 590

Leu Asn Gly His Met Asn Leu Asn Asn Ile Leu Glu Glu Gly Ile Cys
            595                 600                 605

Gln Val Leu Gly His Leu Trp Leu Glu Ser Gln Thr Tyr Ala Thr Ala
    610                 615                 620
```

Asp Thr Thr Ala Asp Ala Ser Ala Ser Ser Ser Ser Arg Thr
625                 630                 635                 640

Pro Pro Ala Ala Ser Ala Ser Lys Lys Gly Glu Trp Ser Asp Phe Asp
            645                 650                 655

Lys Lys Leu Val Glu Phe Cys Lys Asn Gln Ile Glu Thr Asp Glu Ser
                660                 665                 670

Pro Val Tyr Gly Leu Gly Phe Arg Thr Val Asn Glu Met Val Thr Asn
            675                 680                 685

Ser Ser Leu Gln Glu Thr Leu Lys Glu Ile Leu Arg Arg Arg
            690                 695                 700

<210> SEQ ID NO 298
<211> LENGTH: 529
<212> TYPE: PRT
<213> ORGANISM: Arabidopsis thaliana

<400> SEQUENCE: 298

Met Trp Cys Leu Ser Cys Phe Lys Pro Ser Thr Lys His Asp Pro Ser
1               5                   10                  15

Glu Asp Arg Phe Glu Glu Glu Thr Asn Ile Val Thr Gly Ile Ser Leu
            20                  25                  30

Tyr Glu Asp Val Ile Leu Arg Gln Arg Arg Ser Glu Ala Asp Gln Ile
        35                  40                  45

Glu Trp Ala Ile Gln Asp Ser Phe Asn Pro Glu Thr Ser Arg Cys
50                  55                  60

Arg Gln Arg Glu Glu Asp Asp Gln Ile Ala Arg Gly Leu Gln Tyr Val
65                  70                  75                  80

Glu Glu Thr Glu Leu Asp Lys Ser Val Val Asp Glu Asp Gln Gln
                85                  90                  95

Leu Ser Lys Ile Val Glu Glu Ser Leu Lys Glu Lys Gly Lys Ser Lys
            100                 105                 110

Gln Phe Glu Asp Asp Gln Val Glu Asn Asp Glu Gln Gln Ala Leu Met
        115                 120                 125

Val Gln Glu Ser Leu Tyr Met Val Glu Leu Ser Ala Gln Leu Glu Glu
    130                 135                 140

Asp Lys Asn Ile Ser Thr Ile Pro Pro Leu Asn Glu Asp Ala Gln Leu
145                 150                 155                 160

Gln Lys Val Ile Trp Glu Ser Ala Lys Gly Lys Gly Gln Ile Glu His
                165                 170                 175

Phe Lys Asp Pro Val Glu Glu Asp Gly Asn Leu Pro Arg Val Asp Leu
            180                 185                 190

Asn Val Asn His Pro His Ser Ile Cys Asp Gly Cys Lys Ser Ala Ile
        195                 200                 205

Glu Tyr Gly Arg Ser Val His Ala Leu Gly Val Asn Trp His Pro Glu
    210                 215                 220

Cys Phe Cys Cys Arg Tyr Cys Asp Lys Pro Ile Ala Met His Glu Tyr
225                 230                 235                 240

Lys Glu His Pro Phe Trp Lys Glu Lys Tyr Cys Pro Phe His Glu Val
                245                 250                 255

Asp Gly Thr Pro Lys Cys Cys Ser Cys Glu Arg Leu Glu Pro Trp Gly
            260                 265                 270

Thr Lys Tyr Val Met Leu Ala Asp Asn Arg Trp Leu Cys Val Lys Cys
        275                 280                 285

Met Glu Cys Ala Val Met Asp Thr Tyr Glu Cys Gln Pro Leu His Phe
    290                 295                 300

```
Glu Ile Arg Glu Phe Phe Gly Ser Leu Asn Met Lys Val Glu Lys Glu
305                 310                 315                 320

Phe Pro Leu Leu Leu Val Glu Lys Glu Ala Leu Lys Lys Ala Glu Ala
            325                 330                 335

Gln Glu Lys Ile Asp Asn Gln His Gly Val Val Thr Arg Gly Ile Cys
            340                 345                 350

Leu Ser Glu Gly Gln Ile Val Asn Ser Val Phe Lys Lys Pro Thr Met
        355                 360                 365

Gly Pro Asn Gly Glu Leu Val Ser Leu Gly Thr Glu Pro Gln Lys Val
    370                 375                 380

Val Gly Gly Cys Glu Val Thr Ala Ile Leu Ile Leu Tyr Gly Leu Pro
385                 390                 395                 400

Arg Leu Leu Thr Gly Tyr Ile Leu Ala His Glu Met Met His Ala Trp
                405                 410                 415

Leu Arg Leu Asn Gly Tyr Arg Asn Leu Lys Leu Glu Leu Glu Glu Gly
            420                 425                 430

Ile Cys Gln Val Leu Gly His Met Trp Leu Glu Ser Gln Thr Tyr Ser
            435                 440                 445

Ser Ser Ala Ala Ala Ser Ala Ser Ser Ser Arg Thr Pro Ala
    450                 455                 460

Ala Asn Ala Ser Lys Lys Gly Ala Gln Ser Asp Tyr Glu Lys Lys Leu
465                 470                 475                 480

Val Glu Phe Cys Lys Asp Gln Ile Glu Thr Asp Asp Ser Pro Val Tyr
                485                 490                 495

Gly Val Gly Phe Arg Lys Val Asn Gln Met Val Ser Asp Ser Ser Leu
                500                 505                 510

His Lys Ile Leu Lys Ser Ile Gln His Trp Thr Lys Pro Asp Ser Asn
            515                 520                 525

Leu

<210> SEQ ID NO 299
<211> LENGTH: 451
<212> TYPE: PRT
<213> ORGANISM: Arabidopsis thaliana

<400> SEQUENCE: 299

Met Val Arg Arg Lys Arg Gln Glu Glu Asp Glu Lys Ile Glu Ile Glu
1               5                   10                  15

Arg Val Lys Glu Glu Ser Leu Lys Leu Ala Lys Gln Ala Glu Glu Lys
            20                  25                  30

Arg Arg Leu Glu Glu Ser Lys Glu Gln Gly Lys Arg Ile Gln Val Asp
        35                  40                  45

Asp Asp Gln Leu Ala Lys Thr Thr Ser Lys Asp Lys Gly Gln Ile Asn
    50                  55                  60

His Ser Lys Asp Val Val Glu Glu Asp Val Asn Pro Pro Ser Ser
65                  70                  75                  80

Ile Asp Gly Lys Ser Glu Ile Gly Asp Gly Thr Ser Val Asn Pro Arg
                85                  90                  95

Cys Leu Cys Cys Phe His Cys His Arg Pro Phe Val Met His Glu Ile
            100                 105                 110

Leu Lys Lys Gly Lys Phe His Ile Asp Cys Tyr Lys Glu Tyr Tyr Arg
        115                 120                 125

Asn Arg Asn Cys Tyr Val Cys Gln Gln Lys Ile Pro Val Asn Ala Glu
    130                 135                 140
```

```
Gly Ile Arg Lys Phe Ser Glu His Pro Phe Trp Lys Glu Lys Tyr Cys
145                 150                 155                 160

Pro Ile His Asp Glu Asp Gly Thr Ala Lys Cys Cys Ser Cys Glu Arg
                165                 170                 175

Leu Glu Pro Arg Gly Thr Asn Tyr Val Met Leu Gly Asp Phe Arg Trp
            180                 185                 190

Leu Cys Ile Glu Cys Met Gly Ser Ala Val Met Asp Thr Asn Glu Val
        195                 200                 205

Gln Pro Leu His Phe Glu Ile Arg Glu Phe Phe Glu Gly Leu Phe Leu
    210                 215                 220

Lys Val Asp Lys Glu Phe Ala Leu Leu Leu Val Glu Lys Gln Ala Leu
225                 230                 235                 240

Asn Lys Ala Glu Glu Glu Lys Ile Asp Tyr His Arg Ala Ala Val
                245                 250                 255

Thr Arg Gly Leu Cys Met Ser Glu Gly Gln Ile Val Pro Ser Ile Ile
                260                 265                 270

Lys Gly Pro Arg Met Gly Pro Asp Asn Gln Leu Ile Thr Asp Ile Val
            275                 280                 285

Thr Glu Ser Gln Arg Val Ser Gly Phe Glu Val Thr Gly Ile Leu Ile
    290                 295                 300

Ile Tyr Gly Leu Pro Arg Leu Leu Thr Gly Tyr Ile Leu Ala His Glu
305                 310                 315                 320

Met Met His Ala Trp Leu Arg Leu Asn Gly Tyr Lys Asn Leu Lys Leu
                325                 330                 335

Glu Leu Glu Glu Gly Leu Cys Gln Ala Leu Gly Leu Arg Trp Leu Glu
                340                 345                 350

Ser Gln Thr Phe Ala Ser Thr Asp Ala Ala Ala Ala Ala Val Ala
    355                 360                 365

Ser Ser Ser Ser Phe Ser Ser Ser Thr Ala Pro Pro Ala Ala Ile Thr
370                 375                 380

Ser Lys Lys Ser Asp Asp Trp Ser Ile Phe Glu Lys Lys Leu Val Glu
385                 390                 395                 400

Phe Cys Met Asn Gln Ile Lys Glu Asp Asp Ser Pro Val Tyr Gly Leu
                405                 410                 415

Gly Phe Lys Gln Val Tyr Glu Met Met Val Ser Asn Asn Tyr Asn Ile
            420                 425                 430

Lys Asp Thr Leu Lys Asp Ile Val Ser Ala Ser Asn Ala Thr Pro Asp
        435                 440                 445

Ser Thr Val
    450

<210> SEQ ID NO 300
<211> LENGTH: 1575
<212> TYPE: PRT
<213> ORGANISM: Arabidopsis thaliana

<400> SEQUENCE: 300

Met Glu Pro Pro Ala Ala Arg Val Thr Pro Ser Ile Lys Ala Asp Cys
1               5                   10                  15

Ser His Ser Val Asn Ile Ile Cys Glu Glu Thr Val Leu His Ser Leu
                20                  25                  30

Val Ser His Leu Ser Ala Ala Leu Arg Arg Glu Gly Ile Ser Val Phe
            35                  40                  45

Val Asp Ala Cys Gly Leu Gln Glu Thr Lys Phe Phe Ser Ile Lys Gln
```

```
            50                  55                  60
Asn Gln Pro Leu Thr Asp Gly Ala Arg Val Leu Val Val Ile Ser
 65                  70                  75                  80

Asp Glu Val Glu Phe Tyr Asp Pro Trp Phe Lys Phe Leu Lys Val
                     85                  90                  95

Ile Gln Gly Trp Gln Asn Asn Gly His Val Val Pro Val Phe Tyr
                    100                 105                 110

Gly Val Asp Ser Leu Thr Arg Val Tyr Gly Ile Leu Ser Asn Asn Val
                    115                 120                 125

Leu Thr Asp Ser Glu Leu Val Glu Glu Ile Val Arg Asp Val Tyr Gly
            130                 135                 140

Lys Leu Tyr Pro Ala Glu Arg Val Gly Ile Tyr Ala Arg Leu Leu Glu
145                 150                 155                 160

Ile Glu Lys Leu Leu Tyr Lys Gln His Arg Asp Ile Arg Ser Ile Gly
                    165                 170                 175

Ile Trp Gly Met Pro Gly Ile Gly Lys Thr Thr Leu Ala Lys Ala Val
                    180                 185                 190

Phe Asn His Met Ser Thr Asp Tyr Asp Ala Ser Cys Phe Ile Glu Asn
                    195                 200                 205

Phe Asp Glu Ala Phe His Lys Glu Gly Leu His Arg Leu Leu Lys Glu
            210                 215                 220

Arg Ile Gly Lys Ile Leu Lys Asp Glu Phe Asp Ile Glu Ser Ser Tyr
225                 230                 235                 240

Ile Met Arg Pro Thr Leu His Arg Asp Lys Leu Tyr Asp Lys Arg Ile
                    245                 250                 255

Leu Val Val Leu Asp Asp Val Arg Asp Ser Leu Ala Ala Glu Ser Phe
                    260                 265                 270

Leu Lys Arg Leu Asp Trp Phe Gly Ser Gly Ser Leu Ile Ile Ile Thr
                    275                 280                 285

Ser Val Asp Lys Gln Val Phe Ala Phe Cys Gln Ile Asn Gln Ile Tyr
            290                 295                 300

Thr Val Gln Gly Leu Asn Val His Glu Ala Leu Gln Leu Phe Ser Gln
305                 310                 315                 320

Ser Val Phe Gly Ile Asn Glu Pro Glu Gln Asn Asp Arg Lys Leu Ser
                    325                 330                 335

Met Lys Val Ile Asp Tyr Val Asn Gly Asn Pro Leu Ala Leu Ser Ile
                    340                 345                 350

Tyr Gly Arg Glu Leu Met Gly Lys Lys Ser Glu Met Glu Thr Ala Phe
                    355                 360                 365

Phe Glu Leu Lys His Cys Pro Pro Leu Lys Ile Gln Asp Val Leu Lys
            370                 375                 380

Asn Ala Tyr Ser Ala Leu Ser Asp Asn Glu Lys Asn Ile Val Leu Asp
385                 390                 395                 400

Ile Ala Phe Phe Phe Lys Gly Glu Thr Val Asn Tyr Val Met Gln Leu
                    405                 410                 415

Leu Glu Glu Ser His Tyr Phe Pro Arg Leu Ala Ile Asp Val Leu Val
                    420                 425                 430

Asp Lys Cys Val Leu Thr Ile Ser Glu Asn Thr Val Gln Met Asn Asn
            435                 440                 445

Leu Ile Gln Asp Thr Cys Gln Glu Ile Phe Asn Gly Glu Ile Glu Thr
450                 455                 460

Cys Thr Arg Met Trp Glu Pro Ser Arg Ile Arg Tyr Leu Leu Glu Tyr
465                 470                 475                 480
```

```
Asp Glu Leu Glu Gly Ser Gly Glu Thr Lys Ala Met Pro Lys Ser Gly
            485                 490                 495

Leu Val Ala Glu His Ile Glu Ser Ile Phe Leu Asp Thr Ser Asn Val
            500                 505                 510

Lys Phe Asp Val Lys His Asp Ala Phe Lys Asn Met Phe Asn Leu Lys
            515                 520                 525

Phe Leu Lys Ile Tyr Asn Ser Cys Ser Lys Tyr Ile Ser Gly Leu Asn
            530                 535                 540

Phe Pro Lys Gly Leu Asp Ser Leu Pro Tyr Glu Leu Arg Leu Leu His
545                 550                 555                 560

Trp Glu Asn Tyr Pro Leu Gln Ser Leu Pro Gln Asp Phe Asp Phe Gly
                565                 570                 575

His Leu Val Lys Leu Ser Met Pro Tyr Ser Gln Leu His Lys Leu Gly
            580                 585                 590

Thr Arg Val Lys Asp Leu Val Met Leu Lys Arg Leu Ile Leu Ser His
            595                 600                 605

Ser Leu Gln Leu Val Glu Cys Asp Ile Leu Ile Tyr Ala Gln Asn Ile
    610                 615                 620

Glu Leu Ile Asp Leu Gln Gly Cys Thr Gly Leu Gln Arg Phe Pro Asp
625                 630                 635                 640

Thr Ser Gln Leu Gln Asn Leu Arg Val Val Asn Leu Ser Gly Cys Thr
                645                 650                 655

Glu Ile Lys Cys Phe Ser Gly Val Pro Pro Asn Ile Glu Glu Leu His
            660                 665                 670

Leu Gln Gly Thr Arg Ile Arg Glu Ile Pro Ile Phe Asn Ala Thr His
            675                 680                 685

Pro Pro Lys Val Lys Leu Asp Arg Lys Lys Leu Trp Asn Leu Leu Glu
690                 695                 700

Asn Phe Ser Asp Val Glu His Ile Asp Leu Glu Cys Val Thr Asn Leu
705                 710                 715                 720

Ala Thr Val Thr Ser Asn His Val Met Gly Lys Leu Val Cys Leu
            725                 730                 735

Asn Met Lys Tyr Cys Ser Asn Leu Arg Gly Leu Pro Asp Met Val Ser
            740                 745                 750

Leu Glu Ser Leu Lys Val Leu Tyr Leu Ser Gly Cys Ser Glu Leu Glu
            755                 760                 765

Lys Ile Met Gly Phe Pro Arg Asn Leu Lys Lys Leu Tyr Val Gly Gly
    770                 775                 780

Thr Ala Ile Arg Glu Leu Pro Gln Leu Pro Asn Ser Leu Glu Phe Leu
785                 790                 795                 800

Asn Ala His Gly Cys Lys His Leu Lys Ser Ile Asn Leu Asp Phe Glu
            805                 810                 815

Gln Leu Pro Arg His Phe Ile Phe Ser Asn Cys Tyr Arg Phe Ser Ser
            820                 825                 830

Gln Val Ile Ala Glu Phe Val Glu Lys Gly Leu Val Ala Ser Leu Ala
            835                 840                 845

Arg Ala Lys Gln Glu Glu Leu Ile Lys Ala Pro Glu Val Ile Ile Cys
    850                 855                 860

Ile Pro Met Asp Thr Arg Gln Arg Ser Ser Phe Arg Leu Gln Ala Gly
865                 870                 875                 880

Arg Asn Ala Met Thr Asp Leu Val Pro Trp Met Gln Lys Pro Ile Ser
            885                 890                 895
```

-continued

```
Gly Phe Ser Met Ser Val Val Ser Phe Gln Asp Asp Tyr His Asn
            900                 905                 910
Asp Val Gly Leu Arg Ile Arg Cys Val Gly Thr Trp Lys Thr Trp Asn
        915                 920                 925
Asn Gln Pro Asp Arg Ile Val Glu Arg Phe Phe Gln Cys Trp Ala Pro
    930                 935                 940
Thr Glu Ala Pro Lys Val Val Ala Asp His Ile Phe Val Leu Tyr Asp
945                 950                 955                 960
Thr Lys Met His Pro Ser Asp Ser Glu Glu Asn His Ile Ser Met Trp
                965                 970                 975
Ala His Glu Val Lys Phe Glu Phe His Thr Val Ser Gly Glu Asn Asn
            980                 985                 990
Pro Leu Gly Ala Ser Cys Lys Val Thr Glu Cys Gly Val Glu Val Ile
        995                 1000                1005
Thr Ala Ala Thr Gly Asp Thr Ser Val Ser Gly Ile Ile Arg Glu
    1010                1015                1020
Ser Glu Thr Ile Thr Ile Ile Glu Lys Glu Asp Thr Ile Ile Asp
    1025                1030                1035
Glu Glu Asp Thr Pro Leu Leu Ser Arg Lys Pro Glu Glu Thr Asn
    1040                1045                1050
Arg Ser Arg Ser Ser Ser Glu Leu Gln Lys Leu Ser Ser Thr Ser
    1055                1060                1065
Ser Lys Pro Lys Asn Leu Arg Ser Arg Ser Arg Arg Thr Thr Ala
    1070                1075                1080
Leu Glu Glu Ala Leu Glu Glu Ala Leu Lys Glu Arg Glu Lys Leu
    1085                1090                1095
Glu Asp Thr Arg Glu Leu Gln Ile Ala Leu Ile Glu Ser Lys Lys
    1100                1105                1110
Ile Lys Lys Ile Lys Gln Ala Asp Glu Arg Asp Gln Ile Lys His
    1115                1120                1125
Ala Asp Glu Arg Glu Gln Arg Lys His Ser Lys Asp His Glu Glu
    1130                1135                1140
Glu Glu Ile Glu Ser Asn Glu Lys Glu Glu Arg Arg His Ser Lys
    1145                1150                1155
Asp Tyr Val Ile Glu Glu Leu Val Leu Lys Gly Lys Gly Lys Arg
    1160                1165                1170
Lys Gln Leu Asp Asp Asp Lys Ala Asp Glu Lys Glu Gln Ile Lys
    1175                1180                1185
His Ser Lys Asp His Val Glu Glu Val Asn Pro Pro Leu Ser
    1190                1195                1200
Lys Cys Lys Asp Cys Lys Ser Ala Ile Glu Asp Gly Ile Ser Ile
    1205                1210                1215
Asn Ala Tyr Gly Ser Val Trp His Pro Gln Cys Phe Cys Cys Leu
    1220                1225                1230
Arg Cys Arg Glu Pro Ile Ala Met Asn Glu Ile Ser Asp Leu Arg
    1235                1240                1245
Gly Met Tyr His Lys Pro Cys Tyr Lys Glu Leu Arg His Pro Asn
    1250                1255                1260
Cys Tyr Val Cys Glu Lys Lys Ile Pro Arg Thr Ala Glu Gly Leu
    1265                1270                1275
Lys Tyr His Glu His Pro Phe Trp Met Glu Thr Tyr Cys Pro Ser
    1280                1285                1290
His Asp Gly Asp Gly Thr Pro Lys Cys Cys Ser Cys Glu Arg Leu
```

```
                    1295                1300                1305

Glu His Cys Gly Thr Gln Tyr Val Met Leu Ala Asp Phe Arg Trp
    1310                1315                1320

Leu Cys Arg Glu Cys Met Asp Ser Ala Ile Met Asp Ser Asp Glu
    1325                1330                1335

Cys Gln Pro Leu His Phe Glu Ile Arg Glu Phe Phe Glu Gly Leu
    1340                1345                1350

His Met Lys Ile Glu Glu Glu Phe Pro Val Tyr Leu Val Glu Lys
    1355                1360                1365

Asn Ala Leu Asn Lys Ala Glu Lys Glu Lys Ile Gly Asp Gln
    1370                1375                1380

Cys Leu Met Val Val Arg Gly Ile Cys Leu Ser Glu Glu Gln Ile
    1385                1390                1395

Val Thr Ser Val Ser Gln Gly Val Arg Arg Met Leu Asn Lys Gln
    1400                1405                1410

Ile Leu Asp Thr Val Thr Glu Ser Gln Arg Val Val Arg Lys Cys
    1415                1420                1425

Glu Val Thr Ala Ile Leu Ile Leu Tyr Gly Leu Pro Arg Leu Leu
    1430                1435                1440

Thr Gly Tyr Ile Leu Ala His Glu Met Met His Ala Tyr Leu Arg
    1445                1450                1455

Leu Asn Gly Tyr Arg Asn Leu Asn Met Val Leu Glu Glu Gly Leu
    1460                1465                1470

Cys Gln Val Leu Gly Tyr Met Trp Leu Glu Cys Gln Thr Tyr Val
    1475                1480                1485

Phe Asp Thr Ala Thr Ile Ala Ser Ser Ser Ser Ser Arg Thr
    1490                1495                1500

Pro Leu Ser Thr Thr Thr Ser Lys Lys Val Asp Pro Ser Asp Phe
    1505                1510                1515

Glu Lys Arg Leu Val Asn Phe Cys Lys His Gln Ile Glu Thr Asp
    1520                1525                1530

Glu Ser Pro Phe Phe Gly Asp Gly Phe Arg Lys Val Asn Lys Met
    1535                1540                1545

Met Ala Ser Asn Asn His Ser Leu Lys Asp Thr Leu Lys Glu Ile
    1550                1555                1560

Ile Ser Ile Ser Lys Thr Pro Gln Tyr Ser Lys Leu
    1565                1570                1575

<210> SEQ ID NO 301
<211> LENGTH: 515
<212> TYPE: PRT
<213> ORGANISM: Arabidopsis thaliana

<400> SEQUENCE: 301

Gly Asn Asn Lys His Asn His Asn Val Tyr Tyr Asp Asn Tyr Pro Thr
1               5                   10                  15

Ala Ser His Asp Asp Glu Pro Ser Ala Ala Asp Thr Asp Ala Asp Asn
                20                  25                  30

Asp Glu Pro His His Thr Gln Glu Pro Ser Thr Ser Glu Asp Asn Thr
            35                  40                  45

Ser Asn Asp Gln Glu Asn Glu Asp Ile Asp Arg Ala Ile Ala Leu Ser
        50                  55                  60

Leu Leu Glu Glu Asn Gln Glu Gln Thr Ser Ile Ser Gly Lys Tyr Ser
65                  70                  75                  80
```

```
Met Pro Val Asp Glu Asp Glu Gln Leu Ala Arg Ala Leu Gln Glu Ser
             85                  90                  95

Met Val Val Gly Asn Ser Pro Arg His Lys Gly Ser Thr Tyr Asp
        100                 105                 110

Asn Gly Asn Ala Tyr Gly Ala Gly Asp Leu Tyr Gly Asn Gly His Met
            115                 120                 125

Tyr Gly Gly Gly Asn Val Tyr Ala Asn Gly Asp Ile Tyr Tyr Pro Arg
        130                 135                 140

Pro Ile Thr Phe Gln Met Asp Phe Arg Ile Cys Ala Gly Cys Asn Met
145                 150                 155                 160

Glu Ile Gly His Gly Arg Phe Leu Asn Cys Leu Asn Ser Leu Trp His
                165                 170                 175

Pro Glu Cys Phe Arg Cys Tyr Gly Cys Ser Gln Pro Ile Ser Glu Tyr
            180                 185                 190

Glu Phe Ser Thr Ser Gly Asn Tyr Pro Phe His Lys Ala Cys Tyr Arg
            195                 200                 205

Glu Arg Tyr His Pro Lys Cys Asp Val Cys Ser His Phe Ile Pro Thr
        210                 215                 220

Asn His Ala Gly Leu Ile Glu Tyr Arg Ala His Pro Phe Trp Val Gln
225                 230                 235                 240

Lys Tyr Cys Pro Ser His Glu His Asp Ala Thr Pro Arg Cys Cys Ser
            245                 250                 255

Cys Glu Arg Met Glu Pro Arg Asn Thr Arg Tyr Val Glu Leu Asn Asp
                260                 265                 270

Gly Arg Lys Leu Cys Leu Glu Cys Leu Asp Ser Ala Val Met Asp Thr
        275                 280                 285

Met Gln Cys Gln Pro Leu Tyr Leu Gln Ile Gln Asn Phe Tyr Glu Gly
        290                 295                 300

Leu Asn Met Lys Val Glu Gln Glu Val Pro Leu Leu Leu Val Glu Arg
305                 310                 315                 320

Gln Ala Leu Asn Glu Ala Arg Glu Gly Glu Lys Asn Gly His Tyr His
                325                 330                 335

Met Pro Glu Thr Arg Gly Leu Cys Leu Ser Glu Glu Gln Thr Val Ser
            340                 345                 350

Thr Val Arg Lys Arg Ser Lys His Gly Thr Gly Lys Trp Ala Gly Asn
            355                 360                 365

Ile Thr Glu Pro Tyr Lys Leu Thr Arg Gln Cys Glu Val Thr Ala Ile
        370                 375                 380

Leu Ile Leu Phe Gly Leu Pro Arg Leu Leu Thr Gly Ser Ile Leu Ala
385                 390                 395                 400

His Glu Met Met His Ala Trp Met Arg Leu Lys Gly Phe Arg Thr Leu
                405                 410                 415

Ser Gln Asp Val Glu Glu Gly Ile Cys Gln Val Met Ala His Lys Trp
            420                 425                 430

Leu Asp Ala Glu Leu Ala Ala Gly Ser Thr Asn Ser Asn Ala Ala Ser
        435                 440                 445

Ser Ser Ser Ser Ser Gln Gly Leu Lys Lys Gly Pro Arg Ser Gln Tyr
        450                 455                 460

Glu Arg Lys Leu Gly Glu Phe Phe Lys His Gln Ile Glu Ser Asp Ala
465                 470                 475                 480

Ser Pro Val Tyr Gly Asp Gly Phe Arg Ala Gly Arg Leu Ala Val His
            485                 490                 495

Lys Tyr Gly Leu Arg Lys Thr Leu Glu His Ile Gln Met Thr Gly Arg
```

```
                   500                 505                 510

Phe Pro Val
        515

<210> SEQ ID NO 302
<211> LENGTH: 530
<212> TYPE: PRT
<213> ORGANISM: Arabidopsis thaliana

<400> SEQUENCE: 302

Gly Gln Cys Asn Gly Arg Tyr Arg Glu Asp Arg Asn Leu Glu Gly Pro
1               5                   10                  15

Arg Tyr Ser Ala Glu Gly Ser Asp Phe Asp Lys Glu Glu Ile Glu Cys
            20                  25                  30

Ala Ile Ala Leu Ser Leu Ser Glu Gln Glu His Val Ile Pro Gln Asp
        35                  40                  45

Asp Lys Gly Lys Lys Ile Ile Glu Tyr Lys Ser Glu Thr Glu Glu Asp
    50                  55                  60

Asp Asp Asp Glu Asp Glu Asp Glu Glu Tyr Met Arg Ala Gln Leu
65                  70                  75                  80

Glu Ala Ala Glu Glu Glu Arg Arg Val Ala Gln Ala Gln Ile Glu
                85                  90                  95

Glu Glu Glu Lys Arg Arg Ala Glu Ala Gln Leu Glu Glu Thr Glu Lys
            100                 105                 110

Leu Leu Ala Lys Ala Arg Leu Glu Glu Glu Met Arg Arg Ser Lys
        115                 120                 125

Ala Gln Leu Glu Glu Asp Glu Leu Leu Ala Lys Ala Leu Gln Glu Ser
    130                 135                 140

Met Asn Val Gly Ser Pro Pro Arg Tyr Asp Pro Gly Asn Ile Leu Gln
145                 150                 155                 160

Pro Tyr Pro Phe Leu Ile Pro Ser Ser His Arg Ile Cys Val Gly Cys
                165                 170                 175

Gln Ala Glu Ile Gly His Gly Arg Phe Leu Ser Ala Trp Val Ala Phe
            180                 185                 190

Gly Ile Leu Asn Val Ser Val Ala Met His Phe Ser Met Ser Gly Asn
        195                 200                 205

Arg Pro Tyr His Lys Leu Cys Tyr Lys Glu Gln His Pro Lys Cys
    210                 215                 220

Asp Val Cys His Asn Phe Ile Pro Thr Asn Pro Ala Gly Leu Ile Glu
225                 230                 235                 240

Tyr Arg Ala His Pro Phe Trp Met Gln Lys Tyr Cys Pro Ser His Glu
                245                 250                 255

Arg Asp Gly Thr Pro Arg Cys Cys Ser Cys Glu Arg Met Glu Pro Lys
            260                 265                 270

Asp Thr Lys Tyr Leu Ile Leu Asp Asp Gly Arg Lys Leu Cys Leu Glu
        275                 280                 285

Cys Leu Asp Ser Ala Ile Met Asp Thr His Glu Cys Gln Pro Leu Tyr
    290                 295                 300

Leu Glu Ile Arg Glu Phe Tyr Glu Gly Leu His Met Lys Val Glu Gln
305                 310                 315                 320

Ser Asn Ser Tyr Ala Phe Gly Gly Glu Ile Ser Ser Lys Arg Ala Met
                325                 330                 335

Glu Gly Glu Lys His Gly His His Leu Pro Glu Thr Arg Gly Leu
            340                 345                 350
```

Cys Leu Ser Glu Glu Gln Thr Val Thr Thr Val Leu Arg Arg Pro Arg
            355                 360                 365

Ile Gly Ala Gly Tyr Lys Leu Ile Asp Met Ile Thr Glu Pro Cys Arg
    370                 375                 380

Leu Ile Arg Arg Cys Glu Val Thr Ala Ile Leu Ile Leu Tyr Gly Leu
385                 390                 395                 400

Pro Arg Leu Leu Thr Gly Ser Ile Leu Ala His Glu Met Met His Ala
                405                 410                 415

Trp Leu Arg Leu Asn Gly Tyr Pro Asn Leu Arg Pro Glu Val Glu Glu
            420                 425                 430

Gly Ile Cys Gln Val Leu Ala His Met Trp Leu Glu Ser Glu Thr Tyr
        435                 440                 445

Ala Gly Ser Thr Leu Val Asp Ile Ala Ser Ser Ser Ser Ala Val
    450                 455                 460

Val Ser Ala Ser Ser Lys Lys Gly Glu Arg Ser Asp Phe Glu Lys Lys
465                 470                 475                 480

Leu Gly Glu Phe Phe Lys His Gln Ile Glu Ser Asp Ser Ser Ala
                485                 490                 495

Tyr Gly Asp Gly Phe Arg Gln Gly Asn Gln Ala Val Leu Lys His Gly
            500                 505                 510

Leu Arg Arg Thr Leu Asp His Ile Arg Leu Thr Gly Thr Phe Pro Lys
        515                 520                 525

Trp Ile
    530

<210> SEQ ID NO 303
<211> LENGTH: 463
<212> TYPE: PRT
<213> ORGANISM: Arabidopsis thaliana

<400> SEQUENCE: 303

Gly Ala His Thr Asn His His Pro Pro Gln Phe Gln Glu Asp Glu Asn
1               5                   10                  15

Met Val Phe Pro Leu Pro Pro Ser Ser Leu Asp Asp Arg Ser Arg Gly
            20                  25                  30

Ala Arg Asp Lys Glu Glu Leu Asp Arg Ser Ile Ser Leu Ser Leu Ala
        35                  40                  45

Asp Asn Thr Lys Arg Pro His Gly Tyr Gly Trp Ser Met Asp Asn Asn
    50                  55                  60

Arg Asp Phe Pro Arg Pro Phe His Gly Gly Leu Asn Pro Ser Ser Phe
65                  70                  75                  80

Ile Pro Pro Tyr Glu Pro Ser Tyr Gln Tyr Arg Arg Arg Gln Arg Ile
                85                  90                  95

Cys Gly Gly Cys Asn Ser Asp Ile Gly Ser Gly Asn Tyr Leu Gly Cys
            100                 105                 110

Met Gly Thr Phe Phe His Pro Glu Cys Phe Arg Cys His Ser Cys Gly
        115                 120                 125

Tyr Ala Ile Thr Glu His Glu Phe Ser Leu Ser Gly Thr Lys Pro Tyr
    130                 135                 140

His Lys Leu Cys Phe Lys Glu Leu Thr His Pro Lys Cys Glu Val Cys
145                 150                 155                 160

His His Phe Ile Pro Thr Asn Asp Ala Gly Leu Ile Glu Tyr Arg Cys
                165                 170                 175

His Pro Phe Trp Asn Gln Lys Tyr Cys Pro Ser His Glu Tyr Asp Lys
            180                 185                 190

```
Thr Ala Arg Cys Cys Ser Cys Glu Arg Leu Glu Ser Trp Asp Val Arg
        195                 200                 205

Tyr Tyr Thr Leu Glu Asp Gly Arg Ser Leu Cys Leu Glu Cys Met Glu
    210                 215                 220

Thr Ala Ile Thr Asp Thr Gly Glu Cys Gln Pro Leu Tyr His Ala Ile
225                 230                 235                 240

Arg Asp Tyr Tyr Glu Gly Met Tyr Met Lys Leu Asp Gln Gln Ile Pro
            245                 250                 255

Met Leu Leu Val Gln Arg Glu Ala Leu Asn Asp Ala Ile Val Gly Glu
        260                 265                 270

Lys Asn Gly Tyr His His Met Pro Glu Thr Arg Gly Leu Cys Leu Ser
        275                 280                 285

Glu Glu Gln Thr Val Thr Ser Val Leu Arg Arg Pro Arg Leu Gly Ala
        290                 295                 300

His Arg Leu Val Gly Met Arg Thr Gln Pro Gln Arg Leu Thr Arg Lys
305                 310                 315                 320

Cys Glu Val Thr Ala Ile Leu Val Leu Tyr Gly Leu Pro Arg Leu Leu
                325                 330                 335

Thr Gly Ala Ile Leu Ala His Glu Leu Met His Gly Trp Leu Arg Leu
            340                 345                 350

Asn Gly Phe Arg Asn Leu Asn Pro Glu Val Glu Glu Gly Ile Cys Gln
        355                 360                 365

Val Leu Ser Tyr Met Trp Leu Glu Ser Glu Val Leu Ser Asp Pro Ser
        370                 375                 380

Thr Arg Asn Leu Pro Ser Thr Ser Ser Val Ala Thr Ser Ser Ser Ser
385                 390                 395                 400

Ser Phe Ser Asn Lys Lys Gly Gly Lys Ser Asn Val Glu Lys Lys Leu
                405                 410                 415

Gly Glu Phe Phe Lys His Gln Ile Ala His Asp Ala Ser Pro Ala Tyr
            420                 425                 430

Gly Gly Gly Phe Arg Ala Ala Asn Ala Ala Ala Cys Lys Tyr Gly Leu
        435                 440                 445

Arg Arg Thr Leu Asp His Ile Arg Leu Thr Gly Thr Phe Pro Leu
        450                 455                 460

<210> SEQ ID NO 304
<211> LENGTH: 450
<212> TYPE: PRT
<213> ORGANISM: Arabidopsis thaliana

<400> SEQUENCE: 304

Met Val Arg Arg Lys Arg Gln Glu Glu Asp Glu Lys Ile Glu Ile Glu
1               5                   10                  15

Arg Val Lys Glu Glu Ser Leu Lys Leu Ala Lys Gln Ala Glu Glu Lys
            20                  25                  30

Arg Arg Leu Glu Glu Ser Lys Glu Gln Gly Lys Arg Ile Gln Val Asp
        35                  40                  45

Asp Asp Gln Leu Ala Lys Thr Thr Ser Lys Asp Lys Gly Gln Ile Asn
    50                  55                  60

His Ser Lys Asp Val Val Glu Glu Asp Val Asn Pro Pro Ser Ile
65                  70                  75                  80

Asp Gly Lys Ser Glu Ile Gly Asp Gly Thr Ser Val Asn Pro Arg Cys
                85                  90                  95

Leu Cys Cys Phe His Cys His Arg Pro Phe Val Met His Glu Ile Leu
```

```
              100                 105                 110
Lys Lys Gly Lys Phe His Ile Asp Cys Tyr Lys Glu Tyr Tyr Arg Asn
            115                 120                 125

Arg Asn Cys Tyr Val Cys Gln Gln Lys Ile Pro Val Asn Ala Glu Gly
        130                 135                 140

Ile Arg Lys Phe Ser Glu His Pro Phe Trp Lys Glu Lys Tyr Cys Pro
145                 150                 155                 160

Ile His Asp Glu Asp Gly Thr Ala Lys Cys Cys Ser Cys Glu Arg Leu
                165                 170                 175

Glu Pro Arg Gly Thr Asn Tyr Val Met Leu Gly Asp Phe Arg Trp Leu
            180                 185                 190

Cys Ile Glu Cys Met Gly Ser Ala Val Met Asp Thr Asn Glu Val Gln
        195                 200                 205

Pro Leu His Phe Glu Ile Arg Glu Phe Phe Gly Leu Phe Leu Lys
    210                 215                 220

Val Asp Lys Glu Phe Ala Leu Leu Leu Val Glu Lys Gln Ala Leu Asn
225                 230                 235                 240

Lys Ala Glu Glu Glu Lys Ile Asp Tyr His Arg Ala Ala Val Thr
                245                 250                 255

Arg Gly Leu Cys Met Ser Glu Glu Gln Ile Val Pro Ser Ile Ile Lys
            260                 265                 270

Gly Pro Arg Met Gly Pro Asp Asn Gln Leu Ile Thr Asp Ile Val Thr
        275                 280                 285

Glu Ser Gln Arg Val Ser Gly Phe Glu Val Thr Gly Ile Leu Ile Ile
    290                 295                 300

Tyr Gly Leu Pro Arg Leu Leu Thr Gly Tyr Ile Leu Ala His Glu Met
305                 310                 315                 320

Met His Ala Trp Leu Arg Leu Asn Gly Tyr Lys Asn Leu Lys Leu Glu
                325                 330                 335

Leu Glu Glu Gly Leu Cys Gln Ala Leu Gly Leu Arg Trp Leu Glu Ser
            340                 345                 350

Gln Thr Phe Ala Ser Thr Asp Ala Ala Ala Ala Ala Val Ala Ser
        355                 360                 365

Ser Ser Ser Phe Ser Ser Ser Thr Ala Pro Ala Ala Ile Thr Ser
    370                 375                 380

Lys Lys Ser Asp Asp Trp Ser Ile Phe Glu Lys Lys Leu Val Glu Phe
385                 390                 395                 400

Cys Met Asn Gln Ile Lys Glu Asp Asp Ser Pro Val Tyr Gly Leu Gly
                405                 410                 415

Phe Lys Gln Val Tyr Glu Met Met Val Ser Asn Asn Tyr Asn Ile Lys
            420                 425                 430

Asp Thr Leu Lys Asp Ile Val Ser Ala Ser Asn Ala Thr Pro Asp Ser
        435                 440                 445

Thr Val
    450

<210> SEQ ID NO 305
<211> LENGTH: 514
<212> TYPE: PRT
<213> ORGANISM: Arabidopsis thaliana

<400> SEQUENCE: 305

Gly Cys Phe Pro Leu Gln Pro Lys Asn Leu Arg Ser Arg Ser Arg Arg
1               5                   10                  15
```

-continued

Thr Thr Ala Leu Glu Glu Ala Leu Glu Glu Ala Leu Lys Glu Arg Glu
        20                  25                  30

Lys Leu Glu Asp Thr Arg Glu Leu Gln Ile Ala Leu Ile Glu Ser Lys
            35                  40                  45

Lys Ile Lys Lys Ile Lys Gln Ala Asp Glu Arg Asp Gln Ile Lys His
        50                  55                  60

Ala Asp Glu Arg Glu Gln Arg Lys His Ser Lys Asp His Glu Glu Glu
65                  70                  75                  80

Glu Ile Glu Ser Asn Glu Lys Glu Arg Arg His Ser Lys Asp Tyr
                85                  90                  95

Val Ile Glu Glu Leu Val Leu Lys Gly Lys Gly Lys Arg Lys Gln Leu
                100                 105                 110

Asp Asp Asp Lys Ala Asp Glu Lys Glu Gln Ile Lys His Ser Lys Asp
            115                 120                 125

His Val Glu Glu Val Asn Pro Pro Leu Ser Lys Cys Lys Asp Cys
        130                 135                 140

Lys Ser Ala Ile Glu Asp Gly Ile Ser Ile Asn Ala Tyr Gly Ser Val
145                 150                 155                 160

Trp His Pro Gln Cys Phe Cys Cys Leu Arg Cys Arg Glu Pro Ile Ala
                165                 170                 175

Met Asn Glu Ile Ser Asp Leu Arg Gly Met Tyr His Lys Pro Cys Tyr
            180                 185                 190

Lys Glu Leu Arg His Pro Asn Cys Tyr Val Cys Glu Lys Ile Pro
        195                 200                 205

Arg Thr Ala Glu Gly Leu Lys Tyr His Glu His Pro Phe Trp Met Glu
210                 215                 220

Thr Tyr Cys Pro Ser His Asp Gly Asp Gly Thr Pro Lys Cys Cys Ser
225                 230                 235                 240

Cys Glu Arg Leu Glu His Cys Gly Thr Gln Tyr Val Met Leu Ala Asp
            245                 250                 255

Phe Arg Trp Leu Cys Arg Glu Cys Met Asp Ser Ala Ile Met Asp Ser
            260                 265                 270

Asp Glu Cys Gln Pro Leu His Phe Glu Ile Arg Glu Phe Phe Glu Gly
        275                 280                 285

Leu His Met Lys Ile Glu Glu Phe Pro Val Tyr Leu Val Glu Lys
        290                 295                 300

Asn Ala Leu Asn Lys Ala Glu Lys Glu Glu Lys Ile Asp Lys Gln Gly
305                 310                 315                 320

Asp Gln Cys Leu Met Val Val Arg Gly Ile Cys Leu Ser Glu Glu Gln
            325                 330                 335

Ile Val Thr Ser Val Ser Gln Gly Val Arg Arg Met Leu Asn Lys Gln
            340                 345                 350

Ile Leu Asp Thr Val Thr Glu Ser Gln Arg Val Val Arg Lys Cys Glu
        355                 360                 365

Val Thr Ala Ile Leu Ile Leu Tyr Gly Leu Pro Arg Leu Leu Thr Gly
        370                 375                 380

Tyr Ile Leu Ala His Glu Met Met His Ala Tyr Leu Arg Leu Asn Gly
385                 390                 395                 400

Tyr Arg Asn Leu Asn Met Val Leu Glu Glu Gly Leu Cys Gln Val Leu
            405                 410                 415

Gly Tyr Met Trp Leu Glu Cys Gln Thr Tyr Val Phe Asp Thr Ala Thr
            420                 425                 430

Ile Ala Ser Ser Ser Ser Ser Ser Arg Thr Pro Leu Ser Thr Thr Thr

```
                435                 440                 445
Ser Lys Lys Val Asp Pro Ser Asp Phe Glu Lys Arg Leu Val Asn Phe
    450                 455                 460

Cys Lys His Gln Ile Glu Thr Asp Glu Ser Pro Phe Phe Gly Asp Gly
465                 470                 475                 480

Phe Arg Lys Val Asn Lys Met Met Ala Ser Asn Asn His Ser Leu Lys
                485                 490                 495

Asp Thr Leu Lys Glu Ile Ile Ser Ile Ser Lys Thr Pro Gln Tyr Ser
            500                 505                 510

Lys Leu
```

<210> SEQ ID NO 306
<211> LENGTH: 522
<212> TYPE: PRT
<213> ORGANISM: Arabidopsis thaliana

<400> SEQUENCE: 306

```
Lys Met Leu Phe Glu Asp Gly Val Val Thr Val Val Ser Ala Pro
1               5                   10                  15

Tyr Ala Leu Gly Lys Thr Thr Leu Val Thr Lys Leu Cys His Asp Ala
                20                  25                  30

Asp Val Lys Glu Lys Phe Lys Gln Ile Phe Phe Ile Ser Val Ser Lys
            35                  40                  45

Phe Pro Asn Val Arg Leu Ile Gly His Lys Leu Leu Glu His Ile Gly
    50                  55                  60

Cys Lys Ala Asn Glu Tyr Glu Asn Asp Leu Asp Ala Met Leu Tyr Ile
65                  70                  75                  80

Gln Gln Leu Leu Lys Gln Leu Gly Arg Asn Gly Ser Ile Leu Leu Val
                85                  90                  95

Leu Asp Asp Val Trp Ala Glu Glu Ser Leu Leu Gln Lys Phe Leu
                100                 105                 110

Ile Gln Leu Pro Asp Tyr Lys Ile Leu Val Thr Ser Arg Phe Glu Phe
            115                 120                 125

Thr Ser Phe Gly Pro Thr Phe His Leu Lys Pro Leu Ile Asp Asp Glu
130                 135                 140

Val Glu Cys Arg Asp Glu Ile Glu Glu Asn Glu Lys Leu Pro Glu Val
145                 150                 155                 160

Asn Pro Pro Leu Ser Met Cys Gly Gly Cys Asn Ser Ala Val Lys His
                165                 170                 175

Glu Glu Ser Val Asn Ile Leu Gly Val Leu Trp His Pro Gly Cys Phe
            180                 185                 190

Cys Cys Arg Ser Cys Asp Lys Pro Ile Ala Ile His Glu Leu Glu Asn
        195                 200                 205

His Val Ser Asn Ser Arg Gly Lys Phe His Lys Ser Cys Tyr Glu Arg
    210                 215                 220

Tyr Cys Tyr Val Cys Lys Glu Lys Lys Met Lys Thr Tyr Asn Ile His
225                 230                 235                 240

Pro Phe Trp Glu Glu Arg Tyr Cys Pro Val His Glu Ala Asp Gly Thr
                245                 250                 255

Pro Lys Cys Cys Ser Cys Glu Arg Leu Glu Pro Arg Gly Thr Lys Tyr
            260                 265                 270

Gly Lys Leu Ser Asp Gly Arg Trp Leu Cys Leu Glu Cys Gly Lys Ser
        275                 280                 285

Ala Met Asp Ser Asp Glu Cys Gln Pro Leu Tyr Phe Asp Met Arg Asp
```

```
                290                 295                 300
Phe Phe Glu Ser Leu Asn Met Lys Ile Glu Lys Phe Pro Leu Ile
305                 310                 315                 320

Leu Val Arg Lys Glu Leu Leu Asn Lys Lys Glu Lys Ile Asp Asn
                325                 330                 335

His Tyr Glu Val Leu Ile Arg Ala Tyr Cys Met Ser Glu Gln Lys Ile
                340                 345                 350

Met Thr Tyr Val Ser Glu Glu Pro Arg Thr Gly Gln Asn Lys Gln Leu
                355                 360                 365

Ile Asp Met Asp Thr Glu Pro Gln Gly Val Val His Glu Cys Lys Val
                370                 375                 380

Thr Ala Ile Leu Ile Leu Tyr Gly Leu Pro Arg Leu Leu Thr Gly Tyr
385                 390                 395                 400

Ile Leu Ala His Glu Met Met His Ala Trp Leu Arg Leu Asn Gly His
                405                 410                 415

Met Asn Leu Asn Asn Ile Leu Glu Glu Gly Ile Cys Gln Val Leu Gly
                420                 425                 430

His Leu Trp Leu Glu Ser Gln Thr Tyr Ala Thr Ala Asp Thr Thr Ala
                435                 440                 445

Asp Ala Ala Ser Ala Ser Ser Ser Ser Arg Thr Pro Pro Ala Ala
                450                 455                 460

Ser Ala Ser Lys Lys Gly Glu Trp Ser Asp Phe Asp Lys Lys Leu Val
465                 470                 475                 480

Glu Phe Cys Lys Asn Gln Ile Glu Thr Asp Glu Ser Pro Val Tyr Gly
                485                 490                 495

Leu Gly Phe Arg Thr Val Asn Glu Met Val Thr Asn Ser Ser Leu Gln
                500                 505                 510

Glu Thr Leu Lys Glu Ile Leu Arg Arg Arg
                515                 520

<210> SEQ ID NO 307
<211> LENGTH: 482
<212> TYPE: PRT
<213> ORGANISM: Arabidopsis thaliana

<400> SEQUENCE: 307

Glu Tyr Pro Ile Arg Leu Glu Glu Tyr Lys Ser Ile Ser Arg Arg Ala
1               5                   10                  15

Pro Leu Asp Val Asp Glu Gln Phe Ala Lys Ala Val Lys Glu Ser Leu
                20                  25                  30

Lys Asn Lys Gly Lys Gly Lys Gln Phe Glu Asp Glu Gln Val Lys Lys
                35                  40                  45

Asp Glu Gln Leu Ala Leu Ile Val Gln Glu Ser Leu Asn Met Val Glu
                50                  55                  60

Ser Pro Pro Arg Leu Glu Glu Asn Asn Ile Ser Thr Arg Ala Pro
65                  70                  75                  80

Val Asp Glu Asp Glu Gln Leu Ala Lys Ala Val Glu Glu Ser Leu Lys
                85                  90                  95

Gly Lys Gly Gln Ile Lys Gln Ser Lys Asp Glu Val Glu Gly Asp Gly
                100                 105                 110

Met Leu Leu Glu Leu Asn Pro Pro Ser Leu Cys Gly Gly Cys Asn
                115                 120                 125

Phe Ala Val Glu His Gly Gly Ser Val Asn Ile Leu Gly Val Leu Trp
                130                 135                 140
```

His Pro Gly Cys Phe Cys Cys Arg Ala Cys His Lys Pro Ile Ala Ile
145                 150                 155                 160

His Asp Ile Glu Asn His Val Ser Asn Ser Arg Gly Lys Phe His Lys
                165                 170                 175

Ser Cys Tyr Glu Arg Tyr Cys Tyr Val Cys Lys Glu Lys Lys Met Lys
            180                 185                 190

Thr Tyr Asn Asn His Pro Phe Trp Glu Glu Arg Tyr Cys Pro Val His
        195                 200                 205

Glu Ala Asp Gly Thr Pro Lys Cys Cys Ser Cys Glu Arg Leu Glu Pro
    210                 215                 220

Arg Glu Ser Asn Tyr Val Met Leu Ala Asp Gly Arg Trp Leu Cys Leu
225                 230                 235                 240

Glu Cys Met Asn Ser Ala Val Met Asp Ser Asp Glu Cys Gln Pro Leu
                245                 250                 255

His Phe Asp Met Arg Asp Phe Phe Glu Gly Leu Asn Met Lys Ile Glu
            260                 265                 270

Lys Glu Phe Pro Phe Leu Leu Val Glu Lys Gln Ala Leu Asn Lys Ala
        275                 280                 285

Glu Lys Glu Glu Lys Ile Asp Tyr Gln Tyr Glu Val Val Thr Arg Gly
    290                 295                 300

Ile Cys Leu Ser Glu Glu Gln Ile Val Asp Ser Val Ser Gln Arg Pro
305                 310                 315                 320

Val Arg Gly Pro Asn Asn Lys Leu Val Gly Met Ala Thr Glu Ser Gln
                325                 330                 335

Lys Val Thr Arg Glu Cys Glu Val Thr Ala Ile Leu Ile Leu Tyr Gly
            340                 345                 350

Leu Pro Arg Leu Leu Thr Gly Tyr Ile Leu Ala His Glu Met Met His
        355                 360                 365

Ala Tyr Leu Arg Leu Asn Gly His Arg Asn Leu Asn Asn Ile Leu Glu
    370                 375                 380

Glu Gly Ile Cys Gln Val Leu Gly His Leu Trp Leu Asp Ser Gln Thr
385                 390                 395                 400

Tyr Ala Thr Ala Asp Ala Thr Ala Asp Ala Ser Ser Ser Ala Ser Ser
                405                 410                 415

Ser Ser Arg Thr Pro Pro Ala Ala Ser Ala Ser Lys Lys Gly Glu Trp
            420                 425                 430

Ser Asp Phe Asp Lys Lys Leu Val Glu Phe Cys Lys Asn Gln Ile Glu
        435                 440                 445

Thr Asp Asp Ser Pro Val Tyr Gly Leu Gly Phe Arg Thr Val Asn Glu
    450                 455                 460

Met Val Thr Asn Ser Ser Leu Gln Glu Thr Leu Lys Glu Ile Leu Arg
465                 470                 475                 480

Gln Arg

<210> SEQ ID NO 308
<211> LENGTH: 453
<212> TYPE: PRT
<213> ORGANISM: Arabidopsis thaliana

<400> SEQUENCE: 308

Lys Gly Lys Ser Lys Gln Phe Glu Asp Asp Gln Val Glu Asn Asp Glu
1               5                   10                  15

Gln Gln Ala Leu Met Val Gln Glu Ser Leu Tyr Met Val Glu Leu Ser
            20                  25                  30

```
Ala Gln Leu Glu Glu Asp Lys Asn Ile Ser Thr Ile Pro Pro Leu Asn
         35                  40                  45
Glu Asp Ala Gln Leu Gln Lys Val Ile Trp Glu Ser Ala Lys Gly Lys
 50                  55                  60
Gly Gln Ile Glu His Phe Lys Asp Pro Val Glu Glu Asp Gly Asn Leu
 65                  70                  75                  80
Pro Arg Val Asp Leu Asn Val Asn His Pro His Ser Ile Cys Asp Gly
                 85                  90                  95
Cys Lys Ser Ala Ile Glu Tyr Gly Arg Ser Val His Ala Leu Gly Val
            100                 105                 110
Asn Trp His Pro Glu Cys Phe Cys Cys Arg Tyr Cys Asp Lys Pro Ile
            115                 120                 125
Ala Met His Glu Phe Ser Asn Thr Lys Gly Arg Cys His Ile Thr Cys
            130                 135                 140
Tyr Glu Arg Ser His Pro Asn Cys His Val Cys Lys Lys Phe Pro
145                 150                 155                 160
Gly Arg Lys Tyr Lys Glu His Pro Phe Trp Lys Glu Tyr Cys Pro
                165                 170                 175
Phe His Glu Val Asp Gly Thr Pro Lys Cys Cys Ser Cys Glu Arg Leu
                180                 185                 190
Glu Pro Trp Gly Thr Lys Tyr Val Met Leu Ala Asp Asn Arg Trp Leu
            195                 200                 205
Cys Val Lys Cys Met Glu Cys Ala Val Met Asp Thr Tyr Glu Cys Gln
            210                 215                 220
Pro Leu His Phe Glu Ile Arg Glu Phe Phe Gly Ser Leu Asn Met Lys
225                 230                 235                 240
Val Glu Lys Glu Phe Pro Leu Leu Val Glu Lys Glu Ala Leu Lys
                245                 250                 255
Lys Ala Glu Ala Gln Glu Lys Ile Asp Asn Gln His Gly Val Val Thr
            260                 265                 270
Arg Gly Ile Cys Leu Ser Glu Gly Gln Ile Val Asn Ser Val Phe Lys
            275                 280                 285
Lys Pro Thr Met Gly Pro Asn Gly Glu Leu Val Ser Leu Gly Thr Glu
            290                 295                 300
Pro Gln Lys Val Val Gly Gly Cys Glu Val Thr Ala Ile Leu Ile Leu
305                 310                 315                 320
Tyr Gly Leu Pro Arg Leu Leu Thr Gly Tyr Ile Leu Ala His Glu Met
                325                 330                 335
Met His Ala Trp Leu Arg Leu Asn Gly Tyr Arg Asn Leu Lys Leu Glu
            340                 345                 350
Leu Glu Glu Gly Ile Cys Gln Val Leu Gly His Met Trp Leu Glu Ser
            355                 360                 365
Gln Thr Tyr Ser Ser Ser Ala Ala Ser Ser Ala Ser Ser Ser Ser
            370                 375                 380
Arg Thr Pro Ala Ala Asn Ala Ser Lys Lys Gly Ala Gln Ser Asp Tyr
385                 390                 395                 400
Glu Lys Lys Leu Val Glu Phe Cys Lys Asp Gln Ile Glu Thr Asp Asp
                405                 410                 415
Ser Pro Val Tyr Gly Val Gly Phe Arg Lys Val Asn Gln Met Val Ser
                420                 425                 430
Asp Ser Ser Leu His Lys Ile Leu Lys Ser Ile Gln His Trp Thr Lys
            435                 440                 445
Pro Asp Ser Asn Leu
```

```
                 450

<210> SEQ ID NO 309
<211> LENGTH: 515
<212> TYPE: PRT
<213> ORGANISM: Brassica rapa

<400> SEQUENCE: 309

Gly Asn Asp His Asp His Asn Gly Tyr Tyr Gln Ser Tyr Pro His Asp
1               5                   10                  15

Glu Pro Ser Ala Asp Thr Asp Pro Asp Pro Asp Pro Asp Glu
            20                  25                  30

Thr His Thr Gln Glu Pro Ser Thr Ser Glu Glu Asp Thr Ser Gly Gln
            35                  40                  45

Glu Asn Glu Asp Ile Asp Arg Ala Ile Ala Leu Ser Leu Ile Glu Asn
        50                  55                  60

Ser Gln Gly Gln Thr Asn Asn Thr Cys Ala Ala Asn Ala Gly Lys Tyr
65                  70                  75                  80

Ala Met Val Asp Glu Asp Gln Leu Ala Arg Ala Ile Gln Glu Ser
                85                  90                  95

Met Val Val Gly Asn Thr Pro Arg Gln Lys His Gly Ser Ser Tyr Asp
            100                 105                 110

Ile Gly Asn Ala Tyr Gly Ala Gly Asp Val Tyr Gly Asn Gly His Met
        115                 120                 125

His Gly Gly Asn Val Tyr Ala Asn Gly Asp Ile Tyr Tyr Pro Arg
    130                 135                 140

Pro Thr Ala Phe Pro Met Asp Phe Arg Ile Cys Ala Gly Cys Asn Met
145                 150                 155                 160

Glu Ile Gly His Gly Arg Tyr Leu Asn Cys Leu Asn Ala Leu Trp His
                165                 170                 175

Pro Glu Cys Phe Arg Cys Tyr Gly Cys Arg His Pro Ile Ser Glu Tyr
            180                 185                 190

Glu Phe Ser Thr Ser Gly Asn Tyr Pro Phe His Lys Ala Cys Tyr Arg
        195                 200                 205

Glu Arg Tyr His Pro Lys Cys Asp Val Cys Ser Leu Phe Ile Pro Thr
    210                 215                 220

Asn His Ala Gly Leu Ile Gly Tyr Arg Ala His Pro Phe Trp Val Gln
225                 230                 235                 240

Lys Tyr Cys Pro Ser His Glu His Asp Ala Thr Pro Arg Cys Cys Ser
                245                 250                 255

Cys Glu Arg Met Glu Pro Arg Asn Thr Gly Tyr Val Glu Leu Asn Asp
            260                 265                 270

Gly Arg Lys Leu Cys Leu Glu Cys Leu Asp Ser Ala Val Met Asp Thr
        275                 280                 285

Phe Gln Cys Gln Pro Leu Tyr Leu Gln Ile Gln Glu Phe Tyr Glu Gly
    290                 295                 300

Leu Phe Met Lys Val Glu Gln Asp Val Pro Leu Leu Val Glu Arg
305                 310                 315                 320

Gln Ala Leu Asn Glu Ala Arg Glu Gly Glu Lys Asn Gly His Tyr His
                325                 330                 335

Met Pro Glu Thr Arg Gly Leu Cys Leu Ser Glu Glu Gln Thr Val Ser
            340                 345                 350

Thr Val Arg Lys Arg Ser Lys His Gly Thr Gly Asn Trp Ala Gly Asn
        355                 360                 365
```

Met Ile Thr Glu Pro Tyr Lys Leu Thr Arg Gln Cys Glu Val Thr Ala
370                 375                 380

Ile Leu Ile Leu Phe Gly Leu Pro Arg Leu Leu Thr Gly Ser Ile Leu
385                 390                 395                 400

Ala His Glu Met Met His Ala Trp Met Arg Leu Lys Gly Phe Arg Thr
            405                 410                 415

Leu Ser Gln Asp Val Glu Gly Ile Cys Gln Val Met Ala His Lys
            420                 425                 430

Trp Leu Glu Ala Glu Leu Ala Ala Gly Ser Arg Asn Ser Asn Val Ala
            435                 440                 445

Ser Ser Ser Ser Ser Arg Gly Val Lys Lys Gly Pro Arg Ser Gln Tyr
450                 455                 460

Glu Arg Lys Leu Gly Glu Phe Phe Lys His Gln Ile Glu Ser Asp Ala
465                 470                 475                 480

Ser Pro Val Tyr Gly Asp Gly Phe Arg Ala Gly Arg Leu Ala Val Asn
                485                 490                 495

Lys Tyr Gly Leu Pro Lys Thr Leu Glu His Ile Gln Met Thr Gly Arg
            500                 505                 510

Phe Pro Val
        515

<210> SEQ ID NO 310
<211> LENGTH: 497
<212> TYPE: PRT
<213> ORGANISM: Brassica rapa

<400> SEQUENCE: 310

Gly Asn Glu His Tyr His His Asn Gly Gly Tyr Tyr Glu Asn Tyr Pro
1               5                   10                  15

His Glu His Ser Glu Pro Ser Ala Glu Thr Asp Ala Asp His Thr Gln
            20                  25                  30

Glu Pro Ser Thr Ser Glu Glu Thr Trp Asn Gly Lys Glu Asn Glu
        35                  40                  45

Glu Val Asp Arg Val Ile Ala Leu Ser Ile Leu Glu Glu Asn Gln
50                  55                  60

Arg Pro Glu Thr Asn Thr Gly Ala Trp Lys His Ala Met Met Asp Asp
65                  70                  75                  80

Asp Glu Gln Leu Ala Arg Ala Ile Gln Glu Ser Met Ile Ala Arg Asn
                85                  90                  95

Gly Thr Thr Tyr Asp Phe Gly Asn Ala Tyr Gly Asn Gly His Met His
            100                 105                 110

Gly Gly Gly Asn Val Tyr Asp Asn Gly Asp Ile Tyr Tyr Pro Arg Pro
        115                 120                 125

Ile Ala Phe Ser Met Asp Phe Arg Ile Cys Ala Gly Cys Asn Met Glu
130                 135                 140

Ile Gly His Gly Arg Tyr Leu Asn Cys Leu Asn Ala Leu Trp His Pro
145                 150                 155                 160

Gln Cys Phe Arg Cys Tyr Gly Cys Ser His Pro Ile Ser Glu Tyr Glu
                165                 170                 175

Phe Ser Thr Ser Gly Asn Tyr Pro Phe His Lys Ala Cys Tyr Arg Glu
            180                 185                 190

Arg Phe His Pro Lys Cys Asp Val Cys Ser Leu Phe Ile Ser Thr Asn
        195                 200                 205

His Ala Gly Leu Ile Glu Tyr Arg Ala His Pro Phe Trp Val Gln Lys
210                 215                 220

```
Tyr Cys Pro Ser His Glu His Asp Ala Thr Pro Arg Cys Cys Ser Cys
225                 230                 235                 240

Glu Arg Met Glu Pro Arg Asn Thr Gly Tyr Phe Glu Leu Asn Asp Gly
                245                 250                 255

Arg Lys Leu Cys Leu Glu Cys Leu Asp Ser Ser Val Met Asp Thr Phe
            260                 265                 270

Gln Cys Gln Pro Leu Tyr Leu Gln Ile Gln Glu Phe Tyr Glu Gly Leu
        275                 280                 285

Asn Met Thr Val Glu Gln Glu Val Pro Leu Leu Val Glu Arg Gln
    290                 295                 300

Ala Leu Asn Glu Ala Arg Glu Gly Glu Arg Asn Gly His Tyr His Met
305                 310                 315                 320

Pro Glu Thr Arg Gly Leu Cys Leu Ser Glu Glu Gln Thr Val Arg Thr
                325                 330                 335

Val Arg Lys Arg Ser Lys Gly Asn Trp Ser Gly Asn Met Ile Thr Glu
            340                 345                 350

Gln Phe Lys Leu Thr Arg Arg Cys Glu Val Thr Ala Ile Leu Ile Leu
        355                 360                 365

Phe Gly Leu Pro Arg Leu Leu Thr Gly Ser Ile Leu Ala His Glu Met
370                 375                 380

Met His Ala Trp Met Arg Leu Lys Gly Phe Arg Pro Leu Ser Gln Asp
385                 390                 395                 400

Val Glu Glu Gly Ile Cys Gln Val Met Ala His Lys Trp Leu Glu Ala
                405                 410                 415

Glu Leu Ala Ala Gly Ser Arg Asn Ser Asn Ala Ala Ser Ser Ser Ser
            420                 425                 430

Ser Ser Tyr Gly Gly Val Lys Lys Gly Pro Arg Ser Gln Tyr Glu Arg
        435                 440                 445

Lys Leu Gly Glu Phe Phe Lys His Gln Ile Glu Ser Asp Ala Ser Pro
450                 455                 460

Val Tyr Gly Asp Gly Phe Arg Ala Gly Arg Leu Ala Val Asn Lys Tyr
465                 470                 475                 480

Gly Leu Trp Arg Thr Leu Glu His Ile Gln Met Thr Gly Arg Phe Pro
                485                 490                 495

Val

<210> SEQ ID NO 311
<211> LENGTH: 548
<212> TYPE: PRT
<213> ORGANISM: Brassica rapa

<400> SEQUENCE: 311

Gly Gln Ala Asn Arg Arg Tyr Asn Arg Glu Asp Arg Ser Leu Asp Thr
1               5                   10                  15

Pro Arg Tyr Ser Ala Glu Gly Ser Asp Phe Asp Lys Glu Glu Ile Glu
                20                  25                  30

Cys Ala Ile Ala Leu Ser Leu Ser Glu Gln Glu His Val Ile Pro Gln
            35                  40                  45

Asp Asp Lys Gly Lys Lys Val Ile Glu Tyr Lys Ser Glu Thr Glu Glu
        50                  55                  60

Asp Asp Asp Glu Asp Glu Asp Glu Glu Asp Asp Glu Glu
65                  70                  75                  80

His Met Arg Ala Gln Val Glu Ala Ala Glu Glu Glu Lys Lys Val
                85                  90                  95
```

-continued

```
Ala Gln Ala Gln Ile Glu Glu Glu Lys Arg Ala Glu Glu Ala
            100                 105                 110
Glu Leu Glu Glu Leu Glu Lys Gln Leu Ala Lys Ala Arg Leu Glu Glu
            115                 120                 125
Glu Glu Val Arg Arg Ala Lys Ala Gln Leu Glu Glu Asp Glu Gln Leu
        130                 135                 140
Ala Lys Ala Ile Gln Glu Ser Met Asn Val Gly Ser Pro Pro Gly
145                 150                 155                 160
Tyr Asp Ser Gly Ser Val Phe Pro Ser Tyr Pro Phe Leu Val Pro Ser
                165                 170                 175
Arg Ile Cys Thr Gly Cys Arg Ala Glu Ile Gly His Gly Arg Phe Leu
            180                 185                 190
Ser Cys Met Gly Gly Val Trp His Pro Glu Cys Phe Cys His Ala
            195                 200                 205
Cys Asp Lys Pro Ile Ile Asp Cys Glu Val Phe Ser Met Ser Gly Asn
    210                 215                 220
Arg Pro Tyr His Lys Leu Cys Tyr Lys Glu Gln His His Pro Lys Cys
225                 230                 235                 240
Asp Val Cys His Asn Phe Ile Pro Thr Asn Pro Ala Gly Leu Ile Glu
                245                 250                 255
Tyr Arg Ala His Pro Phe Trp Met Gln Lys Tyr Cys Pro Ser His Glu
            260                 265                 270
Arg Asp Gly Thr Pro Arg Cys Cys Ser Cys Glu Arg Met Glu Pro Lys
            275                 280                 285
Asp Thr Lys Tyr Leu Ile Leu Asp Asp Gly Arg Lys Leu Cys Leu Glu
    290                 295                 300
Cys Leu Asp Ser Ala Ile Met Asp Thr Asn Glu Cys Gln Pro Leu Tyr
305                 310                 315                 320
Leu Glu Ile Arg Glu Phe Tyr Glu Gly Leu His Met Lys Val Glu Gln
                325                 330                 335
Gln Ile Pro Met Leu Leu Val Glu Arg Ser Ala Leu Asn Glu Ala Met
            340                 345                 350
Glu Gly Glu Lys His Gly His His His Leu Pro Glu Thr Arg Gly Leu
            355                 360                 365
Cys Leu Ser Glu Glu Gln Thr Val Thr Thr Val Leu Arg Arg Pro Lys
    370                 375                 380
Ile Gly Ala Gly Tyr Lys Leu Ile Asp Met Ile Thr Glu Pro Cys Arg
385                 390                 395                 400
Leu Val Arg Arg Cys Glu Val Thr Ala Ile Leu Ile Leu Tyr Gly Leu
                405                 410                 415
Pro Arg Arg Leu Leu Thr Gly Ser Ile Leu Ala His Glu Met Met His
            420                 425                 430
Ala Trp Leu Arg Leu Asn Gly Tyr Pro Asn Leu Arg Pro Glu Val Glu
            435                 440                 445
Glu Gly Ile Cys Gln Val Leu Ala His Met Trp Leu Glu Ser Glu Thr
    450                 455                 460
Tyr Ala Gly Ser Thr Leu Ile Asp Ile Ala Ser Ser Ser Ser Ser Ser
465                 470                 475                 480
Ser Ser Ala Ala Val Ala Ile Ala Ser Ser Lys Gly Glu Arg Ser
                485                 490                 495
Asp Phe Glu Lys Lys Leu Gly Glu Phe Phe Lys His Gln Ile Glu Ser
            500                 505                 510
```

```
Asp Ser Ser Ser Ala Tyr Gly Asp Gly Phe Arg Gln Gly Asn Gln Ala
            515                 520                 525

Val Leu Thr His Gly Leu Lys Arg Thr Leu Asp His Ile Arg Leu Thr
530                 535                 540

Gly Thr Phe Pro
545

<210> SEQ ID NO 312
<211> LENGTH: 464
<212> TYPE: PRT
<213> ORGANISM: Brassica rapa

<400> SEQUENCE: 312

Gly Ala Arg Thr Asn Arg His Pro Pro Gln Phe Gln Glu Asp Glu Asn
1               5                   10                  15

Met Val Phe Pro Leu Pro Pro Ser Ser Ser Asp Arg Ser Arg Ala
            20                  25                  30

Ser Arg Asp Lys Glu Glu Leu Asp Arg Ala Leu Ser Val Ser Leu Ala
            35                  40                  45

Asp Asp Thr Asn Arg Pro Tyr Gly Tyr Gly Trp Ser Met Asp Asn Asn
        50                  55                  60

Ser Asp Phe Pro Arg Pro Phe His Ser Gly Leu Asn Pro Ser Phe Ile
65                  70                  75                  80

Pro Pro Tyr Glu Pro Ser Tyr Gln Val Arg Arg Pro Gln Arg Ile Cys
                85                  90                  95

Gly Gly Cys Asn Ser Asp Ile Gly Leu Gly Asn Tyr Leu Gly Cys Met
            100                 105                 110

Gly Thr Phe Phe His Pro Asp Cys Phe Cys Asp Ser Cys Arg Tyr
            115                 120                 125

Pro Ile Thr Glu His Glu Phe Ser Leu Ser Gly Thr Lys Pro Tyr His
        130                 135                 140

Gln Ile Cys Phe Lys Glu Leu Thr His Pro Lys Cys Glu Val Cys His
145                 150                 155                 160

His Phe Ile Pro Thr Asn Asp Ala Gly Leu Ile Glu Tyr Arg Cys His
                165                 170                 175

Pro Phe Trp Asn Gln Lys Tyr Cys Pro Ser His Glu His Asp Arg Thr
            180                 185                 190

Ala Arg Cys Cys Ser Cys Glu Arg Leu Glu Ser Trp Glu Val Arg Tyr
            195                 200                 205

Tyr Thr Leu Asp Asp Gly Arg Ser Leu Cys Leu Glu Cys Met Glu Thr
        210                 215                 220

Ala Ile Thr Asp Thr Gly Asp Cys Gln Pro Leu Tyr His Ala Ile Arg
225                 230                 235                 240

Asp Tyr Tyr Glu Gly Met Tyr Met Lys Leu Glu Gln Gln Ile Pro Met
                245                 250                 255

Leu Leu Val Gln Arg Glu Ala Leu Asn Asp Ala Ile Val Gly Glu Lys
            260                 265                 270

His Gly Tyr His His Met Pro Glu Thr Arg Gly Leu Cys Leu Ser Glu
        275                 280                 285

Glu Gln Thr Val Thr Ser Val Leu Lys Arg Pro Arg Leu Gly Ala His
    290                 295                 300

Arg Leu Val Gly Met Arg Thr Gln Pro Gln Lys Leu Thr Arg Lys Cys
305                 310                 315                 320

Glu Val Thr Ala Ile Leu Val Leu Tyr Gly Leu Pro Arg Leu Leu Thr
                325                 330                 335
```

```
Gly Ala Ile Leu Ala His Glu Leu Met His Gly Trp Leu Arg Leu Lys
            340                 345                 350

Gly Tyr Arg Asn Leu Asn Pro Glu Val Glu Gly Ile Cys Gln Val
            355                 360                 365

Leu Ser Tyr Met Trp Leu Glu Ser Glu Val Leu Ser Asp Pro Ser Ser
370                 375                 380

Arg Ser Met Pro Ser Thr Ser Thr Ala Thr Ser Ser Ser Ser Ser Ser
385                 390                 395                 400

Ser Ser Ser Ser Asn Lys Lys Gly Gly Lys Thr Asn Val Glu Lys Lys
                405                 410                 415

Leu Gly Glu Phe Phe Lys His Gln Ile Ala His Asp Ala Ser Pro Ala
            420                 425                 430

Tyr Gly Gly Gly Phe Arg Ala Ala Asn Ala Ala Val Cys Lys Tyr Gly
            435                 440                 445

Leu Arg Arg Thr Leu Asp His Ile Arg Phe Thr Gly Thr Phe Pro Leu
            450                 455                 460

<210> SEQ ID NO 313
<211> LENGTH: 508
<212> TYPE: PRT
<213> ORGANISM: Brassica rapa

<400> SEQUENCE: 313

Ser Ser Thr Lys Gln Asp Asp Pro Ser Glu Asp His Tyr Lys Thr Val
1               5                   10                  15

Ile Lys Ile Ser Arg His Glu Lys Glu Asp Gly Ile Val Arg Gln Lys
            20                  25                  30

Arg Glu Lys Ala Glu Gln Val Gln Thr Glu Arg Ala Lys Glu Met Ser
            35                  40                  45

Leu Lys Gln Phe Glu Lys Glu Val Ala Glu Arg Arg Leu Gln Glu Ser
        50                  55                  60

Lys Glu Glu Gly Lys Arg Lys Gln Val Asp Asp Asp Asp Asp Asp Gln
65                  70                  75                  80

Val Asp Thr Glu Gln Ile Glu Met Asn Lys Val Met Glu Glu Ser Leu
                85                  90                  95

Lys Leu Phe Gln Lys Glu Glu Lys Arg Arg Leu Glu Lys Ser Lys
            100                 105                 110

Glu Glu Gly Lys Arg Lys Gln Val Glu Glu Gly Gln Phe Lys His
            115                 120                 125

Ser Lys Asp Lys Glu Val Ala Pro Pro Ser Ile Cys Asn Gly Cys Lys
130                 135                 140

Ser Glu Ile Lys Asp Gly Leu Ser Val Lys Ala Phe Gly Asp Leu Trp
145                 150                 155                 160

His Pro His Cys Leu Cys Cys Leu His Cys His Lys Ser Ile Ala Leu
                165                 170                 175

Asp Lys Ile Ala Lys Arg Gly Lys Phe His Lys Ser Cys Tyr Lys Glu
            180                 185                 190

His Arg His Pro Thr Cys Cys Val Cys Gln Lys Lys Ile Pro Pro Thr
            195                 200                 205

Glu Glu Gly Ile Lys Tyr Asn Glu His Pro Phe Trp Lys Glu Lys Tyr
            210                 215                 220

Cys Pro Cys His Asp Arg Asp Gly Thr Ala Lys Cys Cys Ser Cys Glu
225                 230                 235                 240

Arg Leu Glu Pro Arg Gly Thr Asn Phe Val Met Leu Gly Asp Asp Arg
```

245                 250                 255

Trp Leu Cys Leu Gln Cys Ile Gly Ser Ser Val Met Asp Thr Tyr Glu
            260                 265                 270

Cys Ile Asp Leu His Val Glu Ile Arg Glu Phe Phe Asp Gly Ser Phe
            275                 280                 285

Leu Pro Val Asp Lys Glu Phe Pro Leu Leu Val Glu Lys Gln Ala
290                 295                 300

Leu Asn Lys Ala Glu Lys Glu Lys Ile Asp Tyr Gln His Ala Val
305                 310                 315                 320

Val Thr Arg Gly Ile Cys Leu Ser Glu Glu Gln Ser Val Thr Ser Val
            325                 330                 335

Lys Glu Arg Pro Lys Arg Gly Pro Asn Asn Thr Leu Ile Asn Met Val
            340                 345                 350

Thr Glu Thr Gln Met Val Ser Gly Cys Glu Val Thr Ala Ile Leu Ile
            355                 360                 365

Ile Tyr Gly Leu Pro Arg Leu Leu Thr Gly Tyr Ile Leu Ala His Glu
            370                 375                 380

Met Met His Ala Tyr Leu Arg Leu Asn Gly Tyr Lys Asn Leu Lys Leu
385                 390                 395                 400

Glu Leu Glu Glu Gly Leu Cys Gln Val Leu Gly Leu Arg Trp Leu Glu
            405                 410                 415

Ser His Thr Phe Ser Ser Asp Asp Ala Thr Ala Ala Ser Ser Ser Ser
            420                 425                 430

Asn Ala Pro Pro Ala Ala Ala Ser Thr Leu Lys Lys Gly Asp Asp Trp
            435                 440                 445

Ser Asp Phe Glu Lys Lys Leu Ala Glu Phe Cys Ile His Gln Ile Lys
            450                 455                 460

Glu Asp Asp Ser Pro Val Tyr Gly Leu Gly Phe Lys Gln Val His Glu
465                 470                 475                 480

Ile Trp Val Ser Asn His Tyr Ile Leu Lys Asp Thr Leu Lys Asp Ile
            485                 490                 495

Val Asn Ala Ser Lys Asn Ala Pro Val Ser Lys Phe
            500                 505

<210> SEQ ID NO 314
<211> LENGTH: 495
<212> TYPE: PRT
<213> ORGANISM: Brachypodium distachyon

<400> SEQUENCE: 314

Gly Gln Arg Gln Ser Arg Pro Ala Glu Glu Ala Val Trp Asn Glu Pro
1               5                   10                  15

Ser Ser Ser Thr Val Val Thr Asp Val Leu Ser Glu Phe Asp Asn Glu
            20                  25                  30

Asp Ile Asp Arg Ala Ile Ala Leu Ser Leu Ser Glu Glu Gln Arg Lys
            35                  40                  45

Ser Lys Gly Thr Gly Lys Asp Leu His Leu Asp Glu Asp Glu Gln Leu
        50                  55                  60

Ala Arg Ala Ile His Glu Ser Leu Asn Val Glu Ser Pro Pro Cys Ala
65                  70                  75                  80

Arg Asp Asn Gly Ser Pro Pro His Ala Arg Asp Asn Ser Ser Pro Pro
                85                  90                  95

His Ala Arg Glu Asn Ser Ser His Pro Arg Ala Arg Glu Asn Gly Ile
            100                 105                 110

Ala Asn Gly Gly Asn Ser Ile Gln His Ser Pro Phe Met Phe Ser Ser
            115                 120                 125

Gly Phe Arg Thr Cys Ala Gly Cys His Ser Glu Ile Gly His Gly Arg
        130                 135                 140

Phe Leu Ser Cys Met Gly Ala Val Trp His Pro Glu Cys Phe Cys Cys
145                 150                 155                 160

His Ala Cys Ser Gln Pro Ile Tyr Asp Tyr Glu Phe Ser Met Ser Gly
                165                 170                 175

Asn His Pro Tyr His Lys Thr Cys Tyr Lys Glu Arg Phe His Pro Lys
            180                 185                 190

Cys Asp Val Cys Lys Gln Phe Ile Pro Thr Asn Met Asn Gly Leu Ile
        195                 200                 205

Glu Tyr Arg Ala His Pro Phe Trp Leu Gln Lys Tyr Cys Pro Ser His
    210                 215                 220

Glu Val Asp Gly Thr Pro Arg Cys Cys Ser Cys Glu Arg Met Glu Pro
225                 230                 235                 240

Arg Glu Ser Arg Tyr Val Leu Leu Asp Asp Gly Arg Lys Leu Cys Leu
                245                 250                 255

Glu Cys Leu Asp Ser Ala Val Met Asp Thr Thr Glu Cys Gln Pro Leu
            260                 265                 270

Tyr Leu Glu Ile Gln Glu Phe Tyr Glu Gly Leu Asn Met Lys Val Glu
        275                 280                 285

Gln Gln Val Pro Leu Leu Val Glu Arg Gln Ala Leu Asn Glu Ala
    290                 295                 300

Met Glu Gly Glu Lys Thr Gly His His His Leu Pro Glu Thr Arg Gly
305                 310                 315                 320

Leu Cys Leu Ser Glu Glu Gln Thr Val Ser Thr Ile Leu Arg Arg Pro
                325                 330                 335

Arg Met Thr Gly Asn Lys Ile Met Glu Met Ile Thr Glu Pro Tyr Arg
            340                 345                 350

Leu Thr Arg Arg Cys Glu Val Thr Ala Ile Leu Ile Leu Tyr Gly Leu
        355                 360                 365

Pro Arg Leu Leu Thr Gly Ser Ile Leu Ala His Glu Met Met His Ala
    370                 375                 380

Trp Leu Arg Leu Lys Gly Tyr Arg Thr Leu Ser Pro Glu Ile Glu Glu
385                 390                 395                 400

Gly Ile Cys Gln Val Leu Ala His Met Trp Ile Glu Ser Glu Ile Met
                405                 410                 415

Ala Gly Ser Ser Ser Asn Ala Ala Ser Thr Ser Ser Ser Ser Ser Ser
            420                 425                 430

Ser Ile Ser Ser Lys Lys Gly Gly Arg Ser Gln Phe Glu Arg Lys Leu
        435                 440                 445

Gly Asp Phe Phe Lys His Gln Ile Glu Ser Asp Thr Ser Val Ala Tyr
    450                 455                 460

Gly Asn Gly Phe Arg Ser Gly Asn Gln Ala Val Leu Gln Tyr Gly Leu
465                 470                 475                 480

Lys Arg Thr Leu Glu His Ile Trp Leu Thr Gly Thr Trp Pro Phe
                485                 490                 495

<210> SEQ ID NO 315
<211> LENGTH: 497
<212> TYPE: PRT
<213> ORGANISM: Brachypodium distachyon

<400> SEQUENCE: 315

```
Gly Gln Asp Gln Ser Lys Pro Ala Glu Glu Thr Val Trp Asn Glu Pro
1               5                   10                  15

Ser Ser Ser Thr Ala Val Asn Tyr Ala Leu Ser Glu Phe Asp Asn Glu
            20                  25                  30

Asp Ile Asp Arg Ala Ile Ala Leu Ser Leu Ser Glu Glu Glu Gln Arg
        35                  40                  45

Lys Ser Lys Gly Thr Gly Lys Asp Gln His Leu Asp Glu Asp Glu Gln
50                  55                  60

Leu Ala Arg Ala Ile Gln Glu Ser Leu Asn Val Glu Ser Pro Pro Arg
65                  70                  75                  80

Ala Arg Glu Lys Ser Ser His Pro Arg Ala Arg Glu Asn Gly Ser Ala
                85                  90                  95

Asn Gly Gly Asn Ser Tyr Gln Leu Pro Leu Met Phe Ser Ser Gly Phe
                100                 105                 110

Arg Thr Cys Ala Gly Cys His Ser Glu Ile Gly His Gly Arg Phe Leu
            115                 120                 125

Ser Cys Met Gly Ala Val Trp His Pro Glu Cys Phe Cys His Gly
    130                 135                 140

Cys Ser Gln Pro Ile Tyr Asp Tyr Glu Phe Ser Met Ser Gly Asn His
145                 150                 155                 160

Pro Tyr His Lys Thr Cys Tyr Lys Glu Arg Phe His Pro Lys Cys Asp
                165                 170                 175

Val Cys Gln Gln Phe Ile Pro Thr Asn Thr Asn Gly Leu Ile Glu Tyr
            180                 185                 190

Arg Ala His Pro Phe Trp Leu Gln Lys Tyr Cys Pro Ser His Glu Val
            195                 200                 205

Asp Gly Thr Pro Arg Cys Cys Ser Cys Glu Arg Met Glu Ile Ser Cys
            210                 215                 220

Cys Leu Gln Asn Met Asp Gln Phe Thr Pro Ile Trp Val Val Tyr Gln
225                 230                 235                 240

Pro Arg Glu Ser Arg Tyr Val Leu Leu Asp Asp Gly Arg Lys Leu Cys
                245                 250                 255

Leu Glu Cys Leu Asp Ser Ala Val Met Asp Thr Thr Glu Cys Gln Pro
            260                 265                 270

Leu Tyr Leu Glu Ile Gln Glu Phe Tyr Glu Gly Leu Asn Met Lys Val
        275                 280                 285

Glu Gln Gln Val Pro Leu Leu Leu Val Glu Arg Gln Ala Leu Asn Glu
        290                 295                 300

Ala Met Glu Gly Glu Lys Thr Gly His His His Leu Pro Glu Thr Arg
305                 310                 315                 320

Gly Leu Cys Leu Ser Glu Glu Gln Thr Val Ser Thr Ile Leu Arg Arg
            325                 330                 335

Pro Arg Met Ala Gly Asn Lys Ile Met Glu Met Arg Thr Glu Pro Tyr
            340                 345                 350

Arg Leu Thr Arg Arg Cys Glu Val Thr Ala Ile Leu Ile Leu Tyr Gly
        355                 360                 365

Leu Pro Arg Leu Val Thr Val Ile Glu Leu Lys Lys Thr Ile Tyr Cys
    370                 375                 380

Phe His Ala Asn Asp Glu Tyr Val Phe Thr Gly Tyr Arg Thr Leu Ser
385                 390                 395                 400

Pro Asp Ile Glu Glu Gly Ile Cys Gln Val Leu Ala His Met Trp Ile
                405                 410                 415
```

```
Glu Ser Glu Ile Thr Ala Gly Ser Gly Ser Asn Ala Ala Ser Thr Ser
                420                 425                 430

Ser Ser Ser Thr Ser Ser Lys Lys Gly Gly Arg Ser Gln Phe Glu Arg
            435                 440                 445

Lys Leu Gly Asp Phe Phe Lys His Gln Ile Glu Ser Asp Thr Ser Val
        450                 455                 460

Ala Tyr Gly Asp Gly Phe Arg Ala Gly Asn Gln Ala Val Leu Gln Tyr
465                 470                 475                 480

Gly Leu Lys Arg Thr Leu Glu His Ile Arg Leu Thr Gly Thr Leu Pro
                485                 490                 495

Phe

<210> SEQ ID NO 316
<211> LENGTH: 466
<212> TYPE: PRT
<213> ORGANISM: Brachypodium distachyon

<400> SEQUENCE: 316

Arg Arg Gln Pro Arg Val Thr Ala Gly Glu Glu Ser Thr Leu Trp Glu
1               5                   10                  15

Gln Glu Pro Leu Arg Pro Lys Arg Glu Asp Pro Arg His Asp Asn
            20                  25                  30

Glu Glu Leu Asp Arg Gln Ile Ala Leu Ser Leu Ala Glu Asp Ala Lys
        35                  40                  45

His Pro Lys Glu Arg Asn His Asn Lys Gly Glu Asn Asp Glu Asp Leu
    50                  55                  60

Ala Lys Ala Ile Gln Asp Ser Leu Asn Met Asn Pro Tyr Met Pro His
65                  70                  75                  80

His Pro Tyr Ala Pro Ser Gln Ala Leu Pro Arg Ala His Arg Val Cys
                85                  90                  95

Gly Gly Cys Lys His Glu Val Gly His Gly His Tyr Leu Ser Cys Met
            100                 105                 110

Gly Met Tyr Trp His Pro Gln Cys Phe Arg Cys Ser Ser Cys Gly His
        115                 120                 125

Pro Ile Arg Glu Thr Glu Phe Thr Leu Leu Gly Ala Glu Pro Tyr His
    130                 135                 140

Lys Leu Cys Tyr Lys Glu Leu His His Pro Lys Cys Asp Val Cys Leu
145                 150                 155                 160

His Phe Ile Ala Thr Asn Arg Thr Gly Leu Ile Glu Tyr Arg Ala His
                165                 170                 175

Pro Phe Trp Gly Gln Lys Tyr Cys Pro Ser His Glu Leu Asp Arg Thr
            180                 185                 190

Pro Arg Cys Cys Ser Cys Glu Lys Met Glu Pro Arg Asn Thr Lys Tyr
        195                 200                 205

Met Ser Leu Gly Asp Gly Arg Ser Leu Cys Met Glu Cys Leu Asp Ser
    210                 215                 220

Ala Val Met Asp Thr Gly Glu Cys Gln Pro Leu Tyr His Ser Ile Arg
225                 230                 235                 240

Asp Tyr Tyr Glu Gly Met Asn Met Lys Leu Asp Gln Gln Ile Pro Met
                245                 250                 255

Leu Leu Val Glu Arg Gln Ala Leu Asn Glu Ala Met Glu Gly Glu Cys
            260                 265                 270

Arg Gly Pro His His Met Pro Glu Thr Arg Gly Leu Cys Leu Ser Glu
        275                 280                 285
```

Glu Gln Thr Val Ser Ser Ile Leu Arg Arg Pro Arg Ile Gly Gly Asn
290                 295                 300

Arg Leu Leu Asp Met Arg Thr Gln Pro Gln Lys Leu Thr Arg Arg Cys
305                 310                 315                 320

Glu Val Thr Ala Ile Leu Val Leu Tyr Gly Leu Pro Arg Leu Leu Thr
                325                 330                 335

Gly Ser Ile Leu Ala His Glu Leu Met His Gly Trp Leu Arg Leu Lys
                340                 345                 350

Gly Tyr Arg Asn Leu Lys Pro Glu Val Glu Gly Ile Cys Gln Val
                355                 360                 365

Met Ser Tyr Leu Trp Leu Glu Ala Glu Ile Leu Pro Ala Ala Thr Arg
370                 375                 380

His Ala His Pro Ser Ser Tyr Ala Ser Ser Ser Ser Ser Ser
385                 390                 395                 400

His Tyr Arg Pro Pro Ser Ser Lys Lys Gly Ile Ser His Thr Glu
                405                 410                 415

Lys Lys Leu Gly Glu Phe Phe Met His Gln Ile Ala Asn Asp Thr Ser
                420                 425                 430

Ala Ala Tyr Gly Asp Gly Phe Arg Thr Ala Tyr Lys Ala Val Asn Gln
                435                 440                 445

Tyr Gly Leu Arg Gln Thr Leu Asn His Ile Arg Leu Thr Gly Gly Phe
450                 455                 460

Pro Leu
465

<210> SEQ ID NO 317
<211> LENGTH: 469
<212> TYPE: PRT
<213> ORGANISM: Oryza sativa

<400> SEQUENCE: 317

Gly Gln Tyr His Ser Lys Pro Ala Glu Glu Thr Ile Trp Asn Gly Pro
1               5                   10                  15

Ser Asn Ser Ala Val Val Thr Asp Val Pro Ser Glu Phe Asp Asn Glu
                20                  25                  30

Asp Ile Ala Arg Ala Ile Ser Leu Ser Leu Leu Glu Glu Glu Gln Arg
            35                  40                  45

Lys Ala Lys Ala Ile Glu Lys Asp Met His Leu Glu Glu Asp Glu Gln
50                  55                  60

Leu Ala Arg Ala Ile Gln Glu Ser Leu Asn Val Glu Ser Pro Pro Arg
65                  70                  75                  80

Ala Arg Glu Asn Gly Asn Ala Asn Gly Gly Asn Met Tyr Gln Pro Leu
                85                  90                  95

Pro Phe Met Phe Ser Ser Gly Phe Arg Thr Cys Ala Gly Cys His Ser
            100                 105                 110

Glu Ile Gly His Gly Arg Phe Leu Ser Cys Met Gly Ala Val Trp His
        115                 120                 125

Pro Glu Cys Phe Arg Cys His Ala Cys Asn Gln Pro Ile Tyr Asp Tyr
    130                 135                 140

Glu Phe Ser Met Ser Gly Asn His Pro Tyr His Lys Thr Cys Tyr Lys
145                 150                 155                 160

Glu Arg Phe His Pro Lys Cys Asp Val Cys Lys Gln Phe Ile Pro Thr
                165                 170                 175

Asn Met Asn Gly Leu Ile Glu Tyr Arg Ala His Pro Phe Trp Leu Gln
            180                 185                 190

```
Lys Tyr Cys Pro Ser His Glu Val Asp Gly Thr Pro Arg Cys Cys Ser
            195                 200                 205

Cys Glu Arg Met Glu Pro Arg Glu Ser Arg Tyr Val Leu Leu Asp Asp
    210                 215                 220

Gly Arg Lys Leu Cys Leu Glu Cys Leu Asp Ser Ala Val Met Asp Thr
225                 230                 235                 240

Ser Glu Cys Gln Pro Leu Tyr Leu Glu Ile Gln Glu Phe Tyr Glu Gly
                245                 250                 255

Leu Asn Met Lys Val Glu Gln Gln Val Pro Leu Leu Val Glu Arg
            260                 265                 270

Gln Ala Leu Asn Glu Ala Met Glu Gly Lys Thr Gly His His His
            275                 280                 285

Leu Pro Glu Thr Arg Gly Leu Cys Leu Ser Glu Gln Thr Val Ser
    290                 295                 300

Thr Ile Leu Arg Arg Pro Arg Met Ala Gly Asn Lys Val Met Glu Met
305                 310                 315                 320

Ile Thr Glu Pro Tyr Arg Leu Thr Arg Arg Cys Glu Val Thr Ala Ile
                325                 330                 335

Leu Ile Leu Tyr Gly Leu Pro Arg Leu Leu Thr Gly Ser Ile Leu Ala
            340                 345                 350

His Glu Met Met His Ala Trp Leu Arg Leu Lys Gly Tyr Arg Thr Leu
            355                 360                 365

Ser Pro Asp Val Glu Glu Gly Ile Cys Gln Val Leu Ala His Met Trp
    370                 375                 380

Ile Glu Ser Glu Ile Ile Ala Gly Ser Gly Ser Asn Gly Ala Ser Thr
385                 390                 395                 400

Ser Ser Ser Ser Ser Ala Ser Thr Ser Ser Lys Lys Gly Gly Arg Ser
                405                 410                 415

Gln Phe Glu Arg Lys Leu Gly Asp Phe Phe Lys His Gln Ile Glu Ser
            420                 425                 430

Asp Thr Ser Met Ala Tyr Gly Asp Gly Phe Arg Ala Gly Asn Arg Ala
            435                 440                 445

Val Leu Gln Tyr Gly Leu Lys Arg Thr Leu Glu His Ile Arg Leu Thr
    450                 455                 460

Gly Thr Phe Pro Phe
465

<210> SEQ ID NO 318
<211> LENGTH: 465
<212> TYPE: PRT
<213> ORGANISM: Oryza sativa

<400> SEQUENCE: 318

Arg Arg Arg Pro Arg Val Thr Ala Gly Glu Glu Thr Thr Leu Trp Glu
1               5                   10                  15

Glu Pro Val Arg Pro Lys Lys Glu Glu Pro Arg His Asn Asn Glu
            20                  25                  30

Glu Met Asp His Ala Leu Ala Leu Ala Leu Ala Asp Asp Ala Lys Asn
        35                  40                  45

Thr Lys Glu Arg Asn His Asp Lys Gly Glu Asn Asp Glu Glu Leu Ala
    50                  55                  60

Arg Ala Ile Gln Asp Ser Leu Asn Met Asn Pro Tyr Gln Pro Tyr Asn
65                  70                  75                  80

Pro Cys Ala Pro Ser Gln Thr Gln Ala Arg Ser Arg Gly Tyr Arg Val
```

```
                85                  90                  95
Cys Gly Gly Cys Lys His Glu Ile Gly His Gly His Tyr Leu Ser Cys
            100                 105                 110

Leu Gly Met Tyr Trp His Pro Gln Cys Phe Arg Cys Ser Ser Cys Arg
            115                 120                 125

His Pro Ile Arg Glu Met Glu Phe Thr Leu Leu Gly Thr Asp Pro Tyr
130                 135                 140

His Lys Leu Cys Tyr Lys Glu Leu His Pro Lys Cys Asp Val Cys
145                 150                 155                 160

Leu Gln Phe Ile Pro Thr Asn Arg Thr Gly Leu Ile Glu Tyr Arg Ala
                165                 170                 175

His Pro Phe Trp Gly Gln Lys Tyr Cys Pro Leu His Glu His Asp Arg
            180                 185                 190

Thr Pro Arg Cys Cys Ser Cys Glu Lys Met Glu Pro Arg Asn Thr Lys
            195                 200                 205

Tyr Met Ser Leu Gly Asp Gly Arg Ser Leu Cys Met Glu Cys Leu Asp
210                 215                 220

Ser Ala Ile Met Asp Thr Gly Glu Cys Gln Pro Leu Tyr His Ser Ile
225                 230                 235                 240

Arg Asp Tyr Tyr Glu Gly Met Asn Met Lys Leu Asp Gln Gln Ile Pro
                245                 250                 255

Met Leu Leu Val Glu Arg Gln Ala Leu Asn Glu Ala Met Glu Gly Glu
            260                 265                 270

Ser Lys Gly Pro His His Met Pro Glu Thr Arg Gly Leu Cys Leu Ser
            275                 280                 285

Glu Glu Gln Thr Val Thr Ser Ile Leu Arg Arg Pro Arg Ile Gly Ala
290                 295                 300

Asn Arg Leu Leu Asp Met Lys Thr Gln Pro Gln Lys Leu Thr Arg Arg
305                 310                 315                 320

Cys Glu Val Thr Ala Ile Leu Val Leu Phe Gly Leu Pro Arg Leu Leu
                325                 330                 335

Thr Gly Ser Ile Leu Ala His Glu Leu Met His Gly Trp Leu Arg Leu
            340                 345                 350

Lys Gly Tyr Arg Asn Leu Lys Ala Glu Ile Glu Glu Gly Ile Cys Gln
            355                 360                 365

Val Met Ser Tyr Leu Trp Leu Glu Ser Glu Ile Leu Pro Ser Thr Ser
370                 375                 380

Arg Tyr Gly Gln Ala Ser Thr Ser Tyr Ala Ser Ser Ser Ser Ser Ser
385                 390                 395                 400

Cys Arg Pro Pro Pro Ser Lys Lys Gly Gly Ile Ser His Thr Glu Lys
                405                 410                 415

Lys Leu Gly Glu Phe Phe Leu His Gln Ile Ala Asn Asp Thr Ser Ser
            420                 425                 430

Ala Tyr Gly Asp Gly Phe Arg Ala Ala Tyr Ala Ala Val Asn Lys Tyr
            435                 440                 445

Gly Leu Arg Gln Ser Leu Asn His Ile Arg Leu Thr Gly Gly Phe Pro
450                 455                 460

Val
465

<210> SEQ ID NO 319
<211> LENGTH: 474
<212> TYPE: PRT
<213> ORGANISM: Oryza sativa
```

<400> SEQUENCE: 319

```
Gly His Tyr Asn Gly Asn Thr His Glu Gly His Ser Ala Trp His Thr
1               5                   10                  15

Lys Ala Tyr Glu His Asp Ser Asp His Glu Asp Ile Asp Arg Ala Ile
            20                  25                  30

Ala Leu Ser Leu Ser Glu Glu Asp Gln Arg Lys Gly Lys Ala Val Asp
        35                  40                  45

Glu Val Asp Ile Asp His Arg Leu His Glu Asp Glu Gln Leu Ala Arg
50                  55                  60

Ala Leu Gln Glu Ser Leu Asn Asp Glu Pro Pro Arg Gln Asn Val Pro
65                  70                  75                  80

Val Lys Asp Val His Ser Glu Ser Thr Pro Ala Thr Phe Met Pro Pro
                85                  90                  95

Tyr Ile Phe Pro Ser Thr Gly Leu Arg Val Cys Ala Gly Cys Lys Thr
            100                 105                 110

Pro Ile Gly Gln Gly Arg Phe Leu Ser Cys Met Asp Ser Val Trp His
        115                 120                 125

Pro Gln Cys Phe Arg Cys Phe Ala Cys Asp Arg Pro Ile Ser Glu Tyr
130                 135                 140

Glu Phe Ala Val His Glu Gly Asn Pro Tyr His Arg Ser Cys Tyr Lys
145                 150                 155                 160

Glu Leu Phe His Pro Lys Cys Asp Val Cys Lys Asn Phe Ile Pro Thr
                165                 170                 175

Asn Lys Asp Gly His Ile Glu Tyr Arg Ala His Pro Phe Trp Met Gln
            180                 185                 190

Lys Tyr Cys Pro Ala His Glu Thr Asp Arg Thr Pro Arg Cys Cys Ser
        195                 200                 205

Cys Glu Arg Met Glu Pro Lys Asp Ser Lys Tyr Ile Thr Leu Asp Asp
210                 215                 220

Gly Arg Lys Leu Cys Leu Glu Cys Leu Asn Thr Ser Ile Met Asp Thr
225                 230                 235                 240

Asp Glu Cys Gln Pro Leu Tyr Ile Asp Ile Gln Glu Phe Tyr Glu Gly
                245                 250                 255

Leu Asn Met Lys Val Glu Gln Gln Ile Pro Leu Leu Leu Val Glu Arg
            260                 265                 270

Gln Ala Leu Asn Glu Ala Met Glu Ala Glu Lys Thr Gly His His Leu
        275                 280                 285

Ala Glu Thr Arg Gly Leu Cys Leu Ser Glu Glu Gln Ile Val Arg Thr
290                 295                 300

Ile Leu Arg Arg Pro Val Ile Gly Pro Gly Asn Lys Ile Val Asp Met
305                 310                 315                 320

Ile Thr Gly Pro Tyr Lys Leu Val Arg Arg Cys Glu Val Thr Ala Ile
                325                 330                 335

Leu Ile Leu Tyr Gly Leu Pro Arg Leu Leu Thr Gly Ser Ile Leu Ala
            340                 345                 350

His Glu Met Met His Ala Tyr Leu Arg Leu Lys Gly Tyr Gln Thr Leu
        355                 360                 365

Asp Pro Lys Val Glu Glu Gly Ile Cys Gln Val Leu Ala His Met Trp
370                 375                 380

Leu Glu Ser Glu Ile Thr Ser Gly Ser Ser Ile Ile Ala Ser Ile
385                 390                 395                 400

Ala Ala Ser Ser Ser Ser Ser Ser Ser Ser Ala Pro Ser Ser Lys
```

```
                    405                 410                 415
Lys Gly Val Gln Thr Asp Phe Glu Lys Lys Leu Gly Glu Phe Phe Lys
            420                 425                 430

His Gln Ile Glu Thr Asp Pro Ser Asp Val Tyr Gly Asp Gly Phe Arg
            435                 440                 445

Asp Gly Ile Lys Ala Val Glu Arg Tyr Gly Leu Arg Lys Thr Leu Asp
450                 455                 460

His Met Lys Leu Thr Gly Val Phe Pro Cys
465                 470

<210> SEQ ID NO 320
<211> LENGTH: 472
<212> TYPE: PRT
<213> ORGANISM: Oryza sativa

<400> SEQUENCE: 320

Arg Phe Leu Ser Ser Gly Tyr Arg Lys Phe Asp Pro Gln Ile Thr Ser
1               5                   10                  15

Ser His Gly Leu Gly Ala Tyr Asp Glu Ser Asp Asn Glu Asp Ile Asp
            20                  25                  30

Arg Ala Ile Ala Leu Ser Leu Ser Glu Glu Gln Asn Lys Gly Lys Ala
        35                  40                  45

Val Asp Ile Asp Tyr Asn Leu Glu Glu Asp Glu Gln Leu Ala Arg Ala
    50                  55                  60

Leu Gln Glu Ser Leu Asn Ala Asp Ser Pro Pro Arg Gln Asn Ile Pro
65                  70                  75                  80

Val Glu Asn Val Pro Ser Glu Pro Pro Arg Leu Pro Pro Ile Leu
                85                  90                  95

Phe Ala Ser Ser Gly Ser Arg Thr Cys Ala Gly Cys Lys Asn Pro Ile
            100                 105                 110

Gly His Gly Arg Phe Leu Ser Cys Met Asp Ser Val Trp His Pro Gln
        115                 120                 125

Cys Phe Arg Cys Phe Ala Cys Asn Lys Pro Ile Ser Glu Tyr Glu Phe
    130                 135                 140

Ala Met His Glu Asp Gln Pro Tyr His Lys Ser Cys Tyr Lys Asp Phe
145                 150                 155                 160

Phe His Pro Lys Cys Asp Val Cys Lys Asn Phe Ile Pro Thr Asn Arg
                165                 170                 175

Asn Gly Leu Ile Glu Tyr Arg Ala His Pro Phe Trp Met Gln Lys Tyr
            180                 185                 190

Cys Pro Ser His Glu Asp Asp Gly Thr Pro Arg Cys Cys Ser Cys Glu
        195                 200                 205

Arg Met Glu Pro Met Asp Ile Lys Tyr Ile Thr Leu Asp Asp Gly Arg
    210                 215                 220

Lys Leu Cys Leu Glu Cys Leu Asn Ser Ser Ile Met Asp Thr Pro Glu
225                 230                 235                 240

Cys Gln Gln Leu Tyr Met Asp Ile Gln Glu Phe Glu Gly Leu Asn
                245                 250                 255

Met Lys Val Glu Gln Gln Val Pro Ile Leu Leu Val Glu Arg Gln Ala
            260                 265                 270

Leu Asn Glu Ala Leu Glu Thr Glu Lys Asn Gly His His Leu Pro Glu
        275                 280                 285

Thr Arg Gly Leu Cys Leu Ser Glu Glu Gln Ile Val Arg Thr Ile Leu
    290                 295                 300
```

-continued

Arg Arg Pro Ile Ile Gly Pro Gly Asn Arg Ile Ile Asp Met Ile Thr
305                 310                 315                 320

Ala Pro Tyr Lys Leu Glu Arg Arg Cys Glu Val Thr Ala Ile Leu Ile
            325                 330                 335

Leu Tyr Gly Leu Pro Arg Leu Gln Thr Gly Ser Ile Leu Ala His Glu
            340                 345                 350

Met Met His Ala Tyr Leu Arg Leu Lys Gly Phe Arg Ser Leu Ser Pro
            355                 360                 365

Gln Val Glu Glu Gly Ile Cys Gln Val Leu Ser His Met Trp Leu Glu
            370                 375                 380

Ser Glu Ile Ile Phe Gly Ser Ser Ile Asp Ile Ser Ala Thr Ser Val
385                 390                 395                 400

Ala Ser Ser Ser Ser Ser Ser Thr Pro Thr Thr Ser Lys Lys Gly
            405                 410                 415

Ala Lys Thr Glu Phe Glu Lys Lys Leu Gly Ala Phe Ile Lys His Gln
            420                 425                 430

Ile Glu Thr Asp Ser Ser Glu Ala Tyr Gly Asp Gly Phe Arg Ala Ala
            435                 440                 445

Asn Arg Ala Val Glu Ser Tyr Gly Leu Arg Ser Thr Leu Asn His Met
450                 455                 460

Lys Met Thr Gly Ser Phe Pro Tyr
465                 470

<210> SEQ ID NO 321
<211> LENGTH: 392
<212> TYPE: PRT
<213> ORGANISM: Physcomitrella patens

<400> SEQUENCE: 321

Met Gln Glu Ser Leu Asn Phe Gly His Arg Asp Pro Tyr Ala Tyr Ser
1               5                   10                  15

Ser Ser Tyr Ala Pro Pro Ser Arg Ser Ser Gly Met Asn Val Cys
            20                  25                  30

Ala Gly Cys Gly Glu Ser Leu Gly Phe Gly Arg Phe Leu Ser Cys Leu
            35                  40                  45

Gly Lys Asn Trp His Pro Asn Cys Phe Cys Cys Lys Lys Cys Asn Asn
50                  55                  60

Ala Ile Ala Glu Arg Glu Phe Ser Val Gln Gly Asn Glu Ala Tyr His
65                  70                  75                  80

Arg Glu Cys Tyr Lys Glu Ile Phe His Pro Lys Cys Glu Val Cys Asn
            85                  90                  95

His Phe Ile Pro Thr Asn Pro Ala Gly Leu Ile Glu Tyr Arg Ser His
            100                 105                 110

Pro Phe Trp Asn Gln Lys Tyr Cys Pro Arg His Glu Arg Asp Gly Thr
            115                 120                 125

Pro Arg Cys Cys Ser Cys Asp Arg Ile Glu Thr Gly Glu Pro Gly Thr
            130                 135                 140

Tyr Ile Ser Leu Ala Gln Ile Thr Gly Ala Gln Gly Ser Leu Ala Asp
145                 150                 155                 160

Asp Arg Lys Val Cys Leu Glu Cys Tyr Asp Thr Ile Val Asp Asn
            165                 170                 175

Gln Ala Cys Gln Pro Leu Tyr Arg Glu Ile Leu Lys Tyr Tyr Arg Ser
            180                 185                 190

Ile Asn Met Pro Ile Ala Gln Glu Ile Pro Met Leu Leu Val Ala Arg
            195                 200                 205

```
Ser Ala Leu Asn Ala Ala Arg Asp Gly Glu Lys Asp Gly His Thr His
            210                 215                 220

Asn Ala Glu Thr Arg Gly Leu Cys Leu Ser Glu Gln Thr Ile Thr
225                 230                 235                 240

Thr Val Tyr Gly Gly Lys Ser Arg Asn Pro Met Arg Tyr Leu Arg
                245                 250                 255

Thr Glu Lys Gln Lys Leu Thr Arg His Cys Glu Val Thr Ala Ile Leu
            260                 265                 270

Val Leu Tyr Gly Leu Pro Arg Leu Leu Thr Gly Ser Ile Leu Ala His
        275                 280                 285

Glu Leu Met His Ala Trp Ile Arg Leu Gln Gly Asn Phe Arg Pro Met
290                 295                 300

Ala Pro His Val Glu Glu Gly Ile Cys Gln Val Met Ser His Ile Trp
305                 310                 315                 320

Leu Thr Ala Glu Leu Lys Lys Leu Lys Gly Ala Arg Ser Ser Ser Asn
                325                 330                 335

Ser Ser Ala Ala Ile Glu Ala Arg Leu Gly Glu Phe Tyr Leu His Gln
            340                 345                 350

Ile Ser Ser Asp Ser Ser Pro Val Tyr Gly Asp Gly Phe Arg His Gly
        355                 360                 365

Met Ala Ala Val Gln Gln Phe Gly Leu Glu Arg Val Leu Asp His Leu
370                 375                 380

Arg Leu Thr Gly Asn Phe Pro Leu
385                 390

<210> SEQ ID NO 322
<211> LENGTH: 366
<212> TYPE: PRT
<213> ORGANISM: Physcomitrella patens

<400> SEQUENCE: 322

Met Ile Leu Cys Val Gly Ile Cys Arg Pro Thr Ala Thr Asn Ile Cys
1               5                   10                  15

Ala Gly Cys Lys Gln Pro Leu Gly Tyr Gly Arg Phe Leu Ser Cys Leu
            20                  25                  30

Gly Lys Asn Trp His Pro His Cys Phe Ala Cys Lys Met Cys Ser Lys
        35                  40                  45

Pro Ile Asp Asp Arg Glu Phe Ser Val Gln Gly Gly Asp Pro Tyr His
    50                  55                  60

Arg Asn Cys Tyr Lys Glu Leu Phe His Pro Lys Cys Glu Val Cys Leu
65                  70                  75                  80

Glu Phe Ile Pro Thr Asn Glu Asp Gly Met Ile Glu Tyr Arg Ser His
                85                  90                  95

Pro Phe Trp Asn Gln Lys Tyr Cys Pro Ser His Glu Ile Asp Gly Thr
            100                 105                 110

Pro Arg Cys Cys Ser Cys Asp Arg Ile Glu Thr Gly Glu Val Lys Tyr
        115                 120                 125

Ala Gly Leu Glu Asp Gly Arg Lys Ile Cys Leu Glu Cys Leu Glu Thr
    130                 135                 140

Ala Val Phe Asp Thr Lys Glu Cys Gln Pro Leu Tyr Arg Glu Val Leu
145                 150                 155                 160

Lys Phe Tyr Lys Asn Val Gly Met Met Ile Asp Gln Glu Val Pro Met
                165                 170                 175

Leu Leu Val Glu Arg Thr Ala Leu Asn Glu Ala Arg Glu Gly Glu Lys
```

```
            180                 185                 190
Glu Gly Ile His Met Thr Ser Glu Thr Arg Gly Leu Cys Leu Ser Glu
                195                 200                 205
Glu Gln Thr Val Thr Thr Val Arg Lys Ser Ser Phe Pro Arg Leu Ser
    210                 215                 220
Phe Asn Phe Trp Thr Glu Pro Lys His Leu Arg Arg His Cys Glu Val
225                 230                 235                 240
Thr Ala Ile Leu Val Leu Tyr Gly Leu Pro Arg Leu Leu Thr Gly Ser
                245                 250                 255
Ile Leu Val His Glu Leu Met His Ala Trp Leu Arg Leu Ala Gly Gly
            260                 265                 270
Phe Pro Arg Met Arg Pro Glu Val Glu Gly Ile Cys Gln Val Met
        275                 280                 285
Ser His Ile Trp Leu Ser Ala Glu Leu Lys Arg Ala Glu Lys Lys Asp
            290                 295                 300
Ser Thr Ser Ala Lys Gly Ile Thr Ser Pro Ala Gln Glu Arg Leu Gly
305                 310                 315                 320
Lys Phe Tyr Leu Tyr Gln Ile Ser Ser Asp Thr Ser Pro Val Tyr Gly
                325                 330                 335
Asp Gly Phe Arg Gln Ala Leu Ala Ser Val Asn Arg Tyr Gly Leu Val
            340                 345                 350
Arg Val Leu Glu His Leu Arg Met Thr Ala Asn Phe Gln Val
            355                 360                 365

<210> SEQ ID NO 323
<211> LENGTH: 465
<212> TYPE: PRT
<213> ORGANISM: Physcomitrella patens

<400> SEQUENCE: 323

Met Ser Thr Ser Thr Leu Asp Asp Leu Lys Arg Tyr Lys Cys Asp Leu
1               5                   10                  15
Ile Thr Ser Met Thr Met Ala Gln Met Leu Gly Leu Cys Asn Ser Gln
            20                  25                  30
Val Ala Asn Glu His Cys Pro Leu Gly Phe Val Lys Leu Ser Gly Arg
        35                  40                  45
Arg Arg Ser Arg Asp Val Pro Asn Thr Glu Asp Asp Glu Ser Leu Ala
    50                  55                  60
Arg Ala Leu Gln Glu Ser Ile Tyr Leu Glu Gln Ser Ala Pro Arg Lys
65                  70                  75                  80
Ile Pro Ala Lys Pro Pro Gly Phe Arg Pro Ile Val Gln Lys Phe Ala
                85                  90                  95
Ser Val His Pro Ser Leu Leu Arg Phe His Ile Tyr Leu Ala Ser Val
            100                 105                 110
Phe Cys Ala Gly Cys Lys Lys Pro Leu Gly Tyr Gly Arg Phe Leu Ser
        115                 120                 125
Cys Leu Gly Lys Asn Trp His Pro Ser Cys Phe Ala Cys Lys Leu Cys
    130                 135                 140
Ser Arg Pro Ile Ala Glu Arg Glu Phe Ser Val Gln Glu Gly Glu Pro
145                 150                 155                 160
Tyr His Arg Asp Cys Tyr Lys Glu Leu Phe His Pro Lys Cys Glu Val
                165                 170                 175
Cys Leu Gln Phe Ile Pro Thr Asn Ala Ala Gly Leu Ile Glu Tyr Arg
            180                 185                 190
```

```
Ser His Pro Phe Trp Asn Gln Lys Tyr Cys Pro Lys His Glu Ala Asp
        195                 200                 205

Gly Thr Pro Arg Cys Cys Ser Cys Asp Arg Val Glu Thr His Asp Glu
    210                 215                 220

Gln Tyr Val Pro Leu Ala Asp Gly Arg Lys Leu Cys Leu Glu Cys Leu
225                 230                 235                 240

Glu Thr Ala Val Phe Asp Thr Lys Glu Cys Gln Pro Leu Tyr Arg Glu
                245                 250                 255

Ile Leu Lys Phe Tyr Lys Asn Val Gly Met Met Ile Asp Gln Glu Val
            260                 265                 270

Pro Met Leu Leu Val Glu Arg Ser Ala Leu Asn Asp Ala Arg Glu Gly
        275                 280                 285

Glu Lys Glu Gly Met His Met Thr Ser Glu Thr Arg Gly Leu Cys Leu
    290                 295                 300

Ser Glu Glu Gln Thr Ile Thr Thr Val Phe Gly Gly Lys Pro Val Phe
305                 310                 315                 320

Ser Arg Gly Pro Trp Ser Leu Trp Thr Glu Pro Arg Gln Leu Arg Arg
                325                 330                 335

His Cys Glu Val Thr Ala Ile Leu Val Leu Tyr Gly Leu Pro Arg Leu
            340                 345                 350

Leu Thr Gly Ala Ile Leu Ala His Glu Leu Met His Ala Trp Leu Arg
        355                 360                 365

Leu Thr Gly Gly Phe Pro His Met Ser Pro Glu Val Glu Glu Gly Ile
    370                 375                 380

Cys Gln Val Met Ser His Ile Trp Leu Ser Ala Glu Leu Lys Arg Ser
385                 390                 395                 400

Gln Asn Arg Thr Ser Thr Asn Ala Thr Ser Pro Ala Gln Glu Arg Leu
                405                 410                 415

Gly Lys Phe Tyr Leu His Gln Ile Ala Asn Asp Thr Ser Pro Ile Tyr
            420                 425                 430

Gly Asn Gly Phe Arg Arg Gly Leu Lys Ala Val Asn Tyr His Gly Leu
        435                 440                 445

Val Arg Val Leu Glu His Leu Arg Met Thr Ala Asn Phe Pro Pro Gly
    450                 455                 460

Pro
465

<210> SEQ ID NO 324
<211> LENGTH: 219
<212> TYPE: PRT
<213> ORGANISM: Physcomitrella patens

<400> SEQUENCE: 324

Met Glu Ser Asn Val Met Asp Thr Arg Gly Cys Gln Pro Leu Tyr Arg
1               5                   10                  15

Glu Ile Leu Lys Phe Tyr Lys Gly Leu Gly Met Pro Ile Glu Gln Glu
            20                  25                  30

Ile Pro Met Leu Leu Val Lys Arg Ala Ala Leu Asn His Ala Arg Glu
        35                  40                  45

Ala Glu Lys Asp Glu His Ile His Ala Pro Thr Arg Gly Leu Cys
    50                  55                  60

Leu Ser Glu Glu Gln Thr Ile Thr Thr Val Phe Val Ser Asp Arg Gly
65                  70                  75                  80

Glu Tyr Gly Asp Tyr Ala His Pro Glu Met Gln Thr Arg Lys Leu Thr
                85                  90                  95
```

```
Arg His Cys Glu Val Thr Ala Ile Leu Val Leu Phe Gly Leu Pro Arg
            100                 105                 110

Leu Leu Thr Gly Ser Ile Leu Ala His Glu Leu Met His Ala Trp Ile
        115                 120                 125

Arg Leu Asp Gly Arg Phe Pro Asn Leu Asp Asn Asp Ile Glu Glu Gly
130                 135                 140

Ile Cys Gln Val Ile Ala His Ile Trp Leu Lys Glu Leu Glu Lys
145                 150                 155                 160

Leu Lys Arg Ser Val Ser Arg Glu Thr Lys Arg Leu Gly Glu Phe Phe
                165                 170                 175

Leu His Gln Ile Glu Thr Asp Ser Ser Pro Ile Tyr Gly Asp Gly Phe
            180                 185                 190

Arg Ala Ala Tyr Thr Ala Tyr Lys Asn Tyr Gly Leu Ala Lys Thr Leu
        195                 200                 205

Asn His Leu Arg Asn Thr Gly Arg Ile Leu Gln
210                 215

<210> SEQ ID NO 325
<211> LENGTH: 403
<212> TYPE: PRT
<213> ORGANISM: Physcomitrella patens

<400> SEQUENCE: 325

Met Gly Ser Ala Tyr Asp Tyr Gly Ala Ser Glu Pro Ile Tyr Pro Ala
1               5                   10                  15

Trp Trp Gly Ile Glu Glu Gly Arg Gln Ser Arg Lys Gln Asp Thr Val
            20                  25                  30

Asp Asp Glu Ser Lys Ala Thr Leu Thr Gln Tyr Ile Glu Glu Glu Ser
        35                  40                  45

Lys Pro Glu Asp Phe Leu Arg Asn Cys Ala Gly Cys Lys Gln Thr Leu
50                  55                  60

Ser His Gly Arg Phe Leu Thr Cys Leu Gly Gln Ser Trp His Pro Ala
65                  70                  75                  80

Cys Phe Cys Cys Arg Ser Cys His Lys Ala Ile Val Asp Arg Glu Phe
                85                  90                  95

Ser Val Gln Glu Lys Gln Pro Tyr His Arg Glu Cys Phe Lys Arg Glu
            100                 105                 110

Phe His Pro Lys Cys Glu Ile Cys Phe Asn Phe Ile Pro Pro Asn Ser
        115                 120                 125

Glu Gly Leu Ile Glu Tyr Arg Ser His Pro Phe Trp Asp Gln Lys Tyr
130                 135                 140

Cys Pro Ser His Glu Arg Asp Gly Arg Arg Cys Cys Ser Cys Asp
145                 150                 155                 160

Arg Ile Glu Arg Val Asp Gln Gly Tyr Thr Pro Leu Gly Asp Gly Arg
                165                 170                 175

Lys Leu Cys Gly Glu Cys Met Asp Ser Met Val Met His Thr Arg Asp
            180                 185                 190

Cys Gln Pro Leu Tyr Arg Glu Ile Leu Lys Phe Tyr Lys Asn Asn Leu
        195                 200                 205

Gly Met Ser Ile Val Gln Glu Ile Pro Met Leu Leu Val Glu Arg Ala
210                 215                 220

Ala Leu Asn His Ala Arg Glu Ala Glu Arg Asp Glu His Ile His Ala
225                 230                 235                 240

Pro Glu Thr Arg Gly Leu Cys Leu Ser Glu Glu Gln Thr Ile Thr Thr
```

```
                        245                 250                 255
Val Arg Leu Val Pro Asp Glu Tyr Gly Asp Tyr Thr His His Glu Met
                260                 265                 270

Gln Thr Arg Lys Leu Thr Arg His Cys Glu Val Thr Ala Ile Leu Val
            275                 280                 285

Leu Phe Gly Leu Pro Ser Leu Leu Thr Gly Ser Ile Leu Ala His Glu
        290                 295                 300

Leu Met His Ala Trp Ile Arg Leu Asp Gly Gly Phe Pro Ser Leu Asp
305                 310                 315                 320

Asn Asp Ile Glu Glu Gly Ile Cys Gln Val Ile Ala His Ile Trp Leu
                325                 330                 335

Lys Glu Glu Leu Glu Lys Leu Lys Arg Lys Gly Asn Val Ser Glu Ala
            340                 345                 350

Thr Ile Arg Leu Gly Asp Phe Phe Leu His Gln Ile Glu Thr Asp Ser
        355                 360                 365

Ser Pro Ile Tyr Gly Asp Gly Phe Arg Ala Ala Tyr Ala Ala Tyr Lys
    370                 375                 380

Glu Tyr Gly Leu Ser Lys Thr Leu Asn His Leu Arg Asn Thr Gly Arg
385                 390                 395                 400

Ile Leu Arg

<210> SEQ ID NO 326
<211> LENGTH: 378
<212> TYPE: PRT
<213> ORGANISM: Physcomitrella patens

<400> SEQUENCE: 326

Met Val Ala Pro Leu Pro Ile Pro Val Ala Ala Pro Thr Thr Lys Asn
1               5                   10                  15

Val Gly Leu Ser Thr Cys Ala Gly Cys His Arg Thr Leu Gly Phe Gly
            20                  25                  30

Arg Phe Leu Thr Cys Ile Asn Gln Asn Trp His Pro Asp Cys Phe Cys
        35                  40                  45

Cys Lys Ser Cys Arg Ser Pro Ile Val Thr Lys Glu Phe Ser Val His
    50                  55                  60

Gly Ser Asp Pro Tyr His Arg Asp Cys Tyr Lys Lys Leu Phe His Pro
65                  70                  75                  80

Lys Cys Glu Ile Cys Tyr Gln Tyr Ile Ser Tyr Asn Ala Gln Gly Gln
                85                  90                  95

Ile Glu Tyr Arg Ser His Pro Phe Trp Asn Gln Arg Tyr Cys Pro Ser
            100                 105                 110

His Glu Arg Asp Gly Ser Lys Cys Cys Cys Ser Cys Asp Arg Ile Glu
        115                 120                 125

Pro Val Asp Arg Arg Tyr Gln Ser Leu Gly Asp Gly Arg Lys Val Cys
    130                 135                 140

Pro Glu Cys Met Glu Ser Ala Val Met Thr Thr Lys Asp Cys Gln Pro
145                 150                 155                 160

Leu Tyr Lys Asn Val Leu Lys Phe Tyr Arg Val Asn Leu Gly Met Pro
                165                 170                 175

Ile Glu Gln Asp Val Pro Met Leu Leu Val Glu Arg Glu Ala Leu Asn
            180                 185                 190

Lys Ala Arg Glu Val Glu Asn Asp Gly His Thr His Thr Pro Glu Thr
        195                 200                 205

Arg Gly Leu Cys Leu Ser Glu Glu Lys Ile Phe Pro Val Arg Gln Pro
```

```
            210                 215                 220
His Leu Phe Arg Phe Arg His Asp Val Ser Arg Phe Glu Gln Val Val
225                 230                 235                 240

Glu Asn Gly Gly Glu Pro Arg Lys Leu Thr Arg His Cys Glu Ile Thr
                245                 250                 255

Ala Ile Leu Val Leu Tyr Gly Leu Pro Met Leu Leu Thr Gly Ser Ile
            260                 265                 270

Leu Ala His Glu Leu Met His Ala Phe Ile Arg Leu Asn Gly Gln Phe
            275                 280                 285

Pro Asn Leu Glu Asn Asp Val Glu Glu Gly Ile Cys Gln Val Ile Ala
            290                 295                 300

His Met Trp Leu Lys Ala Glu Leu Glu Asn Leu Thr Arg Arg Thr Ser
305                 310                 315                 320

Gly Ser Asp Asp Ser Ser Val Ser Lys Arg Leu Gly Glu Phe Phe Leu
                325                 330                 335

His Gln Ile Glu Thr Asp Ser Ser Gln Ile Tyr Gly Asp Gly Phe Arg
                340                 345                 350

Ala Ala Ser Lys Ala Val Ala Ala Tyr Gly Leu Pro Arg Thr Leu His
                355                 360                 365

His Leu Arg Arg Thr Gly Glu Ile Leu Arg
370                 375

<210> SEQ ID NO 327
<211> LENGTH: 345
<212> TYPE: PRT
<213> ORGANISM: Physcomitrella patens

<400> SEQUENCE: 327

Met Phe Asn Gly Asn Arg Gly Leu Cys Arg Ser Val Gly Leu Ala Thr
1               5                   10                  15

Cys Ala Gly Cys His Arg Thr Leu Gly Phe Gly Arg Phe Leu Thr Cys
                20                  25                  30

Leu Asn Gln Asn Trp His Pro Ala Cys Phe Cys Cys Arg Tyr Cys Leu
            35                  40                  45

Gln Gly Ile Val Asp Lys Glu Phe Ser Val His Gly Asn Asp Pro Tyr
    50                  55                  60

His Arg Asp Cys Tyr Lys Lys Leu Phe His Pro Lys Cys Glu Ile Cys
65                  70                  75                  80

Tyr Asn His Ile Pro Leu Asn Pro Lys Gly Gln Ile Glu Tyr Arg Ser
                85                  90                  95

His Pro Phe Trp Asn Gln Arg Tyr Cys Pro Ser His Glu Leu Asp Gly
            100                 105                 110

Ser Gln Cys Cys Cys Ser Cys Asp Arg Ile Gln Pro Val Asp Gln Arg
        115                 120                 125

Tyr Arg Arg Leu Pro Asp Gly Arg Lys Val Cys Ser Glu Cys Met Asp
    130                 135                 140

Ser Ala Val Met Thr Thr Lys Asp Cys Gln Pro Leu Tyr Arg Asp Val
145                 150                 155                 160

Leu Lys Phe Tyr Arg Asn Leu Gly Met Pro Ile Glu Gln Glu Ile Ser
                165                 170                 175

Met Leu Leu Val Glu Arg Glu Ala Leu Asn His Ala Arg Glu Val Glu
            180                 185                 190

Glu Gly Gly His Thr His Ala Pro Glu Thr Arg Gly Leu Cys Leu Ser
        195                 200                 205
```

```
Glu Glu Gln Ile Leu Pro Val Lys Met Arg Lys Leu Thr Arg His Cys
    210                 215                 220

Glu Val Thr Ala Ile Leu Val Leu Tyr Gly Leu Pro Arg Leu Leu Thr
225                 230                 235                 240

Gly Ser Ile Leu Ala His Glu Leu Met His Ala Trp Ile Arg Leu Asp
                245                 250                 255

Gly Arg Tyr Pro Asn Leu Asp Asn Asp Val Glu Glu Gly Ile Cys Gln
                260                 265                 270

Val Ile Ala His Met Trp Leu Lys Ser Glu Leu Glu Thr Leu Met Arg
            275                 280                 285

Thr Gly Val Ser Leu Val Ile Lys Arg Leu Gly Glu Phe Phe Leu His
290                 295                 300

Gln Ile Glu Thr Asp Ser Ser Pro Ile Tyr Gly Asp Gly Phe Arg Thr
305                 310                 315                 320

Ala Ser Ala Ala Val Ser Ser His Gly Leu Thr Arg Thr Leu His His
                325                 330                 335

Leu Arg Gln Thr Gly Glu Ile Leu His
            340                 345

<210> SEQ ID NO 328
<211> LENGTH: 416
<212> TYPE: PRT
<213> ORGANISM: Physcomitrella patens

<400> SEQUENCE: 328

Met Gln Glu Ser Leu Ile Leu Glu Arg Asn Pro Ala Ser His Gly Thr
1               5                   10                  15

Pro Thr Asp Ala Arg Ser Pro His Ser Val Pro Ala Pro Ala Lys Glu
            20                  25                  30

Tyr Glu Phe Thr Phe Gln Ser Pro Glu Leu Ile Met Leu Pro Pro Ala
        35                  40                  45

Val Thr Ile Ala Cys Arg Ser Gly Gly Met Pro Thr Cys Ala Gly Cys
    50                  55                  60

His Arg Thr Leu Gly Ser Gly Lys Phe Leu Thr Cys Leu Asn Gln Asp
65                  70                  75                  80

Trp His Pro Ser Cys Phe Cys Cys Leu Tyr Cys Leu Gln Pro Ile Val
                85                  90                  95

Asp Gln Glu Val Leu Ser Thr Cys Ala Asn Gly Ile Met Gln Phe
            100                 105                 110

Ser Val Gln Glu Ser Asp Pro Tyr His Arg Val Cys Tyr Lys Lys Leu
        115                 120                 125

Phe His Pro Lys Cys Glu Ile Cys Tyr Asn Tyr Ile Gln Ala Asn Ala
    130                 135                 140

Gln Gly Gln Ile Glu Tyr Arg Ser His Pro Phe Trp Asn Gln Lys Tyr
145                 150                 155                 160

Cys Pro Ser His Glu Arg Asp Gly Ser Arg Cys Cys Ser Cys Asp
                165                 170                 175

Arg Ile Glu Pro Val Asp Gln Arg Tyr Gln Ser Leu Pro Asp Gly Arg
            180                 185                 190

Arg Val Cys Ser Glu Cys Leu Gly Ser Ala Met Met Ala Thr Lys Asp
        195                 200                 205

Cys Gln Pro Leu Tyr Arg Asp Ile Ile Arg Phe Tyr Ser Asp Met Gly
    210                 215                 220

Met Arg Ile Glu Gln Glu Ile Pro Met Leu Leu Val Glu Arg Glu Ala
225                 230                 235                 240
```

```
Leu Asn His Ala Arg Glu Ser Glu Glu Gly His Ser His Glu Pro
                245                 250                 255

Glu Thr Arg Gly Leu Cys Leu Ser Glu Gln Thr Phe Pro Val Arg
            260                 265                 270

Gln Arg Lys Ser Phe Phe Glu Leu Asn Leu Gln His Ser Leu Gln Phe
        275                 280                 285

Met Gln Gln Thr Arg His Ser Glu Val Thr Ala Ile Leu Val Leu Cys
290                 295                 300

Gly Leu Pro Arg Leu Leu Thr Gly Ser Ile Leu Ala His Glu Leu Met
305                 310                 315                 320

His Ala Trp Ile Arg Leu Asp Gly Arg Phe Pro Asn Leu Asp Asn Val
                325                 330                 335

Ile Glu Glu Gly Ile Cys Gln Val Ile Ala His Met Trp Leu Ser Ser
            340                 345                 350

Glu Leu Glu Ser Leu Thr Arg Arg Gly Gly Ser Pro Ile Ser Lys Arg
        355                 360                 365

Leu Gly Glu Phe Phe Leu His Gln Ile Glu Thr Asp Ser Ser Pro Thr
370                 375                 380

Tyr Gly Asp Gly Phe Arg Ala Ala Tyr Ala Ala Val Ala Thr Tyr Gly
385                 390                 395                 400

Leu Thr Arg Thr Leu His His Leu Arg His Thr Gly Glu Ile Ile Arg
                405                 410                 415

<210> SEQ ID NO 329
<211> LENGTH: 460
<212> TYPE: PRT
<213> ORGANISM: Selaginella moellendorffi

<400> SEQUENCE: 329

Met Met Arg Leu Leu Arg Cys Ser Ala Leu His Thr Gly Gln Thr Ala
1               5                   10                  15

Ala Lys Gly Gln Arg Gly Gln Glu Asp Glu Gln Gln Arg Arg Thr
            20                  25                  30

Lys Leu Gln Asn Gly Ala Val His Val Asp Pro Gln Ser His Arg Arg
        35                  40                  45

Asn Leu Pro Pro Gly Lys Ser Ser Arg Arg Phe Ala Met Gln Ser Ile
50                  55                  60

Tyr Leu Cys Leu Gly Leu Cys Arg Ser Arg Leu Met Arg Ala Arg Ala
65                  70                  75                  80

Cys Cys Ser Pro Cys Pro Ser Ile Ala Pro Ala Leu Gln Ala Val Ile
                85                  90                  95

Cys Phe Ala Leu Pro Ala Gly Trp Thr Gln Glu Cys Ala Asp Leu Met
            100                 105                 110

His Arg Tyr Met His Arg Tyr Ile Cys Ala Gly Cys Asn Gln Glu Ile
        115                 120                 125

Gly Pro Gly Arg Phe Leu Ser Cys Leu Gly Ser Val Trp His Pro Gln
130                 135                 140

Cys Phe Arg Cys Lys Ala Cys Gly Asp Pro Ile Ser Gly Ser Gln Val
145                 150                 155                 160

Ser Gln Phe Ala Leu Ser Gly Ser Asp Arg Tyr His Lys Glu Cys Tyr
                165                 170                 175

Arg Asp Leu Tyr His Pro Lys Cys Glu Val Cys His Gln Phe Val Ile
            180                 185                 190

Pro Pro Asn Ser Ser Gly Leu Ile Glu Tyr Arg Ala His Pro Phe Trp
```

195                 200                 205
Gly Gln Lys Tyr Cys Pro Leu His Glu Lys Asp Ser Thr Pro Arg Cys
    210                 215                 220

Cys Ser Cys Glu Arg Val Glu Val Arg Met Gln Ala Arg Asp Ala Arg
225                 230                 235                 240

Phe Val Ser Leu Asp Asp Gly Arg Lys Leu Cys Leu Glu Cys Leu Asp
                245                 250                 255

Ser Ala Val Met Asp Thr His Glu Cys Gln His Leu Tyr His Glu Ile
            260                 265                 270

Leu Asp Phe Tyr Glu Gly Met Asn Met Lys Ile Ser Gln Ser Ile Pro
        275                 280                 285

Met Leu Leu Val Glu Arg Gln Ala Leu Asn Glu Ala Arg Glu His Glu
    290                 295                 300

Arg Asp Val Ser Phe Cys Met Gly Tyr His His Leu Pro Glu Thr Arg
305                 310                 315                 320

Gly Leu Cys Leu Ser Glu Glu Gln Thr Val Ser Thr Val Ser Lys Glu
                325                 330                 335

Ser Leu Arg Leu Arg Arg Gln Cys Glu Val Thr Ala Ile Leu Val Leu
            340                 345                 350

Tyr Gly Leu Pro Arg Leu Leu Thr Gly Ser Ile Leu Ala His Glu Leu
        355                 360                 365

Met His Ala Trp Leu Arg Leu Asn Gly Leu Asn Pro Ala Val Glu Glu
    370                 375                 380

Gly Ile Cys Gln Val Met Ala His Thr Trp Leu Glu Ser Gln Ile Gly
385                 390                 395                 400

Gly Lys Gln Lys Pro Lys Ser Ile Asn Asn Asp Arg Phe Gln Glu Phe
                405                 410                 415

Phe Leu His Gln Ile Ala Met Asp Ser Ser Pro Ala Tyr Gly Asp Gly
            420                 425                 430

Phe Arg Ala Gly His Gln Ser Val Val Gln Phe Gly Leu Ser Arg Thr
        435                 440                 445

Leu Glu His Ile Lys Leu Thr Gly Ser Phe Pro Val
    450                 455                 460

<210> SEQ ID NO 330
<211> LENGTH: 428
<212> TYPE: PRT
<213> ORGANISM: Selaginella moellendorffi

<400> SEQUENCE: 330

Met Pro Ser Arg Val Ser Asp Arg Val Ala Ala Arg Glu Leu Gln Ile
1               5                   10                  15

Ser Ser Ser Arg Ser Arg Gly Phe Ser Phe Gln Arg Ser Ser Ile Asp
            20                  25                  30

Arg Ser Met Asp Cys Gln Gly Phe Arg Phe Trp Asp Lys Leu Ser Thr
        35                  40                  45

Met Lys Trp Phe Asp Lys Ile Phe Lys Pro Leu His Gln Lys Val His
    50                  55                  60

Glu Ile Ser His Asn Ser Ser Glu Val Leu Val Leu Leu Ser Phe
65                  70                  75                  80

Val Met Pro Arg Arg Phe Ser Gly Ala His Val Cys Ala Arg Cys Lys
                85                  90                  95

Lys Thr Ile Gly Pro Gly Arg Phe Leu Ser Cys Met Gly Gly Leu Trp
            100                 105                 110

-continued

```
His Pro Glu Cys Phe Arg Cys Thr Ser Cys Asn Lys Pro Ile Ser Gly
        115                 120                 125

Ser Glu Phe Met Gln Phe Ser Val Ser Gly Asn Asp Pro Tyr His Lys
        130                 135                 140

Asp Cys Tyr Lys Glu Leu Phe His Pro Arg Cys Asp Val Cys Asn Leu
145                 150                 155                 160

Phe Val Arg Ala Ser Arg Gln Ser Ile Leu Ile Pro Pro Asn Tyr Ser
                165                 170                 175

Gly Leu Ile Glu Tyr Arg Val His Pro Phe Trp Gly Gln Arg Tyr Cys
            180                 185                 190

Pro Ser His Glu Asp Asp Asn Thr Pro Arg Cys Cys Ser Cys Glu Arg
        195                 200                 205

Leu Glu Leu Lys Thr Lys Asn Ser Lys Tyr Val Val Leu Asp Asp Gly
        210                 215                 220

Arg Lys Leu Cys Leu Glu Cys Met Asp Ser Ala Val Met Asp Thr Asn
225                 230                 235                 240

Glu Gly Gln Pro Leu Tyr Gln Glu Ile Ile Asn Phe Tyr Glu Gly Met
                245                 250                 255

Asn Met Lys Ile Thr Gln Gln Ile Pro Met Leu Leu Val Glu Arg Gln
            260                 265                 270

Ala Leu Asn Glu Ala Arg Ala His Glu Ser Asn His His Leu Thr Glu
        275                 280                 285

Thr Arg Gly Leu Thr Leu Ser Glu Glu Gln Thr Val Thr Ser Val Thr
    290                 295                 300

Glu Ser Met Lys Leu Arg Arg Asn Cys Glu Val Thr Ala Ile Leu Val
305                 310                 315                 320

Leu Tyr Gly Leu Pro Arg Arg Leu Leu Thr Gly Ser Ile Leu Ala His
                325                 330                 335

Glu Leu Met His Ala Trp Leu Arg Leu Asn Gly Leu Asn Pro Val Val
            340                 345                 350

Glu Glu Gly Ile Cys Gln Val Met Ala His Thr Trp Leu Glu Ser Gln
        355                 360                 365

Ile Lys Pro Ala Pro His Gln Phe Asp Thr Ser Lys Leu Arg Glu Phe
    370                 375                 380

Val Met His Gln Ile Ala Met Asp Pro Ser Pro Ala Tyr Gly Asp Gly
385                 390                 395                 400

Phe Arg Ile Gly Gln Ser Ala Val Val Gln Phe Gly Leu Pro Arg Thr
                405                 410                 415

Leu Asp His Ile Lys Leu Thr Gly Asp Phe Pro Val
            420                 425
```